(12) United States Patent
Thomas et al.

(10) Patent No.: US 9,827,258 B2
(45) Date of Patent: *Nov. 28, 2017

(54) BICYCLIC ARYL SPHINGOSINE 1-PHOSPHATE ANALOGS

(71) Applicant: BIOGEN MA INC., Cambridge, MA (US)

(72) Inventors: Jermaine Thomas, Chelsea, MA (US); Xiaogao Liu, Dover, MA (US); Edward Yin-Shiang Lin, Ashland, MA (US); Guo Zhu Zheng, Lexington, MA (US); Bin Ma, Arlington, MA (US); Richard D. Caldwell, Brookline, MA (US); Kevin M. Guckian, Northborough, MA (US); Gnanasambandam Kumaravel, Lexington, MA (US); Arthur G. Taveras, Boston, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,421

(22) Filed: Jan. 3, 2017

(65) Prior Publication Data

US 2017/0239280 A1   Aug. 24, 2017

Related U.S. Application Data

(60) Continuation of application No. 14/874,600, filed on Oct. 5, 2015, now Pat. No. 9,572,824, which is a
(Continued)

(51) Int. Cl.

| *A61K 31/695* | (2006.01) |
| *C07C 229/14* | (2006.01) |
| *C07C 229/22* | (2006.01) |
| *C07C 229/46* | (2006.01) |
| *C07C 229/48* | (2006.01) |

(Continued)

(52) U.S. Cl.
CPC .......... *A61K 31/695* (2013.01); *A61K 31/085* (2013.01); *A61K 31/11* (2013.01); *A61K 31/137* (2013.01); *A61K 31/165* (2013.01); *A61K 31/18* (2013.01); *A61K 31/185* (2013.01); *A61K 31/197* (2013.01); *A61K 31/198* (2013.01); *A61K 31/216* (2013.01); *A61K 31/222* (2013.01); *A61K 31/223* (2013.01); *A61K 31/235* (2013.01); *A61K 31/277* (2013.01); *A61K 31/337* (2013.01); *A61K 31/397* (2013.01); *A61K 31/40* (2013.01); *A61K 31/401* (2013.01); *A61K 31/404* (2013.01); *A61K 31/41* (2013.01); *A61K 31/428* (2013.01); *A61K 31/445* (2013.01); *A61K 31/47* (2013.01); *A61K 31/472* (2013.01); *A61K 31/4709* (2013.01); *A61K 31/517* (2013.01); *A61K 31/662* (2013.01); *A61K 31/683* (2013.01); *A61K 45/06* (2013.01); *C07C 43/247* (2013.01); *C07C 47/575* (2013.01); *C07C 229/14* (2013.01); *C07C 229/22* (2013.01); *C07C 229/46* (2013.01); *C07C 229/48* (2013.01); *C07C 237/08* (2013.01); *C07C 237/52* (2013.01); *C07C 255/54* (2013.01); *C07C 309/14* (2013.01); *C07C 311/51* (2013.01); *C07D 205/04* (2013.01); *C07D 207/16* (2013.01); *C07D 209/08* (2013.01); *C07D 211/60* (2013.01); *C07D 211/62* (2013.01); *C07D 215/20* (2013.01); *C07D 215/227* (2013.01); *C07D 217/04* (2013.01); *C07D 217/24* (2013.01); *C07D 239/74* (2013.01); *C07D 257/04* (2013.01); *C07D 277/64* (2013.01); *C07D 305/08* (2013.01); *C07D 401/06* (2013.01); *C07D 403/06* (2013.01); *C07D 417/06* (2013.01); *C07F 7/081* (2013.01); *C07F 9/3808* (2013.01); *C07F 9/3834* (2013.01); *C07F 9/4006* (2013.01); *C07C 2601/02* (2017.05); *C07C 2601/04* (2017.05); *C07C 2601/08* (2017.05); *C07C 2601/14* (2017.05); *C07C 2601/16* (2017.05)

(58) Field of Classification Search
CPC .................................................. A61K 31/695
See application file for complete search history.

(56) References Cited

U.S. PATENT DOCUMENTS

| 5,041,639 A | 8/1991 | Shroot et al. |
| 5,719,164 A | 2/1998 | Weidmann et al. |

(Continued)

FOREIGN PATENT DOCUMENTS

| CN | 1791592 A | 6/2006 |
| JP | 2007169194 A | 7/2007 |

(Continued)

OTHER PUBLICATIONS

Carrigan et al.; "Synthesis and in Vitro Pharmacology of Substituted Quinoline-2,4-dicarboxylic Acids as Inhibitors of Vesicular Glutamate Transport"; J. Med. Chem.; 45(11):2260-2276 (2002).
European Medicines Agency Press Release Jan. 20, 2012, EMA/CHMP/48716/2012, p. 1-2.
European Supplementary Search Report for European Application No. 10807186.1, dated Jan. 22, 2013.
Examination Report for New Zealand Application No. 597596, dated Oct. 9, 2012.
First Office Action for Chinese Application No. 201080044608.4, issued May 10, 2013. English translation only.
(Continued)

*Primary Examiner* — Timothy R Rozof

(74) *Attorney, Agent, or Firm* — McCarter & English, LLP; Steven G. Davis; Xin Zhang

(57) ABSTRACT

Compounds that have agonist activity at one or more of the S1P receptors are provided. The compounds are sphingosine analogs that, after phosphorylation, can behave as agonists at S1P receptors.

10 Claims, No Drawings

Related U.S. Application Data continuation of application No. 14/306,231, filed on Jun. 17, 2014, now Pat. No. 9,186,367, which is a division of application No. 13/389,054, filed as application No. PCT/US2010/044607 on Aug. 5, 2010, now Pat. No. 8,802,659.

(60) Provisional application No. 61/231,539, filed on Aug. 5, 2009.

(51) Int. Cl.

| | | |
|---|---|---|
| C07C 237/08 | (2006.01) | |
| C07C 237/52 | (2006.01) | |
| C07C 309/14 | (2006.01) | |
| C07C 311/51 | (2006.01) | |
| C07D 205/04 | (2006.01) | |
| C07D 207/16 | (2006.01) | |
| C07D 209/08 | (2006.01) | |
| C07D 211/60 | (2006.01) | |
| C07D 211/62 | (2006.01) | |
| C07D 215/20 | (2006.01) | |
| C07D 217/24 | (2006.01) | |
| C07D 257/04 | (2006.01) | |
| C07D 305/08 | (2006.01) | |
| C07D 403/06 | (2006.01) | |
| C07D 417/06 | (2006.01) | |
| C07F 9/38 | (2006.01) | |
| C07F 9/40 | (2006.01) | |
| A61K 31/085 | (2006.01) | |
| A61K 31/11 | (2006.01) | |
| A61K 31/18 | (2006.01) | |
| A61K 31/197 | (2006.01) | |
| A61K 31/216 | (2006.01) | |
| A61K 31/277 | (2006.01) | |
| A61K 31/337 | (2006.01) | |
| A61K 31/397 | (2006.01) | |
| A61K 31/40 | (2006.01) | |
| A61K 31/404 | (2006.01) | |
| A61K 31/41 | (2006.01) | |
| A61K 31/428 | (2006.01) | |
| A61K 31/445 | (2006.01) | |
| A61K 31/47 | (2006.01) | |
| A61K 31/4709 | (2006.01) | |
| A61K 31/472 | (2006.01) | |
| A61K 31/517 | (2006.01) | |
| A61K 31/662 | (2006.01) | |
| A61K 31/683 | (2006.01) | |
| A61K 45/06 | (2006.01) | |
| C07C 43/247 | (2006.01) | |
| C07C 47/575 | (2006.01) | |
| C07C 255/54 | (2006.01) | |
| C07D 215/227 | (2006.01) | |
| C07D 217/04 | (2006.01) | |
| C07D 239/74 | (2006.01) | |
| C07D 277/64 | (2006.01) | |
| C07D 401/06 | (2006.01) | |
| C07F 7/08 | (2006.01) | |
| A61K 31/137 | (2006.01) | |
| A61K 31/165 | (2006.01) | |
| A61K 31/185 | (2006.01) | |
| A61K 31/198 | (2006.01) | |
| A61K 31/222 | (2006.01) | |
| A61K 31/223 | (2006.01) | |
| A61K 31/235 | (2006.01) | |
| A61K 31/401 | (2006.01) | |

(56) References Cited

U.S. PATENT DOCUMENTS

| | | |
|---|---|---|
| 7,750,021 B2 | 7/2010 | Mi et al. |
| 7,754,896 B2 | 7/2010 | Azzaoui et al. |
| 7,825,109 B2 | 11/2010 | Nakade et al. |
| 7,906,549 B2 | 3/2011 | Habashita et al. |
| 7,919,519 B2 | 4/2011 | Burli et al. |
| 8,039,674 B2 | 10/2011 | Habashita et al. |
| 2004/0209904 A1 | 10/2004 | Dunn et al. |
| 2004/0254215 A1 | 12/2004 | Arend et al. |
| 2008/0027035 A1 | 1/2008 | Edwards et al. |
| 2008/0027036 A1 | 1/2008 | Burli et al. |
| 2009/0131400 A1 | 5/2009 | Mi et al. |
| 2010/0160258 A1 | 6/2010 | Caldwell et al. |
| 2010/0160357 A1 | 6/2010 | Caldwell et al. |
| 2012/0190649 A1 | 7/2012 | Thomas et al. |

FOREIGN PATENT DOCUMENTS

| | | |
|---|---|---|
| WO | 03/061567 A2 | 7/2003 |
| WO | 03/062248 A2 | 7/2003 |
| WO | 03/062252 A1 | 7/2003 |
| WO | 03/105771 A2 | 12/2003 |
| WO | 2004/103309 A2 | 12/2004 |
| WO | 2004/108681 A1 | 12/2004 |
| WO | 2005/000833 A1 | 1/2005 |
| WO | 2005/020882 A2 | 3/2005 |
| WO | 2005/082905 A1 | 9/2005 |
| WO | 2006/001463 A1 | 1/2006 |
| WO | 2006/064757 A1 | 6/2006 |
| WO | 2006/080477 A1 | 8/2006 |
| WO | 2006/088944 A1 | 8/2006 |
| WO | 2006/099610 A2 | 9/2006 |
| WO | 2007/092638 A1 | 8/2007 |
| WO | 2008/074821 A1 | 6/2008 |
| WO | 2009/023854 A1 | 2/2009 |
| WO | 2010/051030 A1 | 5/2010 |
| WO | 2010/051031 A1 | 5/2010 |
| WO | 2010/017561 A1 | 2/2011 |

OTHER PUBLICATIONS

International Preliminary Report on Patentability issued in International Patent Application No. PCT/US2010/044607, issued Feb. 7, 2012.

Kurata et al., "Structure-Activity Relationship Studies of Sphingosine-1-Phosphate Receptor Agonists with N-Cinnamyl-beta-Alanine Moiety", 21 Bioorg. & Med. Chem. Letts. 1390-1393 (2011).

Marsolais et al.; "Chemical modulators of sphingosine-1-phosphate receptors as barrier-oriented therapeutic molecules"; Nature Reviews Drug Discovery; 8(4):297-307 (2009).

Mayo Clinic Multiple Sclerosis Causes 2014 accessed online Jun. 17, 2015 @http://www.mayoclinic.org/diseasesconditions/multiple-sclerosis/basics/causes/con-20026 . . . ; p. 1-8.

Official Action for Eurasian Application No. 201200239, dated Jul. 22, 2013. English translation only.

Official Action for Mexican Patent Application No. MX/a/2012/001650, dated Jun. 28, 2013. English translation only.

Official Letter No. 11204 for Colombian Application No. 12/29572-9, dated Jul. 2, 2013. English translation only.

Patent Examination Report No. 1 for Australian Application No. 2010279337, dated Jul. 17, 2013.

Stedman's Medical Dictionary Online, accessed Jun. 17, 2015 @ http://www.stedmansonline.com/popup.aspx?aid=5231018, 1 p.

Zu Heringdorf, D.M.,"Pharmacology of the sphingosine-1-phosphate signalling system." Sphingolipids: Basic Science and Drug Development. Springer Vienna, 2013. 239-253.

Brinkmann et al., FTY720 (fingolimod) in Multiple Sclerosis: therapeutic effects in the immune and the central nervous system. British Journal of Pharmacology, 2009, 158, pp. 1173-1182.

Cee et al., Discovery of AMG 369, a Thiazolo[5,4-b]pyridine Agonist of S1P1 and S1P5, Americn Chemical Society, ACS Med. Chem Lett. 2011, 2, Published on Web Dec. 29, 2010, pp. 107-112.

(56) References Cited

OTHER PUBLICATIONS

Noguchi et al., Roles for lysophospholipid S1P receptors in multiple sclerosis, Critical Reviews in Biochemistry and Molecular Biology, 2011 46(1) pp. 2-10 Published on Oct. 2010.

BICYCLIC ARYL SPHINGOSINE 1-PHOSPHATE ANALOGS

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl) ethyl] propane 1,3-diol), that following phosphorylation, is an agonist at 4 of 5 S1P receptors, revealed that affecting S1P receptor activity influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds. S1P type 4 receptors ($S1P_4$) are expressed mainly in leukocytes, and specifically $S1P_4$ mediates immunosuppressive effects of S1P by inhibiting proliferation and secretion of effector cytokines, while enhancing secretion of the suppressive cytokine IL-10. See, for example, Wang, W. et. al., (2005) *FASEB J.* 19(12): 1731-3, which is incorporated by reference in its entirety. S1P type 5 receptors ($S1P_5$) are exclusively expressed in oligodendrocytes and oligodendrocyte precursor cells (OPCs) and are vital for cell migration. Stimulation of $S1P_5$ inhibits OPC migration, which normally migrate considerable distances during brain development. See, for example, Novgorodov, A. et al., (2007) *FASEB J,* 21: 1503-1514, which is incorporated by reference in its entirety.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing, tumor growth inhibition, and autoimmune diseases.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response. Generally, compounds can switch from antagonists to agonist depending on what G protein is downstream of the receptor. When $G_q$ is downstream a compound targeting the $S1P_4$ receptor can act as an antagonist. It is possible that with a different G protein ($G_i$) downstream an agonist compound may be an agonist.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of S1P is catalyzed by S1P lyase yielding ethanolamine phosphate and hexadecenal.

SUMMARY

Currently, there is a need for novel, potent, and selective agents that are agonists of the S1P receptor having enhanced potency, selectivity, and oral bioavailability. In addition, there is a need in the art for identification of, as well as the synthesis and use of, such compounds.

In one aspect, a compound can have formula (I):

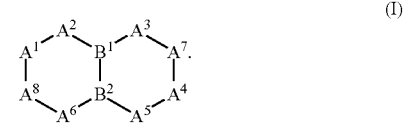

In formula (I), $A^1$ can be —$CX^1$=, —$C(X^1)_2$—, —N=, —$NX^1$—, —O—, —S—, or a bond; $A^2$ can be —$CX_2$=, —$C(X^2)_2$—, —N=, —$NX^2$—, —O—, or —S—; $A^3$ can be —$CX_3$=, —$C(X^3)_2$—, —N=, —$NX^3$—, —O—, —S—, or a bond; $A^4$ can be —$CX^4$=, —$C(X^4)_2$—, —N=, —$NX^4$—, —O—, —S—, or a bond; $A^5$ can be —$CX^5$=, —$C(X^5)_2$—, —N=, —$NX^5$—, —O—, or —S—; $A^6$ can be —$CX^6$=, —$C(X^6)_2$—, —N=, —$NX^6$—, —O—, —S—, or a bond; $A^7$ can be —$C(R^3)$=, —$C(R^3R^f)$—, or —$NR^3$—; and $A^8$ can be —C(—W-Cy)=, —C(—W-Cy)($R^f$)—, or —N(—W-Cy)—.

$B^1$ can be

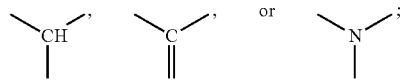

and B² can be

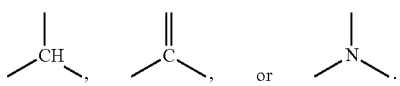

In formula (I), no more than 1 of A¹, A³, A⁴, and A⁶ is a bond; B¹ and B² are not both simultaneously

and no more than 4 ring atoms of A¹-A⁸ and B¹-B² are N, O, or S.

Each of $X^1$, $X^2$, $X^3$, $X^4$, $X^5$, and $X^6$, independently, can be hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —N(R$^f$R$^g$), —N(R$^f$)SO₂R$^g$, —SO₂R$^f$, —S(O)₂N(R$^f$R$^g$), —CO₂R$^f$, trialkylamino, aryl, or heteroaryl.

W can be —C(R$^f$R$^g$)—, —N(R$^f$)—, —O—, —S—, —S(O)—, or —S(O)₂—.

Cy can be cycloalkyl, spirocycloalkyl, cycloalkenyl, spirocycloalkenyl, heterocyclyl, spiroheterocyclyl, aryl, or heteroaryl. Cy can be optionally substituted by 1-6 substituents selected from the group consisting of halo, hydroxy, nitro, cyano, —N(R$^f$R$^g$), alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.

R³ can be -L¹-J-L²-T¹.

L¹ can be —C(O)—, —S(O)₂—, —N(R$^f$)C(O)—, —N(R$^f$)—, —C(R$^f$R$^g$)—, —C(R$^f$R$^g$)—C(R$^f$R$^g$)—, or a bond.

J can be —[C(R$^f$R$^g$)]$_n$—, —N(R$^f$)—[C(R$^f$R$^g$)]$_n$—, or a bond, wherein each n, independently, can be an integer from 0 to 5; or J can be

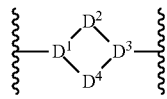

where each of D¹ and D³, independently, can be

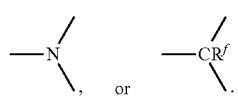

D² can be —[C(R$^f$R$^g$)]$_k$—, —[C(R$^f$R$^g$)]$_k$—N(R$^f$)—, —[C(R$^f$R$^g$)]$_k$—O—, —N(R$^f$)—, or —N(R$^f$)—[(CR$^f$R$^g$)]$_k$—. D⁴ can be —[C(R$^f$R$^g$)]$_m$—. k can be 1 or 2; and m can be 0, 1, 2, or 3. No more than 2 ring atoms of D¹-D⁴ can be N or O.

L² can be —C(R$^f$R$^g$)—, —C(R$^f$G)-, —C(G)₂-, —C(R$^f$R$^g$)—C(R$^f$R$^g$)—, —C(R$^f$R$^g$)—C(R$^f$G)-, —C(R$^f$R$^g$)—C(G)₂-, or a bond.

At least one of L¹, J, and L² can be other than a bond.

T¹ can be —C(O)(OR$^f$), —C(O)N(R$^f$)S(O)₂R$^f$, tetrazolyl, —S(O)₂OR$^f$, —C(O)NHC(O)—R$^f$, —Si(O)OH, —B(OH)₂, —N(R$^f$)S(O)₂R$^f$, —S(O)₂NR$^f$, —O—P(O)(OR$^f$)OR$^f$, or —P(O)₂(OR$^f$).

Each G, independently, can be hydrogen, hydroxy, a halogen, or trifluoromethyl.

Each R$^f$, independently, can be hydrogen, hydroxy, halo, alkyl, haloalkyl, alkenyl, alkynyl, cycloalkyl, cycloalkenyl, aryl, heteroaryl, heterocyclyl or NH₂. Each of alkyl, cycloalkyl, cycloalkenyl, aryl, heteroaryl and heterocycle can be optionally substituted with 1 to 5 substituents independently selected from the group consisting of halo, oxo, —CN, —CHO, —CG₃, —OH, —NO₂, alkyl, —OCG₃, alkoxy, cycloalkoxy, cycloalkenoxy, amino, alkylamino, dialkylamino, acylamino, aminoacyl, alkylsulfonyl, alkylaminosulfonyl, or dialkylaminosulfonyl.

Each R$^g$, independently, can be hydrogen, hydroxy, halo, alkyl, haloalkyl, alkenyl, alkynyl, cycloalkyl, cycloalkenyl, aryl, heteroaryl, or heterocyclyl. Each of alkyl, cycloalkyl, cycloalkenyl, aryl, heteroaryl and heterocycle can be optionally substituted with 1 to 5 substituents independently selected from the group consisting of halo, oxo, —CN, —CHO, —CG₃, —OH, —NO₂, alkyl, —OCG₃, alkoxy, cycloalkoxy, cycloalkenoxy, amino, alkylamino, dialkylamino, acylamino, aminoacyl, alkylsulfonyl, alkylaminosulfonyl, can be dialkylaminosulfonyl.

The compound can be in the form of a pharmaceutically acceptable salt.

In some circumstances, A⁷ can be —CR³═, A⁸ can be —C(—W-Cy)═, B¹ can be

and B² can be

Of A¹-A⁶, 0, 1, or 2 ring atoms of A¹-A⁶ can be N. The remaining ring atoms of A¹-A⁶ can each be C. A¹ can be —CX¹═, A² can be —CX²═, and A⁶ can be —CX⁶═. A³ can be —CX³═, A⁴ can be —CX⁴═, and A⁵ can be —CX⁵═.

In some circumstances, A¹ can be —CX¹═, A² can be —CX²═, A⁶ can be —CX⁶═, A⁸ can be —C(—W-Cy)=, B¹ is

B² can be

and A³, A⁷, A⁴, and A⁵, can be, respectively: —NX³—, —C(R³R^f)—, a bond, and —C(X⁵)₂—; —C(X³)₂—, —NR³—, —C(X⁴)₂—, and —C(X⁵)₂—; —C(X³)₂—, —C(R³R^f)—, —NX⁴—, and —C(X⁵)₂—; —N=, —CR³=, —CX₄=, and —CX₅=; —N=, —CR³=, —N=, and —CX₅=; —CX³=, —CR³=, —N=, and —CX₅=; —N=, —CR³=, —CX₄=, and —N=; —CX³=, —CR³=, —CX₄=, and —N=; —CX³=, —CR³=, —N=, and —N=; —NX³—, —CR³=, a bond, and —CX₅=; or —CX³=, —CR³=, a bond, and —NX⁵—.

In some circumstances, A³ can be —CX³=, A⁴ can be —CX⁴=, A⁵ can be —CX₅=, A⁷ can be —CR³=, B¹ can be

B² can be

and A², A¹, A⁸, and A⁶, can be, respectively: —CX²=, —CX₁=, —C(—W-Cy), and —N=; —CX²=, —N=, —C(—W-Cy), and —N=; —NX²—, —CX¹=, —C(—W-Cy), and a bond; —NX²—, a bond, —C(—W-Cy)=, and —CX⁶=; or —CX²=, a bond, —C(—W-Cy)=, and —NX⁶—.

In some circumstances, each ring atom of A¹, A², A⁵-A⁸ and B¹-B² is C, and each of A³ and A⁴ is, independently, C or N. L¹ can be —C(R^fR^g)— and J can be —NR^f— or

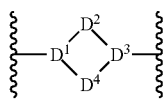

wherein
each of D¹ and D³, independently, is

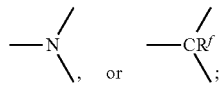

D² is —[C(R^fR^g)]_k—, —[C(R^fR^g)]_k—N(R^f)—, —[C(R^fR^g)]_k—O—, —N(R^f)—, or —N(R^f)—[(CR^fR^g)]_k—; and
D⁴ is —[C(R^fR^g)]_m—;
wherein k is 1 or 2; and m is 0, 1, 2, or 3;
provided that no more than 2 ring atoms of D¹-D⁴ are N or O. Each R^f and R^g, independently, can be hydrogen or alkyl. T¹ can be —C(O)(OR^f). T¹ can be —C(O)N(R^f)S(O₂R^f), —O—P(O)(OR^f)OR^f, —P(O₂)(OR^f), tetrazolyl or —S(O)₂OR^f. X⁶ can be an electron withdrawing group. X⁶ can be halo, alkyl, or haloalkyl. Each G, independently, can be fluoro or hydroxy.

In some circumstances, Cy can have the formula:

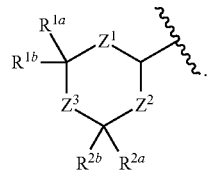

Z¹ can be a bond, —[C(R^dR^e)]_x—, —CR^d=CR^e—, —O—, or —NR^f—.
Z² can be a bond, —[C(R^dR^e)]_y—, —CR^d=CR^e—, —O—, or —NR^f—.
Z³ can be a bond, —[C(R^dR^e)]_z—, —CR^d=CR^e—, —O—, or —NR^f—.
Each of x, y, and z, independently, can be 1, 2, or 3.
Each R^d, and each R^e, independently, can be hydrogen, halo, hydroxy, alkyl, alkenyl, alkoxy, or cycloalkyl.
R^{1a} and R^{1b}, independently, can be hydrogen, halo, hydroxy, nitro, cyano, —NR^fR^g, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. R^{1a} and R^{1b}, when taken together, can be C₂-C₅ alkylene or C₂-C₅ alkenylene.
R^{2a} and R^{2b}, independently, can be hydrogen, halo, hydroxy, nitro, cyano, —NR^fR^g, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.
R^{1a} and R^{2a}, when taken together, can be C₁-C₅ alkylene or C₂-C₅ alkenylene.
R^{1a}, R^{1b}, R^{2a}, and R^{2b} can be each, independently, substituted with 0-5 substituents selected from halo, hydroxy, nitro, cyano, —NR^fR^g, or —CO₂R^f.
R^{1a} and R^{2a} can be both hydrogen. Z¹ can be —CH₂CH₂—. Z² can be —CH₂—. Z³ can be a bond.
R^{1b} can be fluoro, chloro, bromo, iodo, methyl, trifluoromethyl, ethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.
In some circumstances, W is O, Z¹ is —[C(R^dR^e)]_x—, Z² is —[C(R^dR^e)]_y—, and Z³ is —[C(R^dR^e)]_z—. In some circumstances, X² is methyl. In some circumstances, W is —O—. In some circumstances, each ring atom of A¹-A⁸ and B¹-B² is C. In some circumstances, each ring atom of A¹-A³, A⁵-A⁸ and B¹-B² is C, and A⁴ is N. In some circumstances, each ring atom of A¹-A², A⁴-A⁸ and B¹—B² is C, and A³ is N. The compound can be in the form of a pharmaceutically acceptable salt.
In some circumstances, A² can be —CX²=, and X² is fluoro, chloro, bromo, methyl, difluoromethyl, trifluoromethyl, ethyl, propyl, isopropyl or butyl.
In some circumstances, A¹ can be CH; A² can be —CX²=, and X² is fluoro, chloro, bromo, methyl, difluoromethyl, trifluoromethyl, ethyl, propyl, isopropyl or butyl.

$A^3$ can be CH; $A^4$ can be CH; $A^5$ can be CH; $A^6$ can be CH; $A^7$ can be C($R^3$); $A^8$ can be C(—W-Cy); $B^1$ can be

and $B^2$ can be

Each ring atom of $A^1$, $A^2$, $A^1$-$A^8$ and $B^1$-$B^2$ is C, and each of $A^3$ and $A^4$ is, independently, C or N. $L^1$ can be —C($R^fR^g$)— and J can be —$NR^f$— or

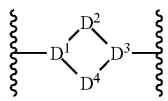

wherein
each of $D^1$ and $D^3$, independently, is

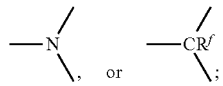

$D^2$ is —[C($R^fR^g$)]$_k$—, —[C($R^fR^g$)]$_k$—N($R^f$)—, —[C($R^fR^g$)]$_k$—O—, —N($R^f$)—, or —N($R^f$)—[(C$R^fR^g$)]$_k$—; and
$D^4$ is —[C($R^fR^g$)]$_m$—;
wherein k is 1 or 2; and m is 0, 1, 2, or 3;
provided that no more than 2 ring atoms of $D^1$-$D^4$ are N or O. Each $R^f$ and $R^g$, independently, can be hydrogen or alkyl. $T^1$ can be —C(O)(O$R^f$). $T^1$ can be —C(O)N($R^f$)S(O$_2R^f$), —O—P(O)(O$R^f$)O$R^f$, —P(O$_2$)(O$R^f$), tetrazolyl or —S(O)$_2$O$R^f$. $X^6$ can be an electron withdrawing group. $X^6$ can be halo, alkyl, or haloalkyl.
Each G, independently, can be fluoro or hydroxy.
In some circumstances, Cy can have the formula:

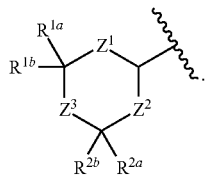

$Z^1$ can be a bond, —[C($R^dR^e$)]$_x$—, —$CR^d$=$CR^e$—, —O—, or —$NR^f$—.
$Z^2$ can be a bond, —[C($R^dR^e$)]$_y$—, —$CR^d$=$CR^e$—, —O—, or —$NR^f$—.
$Z^3$ can be a bond, —[C($R^dR^e$)]$_z$—, —$CR^d$=$CR^e$—, —O—, or —$NR^f$—.
Each of x, y, and z, independently, can be 1, 2, or 3.
Each $R^d$, and each $R^e$, independently, can be hydrogen, halo, hydroxy, alkyl, alkenyl, alkoxy, or cycloalkyl.

$R^{1a}$ and $R^{1b}$, independently, can be hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. $R^{1a}$ and $R^{1b}$, when taken together, can be $C_2$-$C_5$ alkylene or $C_2$-$C_5$ alkenylene.

$R^{2a}$ and $R^{2b}$, independently, can be hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.

$R^{1a}$ and $R^{2a}$, when taken together, can be $C_1$-$C_5$ alkylene or $C_2$-$C_5$ alkenylene.

$R^{1a}$, $R^{1b}$, $R^{2a}$, and $R^{2b}$ can be each, independently, substituted with 0-5 substituents selected from halo, hydroxy, nitro, cyano, —$NR^fR^g$, or —$CO_2R^f$.

$R^{1a}$ and $R^{2a}$ can be both hydrogen. $Z^1$ can be —$CH_2CH_2$—. $Z^2$ can be —$CH_2$—. $Z^3$ can be a bond.

$R^{1b}$ can be fluoro, chloro, bromo, iodo, methyl, triflurormethyl, ethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

In some circumstances, W is O, $Z^1$ is —[C($R^dR^e$)]$_x$—, $Z^2$ is —[C($R^dR^e$)]$_y$—, and $Z^3$ is —[C($R^dR^e$)]$_z$—. In some circumstances, $X^2$ is methyl. In some circumstances, W is —O—.

In another aspect, a pharmaceutical composition includes a pharmaceutically acceptable carrier and a compound of formula (I), as defined above.

In another aspect, a method for prevention or treatment of a pathological condition or symptom in a mammal, wherein the activity of sphingosine 1-phosphate receptors is implicated and agonism of such activity is desired includes administering to said mammal an effective amount of a compound of formula (I).

In another aspect, a method for prevention or treatment of a pathological condition or symptom in a mammal, wherein the activity S1P lyase implicated and inhibition of the S1P lyase is desired includes administering to said mammal an effective amount of a compound of formula (I).

In another aspect, a method for prevention or treatment of a pathological condition or symptom in a mammal, wherein the activity of sphingosine 1-phosphate receptors is implicated and antagonism of such activity is desired includes administering to said mammal an effective amount of a compound of formula (I).

In another aspect, the pathological condition can be multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, tumour metastasis, diseases associated with angiogenesis, vascular diseases, pain conditions, acute viral diseases, inflammatory bowel conditions, insulin or non-insulin dependant diabetes, inhibited cell migration, over-proliferation and secretion of effector cytokines, or lack of secretion of the suppressive cytokine IL-10.

In another aspect, the compound exhibits $S1P_1$ agonist activity. In another aspect, the compound exhibits $S1P_1$ agonist activity and is substantially free of $S1P_3$ agonist and antagonist activity.

In another aspect, the compound exhibits $S1P_5$ antagonist activity. In another aspect, the compound exhibits $S1P_5$ agonist activity.

In another aspect, the compound exhibits $S1P_4$ antagonist activity. In another aspect, the compound exhibits $S1P_4$ agonist activity.

In another embodiment, the invention is directed to the examples having formula (I), pharmaceutically acceptable salts thereof, or when the example having formula (I) is a salt, a free base of that salt.

The compound of formula (I) can be a compound of formula (IIa)-(IId):

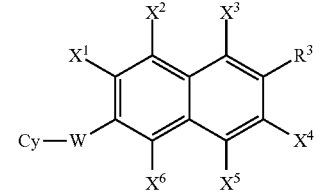
(IIa)

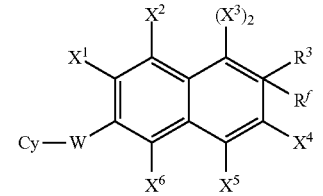
(IIb)

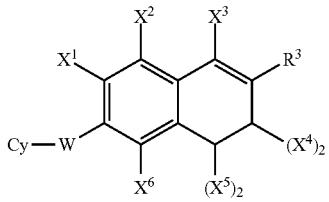
(IIc)

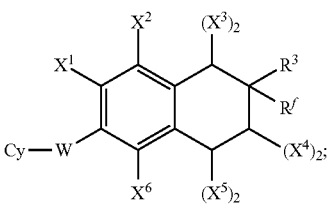
(IId)

a compound of formula (IIIa)-(IIIg):

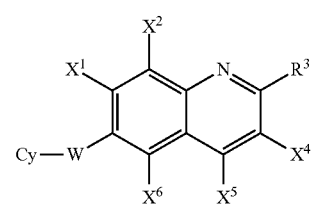
(IIIa)

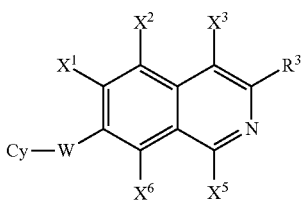
(IIIb)

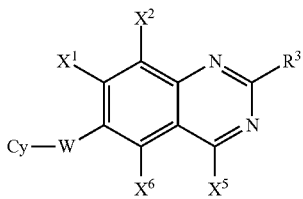
(IIIc)

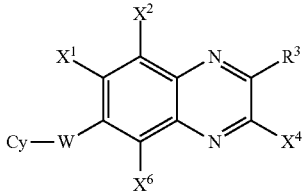
(IIId)

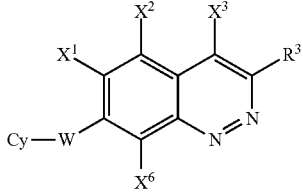
(IIIe)

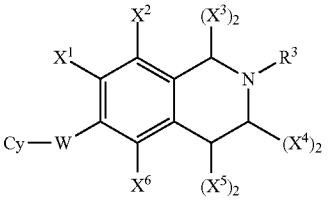
(IIIf)

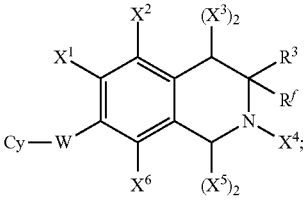
(IIIg)

a compound of formula (IVa)-(IVc):

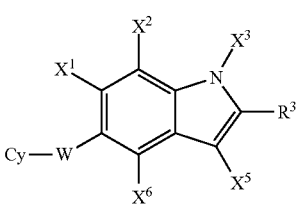
(IVa)

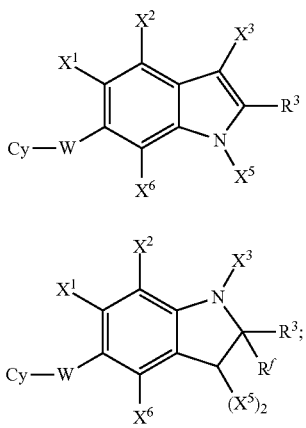

a compound of formula (Va)-(Vc):

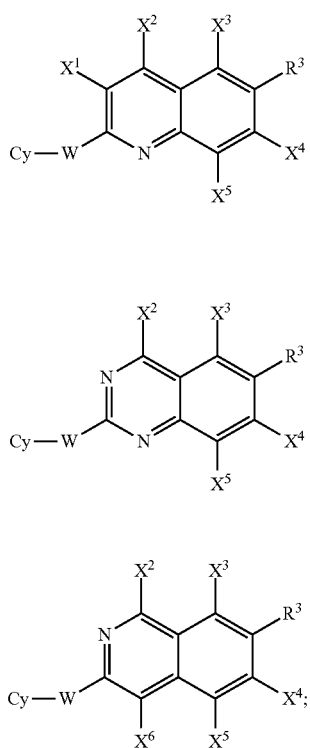

or a compound of formula (VIa)-(VIc):

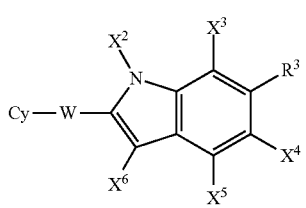

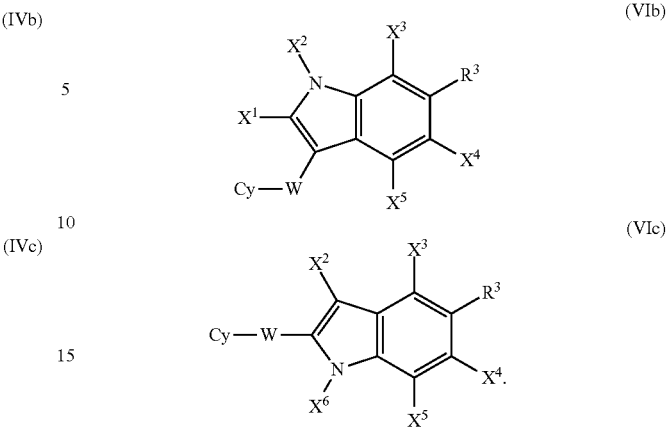

In certain circumstances, the compound is of formula (IIa), (IIIa) or (IIIb).

The details of one or more embodiments are set forth in the accompanying description below. Other features, objects, and advantages will be apparent from the description and from the claims.

DETAILED DESCRIPTION

The following abbreviations are used herein: S1P, sphingosine-1-phosphate; $S1P_{1-5}$, S1P receptor types 1-5; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl, trichloromethyl, or trifluoromethyl and the like.

The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, oroctyl and the like.

The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, or octenyl and the like.

The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like.

The term "($C_1$-$C_{10}$)alkoxy" refers to an alkyl group attached through an oxygen atom. Examples of ($C_1$-$C_{10}$)

alkoxy can be methoxy, ethoxy, propoxy, isopropoxy, butoxy, iso-butoxy, sec-butoxy, pentoxy, 3-pentoxy, or hexyloxy, and the like.

The term "$(C_3-C_{12})$cycloalkyl" refers to a cyclic alkyl group, such as, for example, cyclopropyl, cyclobutyl, cyclopentyl, cyclohexyl, cycloheptyl, or cyclooctyl, and the like. Cyloalkyl groups include bicyclic groups such as decalinyl, bridged bicyclic groups such as norbornyl or bicyclo[2.2.2]octyl, tricyclic, bridged tricyclic such as adamantyl, or spiro-linked bicyclic or tricyclic groups.

The term "$(C_6-C_{14})$aryl" refers to a monocyclic, bicyclic, or tricyclic carbocyclic ring system having one or two aromatic rings including, but not limited to, phenyl, benzyl, naphthyl, tetrahydronaphthyl, indanyl, indenyl, or anthracyl, and the like.

The term "aryl$(C_1-C_{20})$alkyl" or "arylalkyl" or "aralkyl" refers to an alkyl group substituted with a mono or bicyclic carbocyclic ring system having one or two aromatic rings including, a group such as phenyl, naphthyl, tetrahydronaphthyl, indanyl, or indenyl, and the like. Non-limiting examples of arylalkyl include benzyl, or phenylethyl, and the like.

The term "$(C_1-C_{14})$heterocyclic group" refers to an optionally substituted mono- or bicyclic carbocyclic ring system containing one, two, three, or four heteroatoms (optionally in each ring) wherein the heteroatoms are oxygen, sulfur, and nitrogen.

The term "$(C_4-C_{14})$heteroaryl" refers to an optionally substituted mono- or bicyclic cyclic ring system containing one, two, or three heteroatoms (optionally in each ring) wherein the heteroatoms are oxygen, sulfur, or nitrogen. Non-limiting examples of heteroaryl groups include furyl, thienyl, or pyridyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, or boronophosphates, and the like, including associated counterions, e.g., $H^+$, $NH_4^+$, $Na^+$, or $K^+$, and the like if such counterions are present.

The term "alpha-substituted phosphonate" includes phosphonate ($-CH_2PO_3H_2$) groups that are substituted on the alpha-carbon such as $-CHFPO_3H_2$, $-CF_2PO_3H_2$, $-CHOHPO_3H_2$, or $-C{=}OPO_3H_2$) and the like.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

The term "prodrug" refers to a compound that is converted under physiological conditions, e.g., by solvolysis or metabolically, to a compound that is pharmaceutically active, such as a compound of formula (I). A prodrug may be a derivative of a compound of formula (I) that contains a carboxylic or phosphoric acid ester or amide moiety that may be cleaved under physiological conditions. A prodrug containing such a moiety may be prepared according to conventional procedures, for example, by treatment of a compound of this invention containing an amino, amido or hydroxyl moiety with a suitable derivatizing agent, for example, a carboxylic or phosphoric acid halide or acid anhydride, or by converting a carboxyl moiety to an ester or amide. Metabolites of the compounds of formula (I) may also be pharmaceutically active as well.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers (e.g., diastereomers and enantiomers), as well as mixtures thereof (such as a racemic mixture). The compounds can be isotopically-labeled compounds, for example, compounds including various isotopes of hydrogen, carbon, nitrogen, oxygen, phosphorous, fluorine, iodine, or chlorine.

The disclosed compounds may exist in tautomeric forms and the invention includes both mixtures and separate individual tautomers. For example, the following structure:

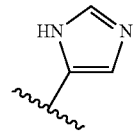

is understood to represent a mixture of the structures:

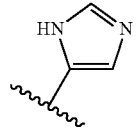 [SMILES: *c1cnc[nH]1]

as well as

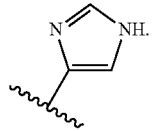 [SMILES: *c1c[nH]cn1]

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, or $S1P_5$), unless the specific subtype is indicated.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof. It is well known in the art how to prepare such optically active forms (for example, resolution of the racemic form by recrystallization techniques, synthesis from optically-active starting materials, by chiral synthesis, or chromatographic separation using a chiral stationary phase) and how to determine S1P agonist activity using the standard tests described herein, or using other similar tests which are well known in the art. In addition, some compounds may exhibit polymorphism.

Potential uses of an S1P receptor agonist, and $S1P_1$ receptor type selective agonists particularly, include, but are not limited to, prevention or treatment of a pathological condition or symptom in a mammal. For example, the condition can include asthma, inflammatory neuropathies, arthritis, lupus erythematosis, psoriasis, ischemia-reperfusion injury, solid tumours, tumour metastasis, diseases associated with angiogenesis, vascular diseases, pain conditions, acute viral diseases, or insulin and non-insulin dependant diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), multiple sclerosis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P agonist compounds are described in provisional U.S. Application No. 60/956,111, filed Aug. 15, 2007, and PCT/US2008/073378, filed Aug. 15, 2008, each of which is incorporated by reference in its entirety.

Potential uses of an S1P receptor antagonist, and $S1P_5$ receptor type selective antagonists particularly, include, but are not limited to, prevention or treatment of a pathological condition or symptom in a mammal. For example, the condition can include inhibited cell migration of oligodendrocyte precursor cells (OPCs). In another example, an $S1P_5$ receptor type selective antagonist may not induce lymphopenia, thereby achieving partial efficacy without immunosuppression.

Potential uses of an S1P receptor antagonist, and $S1P_4$ receptor type selective antagonists particularly, include, but are not limited to, prevention or treatment of a pathological condition or symptom in a mammal.

"Treatment" of multiple sclerosis includes treating various forms of the disease including relapsing-remitting, chronic progressive, and the S1P receptor agonists/antagonists can be used alone or in conjunction with other agents to relieve signs and symptoms of the disease as well as prophylactically.

In addition, the disclosed compounds can be used for altering lymphocyte trafficking as a method for prolonging allograft survival, for example transplantation including solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

Disclosed compounds can be useful for inhibition of sphingosine kinase (i.e., of sphingosine kinase I, sphingosine kinase II, or both). Sphingosine kinase is an intracellular enzyme that catalyzes the formation of S1P from sphingosine and a nucleotide triphosphate (e.g., ATP). Inhibition of sphingosine kinase can reduce the formation of S1P and thereby reduce the supply of S1P available to activate signaling at S1P receptors. Accordingly, sphingosine kinase inhibitors can be useful in modulating immune system function. Therefore, the disclosed compounds can be used to inhibit sphingosine kinase. This inhibition could be in concert with S1P receptor activity, or be independent of activity at any S1P receptor.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Pharmaceutical compositions can include the compounds of formula I. More particularly, such compounds can be formulated as pharmaceutical compositions using standard pharmaceutically acceptable carriers, fillers, solubilizing agents and stabilizers known to those skilled in the art. For example, a pharmaceutical composition including a compound of formula I, or a salt, analog, derivative, or modification thereof, as described herein, is used to administer the appropriate compound to a subject.

The compounds of formula I are useful for treating a disease or disorder including administering to a subject in need thereof of a therapeutically acceptable amount of a compound of formula I, or a pharmaceutical composition comprising a therapeutically effective amount of a compound of formula I, and a pharmaceutically-acceptable carrier.

The disclosed compounds and method are directed to sphingosine 1-phosphate (S1P) analogs that have activity as receptor agonists or receptor antagonists at one or more S1P receptors, specifically the $S1P_1$, $S1P_4$ or $S1P_5$ receptor types. The disclosed compounds and method include both compounds that have a phosphate moiety as well as compounds with hydrolysis-resistant phosphate surrogates such as phosphonates, alpha-substituted phosphonates (particularly where the alpha substitution is a halogen), or phosphothionates.

In cases where compounds of formula I are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium or magnesium salts. Salts derived from organic bases include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. It should also be understood that other carboxylic acid derivatives would be useful, for example, carboxylic acid amides, including carboxamides, lower alkyl carboxamides, or dialkyl carboxamides, and the like.

The compounds of formula I can be formulated as pharmaceutical compositions and administered to a mammalian host, such as a human patient in a variety of forms adapted to the chosen route of administration, e.g., orally or parenterally, as eyedrops, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula I in a liquid composition, such as a lotion, will be from about 0.1 to about 25 weight percent, preferably from about 0.5-10 weight percent. The concentration in a semi-solid or solid composition such as a gel or a powder will be about 0.1-5 wt-%, preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a dose will be in the range of from about 0.1 to about 10 mg/kg of body weight per day.

The compound is conveniently administered in unit dosage form; for example, containing 0.01 to 10 mg, or 0.05 to 1 mg, of active ingredient per unit dosage form. In some embodiments, a dose of 5 mg/kg or less is suitable.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit comprising a compound of formula I and instructional material which describes administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject is a human.

Compounds can have an $EC_{50}$ of between 5 nM and 3 µM when acting as selective agonists for $S1P_1$ receptors. While the $EC_{50}$ of certain compounds acting as agonists to $S1P_1$ and $S1P_3$ receptors can be greater than 5000 nM, these same compounds can have an $EC_{50}$ of 0.2 nM-700 nM when acting as selective antagonists for $S1P_5$ receptors and 50 nM-3 µM when acting as selective antagonists for $S1P_4$ receptors.

In accordance with the disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

The following working examples are provided for the purpose of illustration only, and are not to be construed as limiting in any way the remainder of the disclosure. Therefore, the examples should be construed to encompass any and all variations which become evident as a result of the teaching provided herein.

EXAMPLES

Example 1: cis-4-tert-butylcyclohexyl methanesulfonate

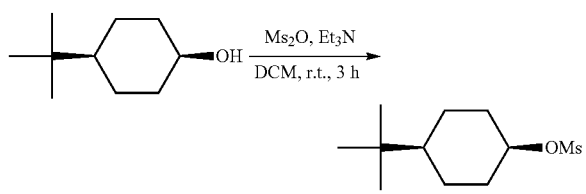

Cis-4-t-butylcyclohexanol (6.0 g, 38.5 mmol, 1.0 eq.) was dissolved in dichloromethane (10 mL). Then methanesulfonic anhydride (8.03 g, 46.2 mmol, 1.1 eq.) was added to the mixture slowly at 0° C. Then triethylamine (6.4 mL, 46.2 mmol, 1.5 eq.) was added to the mixture and the mixture stirred at room temperature for 3 h. The mixture was extracted with dichloromethane and the organic layer was concentrated to give product as a white power (8.0 g, yield: 90%). The product was used to next step without further purification. $^1$H NMR (400 MHz, CDCl$_3$) δ 4.99-4.98 (m, 1H), 3.02 (s, 3H), 2.14-2.12 (m, 2H), 1.65-1.28 (m, 7H), 0.84 (s, 9H).

Example 2: 2-bromo-6-(trans-4-tert-butylcyclohexyloxy)naphthalene

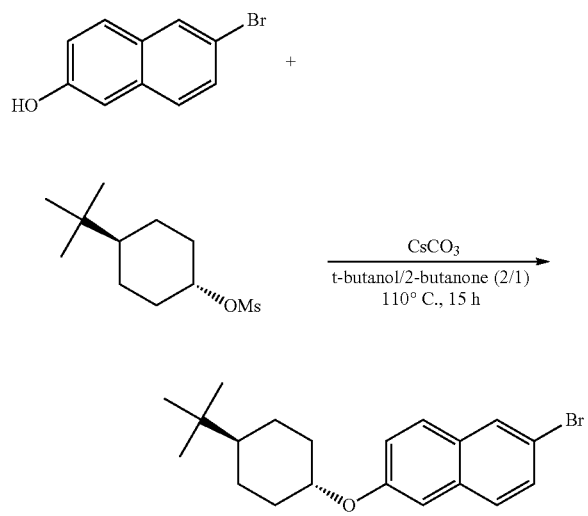

6-bromonaphthalen-2-ol (CAS no. 15231-91-1) (3.0 g, 14.8 mmol, 1.0 eq.) was dissolved in a mixture of t-butanol/2-butanone (4 mL/2 mL). Then cesium carbonate (12 g, 37.2 mmol, 2.5 eq.) was added to the mixture and the mixture was stirred at 110° C. for 10 min. Then trans-4-tert-butylcyclohexyl methanesulfonate (3.48 g, 16.2 mmol, 1.1 eq.) was added to the mixture. The suspension was stirred at 110° C. under a nitrogen atmosphere for 15 h. The reaction mixture was extracted with ethyl acetate and the organic layer was purified by silica gel column chromatography using petroleum ether as eluent to give 2-bromo-6-(trans-4-tert-butylcyclohexyloxy)naphthalene as a slight yellow solid (1.7 g, yield: 32%). ESI-MS: 361.0 (M+H)$^+$. $^1$H NMR (400 MHz, CDCl$_3$) δ 7.89 (s, 1H), 7.63 (d, 1H), 7.56 (d, 1H), 7.47 (d, 1H), 7.15-7.11 (m, 2H), 4.26-4.24 (m, 1H), 2.27-2.25 (m, 2H), 1.89-1.87 (m, 2H), 1.45-1.09 (m, 5H), 0.89 (s, 9H).

Example 3: 6-(trans-4-tert-butylcyclohexyloxy)-2-naphthaldehyde 2-bromo-6-(trans-4-tert-butylcyclohexyloxy)naphthalene (2.249 g, 6.25 mmol, 1.0 eq.) was dissolved in THF (10 mL) under nitrogen atmosphere. Then the mixture was cooled down to −78° C. and a solution of n-BuLi in THF (2.5 M, 7.5 mL, 18.8 mmol, 3.0 eq.) was added to the mixture dropwise. The mixture was stirred at −78° C. for 15 min. Then DMF (2.4 mL, 31.2 mmol, 5.0 eq.) was added to the mixture and stirred at −78° C. for 1 h. When the reaction completed, 1 M HCl was added to adjust the pH to 6. The mixture was extracted with EtOAc and the organic layer was concentrated and purified by silica gel chromatography using petroleum ether/ethyl acetate (10/1) as eluent to give 6-(trans-4-tert-butylcyclohexyloxy)-2-naphthaldehyde as a white solid (1.16 g, 60%). EDI-MS: 311.1 (M+H)$^+$. $^1$H NMR (400 MHz, CDCl$_3$) δ 10.08 (s, 1H), 8.24 (s, 1H), 7.92-7.87 (m, 2H), 7.77 (d, 1H), 7.22-7.19 (m, 2H), 4.42-4.30 (m, 1H), 2.30-2.28 (m, 2H), 1.93-1.90 (m, 2H), 1.48-1.11 (m, 5H), 0.82 (s, 9H).

Example 4: 2-bromo-6-(trans-4-tert-butylcyclohexyloxy)naphthalene (Alternate Synthesis)

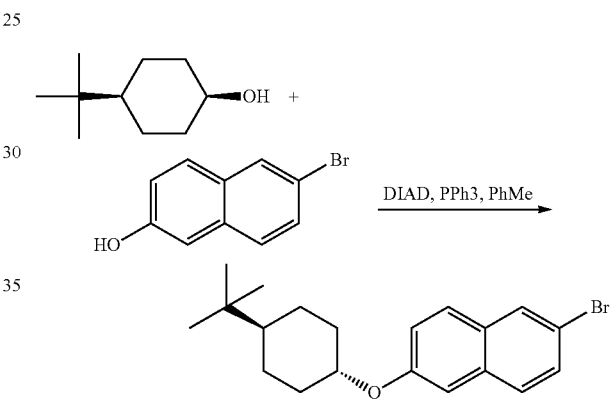

To a solution of 6-bromonaphthalen-2-ol (100.0 g, 450.1 mmol), triphenylphosphine (230 g, 877.8 mmol, 2.0 eq) and cis-4-t-butylcyclohexanol (105.4 g, 675.7 mmol; 1.5 eq) in toluene (1.5 L), was added dropwise diisopropyl azodicarboxylate (170 g, 850.0 mmol, 2.0 eq) at 0° C. The addition took ~2 hrs and the resulting mixture was warmed to 26-30° C. After 24 hrs, thin layer chromatography showed near complete consumption of 6-bromonaphthalen-2-ol. The mixture was then cooled to 5° C. and stirred at that temperature for 2 hrs, over which solids precipitated and were filtered. The filtrate was concentrated to near dryness to afford an oil, which was taken up in 200 mL methylene chloride and purified by silica gel chromatography with 100% petroleum ether. After concentration, 127 g product was obtained as a white solid (yield: 79.1%). EDI-MS: 361.1 (M+H)$^+$.

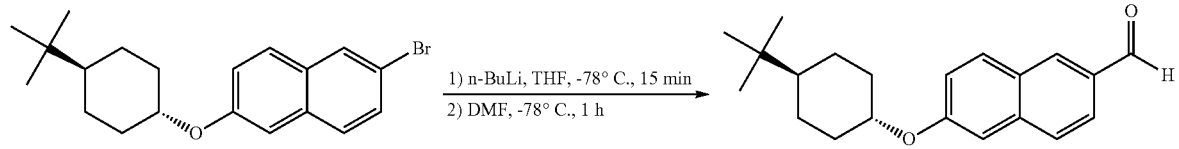 [SMILES: CC(C)(C)[C@H]1CC[C@H](Oc2ccc3cc(Br)ccc3c2)CC1 ; CC(C)(C)[C@H]1CC[C@H](Oc2ccc3cc(C=O)ccc3c2)CC1]

Example 5: 6-bromo-2-(trans-4-tert-butylcyclohexyloxy)-1-iodonaphthalene

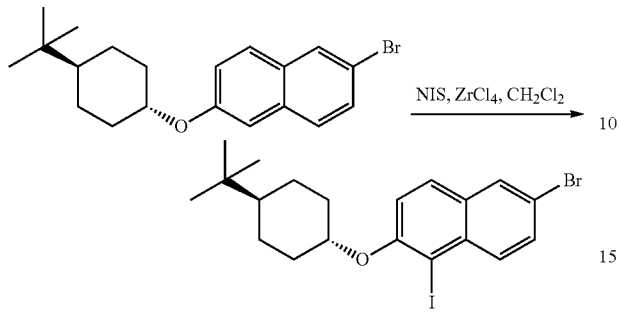

A solution of 2-bromo-6-(trans-4-tert-butylcyclohexyloxy)naphthalene (160.0 g, 444.4 mmol) in methylene chloride (2.5 L) was purged under an atmosphere of argon. N-iodosuccinimide (202.1 g, 888.8 mmol) and zirconium tetrachloride (20.4 g, 88.9 mmol) was added and the reaction was stirred at room temperature under an atmosphere of argon. The reaction was monitored by $^1$H NMR and showed complete conversion to product after 30 minutes. The mixture was then concentrated under reduced pressure to give ~250 g crude as a brown solid. The crude material was purified by silica gel chromatography with hexanes to give 200 g of desired product as a brown solid (yield: 92.6%). EDI-MS: 487.1 (M+H)$^+$.

Example 6: 6-bromo-2-(trans-4-tert-butylcyclohexyloxy)-1-(trifluoromethyl)naphthalene

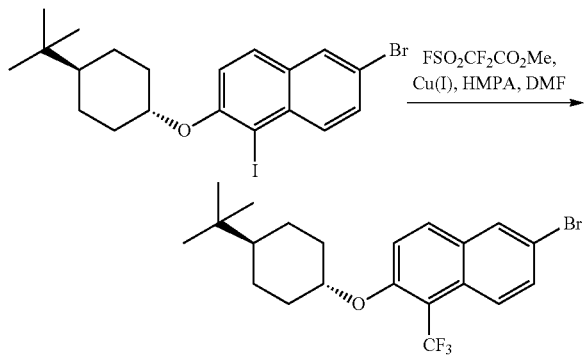

A solution of 6-bromo-2-(trans-4-tert-butylcyclohexyloxy)-1-iodonaphthalene (210.0 g, 433 mmol), hexamethylphosphoramide (386.4 g, 2.16 mol; 5 eq) in N,N-dimethylformamide (2.0 L) was degassed by stirring under vacuum and replacing the vacuum with argon (4 times). To this mixture was added copper(I) iodide (140.0 g, 735 mmol; 1.7 eq) and methyl fluorosulphonyldifluoroacetate (415 g, 2.16 mol; 5 eq). The reaction mixture was warmed to 80° C. under an atmosphere of argon. After stirring for 6 hrs, thin layer chromatography showed complete conversion to product. Saturated NaHCO$_3$ solution was added to adjust the final pH to 9~10 followed by adding EtOAc (3.5 L). The mixture was extracted with EtOAc (2.5 L×3), and washed with brine (1.0 L×4), then dried over Na$_2$SO$_4$ (500 g). The solvent was removed under reduced pressure to give crude 195 g as a sticky off white solid with purity of >90%, which was purified by silica gel chromatography with 0-30% EtOAc in hexanes to give the final product (156 g, 84.3%). EDI-MS: 430.0 (M+H)$^+$.

Example 7: tert-butyl 3-oxo-3-(phenylsulfonamido)propylcarbamate

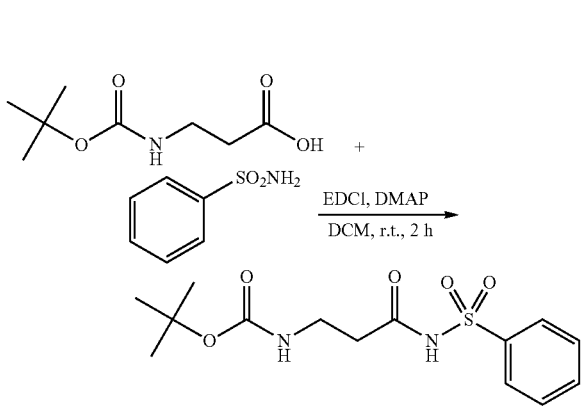

3-(Tert-butoxycarbonylamino)propanoic acid (4 g, 21.2 mmol, 1.0 equiv) was dissolved in DCM (100 mL). Then phenylsulfonamide (15.1 mmol, 0.7 equiv), EDCI (3.45 g, 18.2 mmol, 0.85 equiv) and DMAP (0.37 g, 3 mmol, 0.15 equiv) were added to the mixture and stirred for 2 h at room temperature. The reaction mixture was cooled down to 0° C., ice water (100 mL) was added. The mixture was stirred for 15 min, separated and the water layer was extracted twice with dichloromethane. The combined organic layer was washed by 5% HCl, brine, dried over Na$_2$SO$_4$, concentrated to give tert-butyl 3-oxo-3-(phenylsulfonamido)propylcarbamate 5.3 g, gray oil, 100%. EDI-MS: 329.0 (M+H)$^+$. $^1$H NMR (400 MHz, CDCl$_3$) δ: 9.52~9.43 (brs, 1H), 8.02~7.96 (m, 2H), 7.61~7.55 (m, 1H), 7.50~7.45 (m, 2H), 5.02~4.93 (m, 1H), 3.30~3.24 (m, 2H), 2.48~2.41 (m, 2H), 1.34 (s, 9H).

Example 8: 3-amino-N-(phenylsulfonyl)propanamide

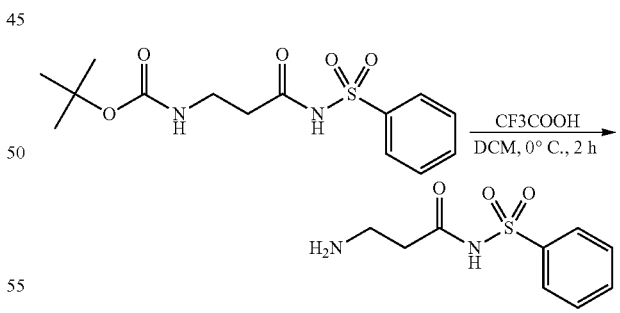

Tert-butyl 3-oxo-3-(phenylsulfonamido)propylcarbamate (3.6 g, 15.1 mmol) was dissolved in dichloromethane (60 mL). Then CF$_3$COOH (1.1 mL, 0.3 mmol, 20 equiv) was added to the mixture at 0° C. and stirred for 2 h at 0° C. The reaction mixture was concentrated and purified by flash chromatography to give 3-amino-N-(phenylsulfonyl)propanamide as a white solid (1.4 g, 40%). EDI-MS: 229.0 (M+H)$^+$. $^1$H NMR (400 MHz, DMSO-d$_6$) δ: 7.79~7.71 (m, 2H), 7.70~7.43 (brs, 3H), 7.42~7.34 (m, 3H), 2.83 (t, 2H), 2.24 (t, 2H).

Example 9: 3-((6-(trans-4-tert-butylcyclohexyloxy)naphthalen-2-yl)methylamino)-N-(phenylsulfonyl)propanamide

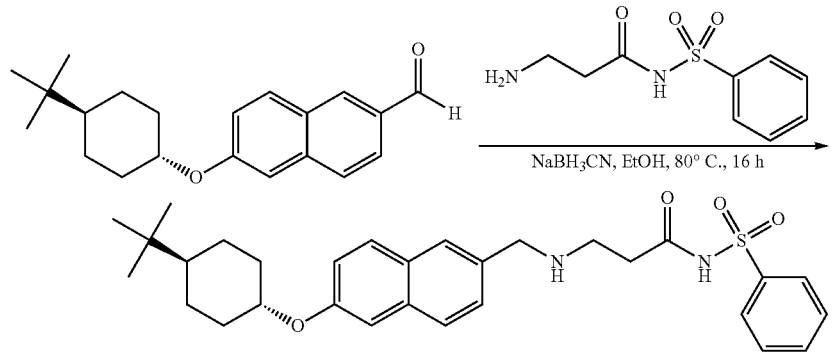

6-(Trans-4-tert-butylcyclohexyloxy)-2-naphthaldehyde (300 mg, 0.96 mmol, 1 equiv) and 3-amino-N-(phenylsulfonyl)propanamide (1.19 mmol, 1.5 equiv) were dissolved in anhydrous ethanol. The mixture was stirred at 80° C. for 1 h. Then NaBH$_3$CN (110 mg, 1.74 mmol, 2 equiv) was added to the mixture and stirred at 80° C. for 16 h. The organic layer was concentrated and purified by preparative thin layer chromatography (mobile phase was methanol:dichloromethane 1:10) to give 3-((6-(trans-4-tert-butylcyclohexyloxy)naphthalen-2-yl)methylamino)-N-(phenylsulfonyl)propanamide as a white solid. 284 mg, white solid, 62%. ESI-MS: 523.0 (M+H)$^+$. HPLC: 99.42%. $^1$H NMR (400 MHz, DMSO-d$_6$) δ: 7.91 (s, 1H), 7.85~7.82 (m, 2H), 7.74~7.72 (m, 2H), 7.53~7.51 (m, 1H), 7.41~7.35 (m, 4H), 7.20~7.15 (m, 1H), 4.45~4.40 (m, 1H), 4.23 (s, 2H), 2.99 (t, 2H), 2.33 (t, 2H), 2.28~2.16 (m, 2H), 1.89~1.78 (m, 2H), 1.41~1.31 (m, 2H), 1.27~1.17 (m, 2H), 1.13~1.06 (m, 1H), 0.89 (s, 9H).

Example 10: 3-((6-(trans-4-tert-butylcyclohexyloxy)-5-(trifluoromethyl)naphthalen-2-yl)methylamino)-N-(phenylsulfonyl)propanamide 6-(trans-4-tert-butylcyclohexyloxy)-5-(trifluoromethyl)-2-naphthaldehyde (300 mg, 0.96 mmol, 1 equiv) and 3-amino-N-(phenylsulfonyl)propanamide (1.19 mmol, 1.5 equiv) were dissolved in anhydrous ethanol. The mixture was stirred at 80° C. for 1 h. Then NaBH$_3$CN (110 mg, 1.74 mmol, 2 equiv) was added to the mixture and stirred at 80° C. for 16 h. The organic layer was concentrated and purified by preparative thin layer chromatography (mobile phase was methanol:dichloromethane 1:10) to give 3-((6-(trans-4-tert-butylcyclohexyloxy)-5-(trifluoromethyl)naphthalen-2-yl)methylamino)-N-(phenylsulfonyl)propanamide as a white solid. 120 mg, white solid, 53%. ESI-MS: 591.0 (M+H)$^+$. HPLC: 98.05%. $^1$H NMR (400 MHz, DMSO-d$_6$) δ: 8.22~8.13 (m, 1H), 8.11~8.04 (m, 2H), 7.79~7.63 (m, 4H), 7.45~7.30 (m, 3H), 4.63~4.49 (m, 1H), 4.27 (s, 2H), 2.99 (t, 2H), 2.32 (t, 2H), 2.19~2.07 (m, 2H), 1.85~1.74 (m, 2H), 1.45~1.30 (m, 2H), 125~1.12 (m, 2H), 1.10~0.97 (m, 1H), 0.86 (s, 9H).

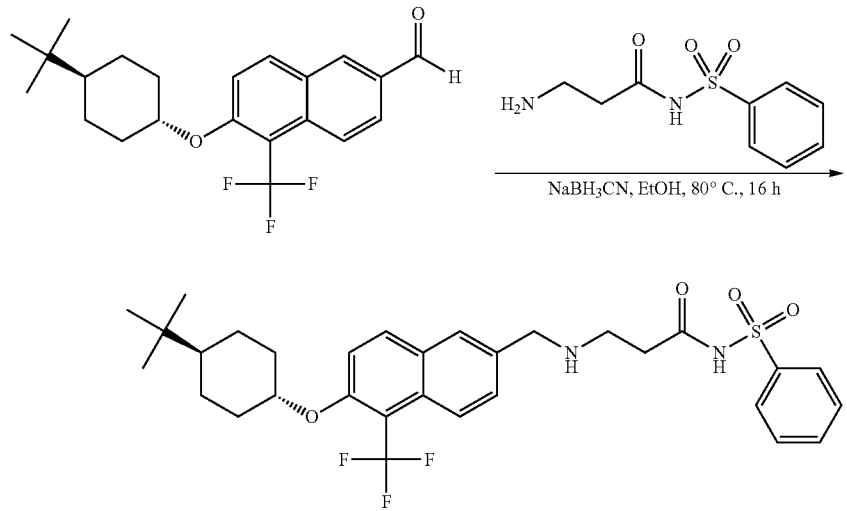

Example 11: methyl 2-((6-(trans-4-tert-butylcyclo-hexyloxy)naphthalen-2-yl)methylamino)propanoate

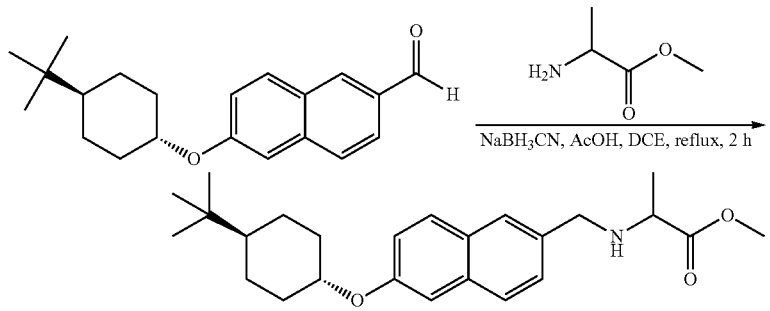

A mixture of 6-(trans-4-tert-butylcyclohexyloxy)-2-naphthaldehyde (155 mg, 0.5 mmol), methyl 2-aminopropanoate (103 mg, 1.0 mmol, 2.0 equiv) and AcOH (59 mg, 1.0 mmol, 2.0 equiv) in anhydrous dichloroethane (20 mL) was refluxed for 30 min, cooled to 23° C., NaBH$_3$CN (60 mg, 1.0 mmol, 2.0 equiv) was added, the resulted mixture was refluxed for 1 h. The reaction mixture was concentrated in vacuum and the residue was purified by chromatography with silica gel (dichloromethane:methanol 20:1) to give methyl 2-((6-(trans-4-tert-butylcyclohexyloxy)naphthalen-2-yl)methylamino)propanoate as a white solid (277 mg, yield: 70%). ESI-MS: 398.1 (M+H)$^+$. HPLC: 96.09%. $^1$H NMR (400 MHz, CD$_3$OD) δ: 7.83 (s, 1H), 7.79 (d, 1H), 7.74 (d, 1H), 7.43 (dd, 1H), 7.22 (d, 1H), 7.10 (dd, 1H), 4.28-4.33 (m, 3H), 4.13 (q, 1H), 3.80 (s, 3H), 2.21 (d, 2H), 1.85 (d, 2H), 1.56 (d, 3H), 1.31-1.37 (m, 2H), 1.17-1.24 (m, 2H), 1.05-1.11 (m, 1H), 0.85 (s, 9H).

Example 12: 2-((6-(trans-4-tert-butylcyclohexyloxy)naphthalen-2-yl)methylamino)propanoic acid

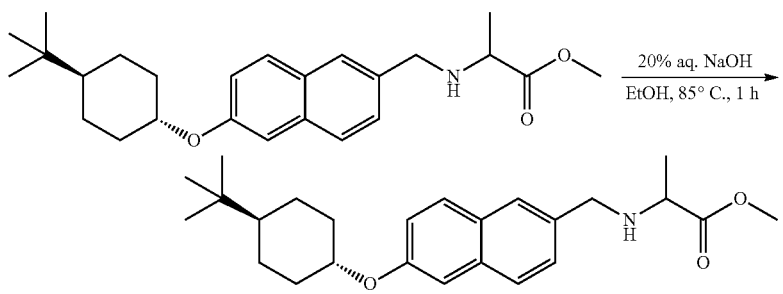

To a solution of methyl 2-((6-(trans-4-tert-butylcyclohexyloxy)naphthalen-2-yl)methylamino)propanoate (100 mg, 0.25 mmol) in ethanol (10 mL) was added aqueous NaOH (3 mL, 20%, 5.0 eq.) and refluxed for 1 hr. Then the reaction was cooled to 0° C., the pH of the solution was adjusted to 6 with 1 M HCl, concentrated and the residue was dissolved in dichloromethane, washed with water, dried and concentrated to give 2-((6-(trans-4-tert-butylcyclohexyloxy)naphthalen-2-yl)methylamino)propanoic acid as a white solid (70 mg, yield: 75%). ESI-MS: 384.1 (M+H)$^+$. HPLC: 97.18%. $^1$H NMR (400 MHz, CD$_3$OD) δ: 7.88 (s, 1H), 7.83 (d, 1H), 7.73 (d, 1H), 7.49 (dd, 1H), 7.26 (d, 1H), 7.15 (dd, 1H), 4.29-4.38 (m, 3H), 4.04 (q, 1H), 2.25 (d, 2H), 1.90 (d, 2H), 1.60 (d, 3H), 1.36-1.44 (m, 2H), 1.21-1.31 (m, 2H), 1.09-1.15 (m, 1H), 0.89 (s, 9H).

Example 13: ethyl 3-((6-(trans-4-tert-butylcyclohexyloxy)naphthalen-2-yl)methylamino) butanoate

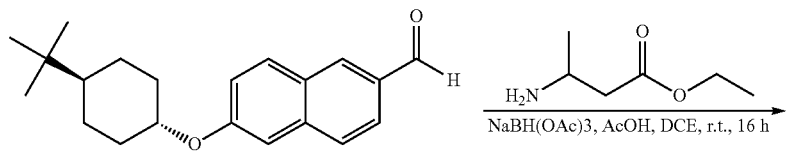

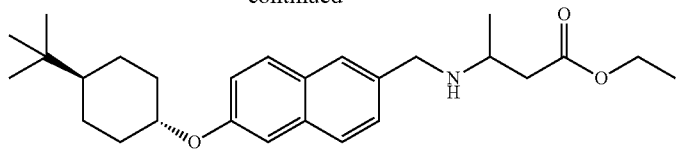

6-(trans-4-tert-butylcyclohexyloxy)-2-naphthaldehyde (30 mg, 0.097 mmol), ethyl 3-aminobutanoate (CAS no. 5303-65-1)(19 mg, 0.145 mmol), and acetic acid (17 mg, 0.291 mmol) were dissolved in dichloroethane (2 mL). The mixture was stirred at r.t. for 10 min under nitrogen atmosphere. Then NaBH(OAc)$_3$ (41 mg, 0.194 mmol) was added to the mixture and the mixture was stirred at r.t. for 15 h. Then saturated NaHCO$_3$ was added to the mixture to adjust the pH to 8. The mixture was extracted with ethyl acetate and the organic layer was purified by silica gel column chromatography using dichloromethane:methanol 10:1 to give product ethyl 3-((6-(trans-4-tert-butylcyclohexyloxy) naphthalen-2-yl)methylamino)butanoate (40 mg, 88%) as a slight yellow solid. ESI-MS: 426.1 (M+H)$^+$. 1H NMR (400 MHz, CDCl$_3$) δ 7.70-7.65 (m, 3H), 7.41 (d, 1H), 7.13-7.09 (m, 2H), 4.28-4.23 (m, 1H), 4.12 (q, 2H), 3.98-3.88 (m, 2H), 3.22-3.18 (m, 1H), 2.53-2.42 (m, 2H), 2.28-2.25 (m, 2H), 1.90-1.87 (m, 2H), 1.45-1.42 (m, 2H), 1.26-1.09 (m, 9H), 0.90 (s, 9H).

Example 14: 3-((6-(trans-4-tert-butylcyclohexyloxy) naphthalen-2-yl)methylamino)butanoic acid

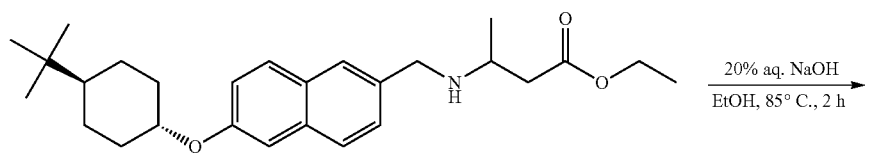

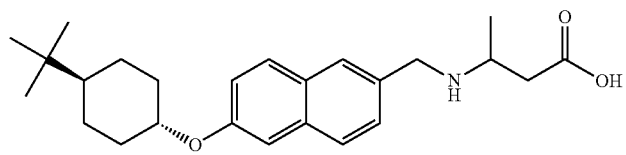

Synthesis was performed as described for 2-((6-(trans-4-tert-butylcyclohexyloxy)naphthalen-2-yl)methylamino)propanoic acid. 9 mg, slight yellow oil, yield: 27%. ESI-MS: 398.1 (M+H)$^+$. HPLC: 91.26%. $^1$H NMR (400 MHz, CDCl$_3$) δ 7.70-7.61 (m, 3H), 7.45 (d, 1H), 7.07 (t, 2H), 4.20-4.17 (m, 2H), 3.98-3.95 (m, 1H), 3.18-3.16 (m, 1H), 2.43-2.42 (m, 2H), 2.24-2.18 (m, 2H), 1.87-1.84 (m, 2H), 1.34-1.17 (m, 8H), 0.91 (s, 9H).

Example 15: ethyl 2-(((6-(trans-4-tert-butylcyclohexyloxy)naphthalen-2-yl)methyl)(methyl)amino) acetate

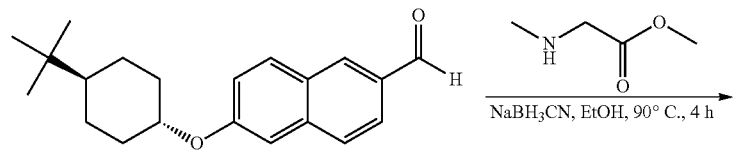

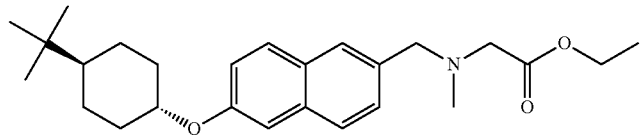

A mixture of 6-(trans-4-tert-butylcyclohexyloxy)-2-naphthaldehyde (155 mg, 0.5 mmol) and ethyl 2-(methylamino)acetate (117 mg, 1.0 mmol, 2.0 equiv) in anhydrous ethanol (20 mL) was refluxed for 2 hr and evaporated in vacuum to dryness. Anhydrous EtOH was added and refluxed for 1 hr, and then the mixture was cooled to 23° C. NaBH$_3$CN (60 mg, 1.0 mmol, 2.0 equiv) was added. The resulted mixture was refluxed for 1 h. The reaction mixture was concentrated in vacuum and the residue was purified by chromatography with silica gel (dichloromethane:methanol 20:1) to give product ethyl 2-(((6-(trans-4-tert-butylcyclohexyloxy)naphthalen-2-yl)methyl)(methyl)amino)acetate as a white solid (82 mg, yield: 40%). ESI-MS: 411.3 (M+H)$^+$. HPLC: 98.93%. $^1$H NMR (400 MHz, CDCl$_3$) δ 7.71-7.67 (m, 3H), 7.00 (d, 1H), 7.14-7.13 (m, 2H), 4.30-4.28 (m, 1H), 4.18 (q, 2H), 3.82 (s, 3H), 3.30 (s, 2H), 2.45 (s, 3H), 2.29-2.27 (m, 2H), 1.91-1.88 (m, 2H), 1.46-1.42 (m, 2H), 1.29-1.22 (m, 3H), 0.90 (s, 9H).

Example 16: 2-(((6-(trans-4-tert-butylcyclohexyloxy)naphthalen-2-yl)methyl)(methyl)amino) acetic acid

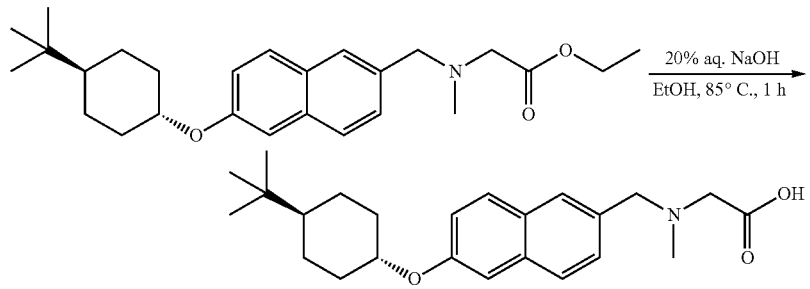

Synthesis was performed as described for 2-((6-(trans-4-tert-butylcyclohexyloxy)naphthalen-2-yl)methylamino)propanoic acid. 14 mg, gray solid, yield: 75%. ESI-MS: 383.3 (M+H)$^+$. HPLC: 95.11%. $^1$H NMR (400 MHz, CD$_3$OD) δ 7.98 (s, 1H), 7.91-7.85 (m, 2H), 7.59-7.57 (m, 1H), 7.33 (s, 1H), 7.22 (d, 1H), 4.55 (s, 2H), 4.42-4.40 (m, 1H), 4.10 (s, 2H), 2.95 (s, 3H), 2.32-2.29 (m, 2H), 1.96-1.93 (m, 2H), 1.47-1.41 (m, 2H), 1.35-1.25 (m, 3H), 0.95 (s, 9H).

Example 17: ethyl 3-((6-(trans-4-tert-butylcyclohexyloxy)naphthalen-2-yl)methylamino)propanoate

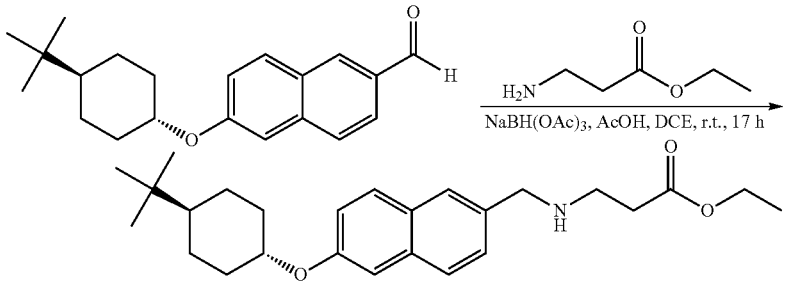

The title compound was synthesized as described for ethyl 3-((6-(trans-4-tert-butylcyclohexyloxy)naphthalen-2-yl)methylamino) butanoate. 730 mg, white solid, 40.9%. ESI-MS: 412.3 (M+H)$^+$. $^1$H NMR (400 MHz, CDCl$_3$) δ: 7.75 (s, 1H), 7.72-7.67 (m, 2H), 7.50 (dd, 1H), 7.12-7.10 (m, 1H), 7.07 (d, 1H), 4.20 (m, 1H), 4.11 (q, 2H), 4.01 (s, 2H), 3.05 (t, 2H), 2.81 (t, 2H), 2.22-2.20 (m, 2H), 1.87-1.84 (m, 2H), 1.41-1.38 (m, 2H), 1.22 (t, 3H), 1.17-1.07 (m, 3H), 0.89 (s, 9H).

Example 18: 3-((6-(trans-4-tert-butylcyclohexyloxy)naphthalen-2-yl)methylamino)propanoic acid

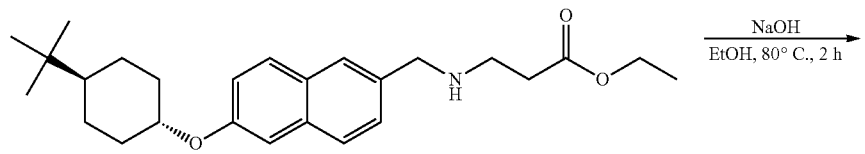

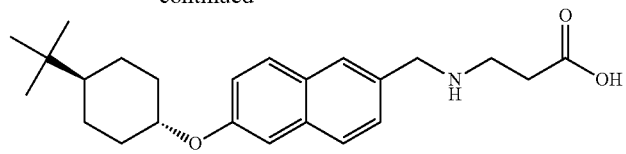

Synthesis was performed as described for 2-((6-(trans-4-tert-butylcyclohexyloxy)naphthalen-2-yl)methylamino)propanoic acid. 593 mg, beige solid, yield: 87.2%. ESI-MS: 384.1 (M+H)+. HPLC: 100%. $^1$H NMR (400 MHz, CD$_3$OD) δ: 7.84 (s, 1H), 7.81-7.75 (m, 2H), 7.45 (dd, 1H), 7.22 (d, 1H), 7.14 (dd, 1H), 4.34-4.32 (m, 1H), 4.28 (s, 2H), 3.17 (t, 2H), 2.49 (t, 2H), 2.28-2.25 (m, 2H), 1.92-1.88 (m, 2H), 1.43-1.40 (m, 2H), 1.25-1.22 (m, 2H), 1.13-1.10 (m, 1H), 0.90 (s, 9H).

Example 19: ethyl 3-(((6-(trans-4-tert-butylcyclohexyloxy)naphthalen-2-yl)methyl)(methyl)amino)propanoate

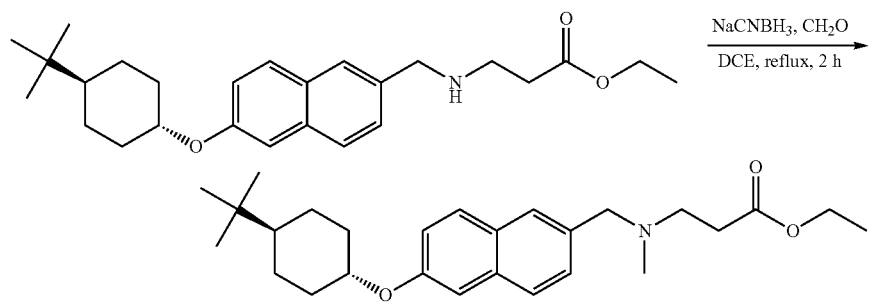

The title compound was synthesized as described for methyl 2-((6-(trans-4-tert-butylcyclohexyloxy)naphthalen-2-yl)methylamino)propanoate. 100 mg, white solid, yield: 70%. ESI-MS: 426.3 (M+H)+. HPLC: 90.71%. 1H NMR (400 MHz, CD3OD) δ: 7.73-7.76 (m, 3H), 7.43 (dd, 1H), 7.24 (d, 1H), 7.12 (dd, 1H), 4.31-4.37 (m, 1H), 4.12-4.17 (m, 2H), 3.87 (s, 2H), 2.96 (t, 2H), 2.66 (t, 2H), 2.40 (s, 3H), 2.28 (d, 2H), 1.91 (d, 2H), 1.39-1.46 (m, 2H), 1.22-1.31 (m, 5H), 1.10-1.17 (m, 1H), 0.93 (s, 9H).

Example 20: 3-(((6-(trans-4-tert-butylcyclohexyloxy)naphthalen-2-yl)methyl)(methyl)amino) propanoic acid

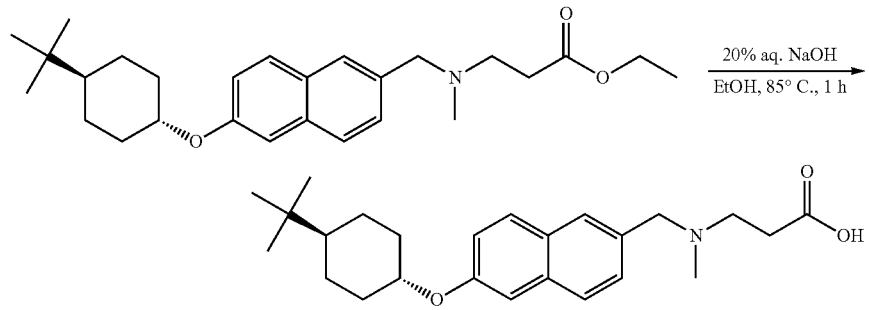

Synthesis was performed as described for 2-((6-(trans-4-tert-butylcyclohexyloxy)naphthalen-2-yl)methylamino)propanoic acid. 70 mg, white solid, yield: 75%. ESI-MS: 398.3 (M+H)+. HPLC: 94.61%. 1H NMR (400 MHz, DMSO-d6) δ: 7.97 (s, 1H), 7.87 (d, 1H), 7.83 (d, 1H), 7.62 (d, 1H), 7.43 (d, 1H), 7.19 (dd, 1H), 4.39-4.44 (m, 3H), 3.27 (br, 2H), 2.85 (t, 2H), 2.67 (s, 3H), 2.21 (d, 2H), 1.82 (d, 2H), 1.32-1.38 (m, 2H), 1.18-1.27 (m, 2H), 1.03-1.08 (m, 1H), 0.88 (s, 9H).

Example 20: methyl 1-((6-(trans-4-tert-butylcyclohexyloxy)naphthalen-2-yl)methyl)azetidine-3-carboxylate

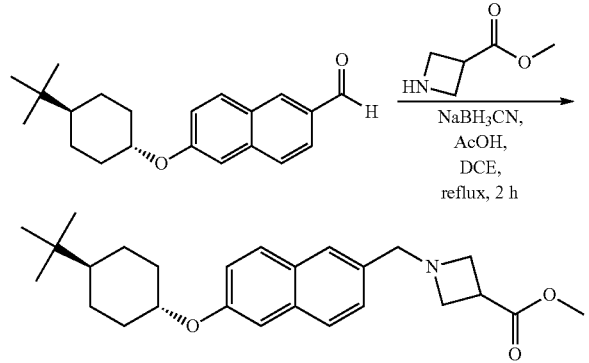

The title compound was synthesized as described for methyl 2-((6-(trans-4-tert-butylcyclohexyloxy)naphthalen-2-yl)methylamino)propanoate. 150 mg, white solid, yield: 61%. ESI-MS: 410.3 (M+H)+. HPLC: 92.03%. 1H NMR (400 MHz, CD3OD) δ: 7.88 (s, 1H), 7.84 (d, 1H), 7.82 (d, 1H), 7.44 (dd, 1H), 7.28 (d, 1H), 7.17 (dd, 1H), 4.51 (s, 2H), 4.32-4.39 (m, 5H), 3.72-3.77 (m, 4H), 2.26 (d, 2H), 1.90 (d, 2H), 1.36-1.47 (m, 2H), 1.24-1.31 (m, 2H), 1.11-1.17 (m, 1H), 0.91 (s, 9H).

Example 21: 1-((6-(trans-4-tert-butylcyclohexyloxy)naphthalen-2-yl)methyl)azetidine-3-carboxylic acid

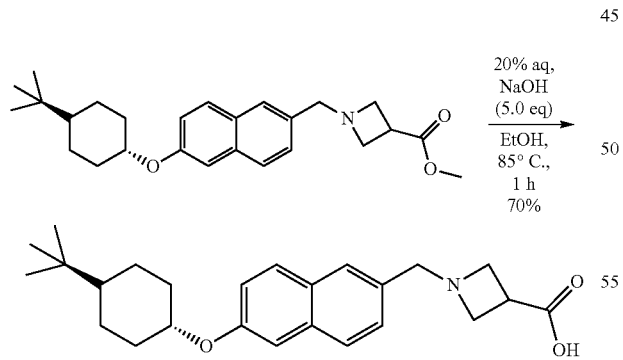

Synthesis was performed as described for 2-((6-(trans-4-tert-butylcyclohexyloxy)naphthalen-2-yl)methylamino)propanoic acid. 70 mg, white solid, yield: 70%. ESI-MS: 396.3 (M+H)+. HPLC: 90.04%. 1H NMR (400 MHz, CD3OD) δ: 7.91 (s, 1H), 7.86 (d, 1H), 7.83 (d, 1H), 7.47 (d, 1H), 7.30 (s, 1H), 7.19 (dd, 1H), 4.53 (s, 2H), 4.30-4.51 (m, 5H), 3.66-3.70 (m, 1H), 2.29 (d, 2H), 1.93 (d, 2H), 1.39-1.48 (m, 2H), 1.24-1.33 (m, 2H), 1.14-1.17 (m, 1H), 0.93 (s, 9H).

Example 22: methyl 1-((6-(trans-4-tert-butylcyclohexyloxy)naphthalen-2-yl)methyl)pyrrolidine-3-carboxylate

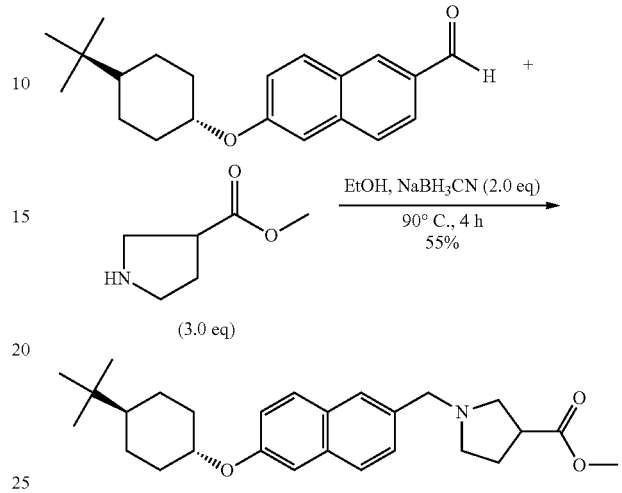

The title compound was synthesized as described for ethyl 2-(((6-(trans-4-tert-butylcyclohexyloxy)naphthalen-2-yl)methyl)(methyl)amino)acetate. 150 mg, white solid, yield: 55%. ESI-MS: 423.3 (M+H)+. HPLC: 98.59%. 1H NMR (400 MHz, CDCl3) δ 7.69-7.67 (m, 3H), 7.42 (d, 1H), 7.12 (t, 2H), 4.27-4.25 (m, 1H), 3.87 (s, 2H), 3.69 (s, 3H), 3.12-3.06 (m, 2H), 2.88-2.84 (m, 2H), 2.73-2.70 (m, 1H), 2.28-2.25 (m, 2H), 2.18-2.16 (m, 2H), 1.90-1.87 (m, 2H), 1.45-1.42 (m, 2H), 1.25-1.12 (m, 3H), 0.89 (s, 9H).

Example 23: 1-((6-(trans-4-tert-butylcyclohexyloxy)naphthalen-2-yl)methyl)pyrrolidine-3-carboxylic acid

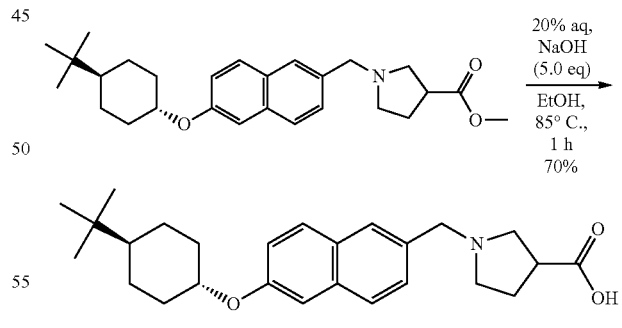

Synthesis was performed as described for 2-((6-(trans-4-tert-butylcyclohexyloxy)naphthalen-2-yl)methylamino)propanoic acid. 80 mg, white solid, yield: 55%. ESI-MS: 409.3 (M+H)+. HPLC: 93.50%. 1H NMR (400 MHz, CD3OD) δ 7.95 (s, 1H), 7.83 (dd, 2H), 7.55 (d, 1H), 7.28 (s, 1H), 7.18 (d, 1H), 4.55-4.47 (m, 2H), 4.41-4.34 (m, 1H) 3.63-3.37 (m, 2H), 3.32 (s, 2H), 3.28-3.20 (m, 1H), 2.42-2.27 (m, 4H), 1.94-1.90 (m, 2H), 1.48-1.38 (m, 2H), 1.33-1.23 (m, 2H), 1.23-1.14 (m, 1H), 0.89 (s, 9H).

Example 24: ethyl 1-((6-(trans-4-tert-butylcyclohexyloxy)naphthalen-2-yl)methyl)piperidine-4-carboxylate

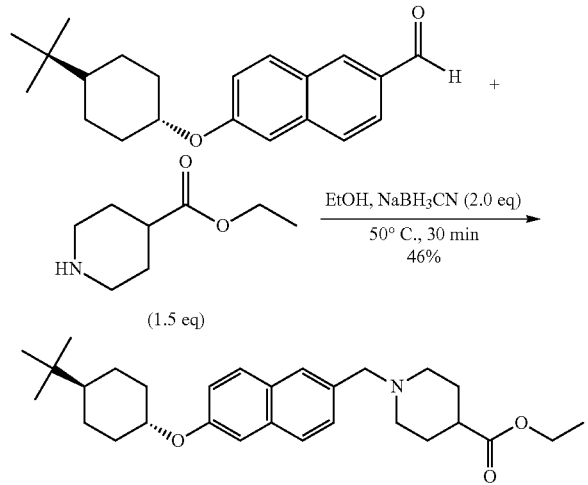

The title compound was synthesized as described for ethyl 2-(((6-(trans-4-tert-butylcyclohexyloxy)naphthalen-2-yl)methyl)(methyl)amino)acetate. 100 mg, white solid, yield: 46%. ESI-MS: 451.3 (M+H)+. HPLC: 92.64%. 1H NMR (400 MHz, CDCl3) δ 7.75-7.72 (m, 3H), 7.48 (dd, 1H), 7.17 (d, 2H), 4.30-4.28 (m, 1H), 4.16 (q, 2H), 3.96 (s, 2H), 3.09-3.08 (m, 2H), 2.53-2.51 (m, 3H), 2.29-2.26 (m, 2H), 2.10-2.03 (m, 4H), 1.91-1.88 (m, 2H), 1.43-1.43 (m, 2H), 1.18-1.13 (m, 6H), 0.88 (s, 9H).

Example 25: 1-((6-(trans-4-tert-butylcyclohexyloxy)naphthalen-2-yl)methyl)piperidine-4-carboxylic acid

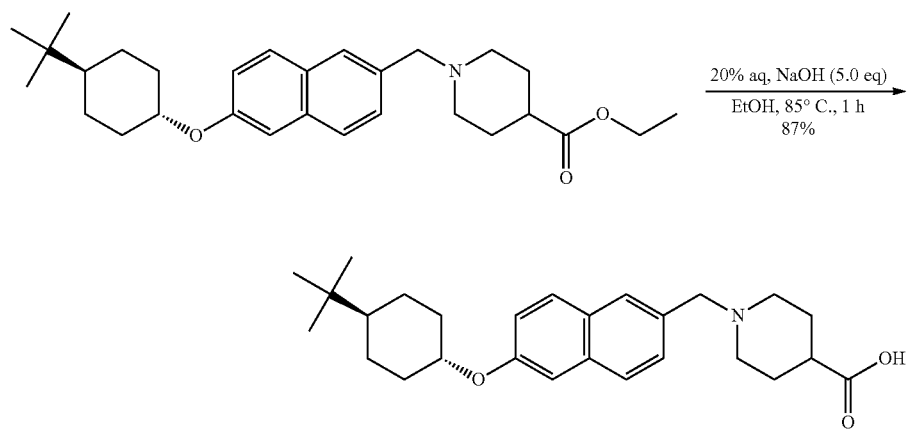

Synthesis was performed as described for 2-((6-(trans-4-tert-butylcyclohexyloxy)naphthalen-2-yl)methylamino)propanoic acid. 70 mg, white solid, yield: 87%. ESI-MS: 423.3 (M+H)+. HPLC: 94.25%. 1H NMR (400 MHz, CD3OD) δ 7.90 (s, 1H), 7.86 (dd, 2H), 7.56 (d, 1H), 7.32 (s, 1H), 7.20 (dd, 1H), 4.46 (s, 2H), 4.42-4.39 (m, 1H), 3.61-3.59 (m, 2H), 3.19-3.15 (m, 2H), 2.72-2.60 (m, 1H), 2.31-2.27 (m, 4H), 1.95-1.92 (m, 4H), 1.46-1.42 (m, 2H), 1.34-1.27 (m, 3H), 0.93 (s, 9H).

Example 26: 6-(trans-4-tert-butylcyclohexyloxy)-5-(trifluoromethyl)-2-naphthaldehyde

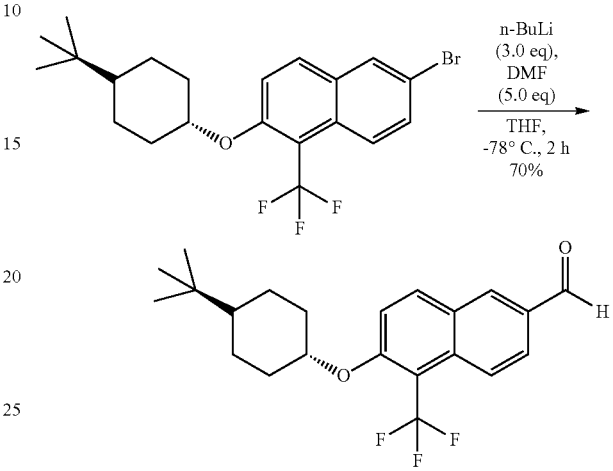

To a solution of 6-bromo-2-(trans-4-tert-butylcyclohexyloxy)-1-(trifluoromethyl)naphthalene (1 g, 2.3 mmol) in THF (30 mL) was added n-BuLi (2.8 mL, 2.5M in THF, 3.0 equiv) dropwise at −78° C. in 30 min, then DMF (840 mg, 11.5 mmol, 5.0 equiv) was added slowly at −78° C. The reaction mixture was stirred at −78° C. for 1.5 h. Then saturated NH4Cl solution was added to the mixture to quench the reaction. The mixture was extracted with EtOAc and purified by silica gel chromatography (petroleum ether: ethyl acetate 10:1) to give product 6-(trans-4-tert-butylcyclohexyloxy)-5-(trifluoromethyl)-2-naphthaldehyde as a yellow solid (608 mg, 70%) ESI-MS: 379.2 (M+H)+. 1H NMR (400 MHz, CDCl3) δ: 10.13 (s, 1H), 8.28 (d, 2H), 8.08 (d, 1H), 7.98-8.01 (dd, 1H), 7.41 (d, 1H), 4.39 (m, 1H), 2.21 (d, 2H), 1.90 (d, 2H), 1.49-1.58 (q, 2H), 1.10-1.17 (m, 3H), 0.86 (s, 9H)

Example 27: methyl 1-((6-(trans-4-tert-butylcyclohexyloxy)-5-(trifluoromethyl)naphthalen-2-yl)methyl)azetidine-3-carboxylate

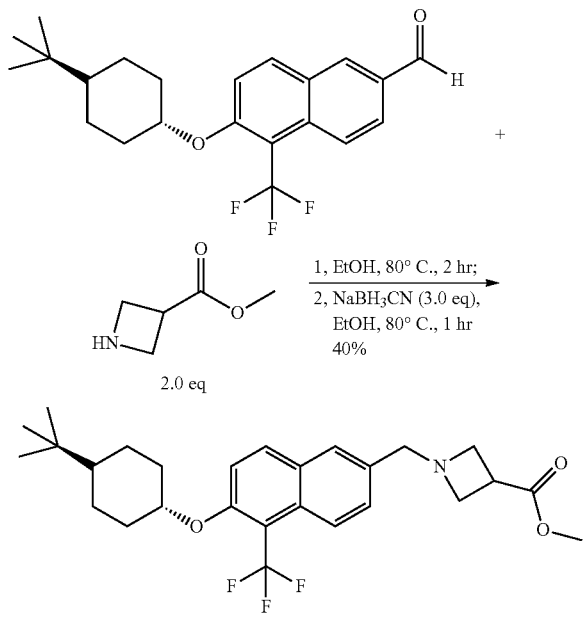

A mixture of 6-(trans-4-tert-butylcyclohexyloxy)-5-(trifluoromethyl)-2-naphthaldehyde (300 mg, 0.8 mmol) and methyl azetidine-3-carboxylate (184 mg, 1.6 mmol, 2.0 equiv) in anhydrous ethanol (20 mL) was refluxed for 2 h. Then the solvent was removed in vacuo, fresh ethanol and NaBH$_3$CN (150 mg, 2.4 mmol, 3.0 equiv) was added, the resulting mixture was refluxed for 1 h. The reaction mixture was concentrated and the residue was purified by chromatography with silica gel (dichloromethane:methanol 20:1) to give product methyl 1-((6-(trans-4-tert-butylcyclohexyloxy)-5-(trifluoromethyl)naphthalen-2-yl)methyl)azetidine-3-carboxylate as a white solid (150 mg, yield: 40%). ESI-MS: 477.3 (M+H)$^+$. HPLC: 85.67% $^1$H NMR (400 MHz, CD$_3$OD) δ: 8.09 (dd, 1H), 8.01 (d, 1H), 7.56 (s, 1H), 7.46-7.51 (m, 2H), 4.42 (m, 1H), 3.77 (s, 2H), 3.71 (s, 3H), 3.57 (t, 2H), 3.45 (t, 2H), 3.35-3.39 (m, 1H), 2.18 (d, 2H), 1.88 (d, 2H), 1.43-1.52 (q, 2H), 1.09-1.22 (m, 3H), 0.89 (s, 9H)

Example 28: 1-((6-(trans-4-tert-butylcyclohexyloxy)-5-(trifluoromethyl)naphthalen-2-yl)methyl)azetidine-3-carboxylic acid

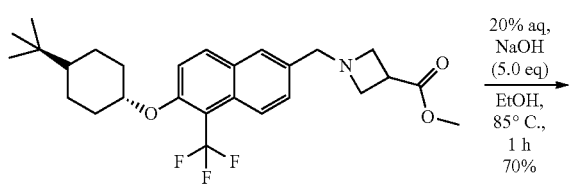

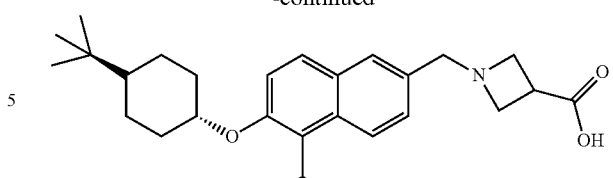

To a solution of methyl 1-((6-(trans-4-tert-butylcyclohexyloxy)-5-(trifluoromethyl)naphthalen-2-yl)methyl)azetidine-3-carboxylate (100 mg, 0.25 mmol) in ethanol (10 mL) was added aqueous NaOH (3 mL, 20%) and refluxed for 1 h. Then the reaction was cooled to 0° C., the pH of the solution was adjusted to 6 with 1 M HCl, and concentrated. The residue was dissolved in dichloromethane, washed with water, dried and concentrated to give 1-((6-(trans-4-tert-butylcyclohexyloxy)-5-(trifluoromethyl)naphthalen-2-yl)methyl)azetidine-3-carboxylic acid as a white solid (70 mg, yield: 70%). ESI-MS: 464.2 (M+H)$^+$. HPLC: 98.64% $^1$H NMR (400 MHz, DMSO-d$_6$) δ: 8.19 (d, 2H), 8.08 (d, 2H), 7.72 (d, 1H), 7.67 (d, 1H), 4.60-4.58 (m, 1H), 4.51 (s, 2H), 4.21 (d, 4H), 3.55-3.67 (m, 1H), 2.13 (d, 2H), 1.80 (d, 2H), 1.35-1.43 (q, 2H), 1.03-1.22 (m, 3H), 0.86 (s, 9H).

Example 29: ethyl 3-((6-(trans-4-tert-butylcyclohexyloxy)-5-(trifluoromethyl)naphthalen-2-yl)methylamino)propanoate

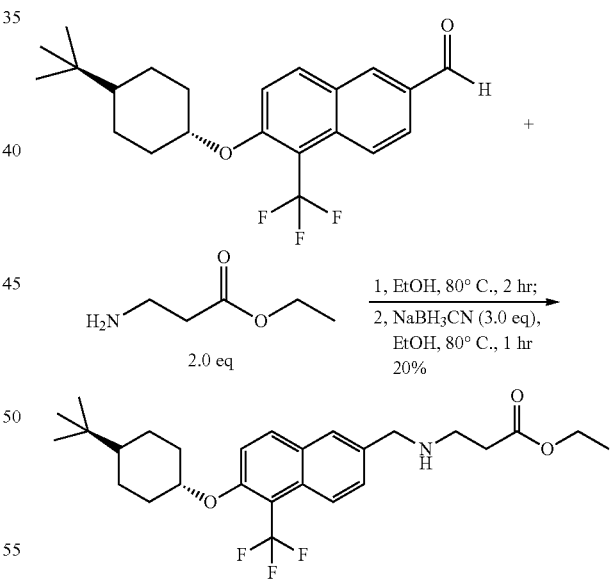

Synthesis was performed as described for methyl 1-((6-(trans-4-tert-butylcyclohexyloxy)-5-(trifluoromethyl)naphthalen-2-yl)methyl)azetidine-3-carboxylate. 50 mg, white solid (yield: 20%). ESI-MS: 480.3 (M+H)$^+$. HPLC: 89.20% $^1$H NMR (400 MHz, DMSO-d$_6$) δ: 8.22 (d, 1H), 8.97 (d, 1H), 7.90 (s, 1H), 7.52 (d, 1H), 7.33 (d, 1H), 4.30-4.28 (m, 1H), 4.14-4.20 (m, 4H), 3.17 (s, 2H), 2.77 (s, 2H), 2.16 (d, 2H), 1.86 (d, 2H), 1.47-1.55 (q, 2H), 1.25 (t, 3H), 1.09-1.13 (m, 3H), 0.87 (s, 9H).

Example 30: 3-((6-(trans-4-tert-butylcyclohexyloxy)-5-(trifluoromethyl)naphthalen-2-yl)methylamino)propanoic acid

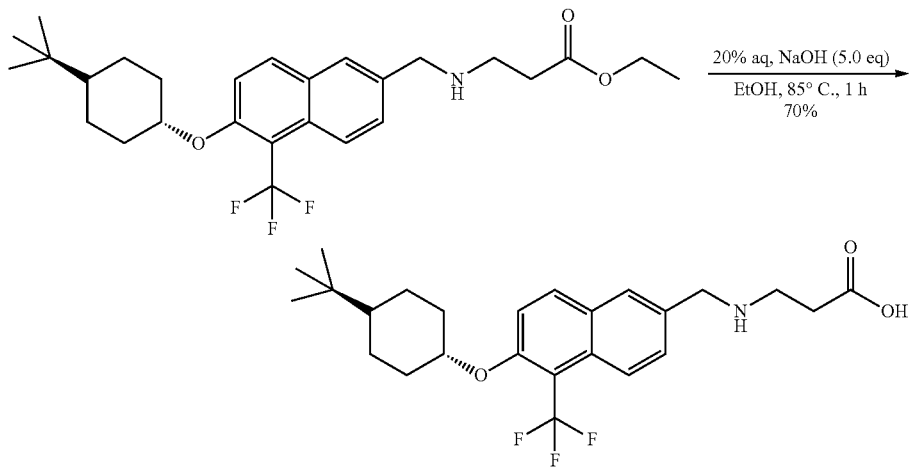

Synthesis was performed as described for 1-((6-(trans-4-tert-butylcyclohexyloxy)-5-(trifluoromethyl)naphthalen-2-yl)methyl)azetidine-3-carboxylic acid. 30 mg, white solid (yield: 70%). ESI-MS: 452.2 (M+H)$^+$. HPLC: 94.35% $^1$H NMR (400 MHz, DMSO-$d_6$) δ: 8.12 (d, 1H), 8.01 (d, 1H), 7.91 (s, 1H), 7.62 (d, 2H), 4.54-4.52 (m, 1H), 3.93 (s, 2H), 2.79 (t, 2H), 2.36 (t, 2H), 2.12 (d, 2H), 1.79 (d, 2H), 1.35-1.41 (q, 2H), 1.03-1.22 (m, 3H), 0.86 (s, 9H).

Example 31: methyl 6-(trans-4-tert-butylcyclohexyloxy)-2-naphthoate

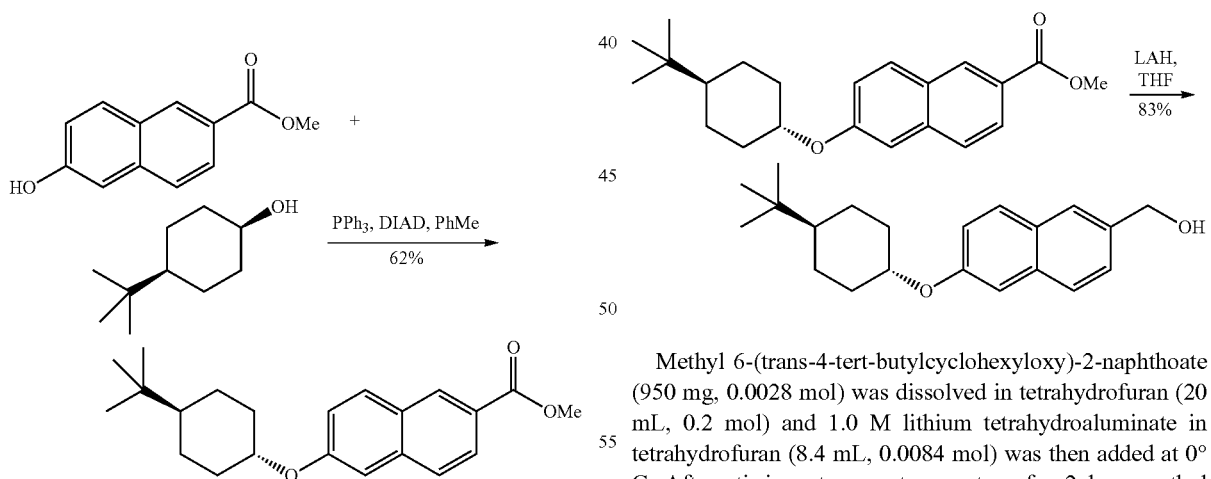

A mixture of cis-4-tert-butylcyclohexanol (927 mg, 0.00593 mol), 6-hydroxy-naphthalene-2-carboxylic acid methyl ester (1.00 g, 0.00494 mol) and triphenylphosphine (1560 mg, 0.00593 mol) in toluene (10 mL, 0.1 mol) was heated to reflux, and diisopropyl azodicarboxylate (1.17 mL, 0.00593 mol) was added dropwise and was stirred and refluxed for 6 hours. The mixture was taken up into dichloromethane and was purified via column chromatography with ethyl acetate:hexane (0:100 to 40:60) to give methyl 6-(trans-4-tert-butylcyclohexyloxy)-2-naphthoate as a white solid (0.95 g, 56%). $^1$H NMR (400 MHz, CDCl$_3$) δ 8.52 (s, 1H), 8.01 (dd, J=8.7, 1.7 Hz, 1H), 7.84 (d, J=9.6 Hz, 1H), 7.73 (d, J=8.7 Hz, 1H), 7.17 (m, 2H), 4.34 (m, 1H), 3.97 (s, 3H), 2.30 (m, 2H), 1.92 (m, 2H), 1.52-1.14 (m, 5H), 0.91 (s, 9H).

Example 32: (6-trans-4-tert-butylcyclohexyloxy)naphthalen-2-yl)methanol

Methyl 6-(trans-4-tert-butylcyclohexyloxy)-2-naphthoate (950 mg, 0.0028 mol) was dissolved in tetrahydrofuran (20 mL, 0.2 mol) and 1.0 M lithium tetrahydroaluminate in tetrahydrofuran (8.4 mL, 0.0084 mol) was then added at 0° C. After stirring at room temperature for 2 hours, ethyl acetate and Rochele's salt was added and the mixture was then stirred at room temperature for 1 hour. After extraction with ethyl acetate followed by concentration under reduced pressure, the product (6-trans-4-tert-Butylcyclohexyloxy)naphthalen-2-yl)methanol was obtained as a white solid (770 mg, 88%). $^1$H NMR (400 MHz, CDCl$_3$) δ 7.71 (m, 2H), 7.45 (d, J=10.1 Hz, 1H), 7.15 (m, 3H), 4.82 (AB, J=16.1, 16.1 Hz, 2H), 4.28 (m, 1H), 2.27-2.31 (m, 2H), 1.89-1.92 (m, 2H), 1.11-1.50 (m, 5H), 0.91 (s, 9H).

Example 33: 6-(trans-4-tert-Butylcyclohexyloxy)-2-naphthaldehyde

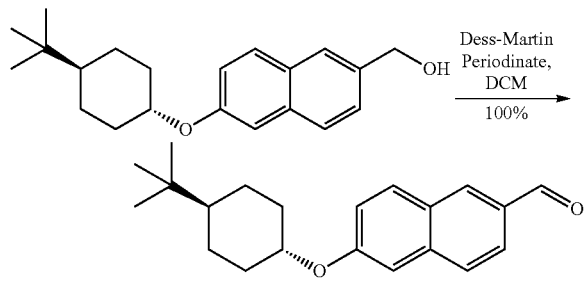

To (6-trans-4-tert-butylcyclohexyloxy)naphthalen-2-yl)methanol (150 mg, 0.480 mmol) in methylene chloride (5 mL, 80 mmol) was added the Dess-Martin periodinane (0.285 g, 0.672 mmol) and the mixture was stirred at room temperature for 1 hour. The crude reaction mixture was then passed through a silica gel plug and the filtrate was then concentrated under reduced pressure to give the product as a white solid (0.150 g, 100%). $^1$H NMR (400 MHz, CDCl$_3$) δ 10.10 (s, 1H), 8.25 (s, 1H), 7.92-7.87 (m, 2H), 7.78 (d, J=8.5 Hz, 1H), 7.23-7.19 (m, 2H), 4.38-4.30 (m, 1H), 2.31-2.29 (m, 2H), 1.94-1.91 (m, 2H), 1.54-1.11 (m, 5H), 0.92 (s, 9H).

Example 34: 3-((6-(trans-4-tert-butylcyclohexyloxy)naphthalen-2-yl)methylamino)-2,2-difluoropropanoic acid

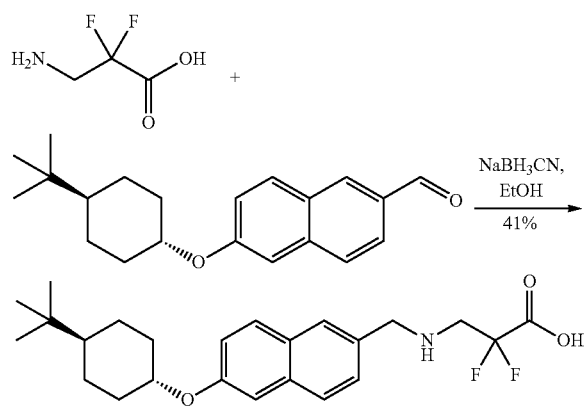

A solution of 6-(4-tert-Butyl-cyclohexyloxy)-naphthalene-2-carbaldehyde (150 mg, 0.483 mmol) and 3-amino-2,2-difluoro-propionic acid (60.4 mg, 0.483 mmol) in ethanol (0.7 mL, 10 mmol) was heated to reflux for 2 h. The yellow solution was then cooled to room temperature and sodium cyanoborohydride (36.4 mg, 0.580 mmol) was added to the stirring solution. The resulting mixture was heated to reflux for 1 h. After cooling to room temperature, citric acid was added, and the solvent removed under vacuum. The resulting solid was suspended in water and collected via filtration. The filtrate was washed thoroughly with water (4×), ether (3×), and hexane (3×). The resulting solid was dried on the filter to give the title compound as a white solid (128.8 mg, 64%). $^1$H NMR (400 MHz, CDCl$_3$) δ: 7.92 (s, 1H), 7.87 (d, J=8.5 Hz, 1H), 7.82 (d, J=9.1 Hz, 1H), 7.52 (dd, J=8.4, 1.8 Hz, 1H), 7.30 (d, J=2.2 Hz, 1H), 7.19 (dd, J=9.0, 2.4 Hz, 1H), 4.45 (s, 2H), 4.40 (m, 1H), 3.61 (t, J=13.8 Hz, 2H), 2.28-2.31 (m, 2H), 1.92-1.95 (m, 2H), 1.49-1.14 (m, 5H), 0.94 (s, 9H).

Example 35: methyl 6-(spiro[5.5]undecan-3-yloxy)-2-naphthoate

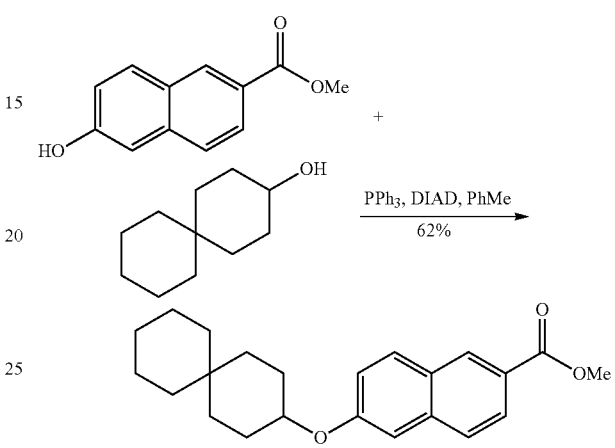

A mixture of spiro[5.5]undecan-3-ol (0.999 g, 0.00593 mol), 6-hydroxy-naphthalene-2-carboxylic acid methyl ester (1.00 g, 0.00494 mol) and triphenylphosphine (1.56 g, 0.00593 mol) in toluene (10 mL, 0.1 mol) was heated to reflux. Diisopropyl azodicarboxylate (1.17 mL, 0.00593 mol) was then added dropwise and the resulting mixture was refluxed for 6 hours. The mixture was then diluted with dichloromethane and subjected to chromatographic purification with ethyl acetate:hexane (0:100 to 40:60) to give methyl 6-(spiro[5.5]undecan-3-yloxy)-2-naphthoate as a white solid. (1.09 g, 62%). $^1$H NMR (400 MHz, CDCl$_3$) δ 8.52 (s, 1H), 8.01 (dd, J=8.7, 1.7 Hz, 1H), 7.84 (d, J=9.6 Hz, 1H), 7.72 (d, J=8.7 Hz, 1H), 7.17 (m, 2H), 4.45 (m, 1H), 3.97 (s, 3H), 1.93-1.28 (m, 18H).

Example 36: (6-(spiro[5.5]undecan-3-yloxy)naphthalen-2-yl)methanol

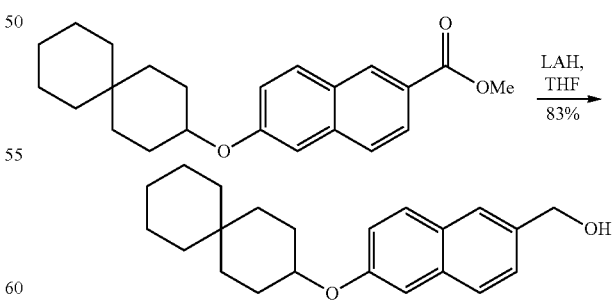

To a solution of 6-(Spiro[5.5]undec-3-yloxy)-naphthalene-2-carboxylic acid methyl ester (0.374 g, 0.00106 mol) in tetrahydrofuran (10 mL, 0.1 mol) was added 1.0 M of lithium tetrahydroaluminate in tetrahydrofuran (3.18 mL, 0.00318 mol) at 0° C. The reaction was then allowed to warm to room temperature while stirring for 2 h, Rochele's salt was then added and stirred the resulting mixture was stirred at room temperature for 1 h. After extraction with ethyl acetate, and solvent removal under vacuum, (6-(spiro[5.5]undecan-3-yloxy)naphthalen-2-yl)methanol was obtained as a white solid (0.28 g, 83%). ESI-MS: 307.5 (M+H)+. 100%). $^1$H NMR (400 MHz, CDCl$_3$) δ 7.74-7.70 (m, 3H), 7.44 (d, J=10.0 Hz, 1H), 7.16 (m, 2H), 4.81 (s, 2H), 4.40 (m, 1H), 1.94-1.26 (m, 18H).

Example 37:
6-(spiro[5.5]undecan-3-yloxy)-2-naphthaldehyde

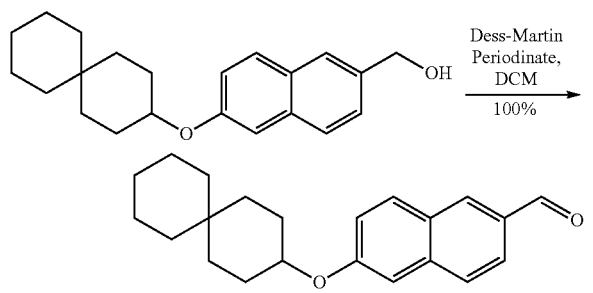

To [6-(Spiro[5.5]undec-3-yloxy)-naphthalen-2-yl]-methanol (150 mg, 0.46 mmol) in methylene chloride (5 mL, 80 mmol) was added Dess-Martin periodinane (0.274 g, 0.647 mmol) and the resulting solution was stirred at room temperature for 1 hour. The crude reaction was then passed through a silica gel plug, the filtrate was removed under vacuum to give 6-(spiro[5.5]undecan-3-yloxy)-2-naphthaldehyde as a colorless solid. (0.150 g, 100%). 1H NMR (400 MHz, CDCl$_3$) δ 10.09 (s, 1H), 8.25 (s, 1H), 7.92-7.89 (m, 2H), 7.78 (d, J=8.7 Hz, 1H), 7.24-7.19 (m, 2H), 4.48 (m, 1H), 1.96-1.29 (m, 18H).

Example 38: 2,2-difluoro-3-((6-(spiro[5.5]undecan-3-yloxy)naphthalen-2-yl)methylamino)propanoic acid

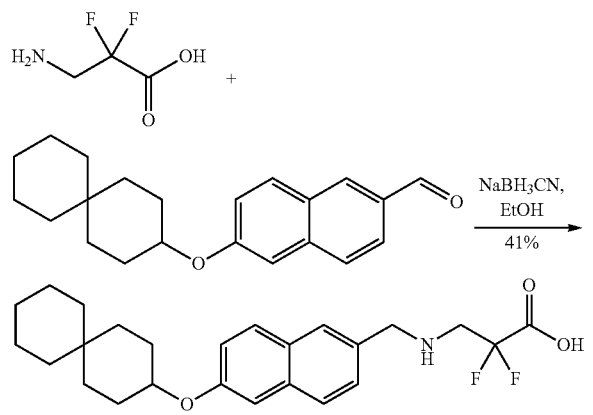

A solution of 6-(spiro[5.5]undec-3-yloxy)-naphthalene-2-carbaldehyde (150 mg, 0.46 mmol) and 3-amino-2,2-difluoro-propionic acid (58.2 mg, 0.465 mmol) in ethanol (0.7 mL, 10 mmol) was heated to reflux for 2 h. The yellow solution was then cooled to room temperature and sodium cyanoborohydride (35.1 mg, 0.558 mmol) was added portionwise. The resulting mixture was heated to reflux for 1 h. The reaction was then cooled to room temperature, and citric acid was added. The solution was stirred for several minutes and the solvent removed under vacuum. The resulting solid was suspended in water and filtered, and the collected solid was washed thoroughly with water (4×), ether (5×), and hexane (5×) to give (82.1 mg, 41%) of 2,2-difluoro-3-((6-(spiro[5.5]undecan-3-yloxy)naphthalen-2-yl)methylamino)propanoic acid. $^1$H NMR (400 MHz, CDCl$_3$) δ: 7.93 (s, 1H), 7.86 (d, J=8.5 Hz, 1H), 7.83 (d, J=9.1 Hz, 1H), 7.52 (dd, J=8.4, 1.8 Hz, 1H), 7.30 (d, J=2.2 Hz, 1H), 7.22 (dd, J=9.0, 2.4 Hz, 1H), 4.52 (m, 1H), 4.45 (s, 2H), 3.60 (t, J=15.9 Hz, 2H), 1.76-1.35 (m, 18H).

Example 39: (R)-ethyl 1-((6-(trans-4-tert-butylcyclohexyloxy)naphthalen-2-yl)methyl)piperidine-3-carboxylate

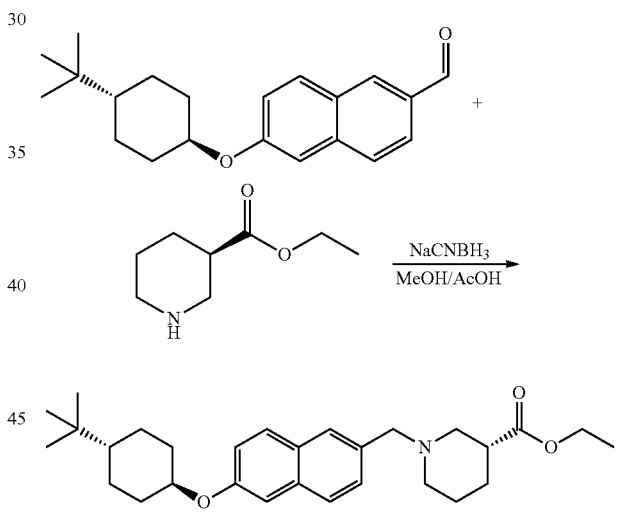

6-(4-tert-Butyl-cyclohexyloxy)-naphthalene-2-carbaldehyde (500 mg, 2 mmol) was combined with (R)-piperidine-3-carboxylic acid ethyl ester (0.51 g, 3.2 mmol) in methanol (10 mL, 200 mmol) and acetic acid (9.2 µL, 0.16 mmol). Sodium cyanoborohydride (0.25 g, 4.0 mmol) was then added and the reaction was stirred overnight at room temperature. The reaction was then quenched with water and extracted three times with ethyl acetate. Organics were combined and dried over MgSO$_4$. Solids were removed via filtration and 10 g of silica gel was added. All solvent was then removed and the resulting silica gel was loaded onto a 24 g column and the product was eluted using a gradient of 0-60% ethyl acetate/hexanes and then dried under vacuum to give the title compound as a colorless oil. EDI-MS: 438.1 (M+H)+.

Example 40: (R)-1-((6-(trans-4-tert-butylcyclohexyloxy)naphthalen-2-yl)methyl)piperidine-3-carboxylic acid

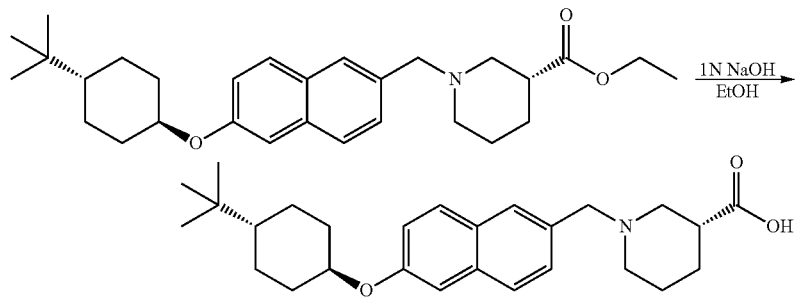

(R)-1-[6-(4-tert-Butyl-cyclohexyloxy)-naphthalen-2-yl-methyl]-piperidine-3-carboxylic acid ethyl ester (363.4 mg, 0.8046 mmol) was dissolved in ethanol (5 mL, 80 mmol) then treated with 1 M aqueous sodium hydroxide (5 mL, 5 mmol). The mixture was stirred vigorously for 18 hours. pH was adjusted to 3-4 with 3 N HCl and reaction was then extracted three times with ethyl acetate. Organics were combined then dried over MgSO$_4$, filtered and concentrated to dryness under reduced pressure. Ethyl ether was then added and a white precipitate formed which was removed via filtration to give a white solid that 86% pure by HPLC. The process was repeated two additional times to give the title compound as a white solid (156 mg, 44%). EDI-MS: 424.2 (M+H)$^+$. $^1$H NMR (400 MHz, MeOD) δ=7.82 (s, 1H), 7.74-7.62 (m, 2H), 7.42 (d, J=2.3, 1 H), 7.19 (d, J=2.3 Hz, 1H), 7.08 (d, J=2.5, 1 H), 4.43-4.34 (m, 1H), 4.33-4.22 (m, 2H), 2.71 (br. s., 1H), 2.16 (d, J=2.0 Hz, 2H), 1.88-167 (m, 4H), 1.40-1.25 (m, 3H), 1.24-1.11 (m, 4H), 1.10-0.95 (m, 5H), 0.79 (s, 9H)

Example 41: (S)-methyl 1-((6-(trans-4-tert-butylcyclohexyloxy)naphthalen-2-yl)methyl)piperidine-3-carboxylate

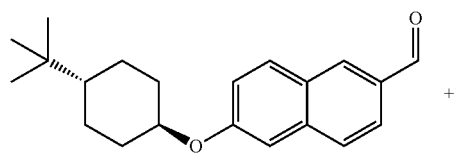

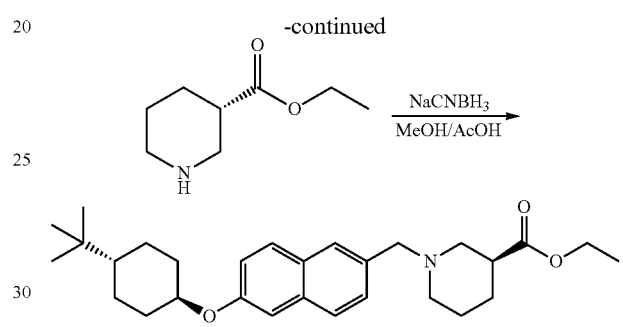

6-(4-tert-Butyl-cyclohexyloxy)-naphthalene-2-carbaldehyde (503.27 mg, 1.6212 mmol) was combined with in methanol (10 mL, 200 mmol) and acetic acid (9.2 μL, 0.16 mmol). Sodium cyanoborohydride (252.76 mg, 4.0221 mmol) was then added and the reaction was stirred overnight at room temperature. The reaction was then quenched with water and extracted three times with ethyl acetate. Organics were combined and dried over MgSO$_4$. Solids were removed via filtration and 7 g of silica gel was added. All solvent was then removed and the resulting silica was loaded onto a 24 g column and the product was eluted using a gradient of 0-60% ethyl acetate/hexanes and then dried under vacuum to give the title compound as a colorless oil (366 mg, 45%). EDI-MS: 438.3 (M+H)$^+$.

Example 42: (S)-1-((6-(trans-4-tert-butylcyclohexyloxy)naphthalen-2-yl)methyl)piperidine-3-carboxylic acid

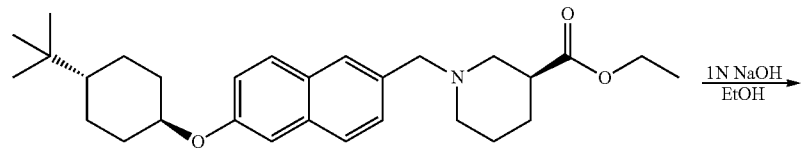

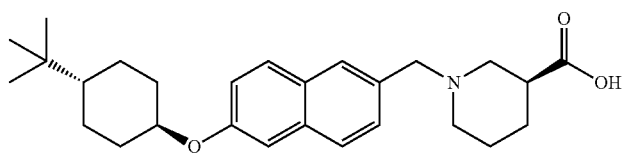

(S)-1-[6-(4-tert-Butyl-cyclohexyloxy)-naphthalen-2-ylmethyl]-piperidine-3-carboxylic acid ethyl ester (151.23 mg, 0.33484 mmol) was dissolved in ethanol (5 mL, 80 mmol) then treated with 1 M sodium hydroxide in water (5 mL, 5 mmol). The mixture was stirred vigorously for 18 hours. pH was adjust to 3-4 with 3 N HCl and reaction was then extracted three times with ethyl acetate. Organics were combined then dried over MgSO$_4$, filtered and concentrated to dryness under reduced pressure. Diethyl ether was then added and a white precipitate formed which was removed via filtration to give the title compound as a white solid (21 mg, 13%). EDI-MS: 424.1 (M+H)$^+$. $^1$H NMR (400 MHz, MeOD) δ=7.82 (s, 1H), 7.74-7.62 (m, 2H), 7.44 (d, J=2.3, 1 H), 7.19 (d, J=2.3 Hz, 1H), 7.08 (d, J=2.5, 1 H), 4.43-4.34 (m, 1H), 4.33-4.22 (m, 2H), 2.71 (br. s., 1H), 2.16 (d, J=2.0 Hz, 2H), 1.88-167 (m, 4H), 1.40-1.25 (m, 3H), 1.24-1.11 (m, 4H), 1.11-0.94 (m, 5H), 0.80 (s, 9H).

Example 43: 4-{[6-(trans-4-tert-Butyl-cyclohexyloxy)-naphthalen-2-ylmethyl]-amino}-butyric acid tert-butyl ester

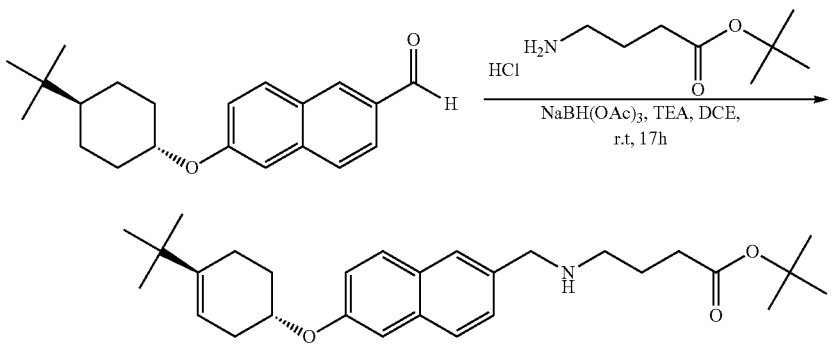

A solution of 6-(4-tert-butyl-cyclohexyloxy)-naphthalene-2-carbaldehyde (45 mg, 0.15 mmol, 4-amino-butyric acid tert-butyl ester HCl salt (115 mg, 0.59 mmol), and triethylamine (81 μL, 0.58 mmol) in 1,2-dichloroethane (1.5 mL) was treated with sodium triacetoxyborohydride (65 mg, 0.29 mmol). After stirring at room temperature over night, the mixture was diluted with dichloromethane and washed with aqueous sodium bicarbonate. The organic phase was dried over MgSO$_4$, filtered and concentrated and residue was purified by silica gel column eluted with ethyl acetate in hexane from 0 to 100% to give colorless oil (33 mg, yield: 50%). ESI-MS: 454.4 (M+H)$^+$; $^1$H NMR (400 MHz, CDCl$_3$) δ=7.65-7.70 (m, 3H), 7.38-7.40 (dd, 1H), 7.10-7.14 (m, 2H), 4.22-4.28 (m, 1H), 3.90 (s, 2H), 2.67 (t, 2H), 2.28 (t, 4H), 1.89 (d, 2H), 1.81 (t, 2H), 1.40 (m, 1H), 1.42 (s, 9H), 1.30 (m, 4H), 0.9 (s, 9H).

Example 44: 4-{[6-(trans-4-tert-Butyl-cyclohexyloxy)-naphthalen-2-ylmethyl]-amino}-butyric acid

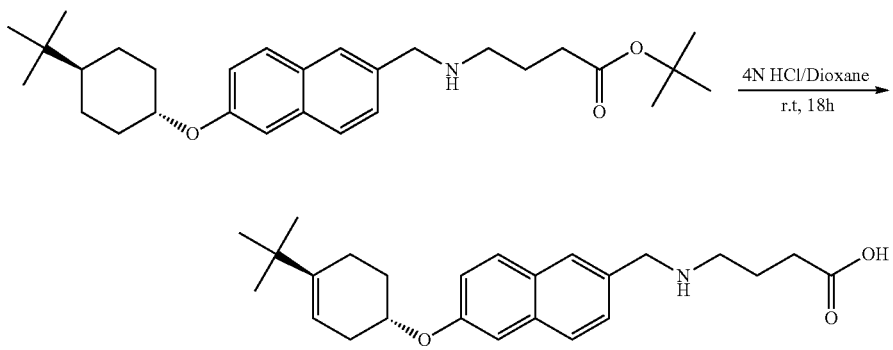

A solution of 4-{[6-(4-tert-butyl-cyclohexyloxy)-naphthalen-2-ylmethyl]-amino}-butyric acid tert-butyl ester (33 mg, 0.073 mmol) in 4 M HCl in dioxane (1.50 mL) was stirred at room temperature overnight to form a white precipitate. The precipitate was filtered and washed with ether to give product as the HCl salt (20 mg, yield: 63%). ESI-MS: 398.1 (M+H)$^+$; (400 MHz, CD$_3$OD) δ=7.90 (s, 1H), 7.84 (d, 1H), 7.81 (d, 1H), 7.49 (dd, 1H), 7.28 (d, 1H), 7.17 (dd, 1H), (m, 2H), 4.37 (m, 1H), 4.33 (s, 2H), 3.15 (t, 2H), 2.47 (t, 2H), 2.28 (t, 2H), 2.0 (m, 2H), 1.92 (d, 2H), 1.43 (q, 2H), 1.27 (q, 2H), 1.13 (m, 1H), 0.92 (s, 9H).

Example 45: {[6-(trans-4-tert-Butyl-cyclohexyloxy)-naphthalen-2-ylmethyl]-amino}-acetic acid ethyl ester

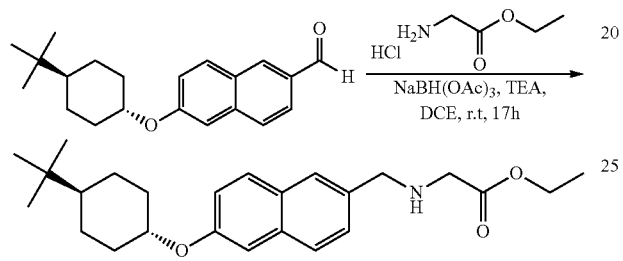

A solution of 6-(4-tert-butyl-cyclohexyloxy)-naphthalene-2-carbaldehyde (90 mg, 0.29 mmol), glycine ethyl ester hydrochloride (162 mg, 1.16 mmol), and triethylamine (0.16 mL, 1.16 mmol) in 1,2-dichloroethane (2 mL) was treated with sodium triacetoxyborohydride (129 mg, 0.58 mmol). The mixture was stirred at room temperature overnight. The solution was diluted with dichloromethane and washed with aqueous sodium bicarbonate. The organic phase was dried over MgSO$_4$ and concentrated. The residue was purified with a silica gel column eluted with ethyl acetate in hexane from 0 to 100% to give product (64 mg, yield: 55%). ESI-MS: 420.30 (M+23)$^+$; $^1$H NMR (400 MHz, CDCl$_3$) δ=7.66-7.70 (m, 3H), 7.41 (dd, 1H), 7.11-7.14 (m, 2H), 4.26 (m, 1H), 4.19 (q, 2H), 3.93 (s, 2H), 3.43 (s, 2H), 2.28 (d, 4H), 1.89 (d, 2H), 1.44 (q, 2H), 1.27 (t, 3H), 1.09-1.20 (m, 3H), 0.89 (s, 9H).

Example 46: {[6-(trans-4-tert-Butyl-cyclohexyloxy)-naphthalen-2-ylmethyl]-amino}-acetic acid To a solution of {[6-(4-tert-butyl-cyclohexyloxy)-naphthalen-2-ylmethyl]-amino}-acetic acid ethyl ester (60 mg, 0.15 mmol) in methanol (1 mL) was added aqueous lithium hydroxide (4.2 M, 0.5 mL, 2 mmol) to form a white precipitate. The mixture slurry was stirred at room temperature for 3 hrs then at 50° C. for 2 hrs. The slurry was neutralized with 1 N HCl to pH 6 and the white precipitate was filtered and dried under vacuum to give white precipitate (48 mg, yield: 86%). ESI-MS: 392.3 (M+23)$^+$; $^1$H NMR (400 MHz, DMSO) δ=7.77-7.82 (m, 3H), 7.48 (dd, 1H), 7.37 (d, 1H), 7.15 (dd, 1H), 4.38 (m, 1H), 4.07 (s, 2H), 3.16 (s, 2H), 2.20 (d, 2H), 1.82 (d, 2H), 1.35 (m, 2H), 1.10-1.25 (m, 3H), 0.89 (s, 9H).

Example 47: (2-{[6-(trans-4-tert-Butyl-cyclohexyloxy)-naphthalen-2-ylmethyl]-amino}-ethyl)-phosphonic acid diethyl ester

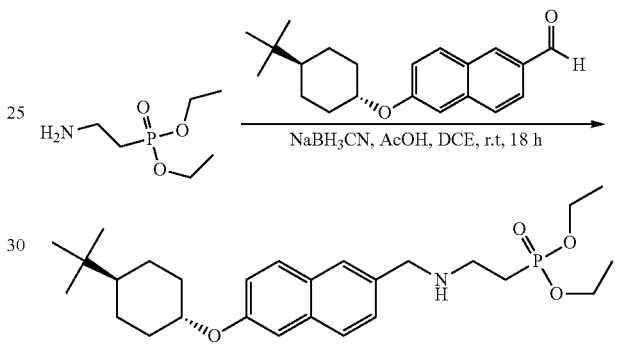

To a solution of (2-amino-ethyl)-phosphonic acid diethyl ester oxalic acid salt (200 mg, 0.74 mmol) in 1,2-dichloroethane (3 mL) was added 6-(4-tert-butyl-cyclohexyloxy)-naphthalene-2-carbaldehyde (343 mg, 1.1 mmol). The mixture was stirred at room temperature for 1 hour, then sodium triacetoxyborohydride (329 mg, 1.5 mmol) was added. After being stirred at room temperature overnight, the reaction mixture was quenched with water, stirred at room temperature for 30 min, then diluted with ethyl acetate, and washed with aqueous NaHCO$_3$. The organic layer was dried over MgSO$_4$ and purified with a silica gel column eluted with ethyl acetate (100%), then eluted with methanol in dichloromethane from 0 to 15% to give sticky oil (130 mg, yield: 25%). ESI-MS: 476.3 (M+H)$^+$.

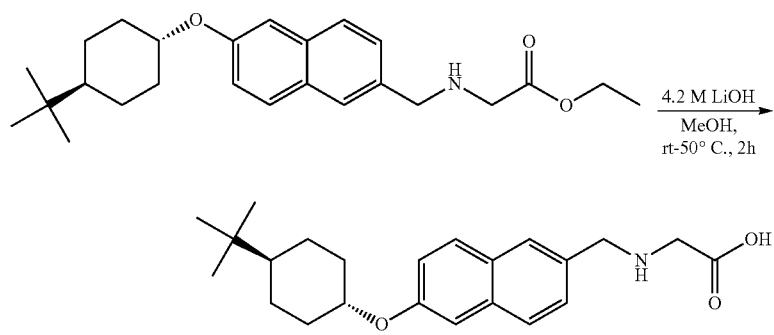

Example 48: (2-{[6-(trans-4-tert-Butyl-cyclohexyloxy)-naphthalen-2-ylmethyl]-amino}-ethyl)phosphonic acid

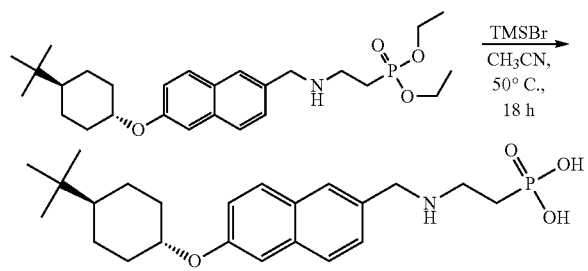

To a solution of (2-{[6-(4-tert-butyl-cyclohexyloxy)-naphthalen-2-ylmethyl]-amino}-ethyl)-phosphonic acid diethyl ester (65.00 mg, 0.14 mmol) in acetonitrile (1 mL) was added bromotrimethylsilane (1 mL, 7.58 mmol). The reaction was then stirred at 50° C. overnight. After the solvent was concentrated, the residue was purified with HPLC (acetonitrile-water, 15-85%) to give white precipitate (33 mg, yield: 58). ESI-MS: 420.2 (M+H)$^+$; $^1$H NMR (400 MHz, DMSO) δ=7.81-7.91 (m, 3H), 7.51 (dd, 1H), 7.41 (d, 1H), 7.19 (dd, 1H), 4.40 (m, 1H), 4.31 (s, 2H), 3.12 (m, 2H), 2.21 (d, 2H), 1.97 (m, 2H), 1.82 (d, 2H), 1.36 (q, 2H), 1.22 (q, 2H), 1.08 (m, 1H), 0.88 (s, 9H).

Example 49: 5-Hydroxy-2,3-dihydro-indole-1-carboxylic acid tert-butyl ester

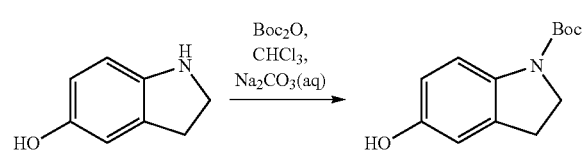

A mixture of 2,3-dihydro-1H-indol-5-ol (1.0 g, 7.8 mmol), di-tert-butyldicarbonate (4.0 g, 18 mmol), chloroform (20 mL) and saturated sodium bicarbonate aq. (8 mL) was stirred at room temperature over night. The organic phase was separated and washed twice with water, dried over MgSO$_4$, filtered and concentrated to give crude product. The crude material was treated with ether and filtered to give product (1.1 g, yield: 60%). ESI-MS: 258.10 (M+23)$^+$, $^1$H NMR (400 MHz, DMSO) δ 9.00 (s, 1H), 7.48 (ws, 1H), 6.61 (d, 1H), 6.51 (dd, 1H), 3.84 (t, 2H), 2.96 (t, 2H), 1.48 (s, 9H).

Example 50: 5-(trans-4-tert-Butyl-Cyclohexyloxy)-2,3-dihydro-indole-1-carboxylic acid tert-butyl ester

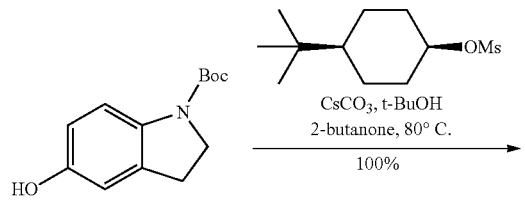

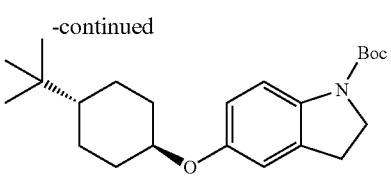

A mixture of 5-hydroxy-2,3-dihydro-indole-1-carboxylic acid tert-butyl ester (0.6 g, 2.6 mmol) in tert-butyl alcohol (8 mL) and 2-butanone (4 mL) was added cesium carbonate (2.5 g, 7.7 mmol) followed by methanesulfonic acid 4-tert-butyl-cyclohexyl ester (1.9 g, 7.7 mmol).

The mixture was heated in a sealed vial at 100° C. over night to form precipitate. The mixture was treated with dichloromethane and the precipitate was filtered off and the solvent was concentrated. The residue was purified with a silica gel column eluted with ethyl acetate in hexanes from 0 to 30% to give precipitate (0.96 g, yield: 100%). ESI-MS: 373.30 (M)$^+$.

Example 51: 5-(trans-4-tert-Butyl-cyclohexyloxy)-2,3-dihydro-1H-indole

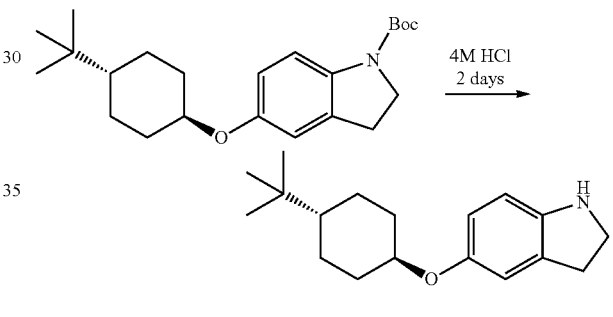

To a solution of 5-(4-tert-butyl-cyclohexyloxy)-2,3-dihydro-indole-1-carboxylic acid tert-butyl ester (0.92 g, 2.5 mmol) in THF (10 mL) was added 4 M HCl in dioxane (6 mL, 25 mmol). The mixture was stirred at room temperature for 48 hrs to form white precipitate. This mixture was partitioned between dichloromethane and aqueous sodium bicarbonate, and the organic phase was dried over MgSO$_4$, filtered and concentrated. The crude was purified with a silica gel column eluted with methanol in dichloromethane from 0 to 8% to give precipitate (0.67 g, yield: 99%). ESI-MS: 274.2 (M+H)$^+$.

Example 52: 3-tert-butoxycarbonylamino-4-[5-(trans-4-tert-butyl-cyclohexyloxy)-2,3-dihydro-indol-1-yl]-4-oxo-butyric acid tert-butyl ester

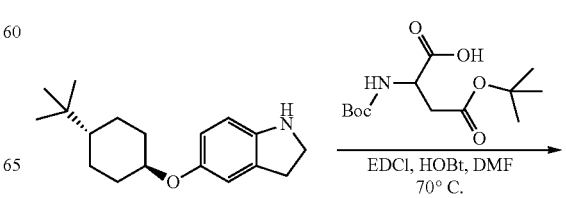

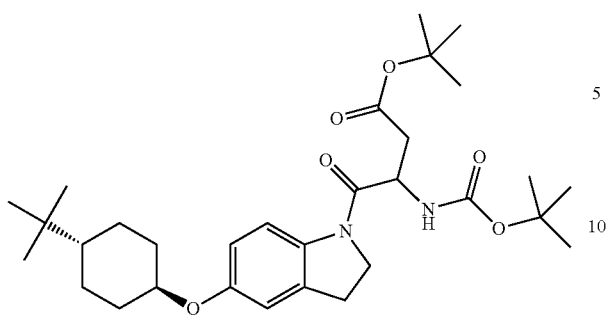

To a solution of 5-(4-tert-butyl-cyclohexyloxy)-2,3-dihydro-1H-indole (110 mg, 0.4 mmol) in dimethylformamide (2 mL) was added HOBT monohydrate (10 mg, 0.1 mmol), 2-tert-butoxycarbonylamino-succinic acid 4-tert-butyl ester (230 mg, 0.8 mmol) and finally N-(3-dimethylaminopropyl)-N'-ethylcarbodiimide hydrochloride (92 mg, 0.48 mmol). The reaction was heated at 50° C. overnight. The solution was diluted with ether and washed twice with water. The organic phase was dried over MgSO$_4$, filtered and concentrated to give crude product (220 mg, yield: 100%). The crude was used directly in Example 53. ESI-MS: 545.4 (M+H)$^+$.

Example 53: 3-amino-4-[5-(trans-4-tert-butyl-cyclohexyloxy)-2,3-dihydro-indol-1-yl]-4-oxo-butyric acid

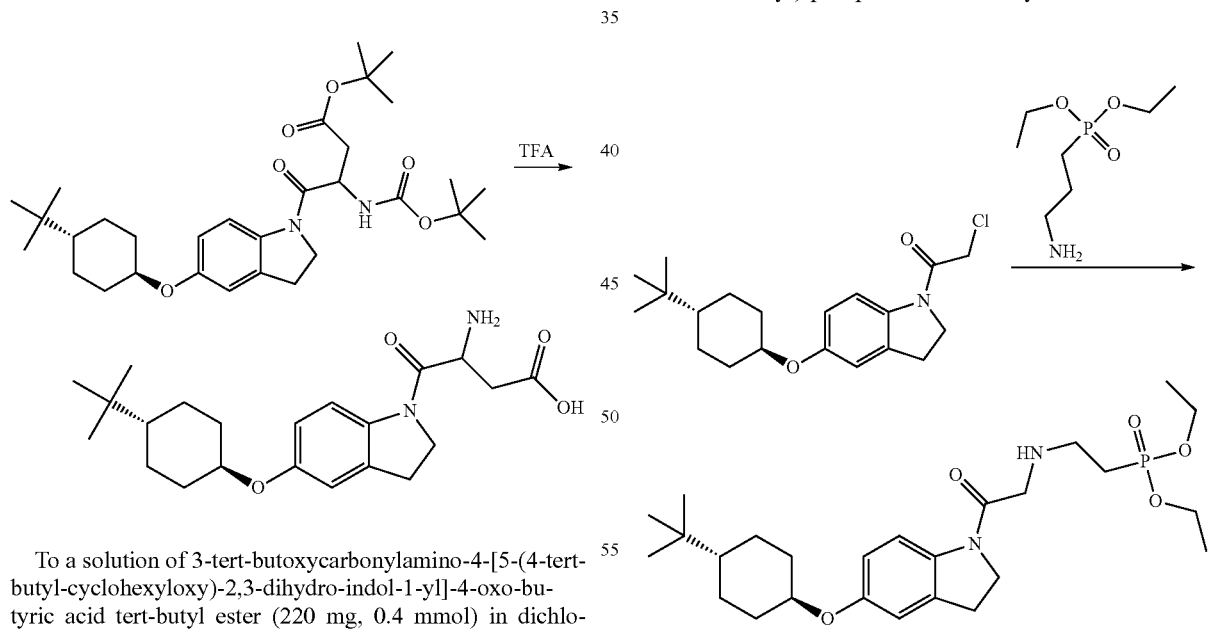

To a solution of 3-tert-butoxycarbonylamino-4-[5-(4-tert-butyl-cyclohexyloxy)-2,3-dihydro-indol-1-yl]-4-oxo-butyric acid tert-butyl ester (220 mg, 0.4 mmol) in dichloromethane (1 mL) was added trifluoroacetic acid (TFA) (0.8 mL, 10 mmol). The reaction was stirred at room temperature over night. The solvent was concentrated and residue was purified with HPLC to give white precipitate product TFA salt (22 mg, yield: 13%). ESI-MS: 389.3 (M+H)$^+$; $^1$H NMR (400 MHz, DMSO) δ 7.96 (d, 1H), 6.92 (d, 1H), 6.76 (dd, 1H), 4.45 (m, 1H), 4.11-4.25 (m, 3H), 3.15 (t, 2H), 3.04 (dd, 1H), 2.70 (dd, 1H), 2.09 (d, 2H), 1.77 (d, 2H), 1.45 (s, 1H), 1.27 (q, 2H), 1.13 (q, 2H), 1.04 (m, 1H), 0.85 (s, 9H).

Example 54: 1-[5-(trans-4-tert-butyl-cyclohexyloxy)-2,3-dihydro-indol-1-yl]-2-chloro-ethanone

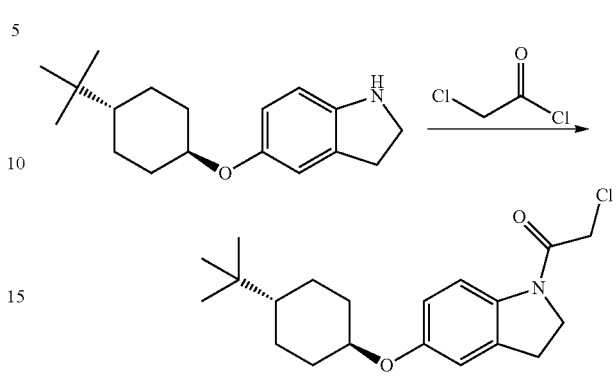

A solution of 5-(4-tert-butyl-cyclohexyloxy)-2,3-dihydro-1H-indole (0.55 g, 2 mmol), triethylamine (0.56 mL, 4 mmol) in dichloromethane (8 mL) was added chloroacetyl chloride (0.2 mL, 2.6 mmol) at 0° C. The solution was stirred from 0° C. to room temperature for 4 hrs.

The solution was diluted with dichloromethane and washed with 5% aqueous citric acid, aqueous sodium bicarbonate, and water, dried over MgSO$_4$, and concentrated. The residue was purified with silica gel column eluted with ethyl acetate in hexane to give product (0.37 g, yield: 52%). ESI-MS: 350.2 (M+H)$^+$.

Example 55: (2-{2-[5-(trans-4-tert-butyl-cyclohexyloxy)-2,3-dihydro-indol-1-yl]-2-oxo-ethylamino}-ethyl)-phosphonic acid diethyl ester To a solution of 1-[5-(4-tert-butyl-cyclohexyloxy)-2,3-dihydro-indol-1-yl]-2-chloro-ethanone (60 mg, 0.2 mmol) and (2-amino-ethyl)-phosphonic acid diethyl ester, oxalic acid salt (93 mg, 0.34 mmol) in dimethylformamide (1.5 mL) was added lithium bromide (18 mg, 0.2 mmol) and potassium carbonate (76 mg, 0.55 mmol). After being stirred at 70° C. overnight, the mixture was diluted with water and extracted with ethyl acetate. The organic phase was washed with 5% aqueous citric acid, aqueous sodium biocarbonate, and water, dried over MgSO$_4$ and concentrated. The residue was purified on a silica gel column to give product (20 mg, yield: 25%). ESI-MS: 495.3 (M+H)$^+$ Example 56: (2-{2-[5-(trans-4-tert-Butyl-cyclohexyloxy)-2,3-dihydro-indol-1-yl]-2-oxo-ethylamino}-ethyl)-phosphonic acid

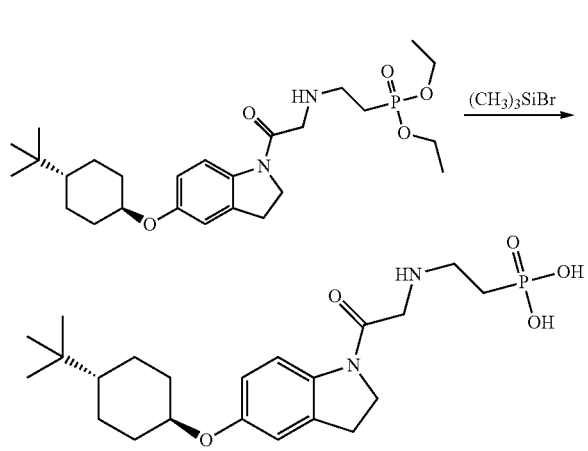

To stirring solution of (2-{2-[5-(4-tert-butyl-cyclohexyloxy)-2,3-dihydro-indol-1-yl]-2-oxo-ethylamino}-ethyl)-phosphonic acid diethyl ester (16 mg, 0.03 mmol) in acetonitrile (0.5 mL) was added bromotrimethylsilane (0.5 mL, 4 mmol). The reaction mixture was stirred at 50° C. overnight. After the solvent was concentrated, the residue was purified by HPLC (acetonitrile-water) to give white precipitate product (7.5 mg, yield: 53%). ESI-MS: 439.2 (M+H)$^+$ Example 57: 3-((2-((trans)-4-tert-butylcyclohexyloxy)quinolin-6-yl)methylamino)propanoic acid

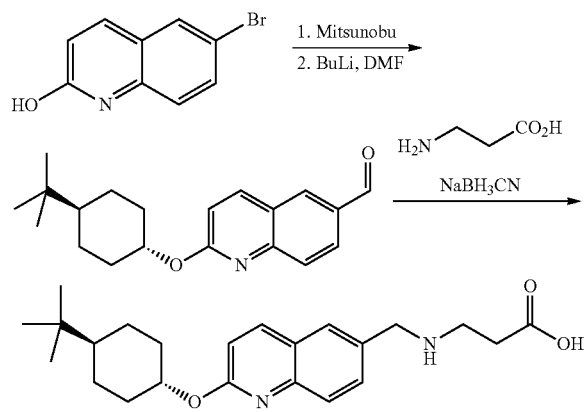

6-bromo-2-hydroxyquinoline was treated with cis-4-tert-butylcyclohexanol under Mitsunobu conditions, affording 6-bromo-2-((trans)-4-tert-butylcyclohexyloxy)quinoline. 6-bromo-2-((trans)-4-tert-butylcyclohexyloxy)quinoline was then exposed to n-butyllithium and DMF, providing 6-formyl-2-((trans)-4-tert-butylcyclohexyloxy)quinoline. This aldehyde was then treated with 3-aminopropionic acid and sodium cyanoborohydride to afford the title compound, 3-((2-((trans)-4-tert-butylcyclohexyloxy)quinolin-6-yl)methylamino)propanoic acid.

Example 58: 3-((6-((trans)-4-tert-butylcyclohexyloxy)quinolin-2-yl)methylamino)propanoic

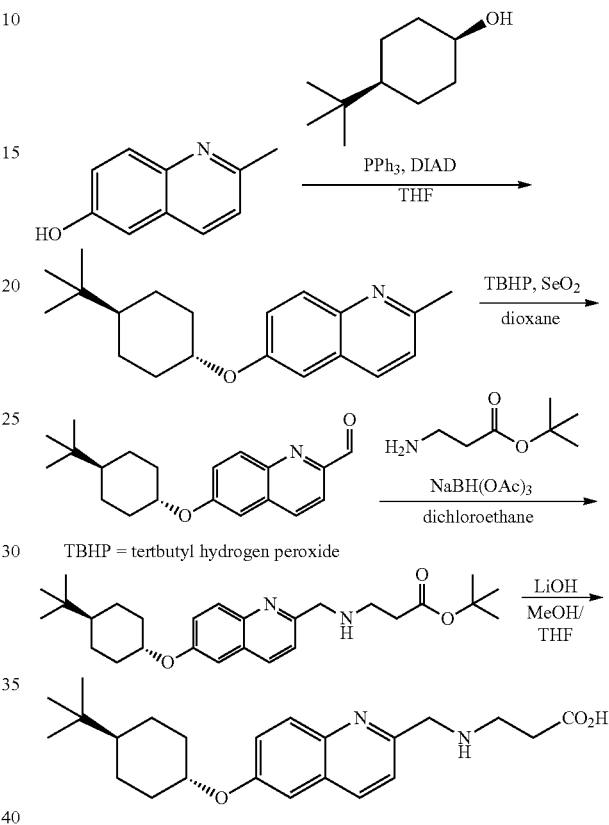

TBHP = tertbutyl hydrogen peroxide 6-hydroxy-2-methylquinoline was treated with cis-4-tert-butylcyclohexanol under Mitsunobu conditions, affording 6-((trans)-4-tert-butylcyclohexyloxy)-2-methylquinoline, which in turn was oxidized with tert-butyl hydrogen peroxide and selenium dioxide in dioxane, providing 6-((trans)-4-tert-butylcyclohexyloxy)-2-formylquinoline. This aldehyde was then treated with t-butyl 3-aminopropionate and sodium cyanoborohydride in dichloroethane to afford t-butyl 3-((((6-((trans)-4-tert-butylcyclohexyloxy)-quinolin-2-yl)methyl)amino)propionate. Treatment with lithium hydroxide in methanol/THF gave the title compound, 3-((6-((trans)-4-tert-butylcyclohexyloxy)quinolin-2-yl)methylamino)propanoic acid.

Example 59: tert-butyl 3-(methylsulfonamido)-3-oxopropylcarbamate

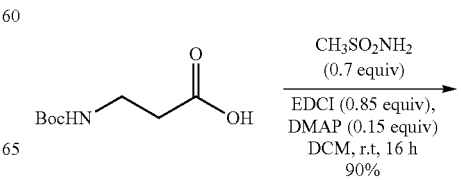

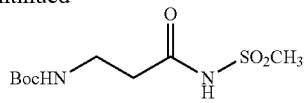

3-(tert-butoxycarbonylamino)propanoic acid (4 g, 21.2 mmol, 1.0 equiv) was dissolved in DCM (100 mL). Then methanesulfonamide (1.43 g, 15.1 mmol, 0.7 equiv), EDCI (3.45 g, 18.2 mmol, 0.85 equiv) and DMAP (0.37 g, 3 mmol, 0.15 equiv) were added to the mixture and stirred for 2 h at r.t. The reaction mixture was cooled down to 0° C., ice water (100 mL) was added. The mixture was stirred for 15 min, separated and the water layer was extracted twice with DCM. The combined organic layer was washed by 5% HCl, brine, dried over $Na_2SO_4$, concentrated to give tert-butyl 3-(methylsulfonamido)-3-oxopropylcarbamate as a gray oil (3.6 g, 90%). ESI-MS $(M+H)^+$: 267.1. $^1$H NMR (400 MHz, DMSO-$d_6$) δ: 6.91~6.83 (brs, 1H), 3.36 (s, 3H), 3.19~3.12 (m, 2H), 2.41 (t, 2H), 1.37 (s, 9H).

Example 60: 3-amino-N-(methylsulfonyl)propanamide

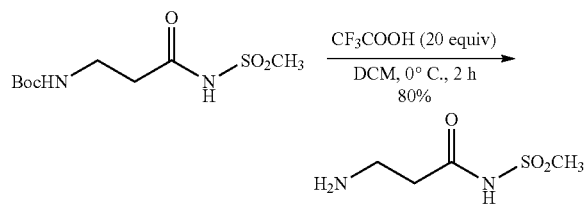

tert-butyl 3-(methylsulfonamido)-3-oxopropylcarbamate (3.6 g, 15.1 mmol) was dissolved in DCM (60 mL). Then $CF_3COOH$ (1.1 mL, 0.3 mmol, 20 equiv) was added to the mixture at 0° C. and stirred for 2 h at 0° C. The reaction mixture was concentrated. The residue was purified by flash chromatography to give 3-amino-N-(methylsulfonyl)propanamide as a transparent solid (1.8 g, 80%). (mobile phase: $CH_3OH/H_2O$=0~5%). ESI-MS $(M+1)^+$: 167.0. $^1$H NMR (400 MHz, $CD_3OD$) δ: 3.21~3.11 (m, 2H), 3.07 (s, 3H), 2.60~2.54 (m, 2H).

Example 61: 3-((6-(((trans)-4-tert-butylcyclohexyloxy)naphthalen-2-yl)methylamino)-N-(methylsulfonyl)propanamide

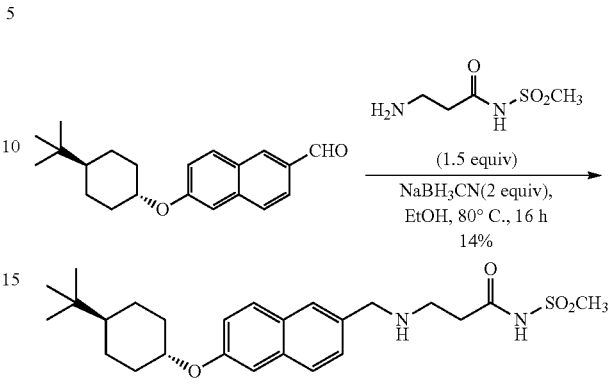

6-((trans)-4-tert-butylcyclohexyloxy)-2-naphthaldehyde (300 mg, 0.96 mmol, 1 equiv) and 3-amino-N-(methylsulfonyl)propanamide (239 mg, 1.19 mmol, 1.5 equiv) were dissolved in anhydrous EtOH. The mixture was stirred at 80° C. for 1 h. Then $NaBH_3CN$ (110 mg, 1.74 mmol, 2 equiv) was added to the mixture and stirred at 80° C. for 16 h. The organic layer was concentrated and purified by prep-TLC to give 3-((6-((trans)-4-tert-butylcyclohexyloxy)naphthalen-2-yl)methylamino)-N-(methylsulfonyl)propanamide as a white solid (62 mg, 14%). (mobile phase: $CH_3OH/DCM$=1:10). ESI-MS $(M+1)^+$: 461.2, HPLC: 96.38%. $^1$H NMR (400 MHz, DMSO-$d_6$) δ: 7.93 (s, 1H), 7.85~7.77 (m, 2H), 7.59~7.49 (m, 1H), 7.43~7.35 (m, 1H), 7.20~7.11 (m, 1H), 4.45~4.33 (m, 1H), 4.20 (s, 2H), 2.98 (t, 2H), 2.77 (s, 3H), 2.35 (t, 2H), 2.26~2.14 (m, 2H), 1.86~1.75 (m, 2H), 1.41~1.30 (m, 2H), 1.27~1.14 (m, 2H), 1.13~1.02 (m, 1H), 0.89 (s, 9H).

Example 62: 3-((6-(((trans)-4-tert-butylcyclohexyloxy)-5-(trifluoromethyl)naphthalen-2-yl)methylamino)-N-(methylsulfonyl)propanamide

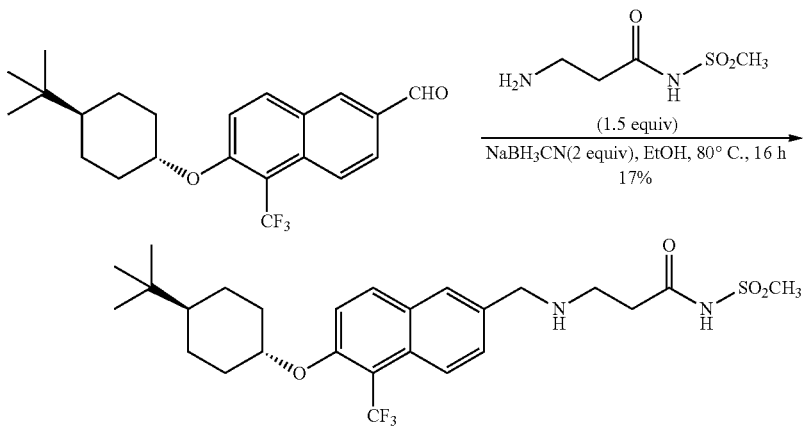

Preparation was done as describe in Example 61 utilizing 6-((trans)-4-tert-butylcyclohexyloxy)-5-(trifluoromethyl)-2-naphthaldehyde in place of 6-((1r,4r)-4-tert-butylcyclohexyloxy)-2-naphthaldehyde. 71 mg, white solid, yield: 17%. (mobile phase: $CH_3OH/DCM$=1:10). ESI-MS $(M+1)^+$:

529.2. HPLC: 98.69%. $^1$H NMR (400 MHz, CD$_3$OD) δ: 8.25~8.20 (m, 1H), 8.13~8.08 (m, 1H), 8.04~8.01 (m, 1H), 7.68~7.63 (m, 1H), 7.60~7.55 (m, 1H), 4.54~4.43 (m, 1H), 4.40 (s, 2H), 3.36 (t, 2H), 3.24 (s, 3H), 2.82 (t, 2H), 2.24~2.16 (m, 2H), 1.94~1.86 (m, 2H), 1.55~1.43 (m, 2H), 1.29~1.16 (m, 2H), 1.15~1.07 (m, 1H), 0.90 (s, 9H).

Example 63: ethyl 3-(tert-butoxycarbonyl((6-((trans)-4-tert-butylcyclohexyloxy)naphthalen-2-yl)methyl)amino)propanoate

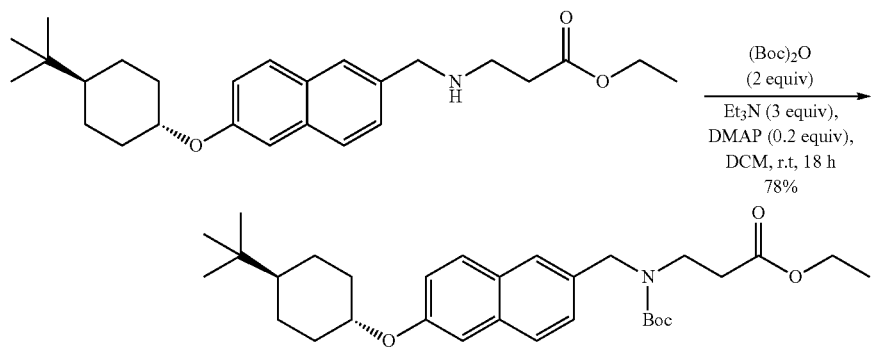

Ethyl 3-((6-(trans-4-tert-butylcyclohexyloxy)naphthalen-2-yl)methylamino)propanoate, (491 mg, 1.2 mmol, 1 equiv) was dissolved in DCM (20 mL). Then Et$_3$N (360 mg, 3.56 mmol, 3 equiv), DMAP (15 mg, 0.13 mmol, 0.1 equiv) and (Boc)$_2$O (520 mg, 2.38 mmol, 2 equiv) was added to the mixture and stirred for 18 h at r.t. The reaction was washed by 5% HCl, brine, dried over Na$_2$SO$_4$, concentrated and purified by prep-TLC to give ethyl 3-(tert-butoxycarbonyl ((6-((trans)-4-tert-butylcyclohexyloxy)naphthalen-2-yl) methyl)amino)propanoate as a yellow oil (478 mg, 78%). (mobile phase:EA/PE=1:8). ESI-MS (M+1)$^+$: 512.3. $^1$H NMR (400 MHz, CDCl$_3$) δ: 7.71~7.63 (m, 2H), 7.61~7.53 (m, 1H), 7.38~7.27 (m, 1H), 7.15~7.10 (m, 2H), 4.57 (s, 2H), 4.30~4.21 (m, 1H), 4.07 (q, 2H), 3.57~3.37 (m, 2H), 2.60~2.45 (m, 2H), 2.31~2.23 (m, 2H), 1.93~1.85 (m, 2H), 1.58~1.36 (m, 11H), 1.26~1.04 (m, 6H), 0.89 (s, 9H).

Example 64: 3-(tert-butoxycarbonyl((6-((trans)-4-tert-butylcyclohexyloxy)naphthalen-2-yl)methyl)amino)propanoic acid To a solution of ethyl 3-(tert-butoxycarbonyl((6-((trans)-4-tert-butylcyclohexyloxy)naphthalen-2-yl)methyl)amino) propanoate (485 mg, 0.94 mmol) in EtOH (10 mL) was added aqueous NaOH (2 mL, 20%, 5.0 equiv) and refluxed for 2 h. Then the reaction was cooled to 0° C., the pH of the solution was adjusted to 6 using 1M HCl, concentrated and the residue was dissolved in DCM, washed with water, dried and concentrated to give 3-(tert-butoxycarbonyl((6-((trans)-4-tert-butylcyclohexyloxy)naphthalen-2-yl)methyl)amino) propanoic acid as a gray oil (392 mg, 75%). ESI-MS (M+H$^+$): 484.3. $^1$H NMR (400 MHz, DMSO-d$_6$) δ: 7.79~7.72 (m, 2H), 7.62~7.57 (m, 1H), 7.35~7.26 (m, 2H), 7.14~7.08 (m, 1H), 4.49 (s, 2H), 4.41~4.30 (m, 1H), 3.38~3.26 (m, 2H), 2.33~2.26 (t, 2H), 2.23~2.15 (m, 2H), 1.95~1.84 (m, 2H), 1.47~1.28 (m, 11H), 1.27~1.15 (m, 2H), 1.11~1.02 (m, 1H), 0.87 (s, 9H).

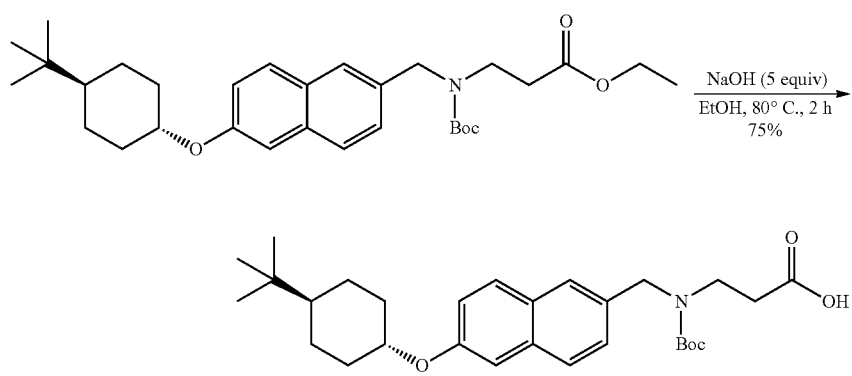

Example 65: tert-butyl (6-((trans)-4-tert-butylcyclohexyloxy)naphthalen-2-yl)methyl(3-(cyclopropanesulfonamido)-3-oxopropyl)carbamate

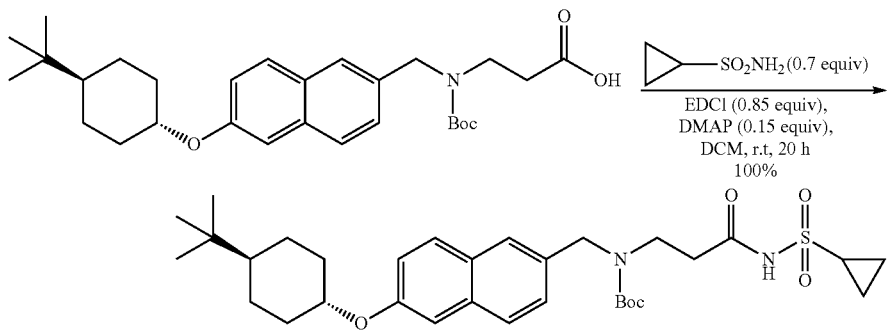

Procedure for tert-butyl 3-(methylsulfonamido)-3-oxopropylcarbamate was utilized to give tert-butyl (6-((trans)-4-tert-butylcyclohexyloxy)naphthalen-2-yl)methyl(3-(cyclopropanesulfonamido)-3-oxopropyl)carbamate. 435 mg, gray oil, 100%. ESI-MS (M+1)$^+$: 587.3. $^1$H NMR (400 MHz, DMSO-d$_6$) δ: 7.80~7.73 (m, 2H), 7.64~7.59 (m, 1H), 7.36~7.27 (m, 2H), 7.15~7.10 (m, 1H), 4.50 (s, 2H), 4.40~4.32 (m, 1H), 3.45~3.45 (m, 2H), 2.94~2.86 (m, 1H), 2.56~2.52 (m, 2H), 2.24~2.15 (m, 2H), 1.85~1.77 (m, 2H), 1.51~1.27 (m, 11H), 1.25~0.99 (m, 7H), 0.87 (s, 9H).

Example 66: 3-((6-((trans)-4-tert-butylcyclohexyloxy)naphthalen-2-yl)methylamino)-N-(cyclopropylsulfonyl)propanamide

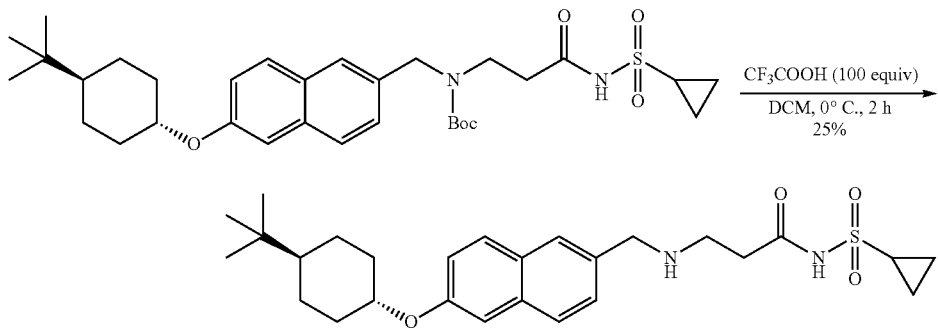

The procedure for 3-amino-N-(methylsulfonyl)propanamide was used to give 3-((6-((trans)-4-tert-butylcyclohexyloxy)naphthalen-2-yl)methylamino)-N-(cyclopropylsulfonyl)propanamide. 92 mg, white solid, 25%. ESI-MS (M+1)$^+$: 487.3. $^1$H NMR (400 MHz, DMSO-d$_6$) δ: 7.94~7.90 (m, 1H), 7.86~7.79 (m, 2H), 7.55~7.50 (m, 1H), 7.41~7.38 (m, 1H), 7.20~7.14 (m, 1H), 4.44~4.34 (m, 1H), 4.23 (s, 2H), 3.02 (t, 2H), 2.79~2.71 (m, 1H), 2.37 (t, 2H), 2.25~2.16 (m, 2H), 1.86~1.76 (m, 2H), 1.41~1.28 (m, 2H), 1.27~1.15 (m, 2H), 1.11~1.03 (m, 1H), 0.88 (s, 9H), 0.83~0.78 (m, 2H), 0.73~0.66 (m, 2H).

Example 67: ethyl 2-((6-((trans)-4-tert-butylcyclohexyloxy)-5-(trifluoromethyl)naphthalen-2-yl)methylamino)acetate

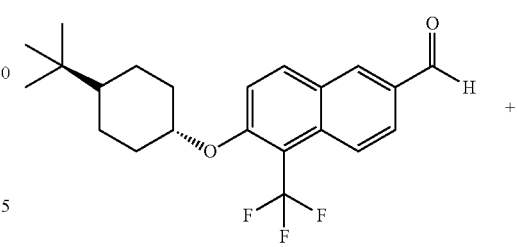

-continued

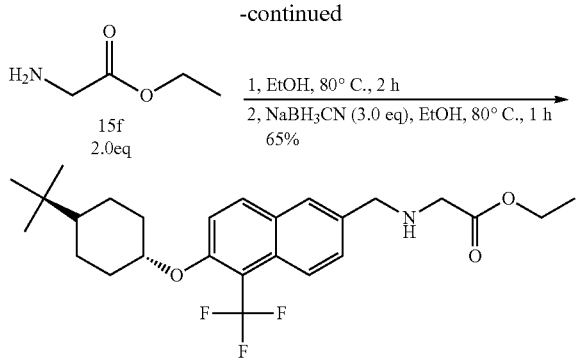

Procedure was done as described in example 27 to give ethyl 2-((6-((trans)-4-tert-butylcyclohexyloxy)-5-(trifluoromethyl)naphthalen-2-yl)methylamino)acetate. ESI-MS (M+H⁺): 466.3. HPLC: 92.65%. $^1$H NMR (400 MHz, CD$_3$OD) δ: 8.09 (d, 1H), 7.99 (d, 1H), 7.78 (s, 1H), 7.56 (dd, 1H), 7.45 (d, 1H), 4.43-4.36 (m, 1H), 4.17 (q, 2H), 3.90 (s, 2H), 3.40 (s, 2H), 2.17 (d, 2H), 1.86 (d, 2H), 1.48 (q, 2H), 1.26-1.13 (m, 5H), 1.10-1.03 (m, 1H), 0.88 (s, 9H).

Example 68: 2-((6-((trans)-4-tert-butylcyclohexyloxy)-5-(trifluoromethyl)naphthalen-2-yl)methylamino)acetic acid

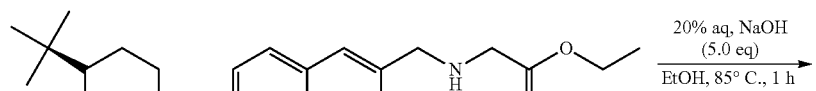

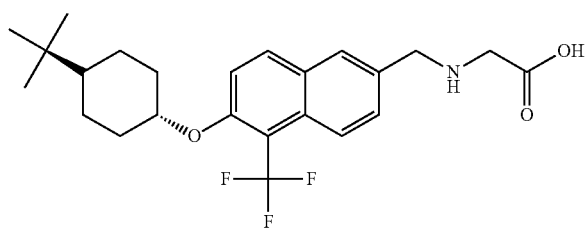

Procedure was done as described in example 28 to give 2-((6-((trans)-4-tert-butylcyclohexyloxy)-5-(trifluoromethyl)naphthalen-2-yl)methylamino)acetic acid. 50 mg, purified by HPLC-preparation (0.05% TFA/water: MeOH=0~95%), white solid (yield: 44%). ESI-MS (M+H⁺): 438.2 HPLC: 96.18%. $^1$H NMR (400 MHz, CD$_3$OD) δ: 8.20 (d, 1H), 8.08 (d, 1H), 7.98 (s, 1H), 7.61 (dd, 1H), 7.55 (d, 1H), 4.50-4.45 (m, 1H), 4.33 (s, 2H), 3.53 (s, 2H), 2.20 (d, 2H), 1.90 (d, 2H), 1.47 (q, 2H), 1.25, (q, 2H), 1.15-1.08 (m, 1H), 0.91 (s, 9H).

Example 69: ethyl 4-((6-((trans)-4-tert-butylcyclohexyloxy)-5-(trifluoromethyl)naphthalen-2-yl)methylamino)butanoate

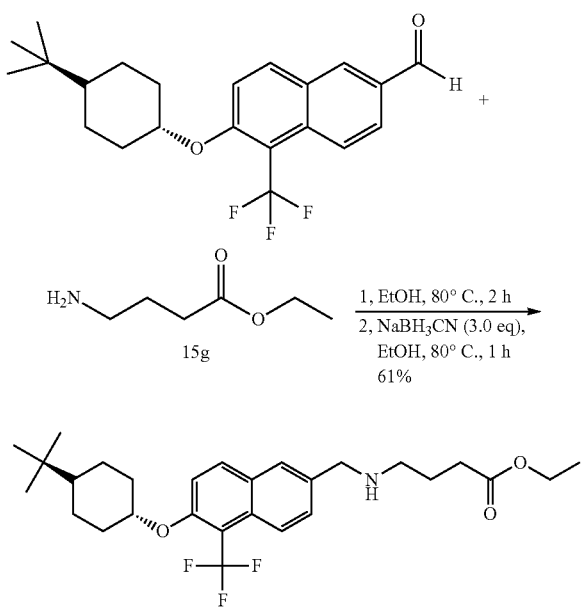

Procedure was done as described in example 27 to give ethyl 4-((6-((trans)-4-tert-butylcyclohexyloxy)-5-(trifluoromethyl)naphthalen-2-yl)methylamino)butanoate 160 mg, purified by HPLC-preparation (0.05% TFA/water: MeOH=0~95%), white solid (yield: 61%). ESI-MS (M+H⁺): 494.3. HPLC: 95.66%. $^1$H NMR (400 MHz, CD$_3$OD) δ: 8.22 (d, 1H), 8.11 (d, 1H), 8.03 (s, 1H), 7.66 (dd, 1H), 7.58 (d, 1H), 4.50-4.46 (m, 1H), 4.37 (s, 2H), 4.13 (q, 2H), 3.16 (t, 2H), 2.49 (t, 2H), 2.21 (d, 2H), 2.04 (t, 2H), 1.90 (d, 2H), 1.49 (q, 2H), 1.34-1.30 (m, 5H), 1.14-1.09 (m, 1H), 0.91 (s, 9H).

Example 70: 4-((6-((trans)-4-tert-butylcyclohexyloxy)-5-(trifluoromethyl)naphthalen-2-yl)methylamino)butanoic acid

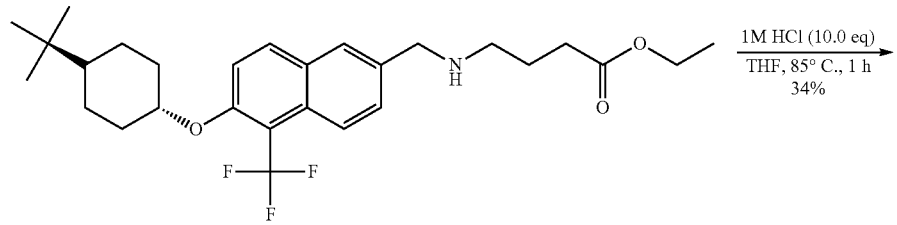

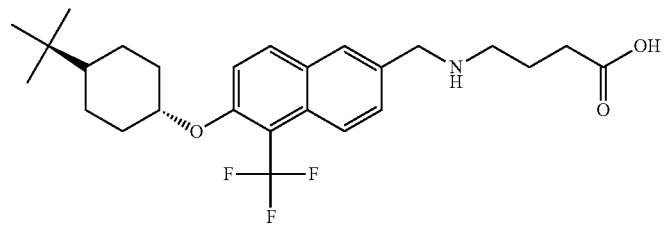

To a solution of ethyl 4-((6-((trans)-4-tert-butylcyclohexyloxy)-5-(trifluoromethyl)naphthalen-2-yl)methylamino)butanoate (150 mg, 0.30 mmol) in THF (15 mL) was added 1M HCl (3 mL) and refluxed for 1 h. Then the reaction was concentrated to give 4-((6-((trans)-4-tert-butylcyclohexyloxy)-5-(trifluoromethyl)naphthalen-2-yl)methylamino)butanoic acid as a white solid, purified by HPLC-preparation (0.05% TFA/water: MeOH=0~95%), 50 mg, white solid (yield: 34%). ESI-MS (M+H$^+$): 466.3 HPLC: 96.13%. $^1$H NMR (400 MHz, CD$_3$OD) δ: 8.20 (d, 1H), 8.10 (d, 1H), 8.01 (d, 1H), 7.65 (dd, 1H), 7.57 (d, 1H), 4.50-4.46 (m, 1H), 4.34 (s, 2H), 3.16 (t, 2H), 2.46 (d, 2H), 2.21 (d, 2H), 1.98 (t, 2H), 1.90 (d, 2H), 1.49 (q, 2H), 1.25 (q, 2H), 1.14-1.08 (m, 1H), 0.91 (s, 9H).

Example 71: methyl 1-((6-((trans)-4-tert-butylcyclohexyloxy)-5-fluoronaphthalen-2-yl)methyl)azetidine-3-carboxylate A mixture of compound methyl 1-((6-(trans-4-tert-butylcyclohexyloxy)-5-(trifluoromethyl)naphthalen-2-yl)methyl)azetidine-3-carboxylate (150 mg, 0.37 mmol) and NFSI (175 mg, 0.56 mmol, 1.5 eq.) was heated to 80° C. and stirred for 4 h under N$_2$ atmosphere. Then the mixture was purified by silica gel chromatography using PE/EA (6/1) as eluent to give product methyl 1-((6-(trans-4-tert-butylcyclohexyloxy)-5-(trifluoromethyl)naphthalen-2-yl)methyl)azetidine-3-carboxylate as a slight yellow oil (40 mg, 34%). EDI-MS (M+1)$^+$: 428.1. $^1$H NMR (400 MHz, CDCl$_3$) δ 7.97 (d, 1H), 7.65-7.62 (m, 1H), 7.52-7.41 (m, 2H), 7.25-7.22 (m, 1H), 4.22-4.17 (m, 1H), 3.74 (s, 2H), 3.71 (s, 3H), 3.59-3.54 (m, 2H), 3.37-3.36 (m, 3H), 2.22-2.19 (m, 2H), 1.86-1.84 (m, 2H), 1.54-1.45 (m, 2H), 1.19-1.08 (m, 3H), 0.86 (s, 9H).

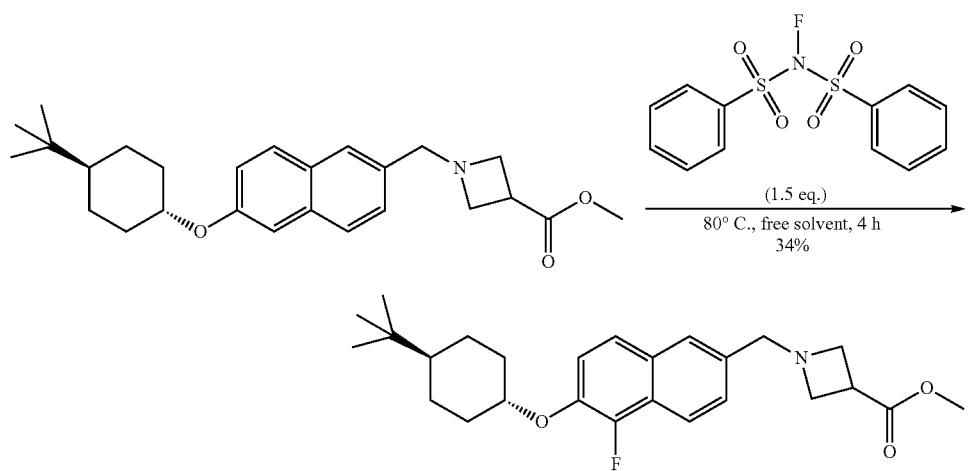

Example 72: ethyl 1-((6-((trans)-4-tert-butylcyclo-hexyloxy)-5-chloronaphthalen-2-yl)methyl)azetidine-3-carboxylate

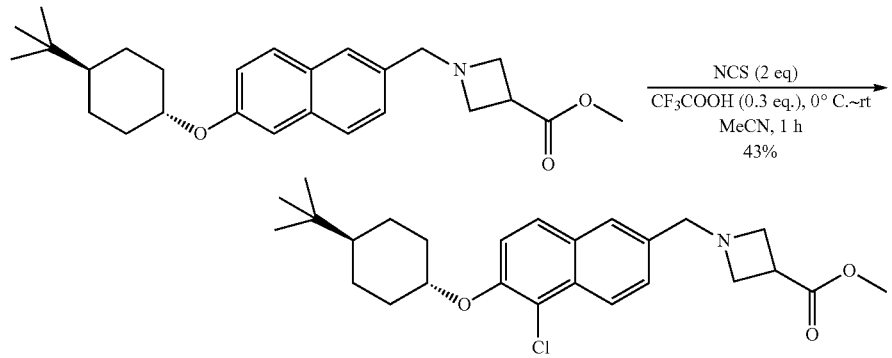

Compound methyl 1-((6-(trans-4-tert-butylcyclohexyloxy)-5-(trifluoromethyl)naphthalen-2-yl)methyl)azetidine-3-carboxylate (140 mg, 0.34 mmol) and NCS (90 mg, 0.68 mmol, 2.0 eq.) were dissolved in MeCN (5 mL). Then $CF_3COOH$ (12 mg, 0.1 mmol, 0.3 eq.) was added to the mixture at 0° C. The mixture was warmed to r.t. and stirred for 1 h. Then the pH of the solution was adjusted to 7 with saturated $Na_2CO_3$, concentrated and the mixture was extracted by EtOAc. The organic layer was concentrated and purified by silica gel chromatography using PE/EA (6/1) to give product methyl 1-((6-((trans)-4-tert-butylcyclohexyloxy)-5-chloronaphthalen-2-yl)methyl)azetidine-3-carboxylate (65 mg, 43%) as a slight yellow oil. EDI-MS (M+1)$^+$: 444.0. $^1$H NMR (400 MHz, $CDCl_3$) δ 8.16 (d, 1H), 7.69-7.66 (m, 2H), 7.50-7.47 (m, 1H), 7.28-7.27 (m, 1H), 4.25-4.19 (m, 1H), 3.77 (s, 2H), 3.72 (s, 3H), 3.59-3.58 (m, 2H), 3.38-3.37 (m, 3H), 2.23-2.20 (m, 2H), 1.88-1.85 (m, 2H), 1.61-1.52 (m, 2H), 1.12-1.07 (m, 3H), 0.87 (s, 9H).

Example 73: 1-((6-((trans)-4-tert-butylcyclohexyloxy)-5-fluoronaphthalen-2-yl)methyl)azetidine-3-carboxylic acid To a solution of methyl 1-((6-((trans)-4-tert-butylcyclohexyloxy)-5-fluoronaphthalen-2-yl)methyl)azetidine-3-carboxylate 40 mg, 0.09 mmol) in EtOH (3 mL) was added aqueous NaOH (2 mL, 1%, 5.0 eq.) and refluxed for 1 h. Then the reaction was cooled to 0° C., the pH of the solution was adjusted to 6 with 1M HCl, concentrated and the residue was washed with DCM and water, dried in vacuum to give product 1-((6-((trans)-4-tert-butylcyclohexyloxy)-5-fluoronaphthalen-2-yl)methyl)azetidine-3-carboxylic acid (30 mg, 78%) as a white solid. EDI-MS (M+1)$^+$: 414.0. HPLC: 91.27%. $^1$H NMR (400 MHz, $CD_3OD$) δ 8.09-8.01 (m, 2H), 7.74-7.71 (m, 1H), 7.59-7.58 (m, 1H), 7.48 (t, 1H), 4.57 (s, 2H), 4.38-4.32 (m, 5H), 3.76-3.70 (m, 1H), 2.21-2.19 (m, 2H), 1.91-1.88 (m, 2H), 1.53-1.44 (m, 2H), 1.24-1.10 (m, 3H), 0.90 (s, 9H).

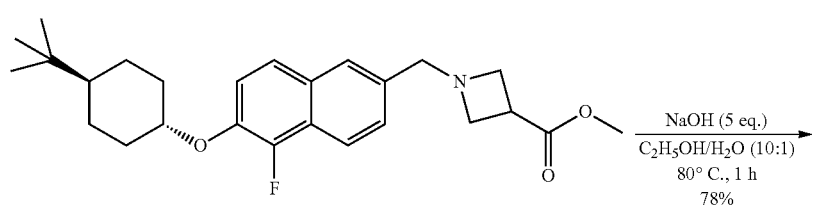

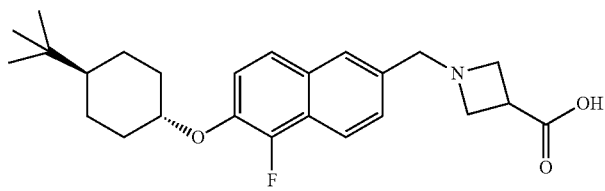

Example 74: 1-((6-((trans)-4-tert-butylcyclohexyloxy)-5-chloronaphthalen-2-yl)methyl)azetidine-3-carboxylic acid

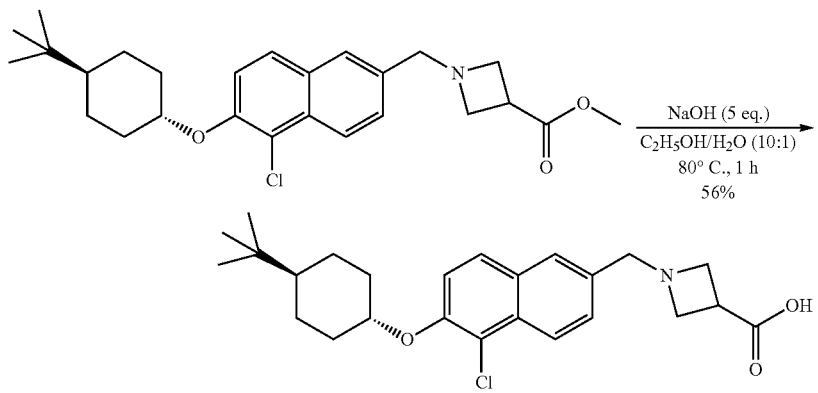

Procedure was done as performed for 1-((6-((trans)-4-tert-butylcyclohexyloxy)-5-fluoronaphthalen-2-yl)methyl)azetidine-3-carboxylic acid to give the title compound solid (35 mg, 56%). EDI-MS (M+1)$^+$: 430.0. HPLC: 91.27%. $^1$H NMR (400 MHz, CD$_3$OD) δ 8.29-8.26 (m, 1H), 8.00-7.90 (m, 2H), 7.64-7.53 (m, 2H), 4.49 (s, 2H), 4.45-4.38 (m, 1H), 4.22-4.19 (m, 4H), 3.49-3.42 (m, 1H), 2.28-2.24 (m, 2H), 1.96-1.92 (m, 2H), 1.60-1.51 (m, 2H), 1.30-1.16 (m, 3H), 0.94 (s, 9H).

Example 75: methyl 3-(benzylamino)-2-methylpropanoate

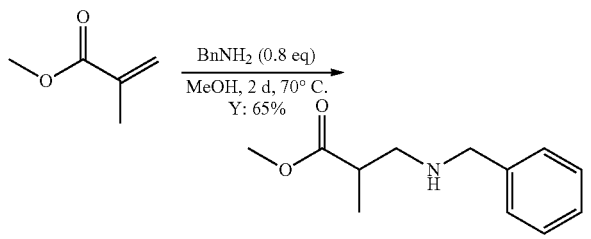

A mixture of methyl methacrylate (7 mL, 0.067 mol, 1.0 equiv), benzylamine (6 mL, 0.055 mol, 0.8 equiv) in methanol (5 mL) was stirred at 70° C. for 2 days. After evaporation of the volatiles, the crude product was purified by flash chromatography (DCM:MeOH=20:1) to give compound methyl 3-(benzylamino)-2-methylpropanoate 9 g, yield: 65%) as a yellow oil. $^1$H NMR (400 MHz, CDCl$_3$) δ: 7.32-7.24 (m, 5H), 3.79 (s, 2H), 3.68 (s, 3H), 2.88-2.85 (m, 1H), 2.71-2.63 (m, 2H), 1.16 (d, 3H).

Example 76: methyl 3-amino-2-methylpropanoate

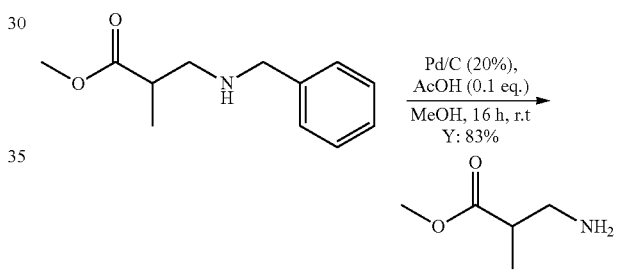

To a solution of methyl 3-(benzylamino)-2-methylpropanoate (3 g, 14 mmol, 1.0 equiv) and acetic acid (87 mg, 1.4 mmol, 0.1 equiv) in methanol (30 mL) was added Pd/C (10%, 0.3 g). The resulting mixture was stirred under hydrogen at 25° C. for 16 h. The catalyst was filtered off, and the filtrate was concentrated to give methyl 3-amino-2-methylpropanoate (1.4 g, yield: 83%) as a yellow oil. $^1$H NMR (400 MHz, CDCl$_3$) δ: 3.72 (s, 3H), 3.06-3.01 (m, 1H), 2.91-2.86 (m, 1H), 2.77-2.72 (m, 1H), 1.95 (s, 2H), 1.22 (d, 3H).

Example 77: methyl 3-((6-((trans)-4-tert-butylcyclohexyloxy)naphthalen-2-yl)methylamino)-2-methylpropanoate

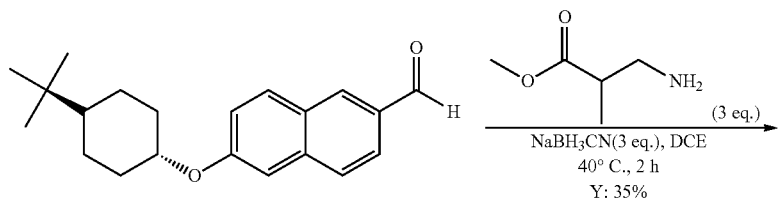

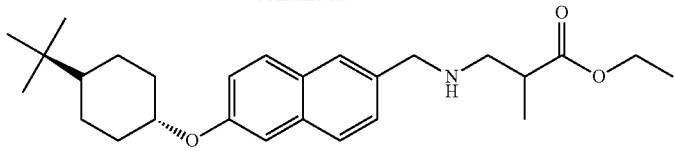

The preparation of methyl 3-((6-((trans)-4-tert-butylcyclohexyloxy)naphthalen-2-yl)methylamino)-2-methylpropanoate was done as described for example 27. 110 mg, pale yellow solid, yield: 35%. ESI-MS (M+H)+: 412.1. HPLC: 93.41%. ¹H NMR (400 MHz, CDCl₃) δ: 7.70-7.65 (m, 3H), 7.34 (d, 1H), 7.10 (dd, 1H), 7.01 (d, 1H), 4.16-4.09 (m, 1H), 3.96 (s, 2H), 3.65 (s, 3H), 3.143-3.138 (m, 1H), 2.92 (d, 2H), 2.16-2.12 (m, 2H), 1.84-1.81 (m, 2H), 1.39-1.26 (m, 2H), 1.15-1.05 (m, 6H), 0.88 (s, 9H).

Example 78: 3-((6-((trans)-4-tert-butylcyclohexyloxy)naphthalen-2-yl)methylamino)-2-methylpropanoic acid

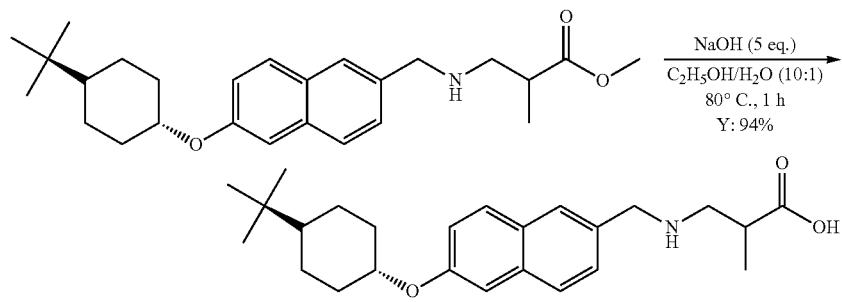

The preparation of 3-((6-((trans)-4-tert-butylcyclohexyloxy)naphthalen-2-yl)methylamino)-2-methylpropanoic acid was done as described for example 77. 100 mg, yellow solid, yield: 94%. ESI-MS (M+H)+: 398.1. HPLC: 97.60%. ¹H NMR (400 MHz, CDCl₃) δ: 7.84 (s, 1H), 7.72-7.68 (m, 2H), 7.59 (d, 1H), 7.15-7.10 (m, 2H), 4.33-4.24 (m, 3H), 3.11-2.82 (m, 3H), 2.25-2.21 (m, 2H), 1.89-1.86 (m, 2H), 1.48-1.11 (m, 9H), 0.89 (s, 9H).

Example 79: ethyl 2-cyano-2-methylpropanoate

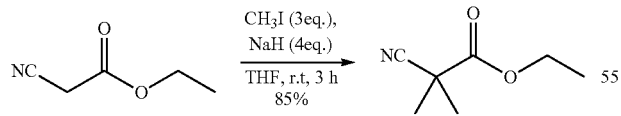

A solution of ethyl 2-cyanoacetate (3 g, 0.026 mol, 1.0 equiv) in tetrahydrofuran (80 mL) was cooled at ice-salt bath, followed by the addition of sodium hydride (2.6 g, 0.104 mol, 4.0 equiv) in several portions. The suspension was stirred at r.t. Then iodomethane (11 g, 0.078 mmol, 3.0 equiv) was added and the reaction mixture was stirred at r.t for 3 h before quenched with water. The mixture was extracted with ethyl acetate and washed with brine, dried over Na₂SO₄ and concentrated to obtain crude product ethyl 2-cyano-2-methylpropanoate (3.2 g, yield: 85%) as a dark green oil. ¹H NMR (400 MHz, CDCl₃) δ: 4.27 (q, 2H), 1.62 (s, 6H), 1.34 (t, 3H).

Example 80: ethyl 3-amino-2,2-dimethylpropanoate

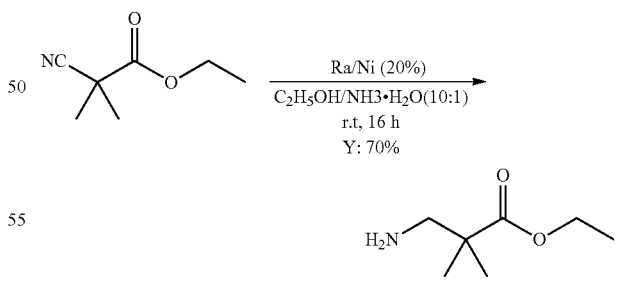

To a solution of ethyl 2-cyano-2-methylpropanoate (0.6 g, 4.2 mmol, 1.0 equiv) in 6 mL of ethanol/ammonium hydroxide (10:1) was added Ra/Ni (20%, 0.12 g). The resulting mixture was stirred under hydrogen at r.t. for 16 h. The catalyst was filtered off, and the filtrate was concentrated to give ethyl 3-amino-2,2-dimethylpropanoate (0.43 g, yield: 70%) as a yellow oil. ¹H NMR (400 MHz, CDCl₃) δ: 4.15 (q, 2H), 2.77 (s, 2H), 1.76 (s, 2H), 1.26 (t, 3H), 1.18 (s, 6H).

Example 81: ethyl 3-((6-((trans)-4-tert-butylcyclohexyloxy)naphthalen-2-yl)methylamino)-2,2-dimethylpropanoate

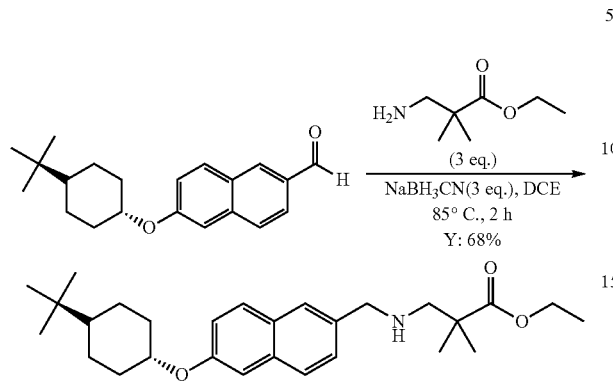

The preparation of ethyl 3-((6-((trans)-4-tert-butylcyclohexyloxy)naphthalen-2-yl)methylamino)-2,2-dimethylpropanoate was performed as described in example 27. 230 mg, colorless oil, yield: 68%. ESI-MS (M+H)$^+$: 440.1. HPLC: 89.40%. $^1$H NMR (400 MHz, CDCl$_3$) δ: 7.70-7.65 (m, 3H), 7.42 (d, 1H), 7.13-7.11 (m, 2H), 4.29-4.23 (m, 1H), 4.12 (q, 2H), 3.95 (s, 2H), 2.70 (s, 2H), 2.29-2.26 (m, 2H), 1.91-1.88 (m, 2H), 1.48-1.42 (m, 2H), 1.25-1.09 (m, 12H), 0.90 (s, 9H).

Example 82: 3-((6-((trans)-4-tert-butylcyclohexyloxy)naphthalen-2-yl)methylamino)-2,2-dimethylpropanoic acid

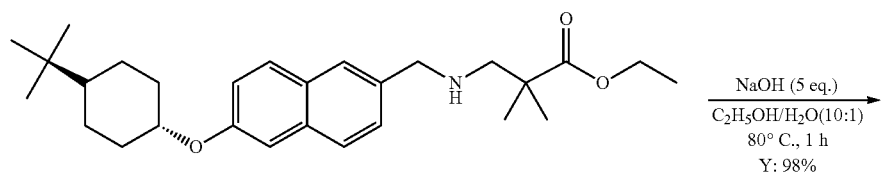

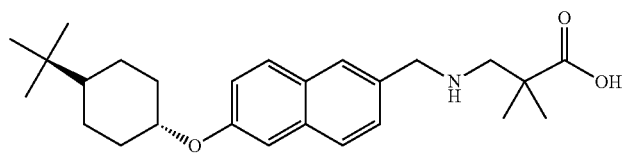

The preparation of 3-((6-((trans)-4-tert-butylcyclohexyloxy)naphthalen-2-yl)methylamino)-2,2-dimethylpropanoic acid was performed as described in example 28. 210 mg, pale yellow solid, yield: 98%. ESI-MS (M+H)$^+$: 412.1. HPLC: 96.40%. $^1$H NMR (400 MHz, CDCl$_3$) δ: 7.75 (s, 1H), 7.69-7.67 (m, 2H), 7.58 (d, 1H), 7.14-7.09 (m, 2H), 4.26-4.21 (m, 3H), 2.78 (s, 2H), 2.24-2.22 (m, 2H), 1.89-1.86 (m, 2H), 1.45-1.37 (m, 2H), 1.28-1.08 (m, 9H), 0.89 (s, 9H).

Example 83: 6-((trans)-4-tert-butylcyclohexyloxy)-2-naphthonitrile

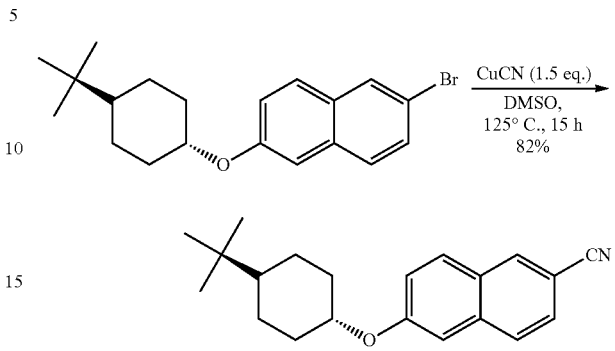

Compound 2-bromo-6-((trans)-4-tert-butylcyclohexyloxy)naphthalene (2.0 g, 5.55 mmol, 1.0 eq.) and CuCN (742 mg, 8.34 mmol, 1.5 eq.) was dissolved in DMSO (5 mL). Then the mixture was stirred at 125° C. for 15 h. Water was added and the mixture was extracted with ethyl acetate and the organic layer was purified by silica gel column chromatography using PE/EA (10/1) to give product as a slight yellow solid (1.423 g, 82%). EDI-MS (M+1)$^+$: 308.0 $^1$H NMR (400 MHz, CDCl$_3$) δ 8.12 (s, 1H), 7.78-7.73 (m, 2H), 7.54 (dd, 1H), 7.22 (dd, 1H), 7.14 (s, 1H), 4.33-4.30 (m, 1H), 2.29-2.25 (m, 2H), 1.93-1.90 (m, 2H), 1.48-1.26 (m, 2H), 1.25-1.10 (m, 3H), 0.91 (s, 9H).

Example 84: (6-((trans)-4-tert-butylcyclohexyloxy)naphthalen-2-yl)methanamine

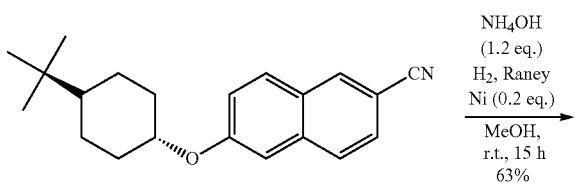

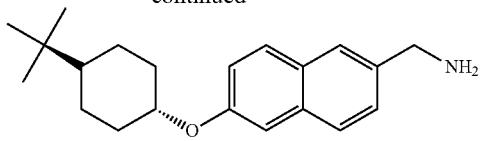

Compound 6-((trans)-4-tert-butylcyclohexyloxy)-2-naphthonitrile (1.7 g, 5.53 mmol, 1.0 eq.) and NH₄OH (0.3 mL, 6.65 mmol, 1.2 eq.) was dissolved in MeOH (5 mL). Then Raney Ni (64 mg, 1.11 mmol, 0.2 eq.) was added to the mixture and the suspension solution was stirred at r.t. under hydrogen atmosphere for 15 h. The mixture was filtrated and purified by silica gel column chromatography using DCM/MeOH (10/1) as eluent to give product as a pale solid (1.76 g, 63%). ESI-MS (M-NH₂)⁺: 295.1. ¹H NMR (400 MHz, CDCl₃) δ 7.71-7.65 (m, 3H), 7.38 (dd, 1H), 7.15-7.11 (m, 2H), 4.28-4.24 (m, 1H), 3.98 (s, 2H), 2.30-2.26 (m, 2H), 1.91-1.87 (m, 2H), 1.76 (s, 2H), 1.46-1.40 (m, 2H), 1.21-1.12 (m, 3H), 0.90 (s, 9H).

Example 85: ethyl 3-((6-((trans)-4-tert-butylcyclohexyloxy)naphthalen-2-yl)methylamino)-2-hydroxypropanoate

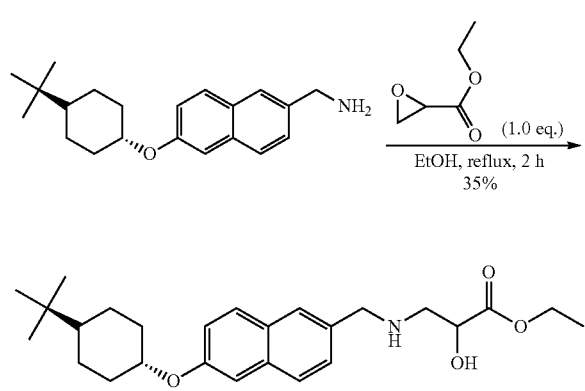

(6-((trans)-4-tert-butylcyclohexyloxy)naphthalen-2-yl)methanamine (311 mg, 1.0 mmol, 1.0 eq.) and ethyl oxirane-2-carboxylate (116 mg, 1.0 mmol, 1.0 eq.) was dissolved in EtOH (5 mL). Then the mixture was refluxed for 2 h. The mixture was concentrated and purified by silica gel column chromatography using DCM/MeOH (10/1) as eluent to give product as a slight yellow oil (311 mg, 35%). EDI-MS (M+1)⁺: 428.1. HPLC: 92.02%. ¹H NMR (400 MHz, CDCl₃) δ 7.70-7.64 (m, 3H), 7.38 (dd, 1H), 7.13-7.11 (m, 2H), 4.31-4.21 (m, 4H), 3.93 (q, 2H), 3.06-2.88 (AB, 2H), 2.60 (b, 2H), 2.28-2.26 (m, 2H), 1.90-1.87 (m, 2H), 1.45-1.41 (m, 2H), 1.26 (t, 3H), 1.20-1.09 (m, 3H), 0.89 (s, 9H).

Example 86: 3-((6-((trans)-4-tert-butylcyclohexyloxy)naphthalen-2-yl)methylamino)-2-hydroxypropanoic acid

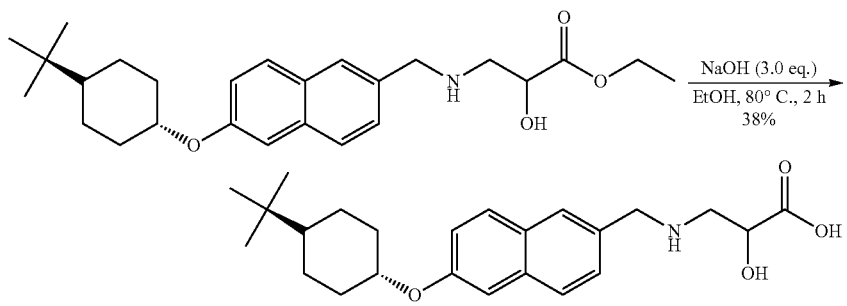

The preparation of 3-((6-((trans)-4-tert-butylcyclohexyloxy)naphthalen-2-yl)methylamino)-2-hydroxypropanoic acid was done as described for example 28. 50 mg, white solid, yield: 38%. ESI-MS (M+H)⁺: 400.2. HPLC: 99.87%. ¹H NMR (400 MHz, CD₃OD) δ: 7.46-7.36 (m, 3H), 7.24 (s, 1H), 6.93-6.87 (m, 2H), 4.23-4.20 (m, 1H), 4.04-4.02 (m, 1H), 3.72 (s, 2H), 2.94-2.92 (m, 2H), 2.10-2.07 (m, 2H), 1.75-1.73 (m, 2H), 1.31-1.24 (m, 2H), 1.07-1.01 (m, 3H), 0.89 (s, 9H).

Example 87: ethyl 1-cyanocyclopropanecarboxylate

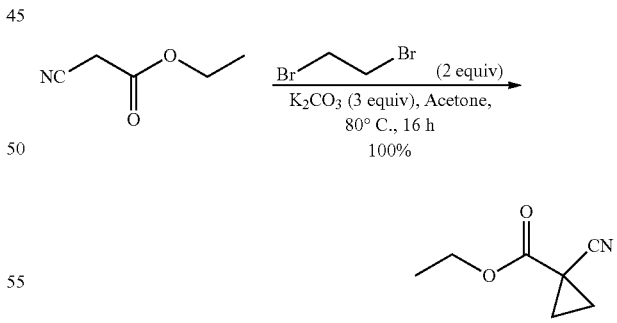

Ethyl 2-cyanoacetate (0.85 g, 7.5 mmol, 1 equiv), 1,2-dibromoethane (1.3 mL, 15 mmol, 2 equiv) and K₂CO₃ (3.18 g, 22.5 mmol, 3 equiv) was dissolved in acetone (6 mL), and the mixture was stirred for 16 h at 80° C. The reaction mixture was filtered, concentrated to give the crude product as a yellow oil (1.84 g, 100%). ¹H NMR (400 MHz, DMSO-d₆) δ: 4.18 (t, 2H), 1.75 (t, 2H), 1.60 (m, 2H), 1.20 (t, 3H).

Example 88: ethyl 1-(aminomethyl)cyclopropanecarboxylate

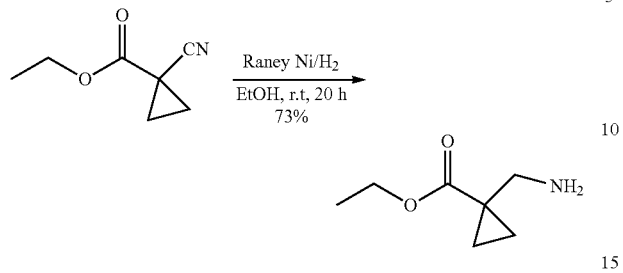

The preparation of ethyl 1-(aminomethyl)cyclopropanecarboxylate as a yellow oil (783 mg, 73%) was performed as described for the synthesis of ethyl 3-amino-2,2-dimethylpropanoate (Example 80). ESI-MS (M+1)$^+$: 144.1. $^1$H NMR (400 MHz, DMSO-d$_6$) δ: 4.03 (t, 2H), 3.59 (s, 2H), 1.17 (t, 3H), 0.99 (t, 2H), 0.84 (t, 2H).

Example 89: ethyl 1-(((6-((trans)-4-tert-butylcyclohexyloxy)naphthalen-2-yl)methylamino)methyl)cyclopropanecarboxylate

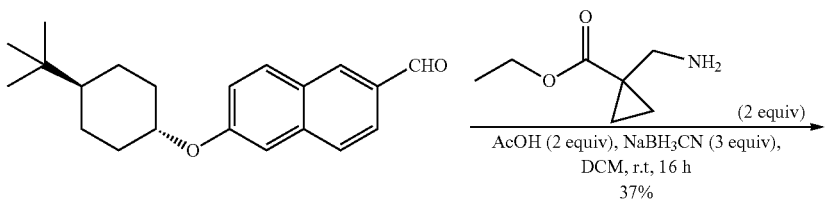

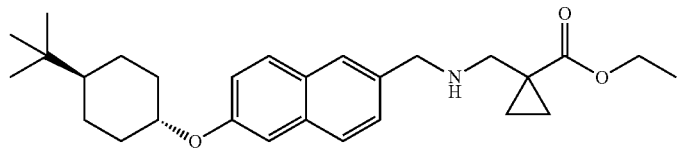

The preparation of ethyl 1-(((6-((trans)-4-tert-butylcyclohexyloxy)naphthalen-2-yl)methylamino)methyl)cyclopropanecarboxylate was performed as described in example 27 as a slight yellow oil (211 mg, 37%). ESI-MS (M+1)$^+$: 438.3. $^1$H NMR (400 MHz, CDCl$_3$) δ: 7.73~7.64 (m, 3H), 7.45~7.39 (m, 1H), 7.19~7.09 (m, 2H), 4.31~4.20 (m, 1H), 4.16~4.07 (m, 2H), 3.66 (s, 2H), 2.73~2.71 (m, 2H), 2.31~2.23 (m, 2H), 1.93~1.85 (m, 2H), 1.50~1.36 (m, 2H), 1.29~1.04 (m, 8H), 0.89 (s, 9H), 0.82~0.76 (m, 2H).

Example 90: 1-(((6-((trans)-4-tert-butylcyclohexyloxy)naphthalen-2-yl)methylamino)methyl)cyclopropanecarboxylic acid

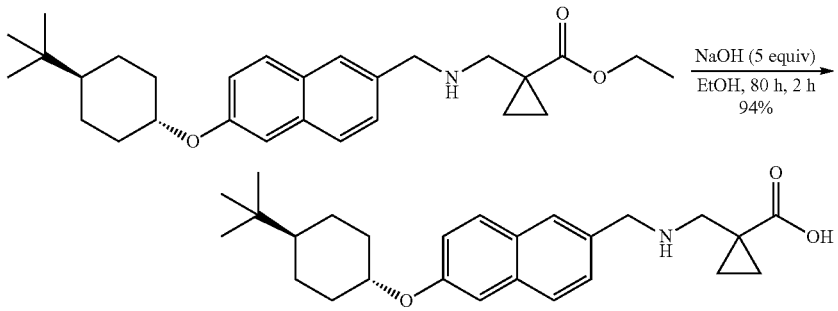

The preparation of 1-(((6-((trans)-4-tert-butylcyclohexyloxy)naphthalen-2-yl)methylamino)methyl)cyclopropanecarboxylic acid was performed as described for example 28 as a white solid (162 mg, 94%). ESI-MS (M+1)+: 410.3. HPLC: 97.07%. ¹H NMR (400 MHz, DMSO-d₆) δ: 7.93~7.73 (m, 3H), 7.59~7.50 (m, 1H), 7.42~7.36 (m, 1H), 7.19~7.10 (m, 1H), 4.43~4.33 (m, 1H), 4.20~4.09 (brs, 2H), 3.00~2.89 (m, 2H), 2.26~2.14 (m, 2H), 1.85~1.75 (m, 2H), 1.40~1.29 (m, 2H), 1.27~1.14 (m, 3H), 1.13~1.00 (m, 2H), 0.96~0.76 (m, 11H).

Example 91: N-((6-((trans)-4-tert-butylcyclohexyloxy)naphthalen-2-yl)methyl)ethanamine

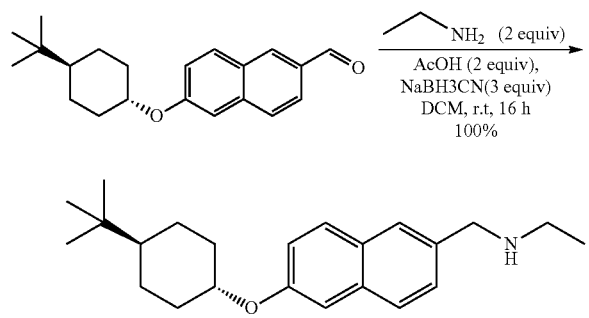

6-((trans)-4-tert-butylcyclohexyloxy)-2-naphthaldehyde (200 mg, 0.64 mmol, 1 equiv), ethanamine (58 mg, 1.05 mmol, 2 equiv) and AcOH (62 mg, 1.05 mmol, 2 equiv) were dissolved in DCM (15 mL), and the mixture was stirred at r.t. for 2 h. Then NaBH₃CN (101 mg, 1.9 mmol, 3 equiv) was added to the mixture and stirred for 16 h at r.t. The reaction mixture was washed by brine, dried over Na₂SO₄, and concentrated to give the title compound as a gray oil (250 mg, 100%). ESI-MS (M+1)+: 340.3. ¹H NMR (400 MHz, CDCl₃) δ: 7.73~7.63 (m, 3H), 7.42~7.31 (m, 1H), 7.16~7.09 (m, 2H), 4.30~4.21 (m, 1H), 3.91 (s, 2H), 2.73 (q, 2H), 2.31~2.23 (m, 2H), 1.93~1.83 (m, 2H), 1.49~1.36 (m, 2H), 1.27~1.18 (m, 2H), 1.15 (t, 3H), 1.12~1.05 (m, 1H), 0.89 (s, 9H).

Example 92: methyl 3-(((6-((trans)-4-tert-butylcyclohexyloxy)naphthalen-2-yl)methyl)(ethyl)amino)propanoate

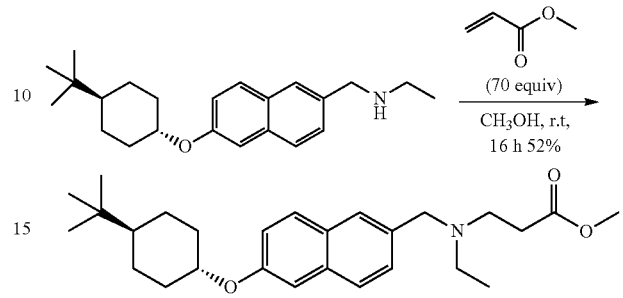

N-((6-((trans)-4-tert-butylcyclohexyloxy)naphthalen-2-yl)methyl)ethanamine (250 mg, 0.64 mmol, 1 equiv) was dissolved in CH₃OH (1 mL). Then methyl acrylate (4 mL, 44 mmol, 70 equiv) was added to the mixture and stirred at r.t. for 16 h. The reaction was concentrated and purified by prep-TLC to give the title compound as a white solid (217 mg, 52%). (mobile phase: EA/PE=1:8). ESI-MS (M+1)+: 426.3, HPLC: 97.34%. ¹H NMR (400 MHz, CDCl₃) δ: 7.71~7.60 (m, 3H), 7.44~7.38 (m, 1H), 7.16~7.09 (m, 2H), 4.30~4.20 (m, 1H), 3.69 (s, 2H), 3.64 (s, 3H), 2.85 (t, 2H), 2.65~2.46 (m, 4H), 2.31~2.24 (m, 2H), 1.92~1.85 (m, 2H), 1.49~1.37 (m, 2H), 1.30~1.10 (m, 3H), 1.05 (t, 3H), 0.89 (s, 9H).

Example 93: 3-(((6-((trans)-4-tert-butylcyclohexyloxy)naphthalen-2-yl)methyl)(ethyl)amino)propanoic acid

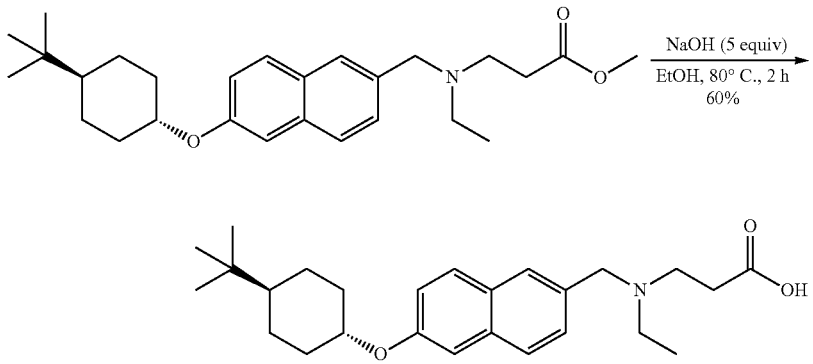

The preparation of 3-(((6-((trans)-4-tert-butylcyclohexyloxy)naphthalen-2-yl)methyl)(ethyl)amino)propanoic acid was performed as described for example 28 to give the title compound as a white solid (126 mg, 60%). ESI-MS (M+1)+: 412.3, HPLC: 96.12%. ¹H NMR (400 MHz, DMSO-d₆) δ: 7.91 (m, 1H), 7.84~7.76 (m, 2H), 7.61~7.55 (m, 1H), 7.40~7.31 (m, 1H), 7.18~7.12 (m, 1H), 4.43~4.34 (m, 1H), 4.12 (s, 2H), 3.03 (t, 2H), 2.90~2.78 (m, 2H), 2.66 (t, 2H), 2.25~2.17 (m, 2H), 1.86~1.76 (m, 2H), 1.41~1.29 (m, 2H), 1.25~1.12 (m, 5H), 1.10~1.02 (m, 1H), 0.89 (s, 9H).

Example 94: N-((6-((trans)-4-tert-butylcyclohexyloxy)naphthalen-2-yl)methyl)propan-1-amine

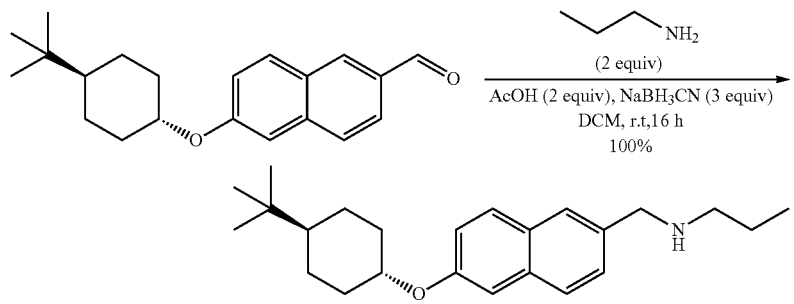

The preparation of N-((6-((trans)-4-tert-butylcyclohexyloxy)naphthalen-2-yl)methyl)propan-1-amine was done as described for N-((6-((trans)-4-tert-butylcyclohexyloxy)naphthalen-2-yl)methyl)ethanamine (Example 91) to give the title compound as a gray oil (429 mg, 100%). ESI-MS (M+1)$^+$: 354.3. $^1$H NMR (400 MHz, DMSO-d$_6$) δ: 7.76~7.66 (m, 3H), 7.44~7.40 (m, 1H), 7.32~7.30 (m, 1H), 7.12~7.06 (m, 1H), 4.40~4.30 (m, 1H), 3.78 (s, 2H), 2.46 (t, 2H), 2.23~2.15 (m, 2H), 1.85~1.76 (m, 2H), 1.44 (q, 2H), 1.39~1.27 (m, 2H), 1.26~1.15 (m, 3H), 0.87 (s, 9H), 0.86 (t, 3H).

Example 95: methyl 3-(((6-((trans)-4-tert-butylcyclohexyloxy)naphthalen-2-yl)methyl)(propyl)amino)propanoate

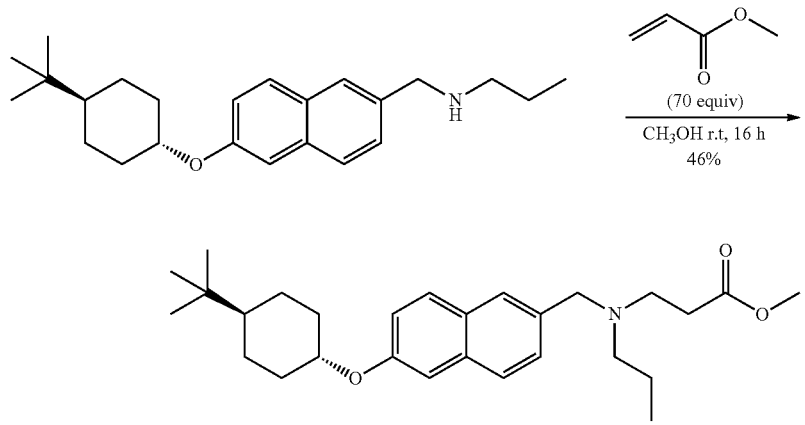

The preparation of methyl 3-(((6-((trans)-4-tert-butylcyclohexyloxy)naphthalen-2-yl)methyl)(propyl)amino)propanoate was performed as described for methyl 3-(((6-((trans)-4-tert-butylcyclohexyloxy)naphthalen-2-yl)methyl)(ethyl)amino)propanoate (Example 93) to give the title compound as a white solid (195 mg, 46%). (mobile phase: EA/PE=1:8). ESI-MS (M+1)$^+$: 440.3, HPLC: 95.63%. $^1$H NMR (400 MHz, CDCl$_3$) δ: 7.71~7.60 (m, 3H), 7.44~7.39 (m, 1H), 7.16~7.09 (m, 2H), 4.30~4.20 (m, 1H), 3.67 (s, 2H), 3.64 (s, 3H), 2.83 (t, 2H), 2.50 (t, 2H), 2.41 (t, 2H), 2.31~2.23 (m, 2H), 1.93~1.84 (m, 2H), 1.55~1.37 (m, 4H), 1.25~1.05 (m, 3H), 0.89 (s, 9H), 0.84 (t, 3H).

Example 96: 3-((((6-((trans)-4-tert-butylcyclohexy-loxy)naphthalen-2-yl)methyl)(propyl)amino)propanoic acid

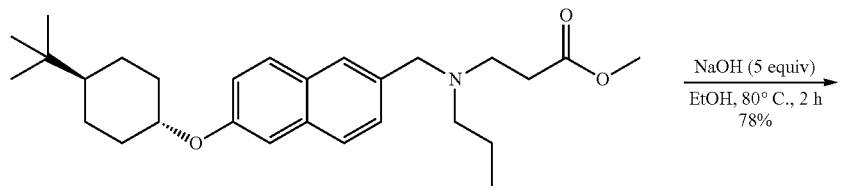

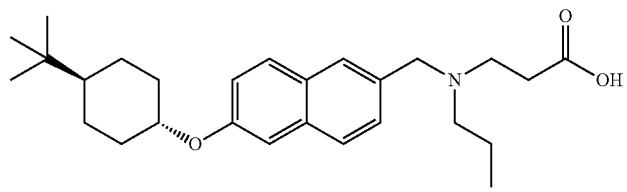

The preparation of 3-((((6-((trans)-4-tert-butylcyclohexyloxy)naphthalen-2-yl)methyl)(propyl)amino)propanoic acid was same performed as described for example 28 as a white solid (147 mg, 78%) ESI-MS (M+1)$^+$: 426.3, HPLC: 99.49%. $^1$H NMR (400 MHz, DMSO-d$_6$) δ: 7.86~7.76 (m, 3H), 7.55~7.49 (m, 1H), 7.39~7.34 (m, 1H), 7.17~7.10 (m, 1H), 4.43~4.33 (m, 1H), 4.02 (s, 2H), 2.96 (t, 2H), 2.70~2.55 (m, 4H), 2.24~1.16 (m, 2H), 1.86~1.76 (m, 2H), 1.63~1.53 (m, 2H), 1.40~1.28 (m, 2H), 1.26~1.14 (m, 2H), 1.07~1.02 (m, 1H), 0.89 (s, 9H), 0.82 (t, 3H).

Example 97: N-((6-((trans)-4-tert-butylcyclohexyloxy)naphthalen-2-yl)methyl)cyclobutanamine

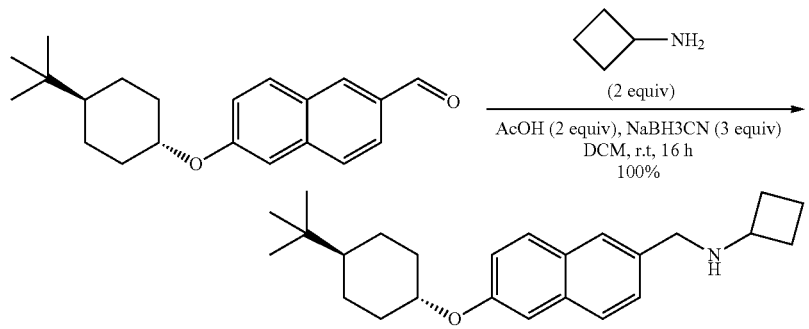

The preparation of N-((6-((trans)-4-tert-butylcyclohexyloxy)naphthalen-2-yl)methyl)cyclobutanamine was performed as described for example 27 to give the title compound as a gray oil (282 mg, 100%). ESI-MS (M+1)$^+$: 366.3. $^1$H NMR (400 MHz, CDCl$_3$) δ: 7.76~7.62 (m, 3H), 7.43~7.37 (m, 1H), 7.17~7.08 (m, 2H), 4.31~4.19 (m, 1H), 3.82 (s, 2H), 3.37~3.29 (m, 1H), 2.37~2.18 (m, 4H), 1.98~1.84 (m, 4H), 1.76~1.67 (m, 2H), 1.49~1.36 (m, 2H), 1.26~1.04 (m, 3H), 0.89 (s, 9H).

Example 98: methyl 3-(((6-((trans)-4-tert-butylcyclohexyloxy)naphthalen-2-yl)methyl)(cyclobutyl)amino)propanoate

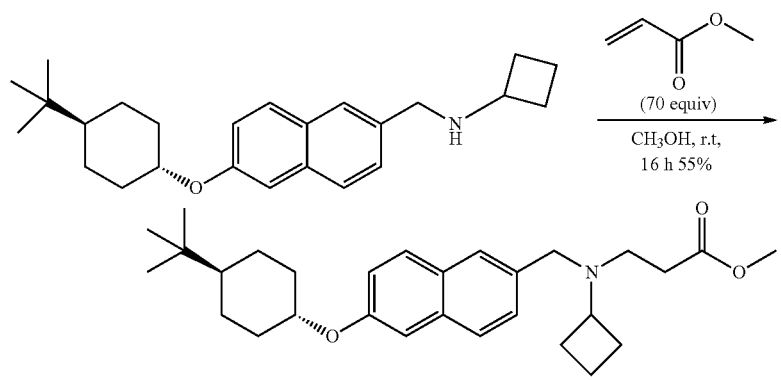

The synthesis of methyl 3-(((6-((trans)-4-tert-butylcyclohexyloxy)naphthalen-2-yl)methyl)(cyclobutyl)amino)propanoate was performed as described for methyl 3-(((6-((trans)-4-tert-butylcyclohexyloxy)naphthalen-2-yl)methyl)(ethyl)amino)propanoate (Example 95) to give the title compound as a white solid (240 mg, 55%). (mobile phase: EA/PE=1:8). ESI-MS (M+1)$^+$: 452.3, HPLC: 97.45%. $^1$H NMR (400 MHz, CDCl$_3$) δ: 7.72~7.58 (m, 3H), 7.44~7.38 (m, 1H), 7.15~7.09 (m, 2H), 4.30~4.20 (m, 1H), 3.62 (s, 2H), 3.60 (s, 3H), 3.20~3.11 (m, 1H), 2.75 (t, 2H), 2.41 (t, 2H), 2.31~2.23 (m, 2H), 1.95~1.83 (m, 4H), 1.71~1.52 (m, 2H), 1.50~1.31 (m, 2H), 1.26~1.05 (m, 5H), 0.89 (s, 9H).

Example 99: 3-(((6-((trans)-4-tert-butylcyclohexyloxy)naphthalen-2-yl)methyl)(cyclobutyl)amino)propanoic acid

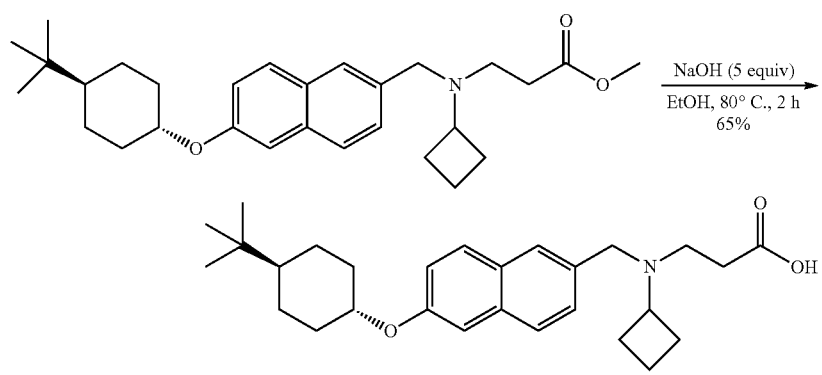

The preparation of 3-(((6-((trans)-4-tert-butylcyclohexyloxy)naphthalen-2-yl)methyl)(cyclobutyl)amino)propanoic acid was performed as described for example 28 to give the title compound as a white solid (152 mg, 65%) ESI-MS (M+1)$^+$: 438.3, HPLC: 98.55%. 1H NMR (400 MHz, DMSO-d$_6$) δ: 7.78~7.66 (m, 3H), 7.44~7.37 (m, 1H), 7.34~7.30 (m, 1H), 7.14~7.06 (m, 1H), 4.41~4.31 (m, 1H), 3.64 (s, 2H), 3.22~3.14 (m, 1H), 2.64 (t, 2H), 2.35 (t, 2H), 2.25~2.14 (m, 2H), 2.03~1.93 (m, 2H), 1.90~1.76 (m, 4H), 1.64~1.49 (m, 2H), 1.40~1.27 (m, 2H), 1.26~1.14 (m, 2H), 1.10~1.01 (m, 1H), 0.87 (s, 9H).

Example 100: N-((6-((trans)-4-tert-butylcyclohexy-loxy)naphthalen-2-yl)methyl)cyclopentanamine

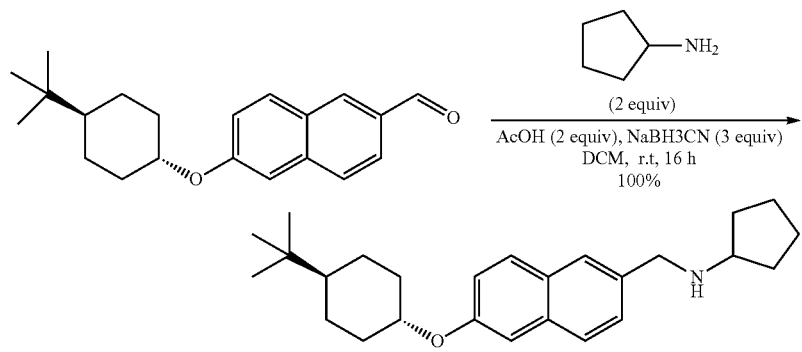

The preparation of N-((6-((trans)-4-tert-butylcyclohexy-loxy)naphthalen-2-yl)methyl)cyclopentanamine was performed as described in example 27 to give the title compound as a gray oil (356 mg, 100%). ESI-MS (M+H)+: 380.3. ¹H NMR (400 MHz, CDCl₃) δ: 7.73~7.63 (m, 3H), 7.44~7.39 (m, 1H), 7.15~7.08 (m, 2H), 4.30~4.20 (m, 1H), 3.90 (s, 2H), 3.18~3.10 (m, 1H), 2.31~2.22 (m, 2H), 1.93~1.84 (m, 2H), 1.78~1.06 (m, 13H), 0.89 (s, 9H).

Example 101: methyl 3-(((6-((trans)-4-tert-butylcyclohexyloxy)naphthalen-2-yl)methyl)(cyclopentyl)amino)propanoate The synthesis of methyl 3-(((6-((trans)-4-tert-butylcyclohexyloxy)naphthalen-2-yl)methyl)(cyclopentyl)amino)propanoate was performed as described for methyl 3-(((6-((trans)-4-tert-butylcyclohexyloxy)naphthalen-2-yl)methyl)(cyclobutyl)amino)propanoate (Example 98) to give the title compound as a white solid (258 mg, 69%). (mobile phase: EA/PE=1:8) ESI-MS (M+1)+: 466.3, HPLC: 95.23%. ¹H NMR (400 MHz, CDCl₃) δ: 7.72~7.61 (m, 3H), 7.45~7.40 (m, 1H), 7.16~7.08 (m, 2H), 4.30~4.21 (m, 1H), 3.72 (s, 2H), 3.60 (s, 3H), 3.15~3.06 (m, 1H), 2.87 (t, 2H), 2.45 (t, 2H), 2.31~2.24 (m, 2H), 1.93~1.85 (m, 2H), 1.83~1.73 (m, 2H), 1.69~1.61 (m, 2H), 1.54~1.36 (m, 6H), 1.26~1.03 (m, 3H), 0.89 (s, 9H).

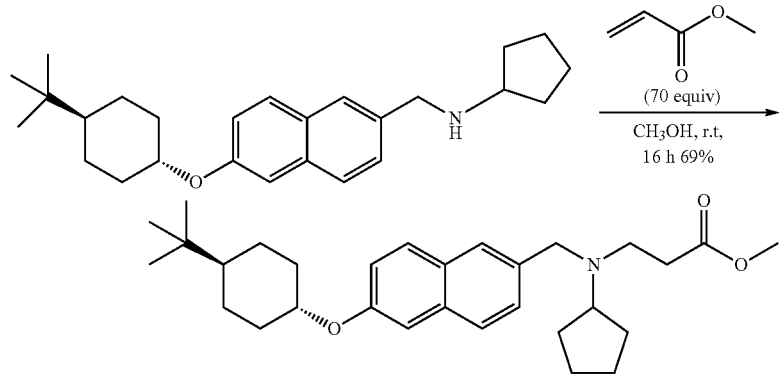

Example 102: 3-(((6-((trans)-4-tert-butylcyclohexyloxy)naphthalen-2-yl)methyl)(cyclopentyl)amino)propanoic acid

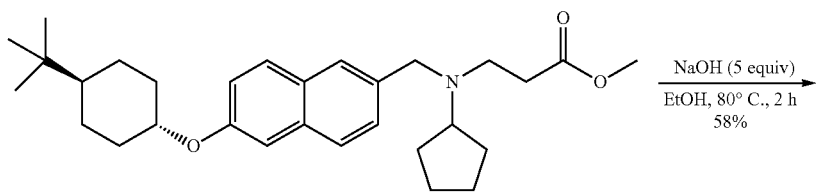

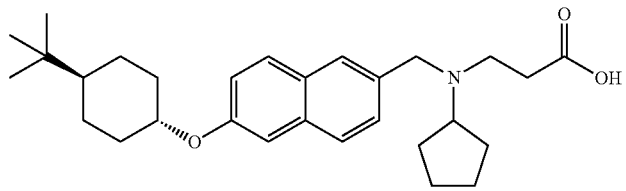

The preparation of 3-(((6-(((trans)-4-tert-butylcyclohexyloxy)naphthalen-2-yl)methyl)(cyclopentyl)amino)propanoic acid was performed as described for example 28 to give the title compound as a white solid (171 mg, 58%) ESI-MS (M+1)+: 452.3, HPLC: 95.83%. $^1$H NMR (400 MHz, DMSO-d$_6$) δ: 8.01~7.93 (m, 1H), 7.86~7.77 (m, 2H), 7.70~7.64 (m, 1H), 7.43~7.37 (m, 1H), 7.21~7.14 (m, 1H), 4.45~4.35 (m, 1H), 4.28 (s, 2H), 3.58~3.45 (m, 1H), 3.11~3.01 (m, 2H), 2.75~2.62 (m, 2H), 2.26~2.14 (m, 2H), 2.06~1.93 (m, 2H), 1.90~1.77 (m, 4H), 1.76~1.65 (m, 2H), 1.59~1.47 (m, 2H), 1.40~1.30 (m, 2H), 1.27~1.16 (m, 2H), 1.12~1.02 (m, 1H), 0.88 (s, 9H).

Example 103: N-((6-(((trans)-4-tert-butylcyclohexyloxy)naphthalen-2-yl)methyl)cyclohexanamine

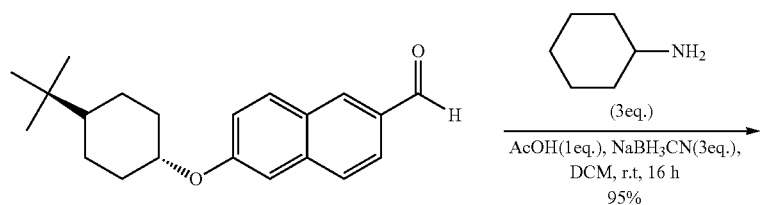

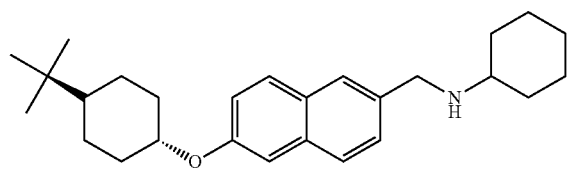

The preparation of N-((6-(((trans)-4-tert-butylcyclohexyloxy)naphthalen-2-yl)methyl)cyclohexanamine was performed as described for example 27 to give the title compound as a white solid (420 mg, 95%). ESI-MS (M+H)+: 394.2. $^1$H NMR (400 MHz, CDCl$_3$) δ: 7.82-7.70 (m, 3H), 7.47-7.45 (m, 1H), 7.15-7.07 (m, 2H), 4.23-4.17 (m, 1H), 4.06 (s, 2H), 2.86-2.80 (m, 1H), 2.22-2.18 (m, 2H), 1.89-1.85 (m, 2H), 1.73-1.59 (m, 4H), 1.43-1.08 (m, 11H), 0.90 (s, 9H).

Example 104: methyl 3-(((6-((trans)-4-tert-butylcyclohexyloxy)naphthalen-2-yl)methyl)(cyclohexyl)amino)propanoate

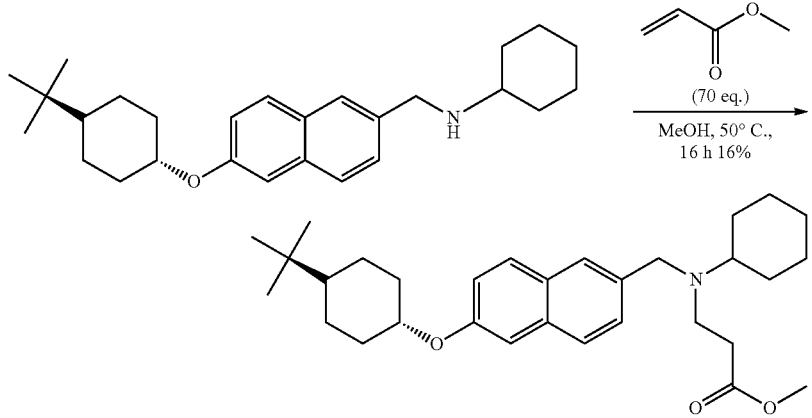

The synthesis of methyl 3-(((6-((trans)-4-tert-butylcyclohexyloxy)naphthalen-2-yl)methyl)(cyclohexyl)amino)propanoate was performed as described for methyl 3-(((6-((trans)-4-tert-butylcyclohexyloxy)naphthalen-2-yl)methyl)(cyclobutyl)amino)propanoate (Example 98) to give the title compound as a white solid (80 mg, 16%) (mobile phase: EA/PE=1:8).

ESI-MS (M+H)$^+$: 480.2. $^1$H NMR (400 MHz, CDCl$_3$) δ: 7.74-7.62 (m, 3H), 7.44-7.41 (m, 1H), 7.14-7.09 (m, 2H), 4.29-4.23 (m, 1H), 3.74 (s, 2H), 3.60 (s, 3H), 2.86 (t, 2H), 2.49-2.39 (m, 3H), 2.29-2.26 (m, 2H), 1.91-1.78 (m, 5H), 1.56-1.10 (m, 12H), 0.90 (s, 9H).

Example 105: 3-(((6-((trans)-4-tert-butylcyclohexyloxy)naphthalen-2-yl)methyl)(cyclohexyl)amino)propanoic acid The preparation of 3-(((6-((trans)-4-tert-butylcyclohexyloxy)naphthalen-2-yl)methyl)(cyclohexyl)amino)propanoic acid was performed as described for example 28 to give the title compound, 65 mg, slight yellow solid, yield: 84%.

ESI-MS (M+H)$^+$: 466.1. HPLC: 96.99%. $^1$H NMR (400 MHz, DMSO-d$_6$) δ: 7.86-7.77 (m, 3H), 7.54 (d, 1H), 7.38 (d, 1H), 7.15 (dd, 1H), 4.41-4.35 (m, 1H), 4.10 (br, 2H), 3.04 (t, 2H), 2.86-2.84 (m, 1H), 2.22-2.19 (m, 2H), 1.97-1.94 (m, 2H), 1.83-1.75 (m, 4H), 1.57-1.07 (m, 13H), 0.88 (s, 9H).

Example 106: methyl 2-(hydroxymethyl)acrylate

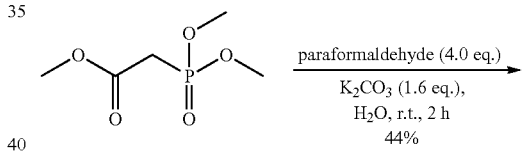

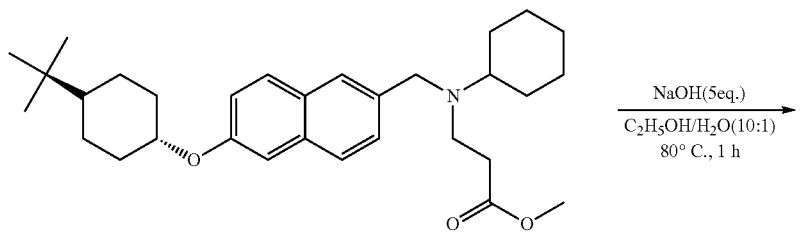

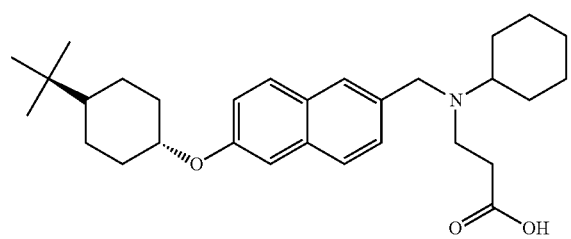

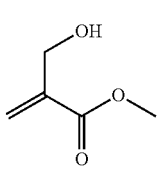

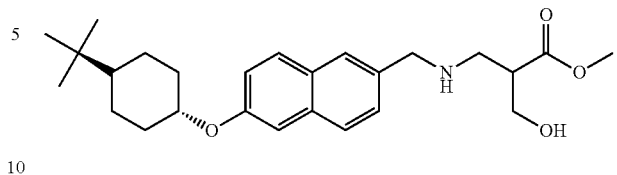

A saturated aqueous solution (10 mL) of K₂CO₃ (3.5 g, 117 mmol, 1.6 eq.) was slowly added to a rapidly stirred solution of trimethylphosphonoacetate (5.46 g, 30 mmol, 1.0 eq.) and paraformaldehyde (6.63 g, 48 mmol, 4.0 eq.) at r.t. After the addition the mixture was stirred for 2 h. Then the mixture was extracted with DCM. The organic layer was concentrated to give the compound (1.5 g, 44%) as a yellow oil. ¹H NMR (400 MHz, CD₃OD) δ: 6.29 (s, 1H), 5.83 (s, 1H), 3.75 (s, 3H), 3.72 (s, 2H).

Example 107: methyl 3-((6-((trans)-4-tert-butylcyclohexyloxy)naphthalen-2-yl)methylamino)-2-(hydroxymethyl)propanoate

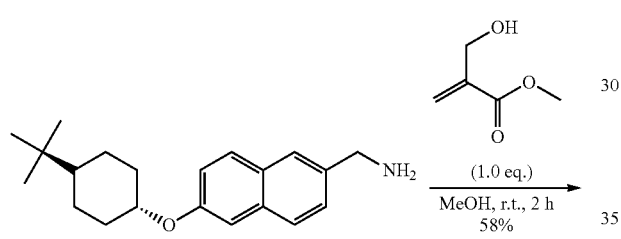

Compounds (6-((trans)-4-tert-butylcyclohexyloxy)naphthalen-2-yl)methanamine (311 mg, 1.0 mmol, 1.0 eq.) and methyl 2-(hydroxymethyl)acrylate (116 mg, 1.0 mmol, 1.0 eq.) was dissolved in MeOH (5 mL). The mixture was stirred at r.t. for 2 h. Then the mixture was concentrated and purified by silica gel column chromatography using DCM/CH₃OH (10/1) to give product (250 mg, 58%) as a slight yellow oil. ESI-MS (M+H)⁺: 428.3. HPLC: 90.18%. ¹H NMR (400 MHz, CDCl₃) δ 7.68 (t, 2H), 7.63 (s, 1H), 7.37 (dd, 1H), 7.14-7.11 (m, 2H), 4.27-4.25 (m, 1H), 4.01-3.96 (m, 2H), 3.91 (s, 2H), 3.71 (s, 3H), 3.18-2.93 (AB, 2H), 2.73-2.71 (m, 1H), 2.28-2.25 (m, 2H), 1.90-1.87 (m, 2H), 1.45-1.40 (m, 2H), 1.25-1.09 (m, 3H), 0.89 (s, 9H).

Example 108: 3-((6-((trans)-4-tert-butylcyclohexyloxy)naphthalen-2-yl)methylamino)-2-(hydroxymethyl)propanoic acid

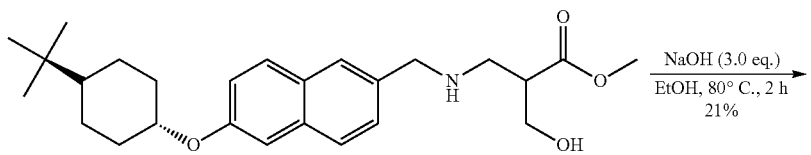

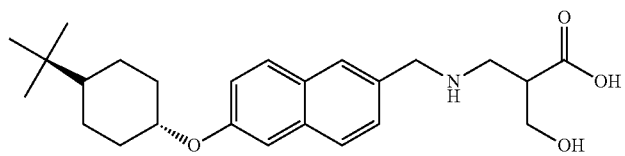

The preparation of 3-((6-(((trans)-4-tert-butylcyclohexyloxy)naphthalen-2-yl)methylamino)-2-(hydroxymethyl)propanoic acid was performed as described for example 28 to give the title compound 50 mg, white solid, yield: 21%. ESI-MS (M+H)$^+$: 414.3. HPLC: 94.23%. $^1$H NMR (400 MHz, CDCl$_3$) δ 7.59 (s, 1H), 7.52 (d, 1H), 7.43 (d, 1H), 7.37-7.35 (m, 1H), 6.93 (d, 1H), 6.88 (s, 1H), 4.07-4.05 (m, 1H), 3.95 (s, 2H), 3.73-3.61 (m, 2H), 3.04-2.83 (AB, 2H), 2.74-2.72 (m, 1H), 2.12-2.09 (m, 2H), 1.79-1.76 (m, 2H), 1.32-1.25 (m, 2H), 1.09-1.01 (m, 3H), 0.85 (s, 9H).

Example 109: ethyl 3-((6-((trans)-4-tert-butylcyclohexyloxy)naphthalen-2-yl)methylamino)cyclobutanecarboxylate

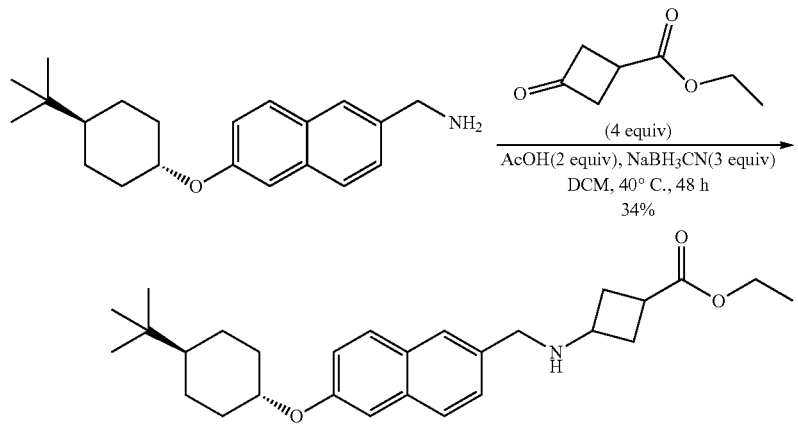

The preparation of ethyl 3-((6-(((trans)-4-tert-butylcyclohexyloxy)naphthalen-2-yl)methylamino)cyclobutanecarboxylate was performed as described for example 27 to give the title compound ESI-MS (M+1)$^+$: 438.3. $^1$H NMR (400 MHz, CDCl$_3$) δ: 7.73~7.63 (m, 3H), 7.42~7.37 (m, 1H), 7.15~7.08 (m, 2H), 4.29~4.21 (m, 1H), 4.11 (q, 2H), 3.85 (d, 2H), 3.30~3.24 (m, 1H), 2.75~2.69 (m, 1H), 2.53~2.46 (m, 2H), 2.30~2.22 (m, 2H), 2.05~1.98 (m, 2H), 1.92~1.85 (m, 2H), 1.47~1.38 (m, 2H), 1.27~1.15 (m, 5H), 1.14~1.05 (m, 1H), 0.89 (s, 9H).

Example 110: 3-((6-(((trans)-4-tert-butylcyclohexyloxy)naphthalen-2-yl)methylamino)cyclobutanecarboxylic acid

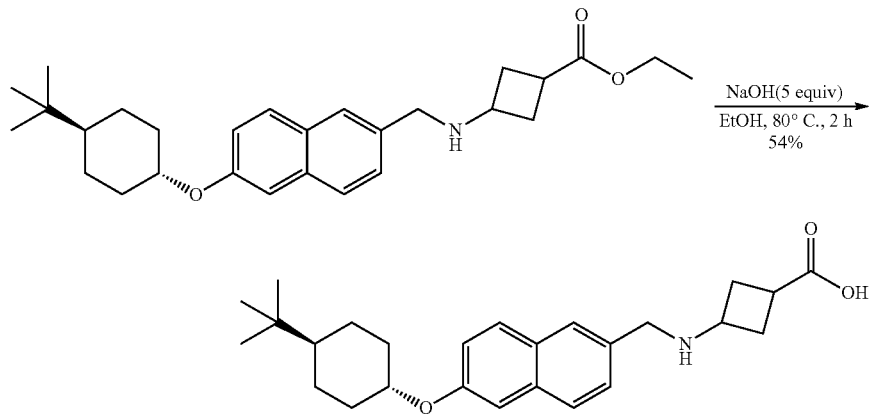

The preparation of 3-((6-(((trans)-4-tert-butylcyclohexyloxy)naphthalen-2-yl)methylamino)cyclobutanecarboxylic acid was performed as described for example 28 to give the title compound ESI-MS (M+1)+: 410.3. HPLC: 96.18%. 1H NMR (400 MHz, CD3OD) δ: 7.85~7.73 (m, 3H), 7.47~7.41 (m, 1H), 7.26~7.21 (m, 1H), 7.16~7.08 (m, 1H), 4.37~4.28 (m, 1H), 4.15~4.07 (m, 2H), 3.65~3.54 (m, 1H), 2.84~2.77 (m, 1H), 2.58~2.51 (m, 2H), 2.30~2.18 (m, 4H), 1.93~1.85 (m, 2H), 1.46~1.33 (m, 2H), 1.30~1.18 (m, 2H), 1.13~1.08 (m, 1H), 0.89 (s, 9H).

Example 111: (S)-methyl 1-((6-((trans)-4-tert-butylcyclohexyloxy)naphthalen-2-yl)methyl)pyrrolidine-2-carboxylate

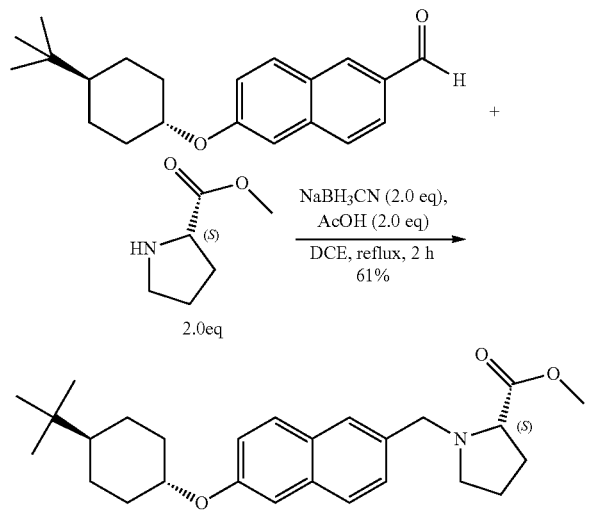

The preparation of (S)-methyl 1-((6-((trans)-4-tert-butylcyclohexyloxy)naphthalen-2-yl)methyl)pyrrolidine-2-carboxylate was performed as described for example 27 to give the title compound. ESI-MS (M+1)+: 424.3. 1H NMR (400 MHz, CDCl3) δ: 7.70~7.64 (m, 3H), 7.45 (d, 1H), 7.13~7.09 (m, 2H), 4.28~4.23 (m, 1H), 4.06~4.00 (m, 1H), 3.77~3.71 (m, 1H), 3.61 (s, 3H), 3.33~3.31 (m, 1H), 3.11~3.07 (m, 1H), 2.45~2.41 (m, 1H), 2.27 (d, 2H), 2.20~2.16 (m, 1H), 2.01~1.96 (m, 1H), 1.89 (d, 2H), 1.73~1.69 (m, 2H), 1.46~1.42 (m, 2H), 1.23~1.09 (m, 3H), 0.89 (s, 9H).

Example 112: (S)-1-((6-((trans)-4-tert-butylcyclohexyloxy)naphthalen-2-yl)methyl)pyrrolidine-2-carboxylic acid

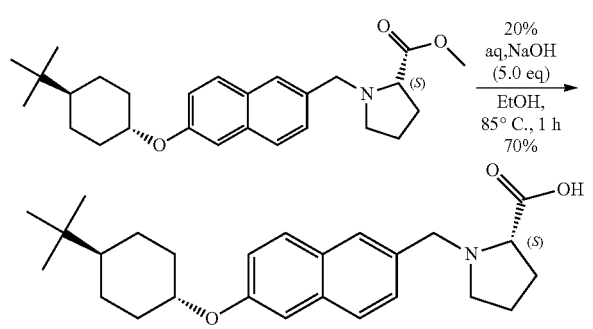

The preparation of (S)-1-((6-((trans)-4-tert-butylcyclohexyloxy)naphthalen-2-yl)methyl)pyrrolidine-2-carboxylic acid was performed as described for example 28 to give the title compound as a white solid (50 mg, 70%). ESI-MS (M+1)+: 410.3. HPLC: 98.10%. 1H NMR (400 MHz, CD3OD) δ: 7.95 (s, 1H), 7.86 (d, 1H), 7.83 (d, 1H), 7.54 (dd, 1H), 7.29 (d, 1H), 7.19 (dd, 1H), 4.69 (d, 1H), 4.46-4.37 (m, 3H), 3.62~3.54 (m, 1H), 3.44-3.40 (m, 1H), 2.66-2.62 (m, 1H), 2.28 (d, 2H), 2.25-2.16 (m, 2H), 2.02-1.98 (m, 1H), 1.93 (d, 2H), 1.46-1.41 (m, 2H), 1.30-1.25 (m, 2H), 1.17~1.13 (m, 1H), 0.91 (s, 9H).

Example 113: methyl 1-((6-((trans)-4-tert-butylcyclohexyloxy)naphthalen-2-yl)methyl)azetidine-2-carboxylate

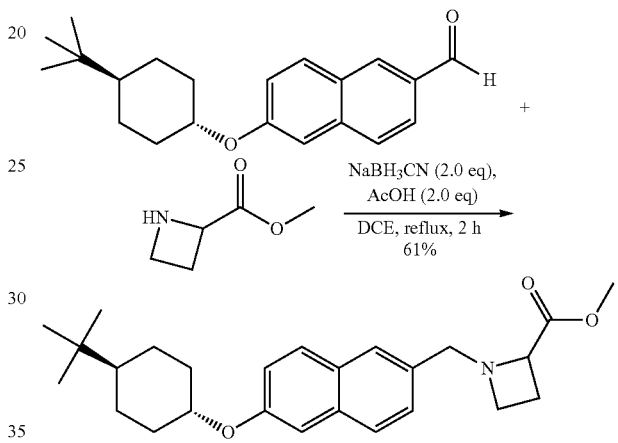

The preparation of methyl 1-((6-((trans)-4-tert-butylcyclohexyloxy)naphthalen-2-yl)methyl)azetidine-2-carboxylate was performed as described for example 27 to give the title compound. ESI-MS (M+1)+: 410.3. 1H NMR (400 MHz, CD3OD) δ: 7.73~7.66 (m, 3H), 7.38 (dd, 1H), 7.21 (d, 1H), 7.09 (dd, 1H), 4.37~4.31 (m, 1H), 3.93~3.83 (m, 1H), 3.73 (d, 2H), 3.56 (s, 3H), 3.29~3.21 (m, 1H), 3.13~3.08 (m, 1H), 2.29~2.25 (m, 4H), 1.92 (d, 2H), 1.45~1.40 (m, 2H), 1.30~1.09 (m, 3H), 0.93 (s, 9H).

Example 114: 1-((6-((trans)-4-tert-butylcyclohexyloxy)naphthalen-2-yl)methyl)azetidine-2-carboxylic acid

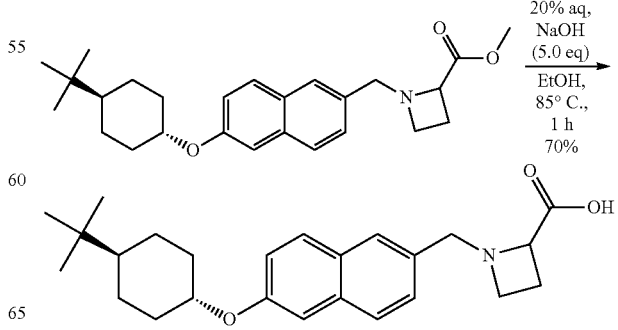

The preparation of 1-((6-((trans)-4-tert-butylcyclohexyloxy)naphthalen-2-yl)methyl)azetidine-2-carboxylic acid was performed as described for example 28 to give the title compound as a white solid (50 mg, 70%). ESI-MS (M+1)⁺: 396.3. HPLC: 96.99%. ¹H NMR (400 MHz, CD₃OD) δ: δ: 7.82 (s, 1H), 7.75 (d, 2H), 7.43 (dd, 1H), 7.14 (d, 2H), 4.94-4.90 (m, 1H), 4.49-4.41 (m, 2H), 4.30-4.23 (m, 1H), 4.06-4.01 (m, 1H), 3.86-3.81 (m, 1H), 2.64-2.59 (m, 2H), 2.23 (d, 2H), 1.87 (d, 2H), 1.44-1.38 (m, 2H), 1.22~1.07 (m, 3H), 0.86 (s, 9H).

Example 115: tert-butyl 3-amino-3-oxopropyl((6-((trans)-4-tert-butylcyclohexyloxy)naphthalen-2-yl)methyl)carbamate

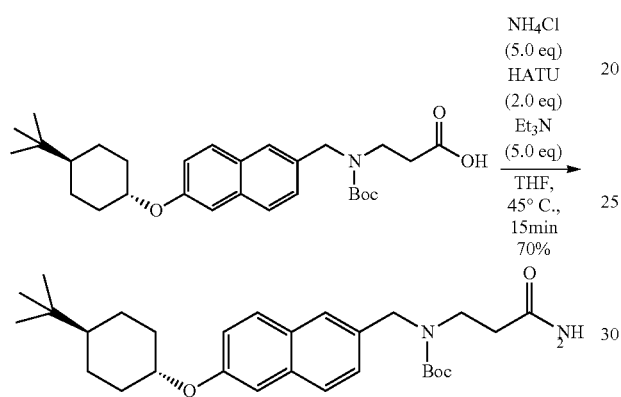

The mixture of 3-(tert-butoxycarbonyl((6-((trans)-4-tert-butylcyclohexyloxy)naphthalen-2-yl)methyl)amino)propanoic acid (483 mg, 1.0 mmol), NH₄Cl (215 mg, 5.0 mmol, 5.0 equiv), Et₃N (510 mg, 5.0 mmol, 5.0 equiv) and HATU (760 mg, 2.0 mmol, 2.0 equiv) in anhydrous THF (20 mL) was stirred at 45° C. for 15 min. The reaction mixture was concentrated in vacuum and the residue was purified by chromatography with silica gel (DCM/MeOH=20/1) to give compound the title compound as a white solid (337 mg, yield: 70%). ESI-MS (M+H⁺): 483.3. ¹H NMR (400 MHz, DMSO-d₆) δ: 7.76 (d, 2H), 7.60 (s, 1H), 7.34 (s, 1H), 7.30 (d, 1H), 7.12 (dd, 1H), 4.49 (s, 2H), 4.38-4.31 (m, 1H), 3.30 (t, 2H), 2.30 (t, 2H), 2.19 (d, 2H), 1.81 (d, 2H), 1.45-1.33 (m, 11H), 1.23-1.16 (m, 3H), 0.88 (s, 9H).

Example 116: N-acetyl-3-((6-((trans)-4-tert-butylcyclohexyloxy)naphthalen-2-yl)methylamino)propanamide

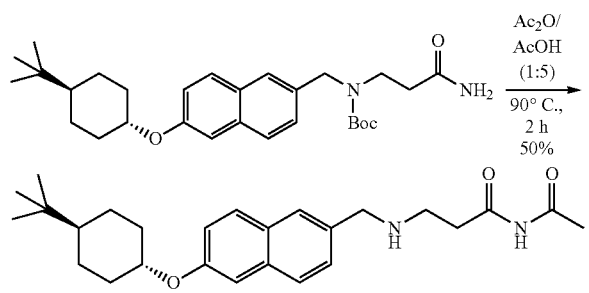

The mixture of tert-butyl 3-amino-3-oxopropyl((6-((trans)-4-tert-butylcyclohexyloxy)naphthalen-2-yl)methyl)carbamate (241 mg, 0.5 mmol) in Ac₂O and AcOH (6 mL, 1:5), was stirred at 90° C. for 2 h. The reaction mixture was concentrated in vacuum and the residue was purified by chromatography with silica gel (DCM/MeOH=15/1) to give the title compound as a white solid (100 mg, yield: 50%). ESI-MS (M+H⁺): 425.3. HPLC: 94.82%. ¹H NMR (400 MHz, CDCl₃) δ: 7.70 (d, 1H), 7.68 (d, 1H), 7.49 (s, 1H), 7.21 (d, 1H), 7.17-7.14 (m, 2H), 6.50 (br, 1H), 5.49 (br, 1H), 4.71 (s, 2H), 4.24-4.30 (m, 1H), 3.71 (t, 2H), 2.57 (t, 2H), 2.27 (d, 2H), 2.18 (s, 3H), 1.89 (d, 2H), 1.48-1.42 (m, 2H), 1.09-1.20 (m, 3H), 0.88 (s, 9H).

Example 116: 6-((trans)-4-tert-butylcyclohexyloxy)-2-naphthonitrile

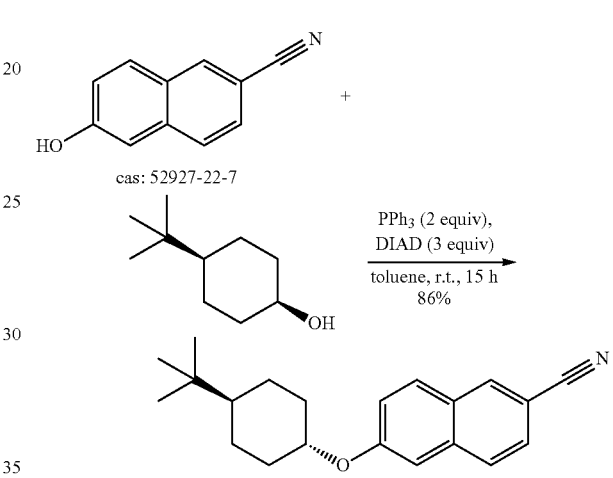

To a vial charged with 6-hydroxy-2-naphthonitrile (3.38 g, 0.02 mol, 1.0 eq.), cis-4-tert-butylcyclohexanol (6.24 g, 0.04 mol, 2.0 eq.), PPh₃ (10.5 g, 0.04 mol, 2.0 eq.) and toluene (20 mL), was added DIAD (12 mL, 0.06 mol, 3.0 eq.) under nitrogen atmosphere at r.t. and stirred for 15 h. Water was added and extracted with EtOAc. The organic layer was purified by silica gel chromatography (PE:EA=10:1) to give the title compound (9.0 g, 86%) as a slight yellow solid. EDI-MS (M+1)⁺: 308.0. ¹H NMR (400 MHz, CDCl₃) δ 8.12 (s, 1H), 7.78-7.73 (m, 2H), 7.54 (dd, 1H), 7.22 (dd, 1H), 7.14 (s, 1H), 4.33-4.30 (m, 1H), 2.29-2.25 (m, 2H), 1.93-1.90 (m, 2H), 1.48-1.26 (m, 2H), 1.25-1.10 (m, 3H), 0.91 (s, 9H).

Example 117: 2-(6-((trans)-4-tert-butylcyclohexyloxy)naphthalen-2-yl)propan-2-amine

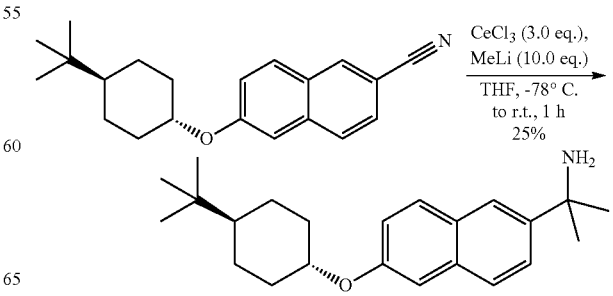

To a vial charged with 6-((trans)-4-tert-butylcyclohexyloxy)-2-naphthonitrile (500 mg, 1.63 mmol, 1.0 eq.), CeCl₃ (1.2 g, 4.89 mmol, 3.0 eq.) and THF (10 mL), was added MeLi (1.5 M solution in diethoxymethane, 10 mL, 16.3 mmol, 10.0 eq.) under nitrogen atmosphere at −78° C. The mixture was stirred at −78° C. for 1 h. Saturated ammonium chloride solution was added and extracted with EtOAc. The organic layer was purified by silica gel chromatography (DCM:MeOH=10:1) to give the title compound (140 mg, 25%) as a slight yellow oil. ¹H NMR (400 MHz, CDCl₃) δ: 7.84 (s, 1H), 7.72-7.66 (m, 2H), 7.59 (d, 1H), 7.13-7.09 (m, 2H), 4.28-4.23 (m, 1H), 2.29 (b, 2H), 2.28-2.25 (m, 2H), 1.90-1.87 (m, 2H), 1.61 (s, 6H), 1.48-1.39 (m, 2H), 1.25-1.09 (m, 3H), 0.89 (s, 9H).

Example 118: methyl 3-(2-(6-((trans)-4-tert-butyl-cyclohexyloxy)naphthalen-2-yl)propan-2-ylamino)propanoate

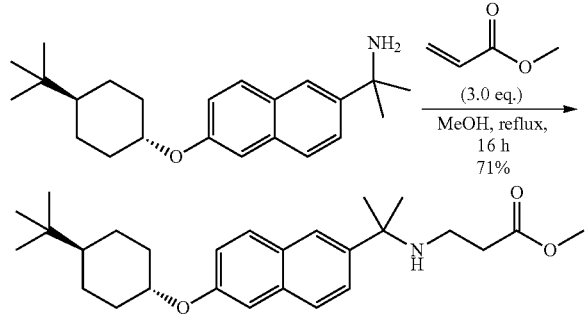

2-(6-((trans)-4-tert-butylcyclohexyloxy)naphthalen-2-yl)propan-2-amine (113 mg, 0.33 mmol, 1.0 eq.) and methyl acrylate (86 mg, 0.99 mmol, 3.0 eq.) was dissolved in MeOH (2 mL). The mixture was reflux for 16 h. The mixture was concentrated and purified by silica gel chromatography (DCM:MeOH=20:1) to give the title compound (100 mg, 71%) as a slight yellow oil. ¹H NMR (400 MHz, CDCl₃) δ: 7.73-7.68 (m, 3H), 7.60 (dd, 1H), 7.13-7.16 (m, 2H), 4.26-4.23 (m, 1H), 3.66 (s, 3H), 2.62 (t, 2H), 2.50 (t, 2H), 2.28-2.26 (m, 2H), 1.90-1.87 (m, 2H), 1.58 (s, 6H), 1.45-1.38 (m, 2H), 1.19-1.09 (m, 3H), 0.89 (s, 9H).

Example 119: 3-(2-(6-((trans)-4-tert-butylcyclohexyloxy)naphthalen-2-yl)propan-2-ylamino)propanoic acid

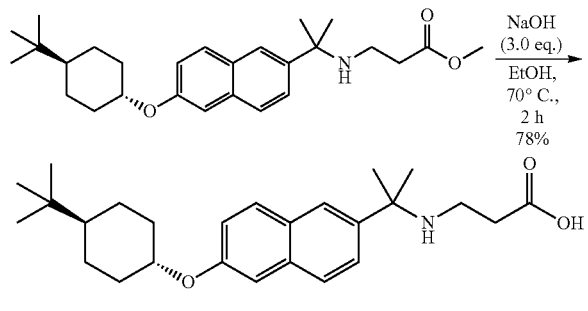

The preparation of 3-(2-(6-((trans)-4-tert-butylcyclohexyloxy)naphthalen-2-yl)propan-2-ylamino)propanoic acid was performed as described in example 28 to give the title compound as a white solid (75 mg, 78%). HPLC: 96.91%. ¹H NMR (400 MHz, CD₃OD) δ: 7.97 (s, 1H), 7.89-7.83 (m, 2H), 7.64 (dd, 1H), 7.27 (s, 1H), 7.17 (dd, 1H), 4.39-4.36 (m, 1H), 2.94 (t, 2H), 2.58 (t, 2H), 2.29-2.27 (m, 2H), 1.94-1.92 (m, 2H), 1.90 (s, 6H), 1.45-1.41 (m, 2H), 1.32-1.13 (m, 3H), 0.92 (s, 9H).

Example 120: 2-((6-((trans)-4-tert-butylcyclohexyloxy)naphthalen-2-yl)methylamino)acetonitrile

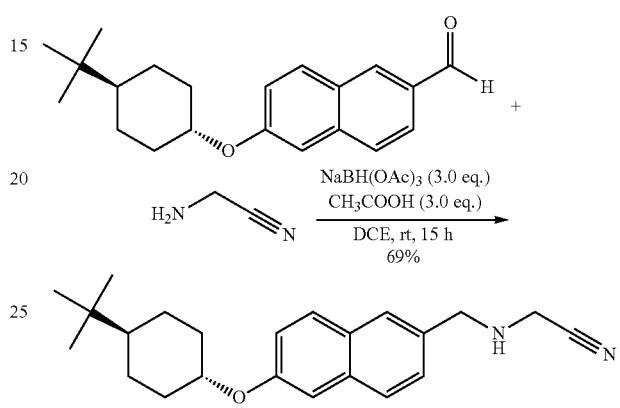

6-((trans)-4-tert-butylcyclohexyloxy)-2-naphthaldehyde (310 mg, 1 mmol), 2-aminoacetonitrile (112 mg, 2 mmol, 2.0 eq) and acetic acid (180 mg, 3 mmol, 3.0 eq) in DCE (10 mL) was stirred at rt for 10 min. Then NaBH(OAc)₃ (636 mg, 3 mmol, 3.0 eq) was added to the mixture and the mixture was stirred at rt for 15 h. Then saturated NaHCO₃ was added to the mixture until pH=8. The mixture was extracted with DCM (20 mL×3). The organic layer was concentrated and the residue was purified by silica gel column chromatography eluting with DCM/CH₃OH (20/1) to give product the title compound as a colorless oil (240 mg, yield: 69%).
ESI-MS (M+H⁺): 351.2. ¹H NMR (400 MHz, CDCl₃) δ: 7.70 (dd, 2H), 7.68 (s, 1H), 7.41 (dd, 1H), 7.13 (d, 2H), 4.30-4.23 (m, 1H), 4.05 (s, 2H), 3.57 (s, 2H), 2.26 (d, 2H), 1.90 (d, 2H), 1.48-1.42 (m, 2H), 1.20-1.09 (m, 3H), 0.90 (s, 9H).

Example 121: N-((1H-tetrazol-5-yl)methyl)-1-(6-((trans)-4-tert-butylcyclohexyloxy)naphthalen-2-yl)methanamine

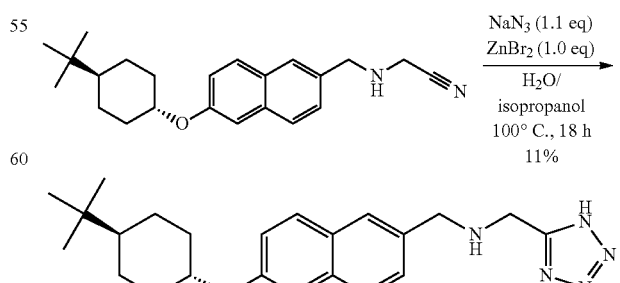

To a solution of 2-((6-(((trans)-4-tert-butylcyclohexyloxy)naphthalen-2-yl)methylamino)acetonitrile (240 mg, 0.69 mmol) in water and isopropanol (10 mL, 1:5) was added NaN$_3$ (50 mg, 0.76 mmol, 1.1 eq) and ZnBr$_2$ (153 mg, 0.69 mmol, 1.0 eq), then refluxed for 18 h. The reaction was cooled to 0° C. and saturated NaHCO$_3$ was added. The mixture was extracted with DCM (20 mL×3) and the aqueous layer was destroyed by NaClO solution. The organic layer was concentrated and the residue was the title compound as a white solid (27 mg, yield: 11%). ESI-MS (M+H$^+$): 394.3. HPLC: 91.15%, $^1$H NMR (400 MHz, CD$_3$OD) δ: 7.82 (s, 1H), 7.79-7.72 (m, 2H), 7.42 (d, 1H), 7.16 (d, 2H), 4.47-4.31 (m, 5H), 2.26 (d, 2H), 1.89 (d, 2H), 1.45-1.41 (m, 2H), 1.24-1.09 (m, 3H), 0.88 (s, 9H)

Example 122: 3-((6-(((trans)-4-tert-butylcyclohexyloxy)naphthalen-2-yl)methylamino)propanenitrile

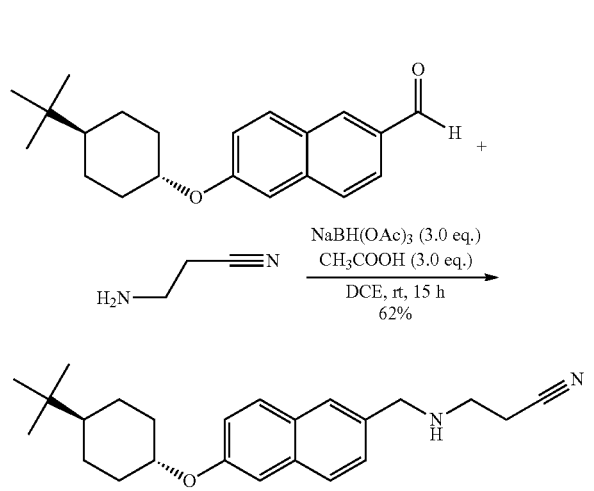

Procedure was followed as described for 2-((6-(((trans)-4-tert-butylcyclohexyloxy)naphthalen-2-yl)methylamino)acetonitrile (Example 120) to give the title compound 240 mg, white solid (yield: 62%). ESI-MS (M+H$^+$): 365.3. $^1$H NMR (400 MHz, CDCl$_3$) δ: 7.69 (dd, 2H), 7.66 (s, 1H), 7.40 (dd, 1H), 7.13 (d, 2H), 4.30-4.23 (m, 1H), 3.95 (s, 2H), 2.97 (t, 2H), 2.56 (t, 2H), 2.29 (d, 2H), 1.90 (d, 2H), 1.46-1.42 (m, 2H), 1.20-1.12 (m, 3H), 0.90 (s, 9H)

Example 123: N-((6-(((trans)-4-tert-butylcyclohexyloxy)naphthalen-2-yl)methyl)-2-(1H-tetrazol-5-yl)ethanamine

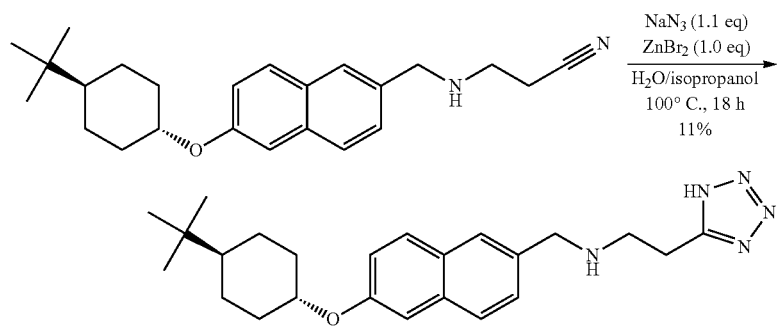

The procedure was followed as described for N-((1H-tetrazol-5-yl)methyl)-1-(6-(((trans)-4-tert-butylcyclohexyloxy)naphthalen-2-yl)methanamine (Example 121) to give the title compound 20 mg, white solid (yield: 11%). ESI-MS (M+H$^+$): 408.3 HPLC: 98.66% $^1$H NMR (400 MHz, CD$_3$OD) δ: 7.93 (s, 1H), 7.85 (dd, 2H), 7.53 (dd, 1H), 7.30 (d, 1H) 7.19 (dd, 1H), 4.45 (s, 2H), 4.42-4.36 (m, 1H), 3.61 (t, 2H), 3.43 (t, 2H), 2.29 (d, 2H), 1.93 (d, 2H), 1.43-1.39 (m, 2H), 1.33-1.11 (m, 3H), 0.88 (s, 9H)

Example 124; 3-((6-(((trans)-4-tert-butylcyclohexyloxy)naphthalen-2-yl)methylamino)propanamide

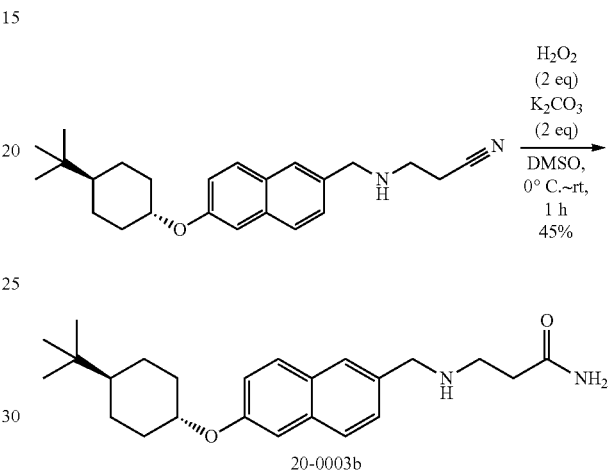

20-0003b

To a solution of 3-((6-(((trans)-4-tert-butylcyclohexyloxy)naphthalen-2-yl)methylamino)propanenitrile (233 mg, 0.64 mmol) in DMSO (2 mL) was added K$_2$CO$_3$ (265 mg, 2 mmol, 3.0 eq), the mixture was then cooled to 0° C., and followed by addition of aq. 30% H$_2$O$_2$ (0.3 mL). The reaction mixture was stirred at rt for 1 h, and quenched with water (10 mL). The solvent was removed by freezing-dried. The crude product was purified by flash chromatography to give the title compound as a white solid (111 mg, 45%) (mobile phase: MeOH/H$_2$O: 0%-80%). ESI-MS (M+1)$^+$: 383.3. HPLC: 97.84%. $^1$H NMR (400 MHz, CD$_3$OD) δ: 7.86~7.79 (m, 3H), 7.53~7.50 (m, 1H), 7.33~7.30 (m, 1H), 7.21~7.16 (m, 1H), 4.42~4.35 (m, 3H), 3.34~3.27 (m, 2H), 2.71 (t, 2H), 2.32~2.24 (m, 2H), 1.96~1.87 (m, 2H), 1.51~1.39 (m, 2H), 1.33~1.20 (m, 2H), 1.17~1.09 (m, 1H), 0.92 (s, 9H).

Example 125: methyl 1-((6-(((trans)-4-tert-butylcyclohexyloxy)-5-iodonaphthalen-2-yl)methyl)azetidine-3-carboxylate

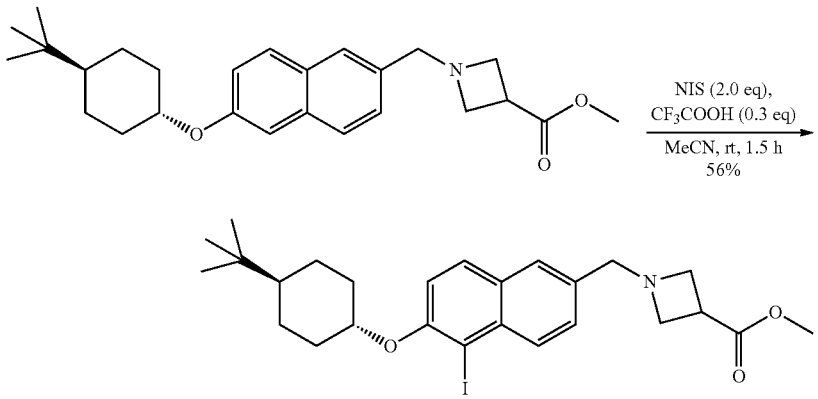

Methyl 1-((6-(((trans)-4-tert-butylcyclohexyloxy)naphthalen-2-yl)methyl)azetidine-3-carboxylate (410 mg, 1 mmol) and NIS (247 mg, 1.1 mmol, 2.0 eq.) were dissolved in CH$_3$CN (5 mL). Then CF$_3$COOH (35 mg, 0.3 mmol, 0.3 eq.) was added to the mixture dropwise at 0° C. The mixture was warmed to r.t. and stirred for another 1.5 h. Then the mixture was extracted with EtOAc and the organic layer was concentrated and purified by silica gel chromatography using PE/EA (1/1) as eluent to give product the title compound as a slight red solid (300 mg, 56%). ESI-MS (M+H$^+$): 536.2. $^1$H NMR (400 MHz, CDCl$_3$) δ: 8.19 (d, 1H), 7.93 (s, 1H), 7.81 (d, 1H), 7.62 (d, 1H), 7.22 (d, 1H), 4.34-4.28 (m, 4H), 3.91-3.67 (m, 1H), 3.80-3.78 (m, 3H), 3.75 (s, 3H), 2.24-2.21 (m, 2H), 1.90-1.88 (m, 2H), 1.62-1.58 (m, 2H), 1.15-1.12 (m, 3H), 0.89 (s, 9H).

Example 126: methyl 1-((6-(((trans)-4-tert-butylcyclohexyloxy)-5-methylnaphthalen-2-yl)methyl)azetidine-3-carboxylate A flask charged with compound methyl 1-((6-(((trans)-4-tert-butylcyclohexyloxy)-5-iodonaphthalen-2-yl)methyl) azetidine-3-carboxylate (300 mg, 0.56 mmol), methylboronic acid (66 mg, 1.1 mmol, 2.0 eq), 2 M aq K$_2$CO$_3$ (5 mL, 3.0 equiv) and [1,1-bis (diphenylphosphino) ferroene] dichloropalladium (II) complex with dichloromethane (1:1) (45 mg, 0.05 mmol, 0.1 equiv) was flushed with nitrogen. 1, 4-Dioxane (20 mL) was added and the reaction was stirred at 90° C. for 5 h. The solution was cooled to room temperature. The solvent was removed and the residue was purified by column chromatography (PE/EA=1:1) to give compound the title compound as a white solid (80 mg, 33%). ESI-MS (M+H$^+$): 424.3. $^1$H NMR (400 MHz, CDCl$_3$) δ: 7.88 (d, 1H), 7.64-7.61 (m, 2H), 7.40 (dd, 1H), 7.23 (d, 1H), 4.10-4.08 (m, 1H), 3.79 (s, 2H), 3.74 (s, 3H), 3.59-3.56 (m, 2H), 3.39-3.36 (m, 3H), 2.53 (s, 3H), 2.20-2.17 (m, 2H), 1.86-1.83 (m, 2H), 1.48-1.43 (m, 2H), 1.10-1.26 (m, 3H), 0.86 (s, 9H)

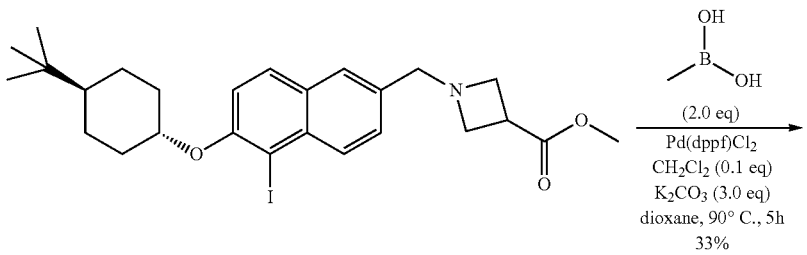

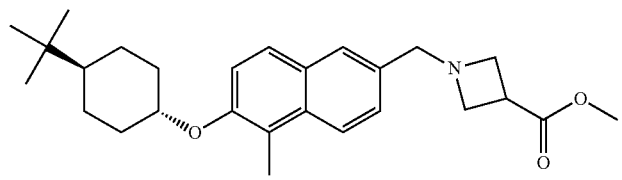

Example 127: 1-((6-((trans)-4-tert-butylcyclohexyloxy)-5-methylnaphthalen-2-yl)methyl)azetidine-3-carboxylic acid

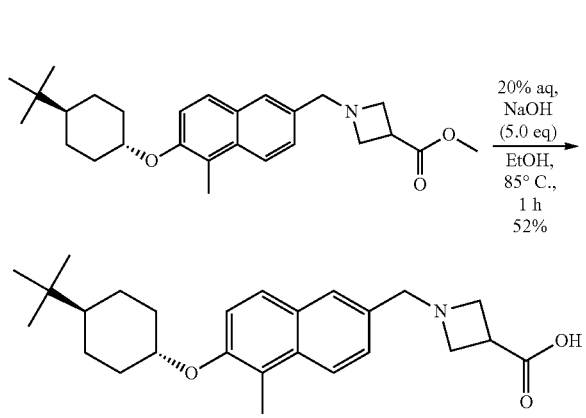

To a solution of methyl 1-((6-((trans)-4-tert-butylcyclohexyloxy)-5-methylnaphthalen-2-yl)methyl)azetidine-3-carboxylate (80 mg, 0.18 mmol) in EtOH (10 mL) was added aqueous NaOH (2 mL, 20%, 5.0 eq) and 85° C. for 1 h. Then the reaction was cooled to 0° C., the pH of the solution was adjusted to 6 using 1M HCl, concentrated and the residue was dissolved in DCM, washed with water, dried and concentrated to give the title compound as a white solid (40 mg, yield: 52%). ESI-MS (M+H$^+$): 410.3. HPLC: 97.77% $^1$H NMR (400 MHz, CD$_3$OD) δ: 8.04 (d, 1H), 7.92 (s, 1H), 7.77 (d, 1H), 7.50 (dd, 1H), 7.41 (d, 1H), 4.54 (s, 2H), 4.34-4.26 (m, 5H), 3.74-3.70 (m, 1H), 2.52 (s, 3H), 2.21-2.18 (m, 2H), 1.91-1.88 (m, 2H), 1.49-1.44 (m, 2H), 1.23-1.11 (m, 3H), 0.90 (s, 9H).

Example 128: (6-bromonaphthalen-2-yloxy)(tert-butyl)dimethylsilane

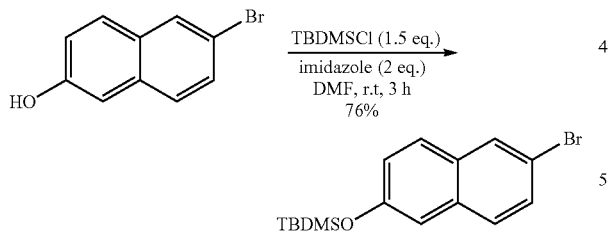

To a solution of compound 6-bromonaphthalen-2-ol (10 g, 0.044 mol, 1.0 equiv) and imidazole (6 g, 0.088 mol, 2.0 equiv) in dry DMF (100 mL) was added TBDMSCl (10 g, 0.066 mol, 1.5 equiv) at 0° C. Then the reaction mixture was warmed to r.t and stirred for 3 h. Then DMF was removed under reduced pressure. The mixture was extracted with ethyl acetate and washed with brine, dried over Na$_2$SO$_4$ and concentrated to obtain crude product. The crude product was purified by silica gel chromatography (PE:EA=30:1) to give compound to give the title compound as a yellow solid (23 g, 76%). ESI-MS (M+H$^+$): 336.9. $^1$H NMR (400 MHz, CDCl$_3$) δ: 7.91-7.92 (m, 1H), 7.64-7.46 (m, 3H), 7.15-7.08 (m, 2H), 1.01 (s, 9H), 0.24 (s, 6H).

Example 129: 6-(tert-butyldimethylsilyloxy)-2-naphthaldehyde

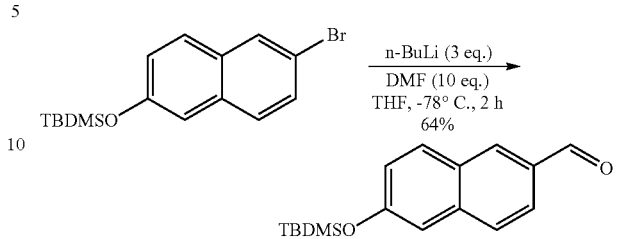

To a solution of (6-bromonaphthalen-2-yloxy)(tert-butyl)dimethylsilane (4 g, 0.01 mol, 1.0 equiv) in dry THF (30 mL) at −78° C. under N$_2$ atmosphere was added n-BuLi (2.5 M, 12 mL, 3.0 equiv) dropwise and stirred for 30 min. Then DMF (7.3 g, 0.1 mol, 10 equiv) was added and stirred for another 1 h, then quenched with water, extracted with ethyl acetate and washed with brine, dried over Na$_2$SO$_4$ and concentrated to obtain crude product. The crude product was purified by silica gel chromatography (PE:EA=20:1) to give compound the title compound (2.2 g, 64%) as a yellow liquid. ESI-MS (M+1)$^+$: 287.0. $^1$H NMR (400 MHz, CDCl$_3$) δ: 10.10 (s, 1H), 8.26 (s, 1H), 7.91-7.88 (m, 2H), 7.78-7.76 (m, 1H), 7.24-7.16 (m, 2H), 1.03 (s, 9H), 0.28 (s, 6H).

Example 130: methyl 1-((6-(tert-butyldimethylsilyloxy)naphthalen-2-yl)methyl)azetidine-3-carboxylate

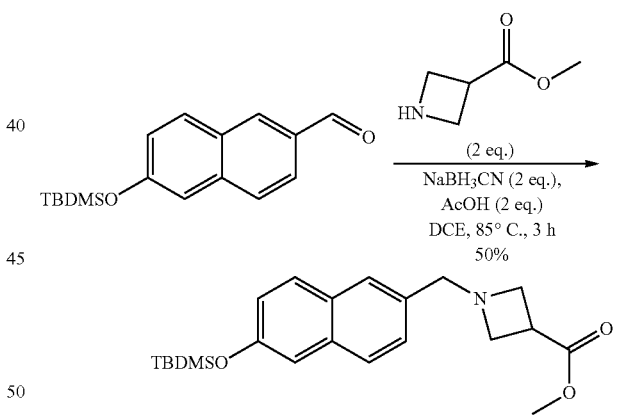

6-(tert-butyldimethylsilyloxy)-2-naphthaldehyde (4.0 g, 14 mmol), AcOH (1.8 g, 28 mmol) and methyl azetidine-3-carboxylate (3.2 g, 28 mmol, 2.0 equiv) in DCE (30 mL) were stirred at 85° C. for 1 h. Then NaBH$_3$CN (1.8 g, 28 mmol, 2.0 equiv) was added to the mixture at 50° C. and stirred for 2 h at 85° C. The reaction mixture was quenched with water, extracted with DCM and washed with brine, dried over Na$_2$SO$_4$ and concentrated to obtain crude product. The crude product was purified by silica gel chromatography (DCM:MeOH=40:1) to give the title compound (2.7 g, 50%) as a yellow oil. ESI-MS (M+1)$^+$: 386.2. $^1$H NMR (400 MHz, CDCl$_3$) δ: 7.72-7.68 (m, 3H), 7.37-7.34 (m, 1H), 7.15-7.10 (m, 2H), 3.94 (s, 2H), 3.81-3.76 (m, 4H), 3.74 (s, 3H), 3.50-3.44 (m, 1H), 1.02 (s, 9H), 0.25 (s, 6H).

Example 131: methyl 1-((6-hydroxynaphthalen-2-yl)methyl)azetidine-3-carboxylate

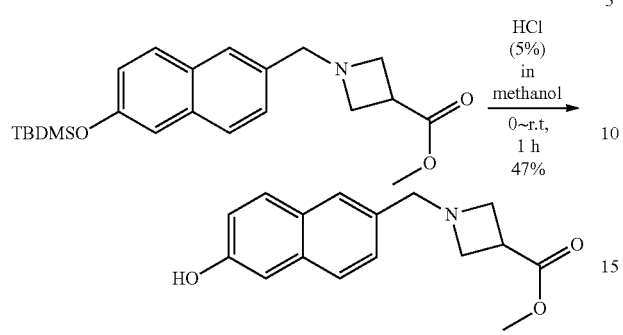

To a solution of methyl 1-((6-(tert-butyldimethylsilyloxy)naphthalen-2-yl)methyl)azetidine-3-carboxylate (4.5 g, 11.7 mmol) in methanol (50 mL) at 0° C. was added con. HCl (5 mL) dropwise. The reaction mixture was stirred at r.t for 1 h. The mixture was neutralized by sat. NaHCO$_3$ and evaporated off most of solvent, extracted with DCM and washed with brine, dried over Na$_2$SO$_4$ and concentrated to obtain crude product. The crude product was purified by silica gel chromatography (DCM:MeOH=40:1), extracted with DCM and washed with brine, dried over Na$_2$SO$_4$ and concentrated to obtain crude product. The crude product was purified by silica gel chromatography (DCM:MeOH=40:1) to give the title compound (1.5 g, 47%) as a gray solid. ESI-MS (M+1)$^+$: 272.0. $^1$H NMR (400 MHz, CDCl$_3$) δ: 8.14 (s, 1H), 7.59-7.52 (m, 2H), 7.39-7.28 (m, 2H), 7.09-7.04 (m, 2H), 3.92 (s, 2H), 3.86-3.82 (m, 2H), 3.70 (s, 3H), 3.63-3.59 (m, 2H), 3.52-3.46 (m, 1H).

Example 132: methyl 1-((6-(4-(trifluoromethyl)cyclohexyloxy)naphthalen-2-yl)methyl)azetidine-3-carboxylate

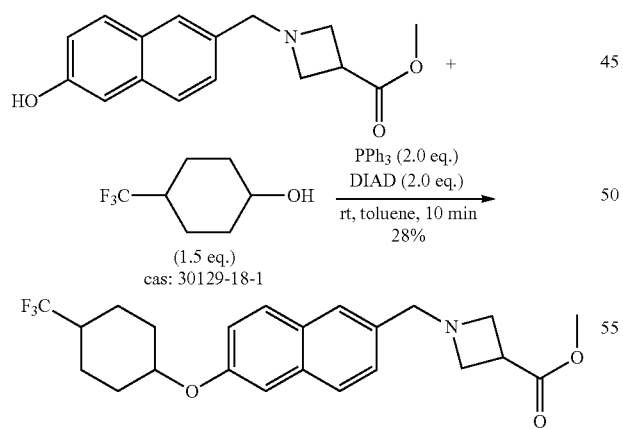

To a vial was added methyl 1-((6-hydroxynaphthalen-2-yl)methyl)azetidine-3-carboxylate (271 mg, 1.0 mmol), 4-(trifluoromethyl) cyclohexanol (252 mg, 1.5 mmol, 1.5 equiv), PPh$_3$ (524 mg, 2.0 mmol, 2.0 equiv) and toluene (0.8 mL) under N$_2$ atmosphere. While stirring, DIAD (404 mg, 2.0 mmol, 2.0 equiv) was added to the reaction mixture quickly at r.t and stirred for 10 min. The reaction mixture was then purified by silica gel chromatography (PE:EA=5:1) to give the title compound (114 mg, 28%) as a slight yellow oil. ESI-MS (M+1)$^+$: 408.2. $^1$H NMR (400 MHz, CD$_3$OD) δ: 7.76 (d, 1H), 7.70 (d, 1H), 7.66 (s, 1H), 7.36 (dd, 1H), 7.24 (d, 1H), 7.17 (dd, 1H), 4.86-4.76 (m, 1H), 3.74 (s, 2H), 3.70 (s, 3H), 3.56-3.51 (m, 2H), 3.32-3.34 (m, 3H), 2.33-2.22 (m, 1H), 2.20 (d, 2H), 1.82-1.67 (m, 6H).

Example 133: methyl 1-((6-((1R,3s,5S)-bicyclo[3.1.0]hexan-3-yloxy)naphthalen-2-yl)methyl)azetidine-3-carboxylate

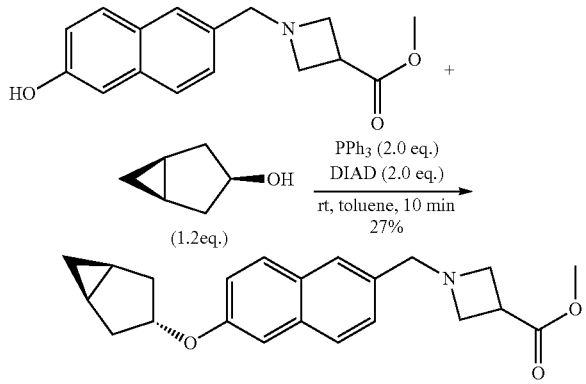

The preparation of the title compound was performed as described for methyl 1-((6-(4-(trifluoromethyl)cyclohexyloxy)naphthalen-2-yl)methyl)azetidine-3-carboxylate (Example 132). 100 mg, slight yellow oil, yield: 27% ESI-MS (M+1)$^+$:351.2. $^1$H NMR (400 MHz, CD$_3$OD) δ: 7.72 (d, 1H), 7.70 (d, 1H), 7.66 (s, 1H), 7.36 (dd, 1H), 7.16 (d, 1H), 7.08 (dd, 1H), 4.67-4.61 (m, 1H), 3.75 (s, 2H), 3.72 (s, 3H), 3.55 (t, 2H), 3.44 (t, 2H), 3.39-3.35 (m, 1H), 2.45 (q, 2H), 1.97-1.93 (m, 2H), 1.44-1.40 (m, 2H), 0.51-0.48 (m, 1H), 0.20 (q, 1H).

Example 134: methyl 1-((6-(bi(cyclohexan)-4-yloxy)naphthalen-2-yl)methyl)azetidine-3-carboxylate

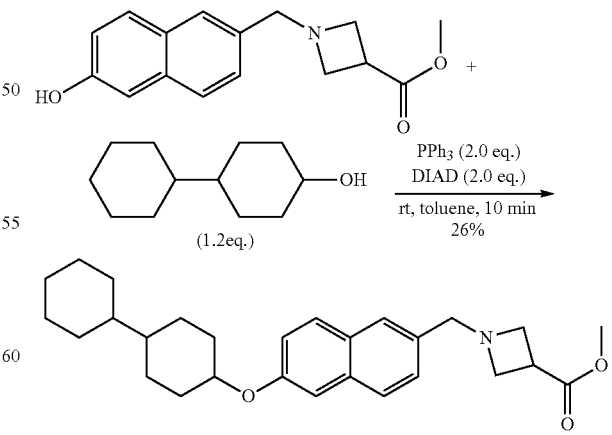

The preparation of the title compound was performed as described for methyl 1-((6-(4-(trifluoromethyl)cyclohexyloxy)naphthalen-2-yl)methyl)azetidine-3-carboxylate (Example 132). 100 mg, slight yellow oil, yield: 26% ESI-MS (M+1)⁺: 435.3 ¹H NMR (400 MHz, CD₃OD) δ: 7.76-7.70 (m, 2H), 7.66 (s, 1H), 7.36 (dd, 1H), 7.21 (d, 1H), 7.10 (dd, 1H), 4.33-4.39 (m, 1H), 3.77 (s, 2H), 3.72 (s, 3H), 3.57 (t, 2H), 3.46 (t, 2H), 3.39-3.35 (m, 1H), 2.26 (d, 2H), 1.89-1.40 (m, 9H), 1.30-1.09 (m, 9H)

Example 135: methyl 1-((6-(cyclohexyloxy)naphthalen-2-yl)methyl)azetidine-3-carboxylate

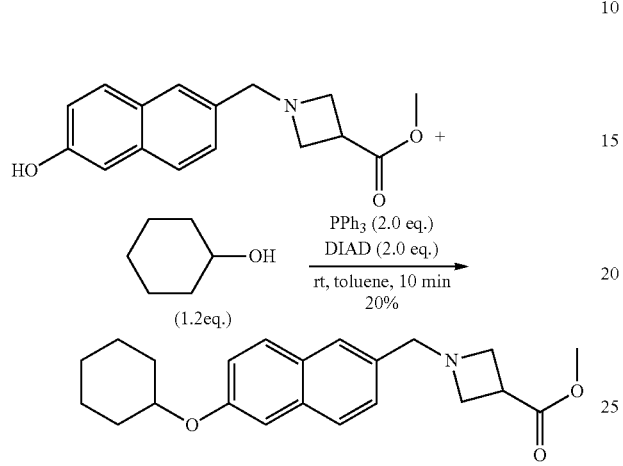

The preparation of the title compound was performed as described for methyl 1-((6-(4-(trifluoromethyl)cyclohexyloxy)naphthalen-2-yl)methyl)azetidine-3-carboxylate (Example 132). 100 mg, slight yellow oil, yield: 20%. ESI-MS (M+1)⁺: 354.2 ¹H NMR (400 MHz, CDCl₃) δ: 7.71-7.63 (m, 3H), 7.37 (dd, 1H), 7.13 (dd, 2H), 5.01-4.95 (m, 2H), 4.42-4.36 (m, 1H), 3.78-3.76 (m, 2H), 3.71 (s, 3H), 3.63-3.61 (m, 1H), 3.40-3.38 (m, 2H), 2.07 (d, 2H), 1.82 (d, 2H), 1.60-1.54 (m, 3H), 1.43-1.37 (m, 3H)

Example 136: methyl 1-((6-((trans)-4-cyclopentylcyclohexyloxy)naphthalen-2-yl)methyl)azetidine-3-carboxylate

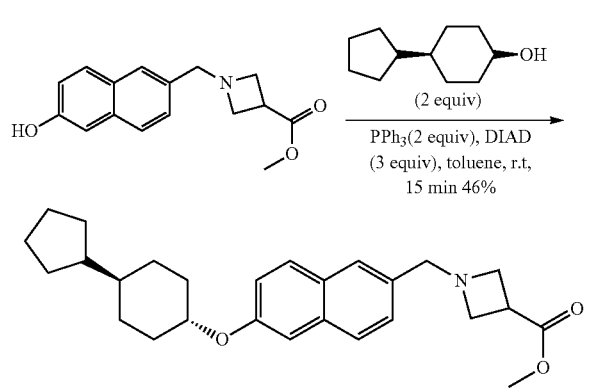

The preparation of the title compound was performed as described or methyl 1-((6-(4-(trifluoromethyl)cyclohexyloxy)naphthalen-2-yl)methyl)azetidine-3-carboxylate (Example 132). 217 mg, slight yellow oil, yield: 46%. ESI-MS (M+1)⁺: 422.3. ¹H NMR (400 MHz, CDCl₃) δ: 7.73~7.59 (m, 3H), 7.38~7.31 (m, 1H), 7.16~7.08 (m, 2H), 4.32~4.22 (m, 1H), 3.72 (s, 2H), 3.71 (s, 3H), 3.57-3.56 (m, 2H), 3.38-3.34 (m, 3H), 2.26~2.17 (m, 2H), 1.96~1.87 (m, 2H), 1.83~1.71 (m, 2H), 1.68~1.39 (m, 12H).

Example 137: methyl 1-((6-(((trans)-4-tert-butylcyclohexyloxy)naphthalen-2-yl)methyl)azetidine-3-carboxylate

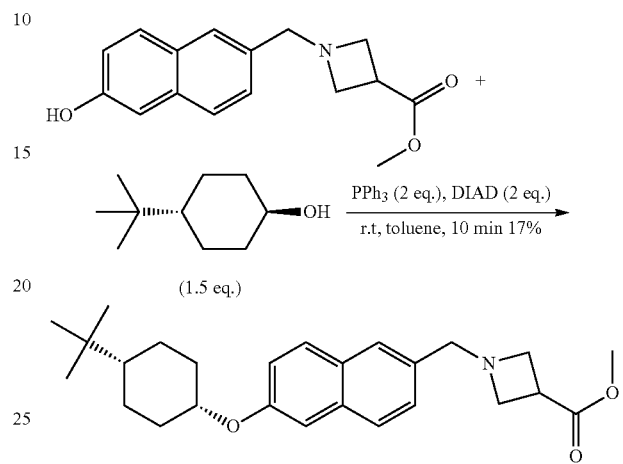

The preparation of the title compound was performed as described for methyl 1-((6-(4-(trifluoromethyl)cyclohexyloxy)naphthalen-2-yl)methyl)azetidine-3-carboxylate (Example 132). 67 mg, slight yellow oil, yield: 17%. ESI-MS (M+1)⁺: 410.3 ¹H NMR (400 MHz, CDCl₃) δ: 7.72-7.65 (m, 3H), 7.38 (d, 1H), 7.16 (dd, 2H), 4.68-6.66 (m, 1H), 3.80 (s, 2H), 3.72 (s, 3H), 3.66-3.64 (m, 2H), 3.42-3.40 (m, 3H), 2.18 (d, 2H), 1.59-1.49 (m, 7H), 0.89 (s, 9H)

Example 138: methyl 1-((6-(4-methylcyclohexyloxy)naphthalen-2-yl)methyl)azetidine-3-carboxylate

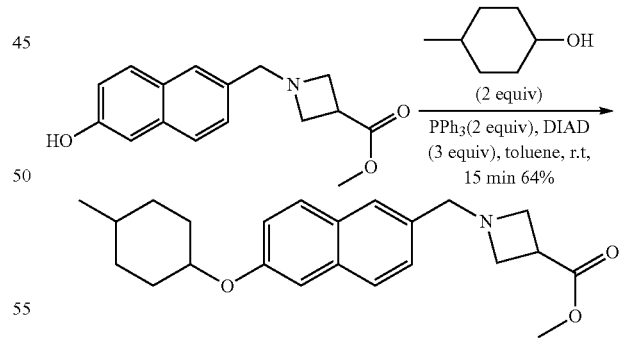

The preparation of the title compound was performed as described for methyl 1-((6-(4-(trifluoromethyl)cyclohexyloxy)naphthalen-2-yl)methyl)azetidine-3-carboxylate (Example 132). 216 mg, slight yellow oil, yield: 64%. ESI-MS (M+1)⁺: 368.2. ¹H NMR (400 MHz, CDCl₃) δ: 7.74~7.61 (m, 3H), 7.38~7.32 (m, 1H), 7.18~7.08 (m, 2H), 4.66~4.24 (m, 1H), 3.75 (s, 2H), 3.71 (s, 3H), 3.62~3.52 (m, 2H), 3.43~3.31 (m, 3H), 2.23~2.01 (m, 2H), 1.65~1.56 (m, 2H), 1.54~1.38 (m, 5H), 0.99~0.90 (m, 3H).

Example 139: methyl 1-((6-(4-propylcyclohexyloxy)naphthalen-2-yl)methyl)azetidine-3-carboxylate

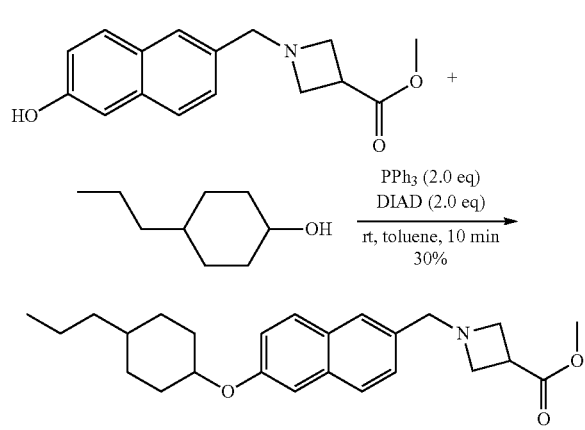

The preparation of the title compound was performed as described for methyl 1-((6-(4-(trifluoromethyl)cyclohexyloxy)naphthalen-2-yl)methyl)azetidine-3-carboxylate (Example 132). ESI-MS (M+1)+: 396.3. ¹H NMR (400 MHz, CDCl₃) δ: 7.72-7.66 (m, 3H), 7.37 (d, 1H), 7.16-7.12 (m, 2H), 4.76-4.66 (m, 1H), 3.74-3.66 (m, 5H), 3.59-3.52 (m, 2H), 3.40-3.33 (m, 3H), 2.25-1.85 (m, 2H), 1.60-1.55 (m, 11H), 0.90 (t, 3H).

Example 140: methyl 1-((6-(4-butylcyclohexyloxy)naphthalen-2-yl)methyl)azetidine-3-carboxylate

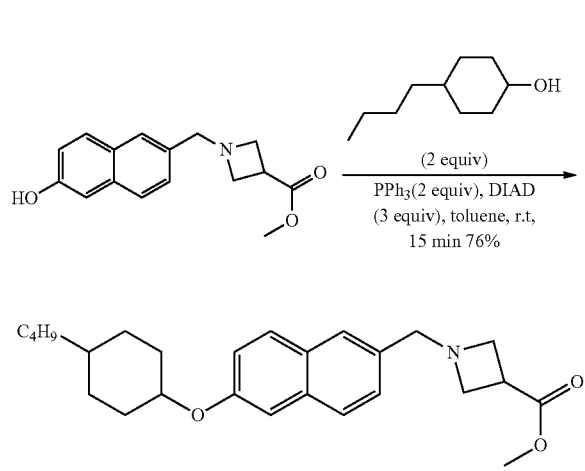

The preparation of the title compound was performed as described for methyl 1-((6-(4-(trifluoromethyl)cyclohexyloxy)naphthalen-2-yl)methyl)azetidine-3-carboxylate (Example 132). 292 mg, slight yellow oil, yield: 76%. ESI-MS (M+1)+: 410.3. ¹H NMR (400 MHz, CDCl₃) δ: 7.73~7.60 (m, 3H), 7.39~7.32 (m, 1H), 7.18~7.09 (m, 2H), 4.67~4.20 (m, 1H), 3.75 (s, 2H), 3.71 (s, 3H), 3.65~3.52 (m, 2H), 3.42~3.33 (m, 3H), 2.25~2.05 (m, 2H), 1.92~1.83 (m, 2H), 1.61~1.37 (m, 6H), 1.17~0.98 (m, 5H), 0.93~0.80 (m, 3H).

Example 141: methyl 1-((6-(4-butylcyclohexyloxy)naphthalen-2-yl)methyl)azetidine-3-carboxylate

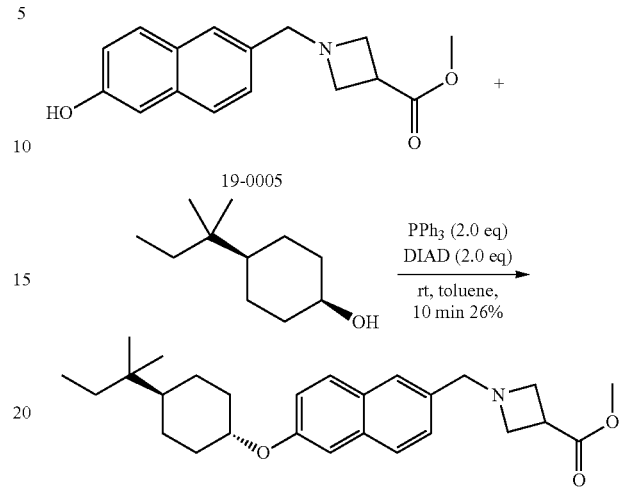

The preparation of the title compound was performed as described for methyl 1-((6-(4-(trifluoromethyl)cyclohexyloxy)naphthalen-2-yl)methyl)azetidine-3-carboxylate (Example 132). ESI-MS (M+1)+: 424.3. ¹H NMR (400 MHz, CD₃OD) δ: 7.73-7.64 (m, 3H), 7.34 (dd, 1H), 7.20 (d, 1H), 7.09 (dd, 1H), 4.40-4.30 (m, 1H), 3.76-3.66 (m, 5H), 3.55-3.32 (m, 5H), 2.28-2.25 (m, 2H), 1.85-1.82 (m, 2H), 1.39-1.27 (m, 7H), 0.91-0.81 (m, 9H).

Example 142: (trans)-methyl 4-hydroxycyclohexanecarboxylate

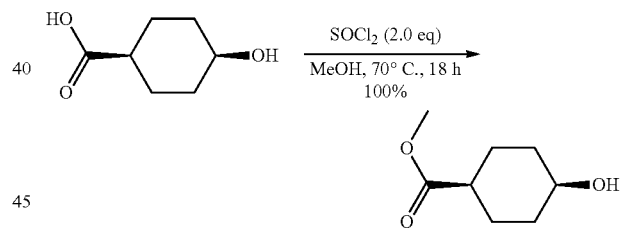

To a solution of (trans)-4-hydroxycyclohexanecarboxylic acid (4.32 g, 30 mmol) in MeOH (20 mL) was added SOCl₂ (7.08 g, 60 mmol, 2.0 eq) dropwise at rt. Then the mixture was stirred at 70° C. for 18 h, and the solvent was removed in vacuo to give the title compound as a colorless oil (4.74 g, yield: 100%). ¹H NMR (400 MHz, DMSO-d₆) δ: 4.33 (br, 1H), 3.68-3.60 (m, 1H), 3.57 (s, 3H), 2.37-2.31 (m, 1H), 1.82-1.74 (m, 2H), 1.53-1.45 (m, 6H).

Example 143: (trans)-methyl 4-(tetrahydro-2H-pyran-2-yloxy)cyclohexanecarboxylate

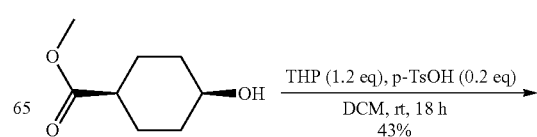

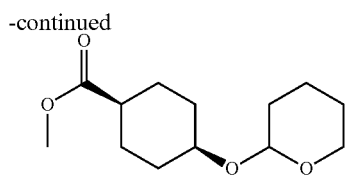

To a solution of (trans)-methyl 4-hydroxycyclohexanecarboxylate (4.74 g, 30 mmol) and THP (3.06 g, 3.6 mmol, 1.2 eq) in DCM (20 mL) was added p-TsOH (1.18 g, 6 mmol, 0.2 eq) slowly at rt. Then the mixture was stirred at rt for 18 h, and the solvent was removed in vacuo. The residue was purified on silica gel (EA/PE=1:20) to give the title compound as a colorless oil (3.12 g, yield: 43%). $^1$H NMR (400 MHz, CDCl$_3$) δ: 4.68 (t, 1H), 3.91-3.88 (m, 1H), 3.84-3.81 (m, 1H), 3.67 (s, 3H), 3.51-3.46 (m, 1H), 2.40-2.36 (m, 1H), 2.00-1.82 (m, 4H), 1.76-1.51 (m, 10H).

Example 144: 2-((trans)-4-(tetrahydro-2H-pyran-2-yloxy)cyclohexyl)propan-2-ol

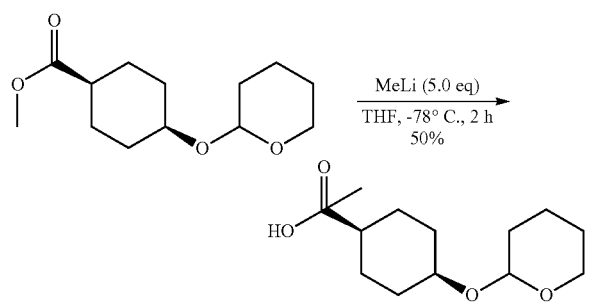

To a solution of (trans)-methyl 4-(tetrahydro-2H-pyran-2-yloxy)cyclohexanecarboxylate (3.12 g, 13 mmol) in THF (10 mL) was added MeLi (65 mL, 1 M, 5.0 eq) dropwise at −78° C., then the mixture was stirred at −78° C. for 2 h. Water (20 mL) was added and the mixture was extracted with EA (30 mL×3), dried and concentrated. The residue was purified on silica gel (EA/PE=1:10) to give the title compound as a colorless oil (1.56 g, yield: 50%). $^1$H NMR (400 MHz, CDCl$_3$) δ: 4.65 (t, 1H), 3.93-3.89 (m, 2H), 3.51-3.47 (m, 1H), 2.05-1.84 (m, 3H), 1.73-1.68 (m, 1H), 1.59-1.53 (m, 7H), 1.35-1.31 (m, 4H), 1.17 (d, 6H).

Example 145: 2-((trans)-4-(2-methoxypropan-2-yl)cyclohexyloxy)tetrahydro-2H-pyran

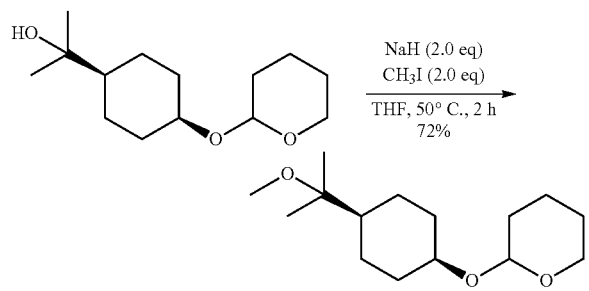

To a solution of 2-((trans)-4-(tetrahydro-2H-pyran-2-yloxy)cyclohexyl)propan-2-ol (1.56 g, 6.5 mmol) in THF (10 mL) was added NaH (300 mg, 13 mmol, 2.0 eq) slowly at r.t. and then CH$_3$I (1.96 g, 13 mmol, 2.0 eq) was added in one portion. The mixture was stirred at 50° C. for 2 h, Water (10 mL) was added and the mixture was extracted with EA (30 mL×3), dried and concentrated to give the title compound as a colorless oil (1.2 g, yield: 72%). $^1$H NMR (400 MHz, CDCl$_3$) δ: 4.64 (t, 1H), 3.93-3.89 (m, 2H), 3.51-3.47 (m, 1H), 3.17 (s, 3H), 1.97-1.85 (m, 3H), 1.70-1.67 (m, 1H), 1.58-1.43 (m, 9H), 1.34-1.27 (m, 2H), 1.09 (d, 6H).

Example 146: (trans)-4-(2-methoxypropan-2-yl)cyclohexanol

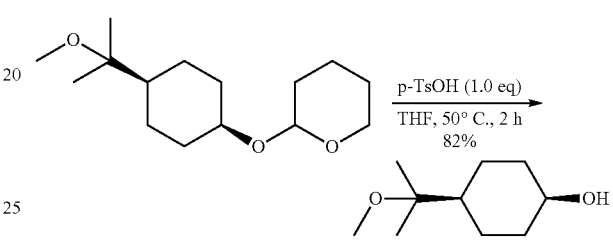

To a solution of 2-((trans)-4-(2-methoxypropan-2-yl)cyclohexyloxy)tetrahydro-2H-pyran (1.2 g, 4.7 mmol) in MeOH (10 mL) was added p-TsOH (8.9 g, 4.7 mmol, 1.0 eq) slowly at rt.

Then the mixture was stirred at rt for 2 h, and the solvent was removed in vacuo. The residue was purified on silica gel (EA/PE=1:3) to give the title compound as a colorless oil (660 mg, yield: 82%). $^1$H NMR (400 MHz, CDCl$_3$) δ: 4.07-4.05 (m, 1H), 3.17 (s, 3H), 1.87-1.82 (m, 2H), 1.55-1.38 (m, 7H), 1.10 (s, 6H).

Example 147: methyl 1-((6-((trans)-4-(2-methoxypropan-2-yl)cyclohexyloxy)naphthalen-2-yl)methyl)azetidine-3-carboxylate

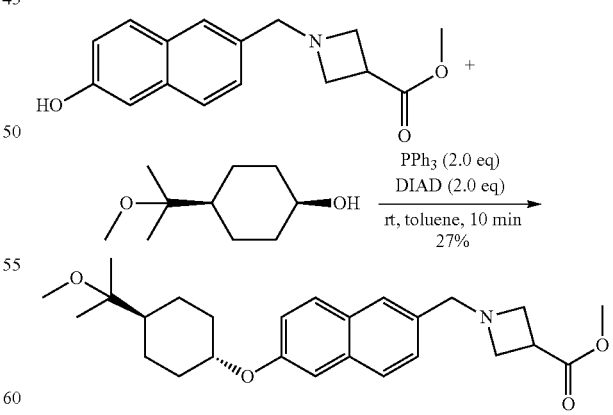

The preparation of the title compound was performed as described for methyl 1-((6-(4-(trifluoromethyl)cyclohexyloxy)naphthalen-2-yl)methyl)azetidine-3-carboxylate. ESI-MS (M+1)$^+$: 426.3. $^1$H NMR (400 MHz, CDCl$_3$) δ: 7.80-7.75 (m, 3H), 7.37 (d, 1H), 7.17-7.14 (m, 2H), 4.32-4.26 (m, 1H), 3.73-3.68 (m, 10H), 3.20 (s, 3H), 2.30-2.28 (m, 2H), 1.89-1.87 (m, 2H), 1.69-1.65 (m, 2H), 1.48-1.42 (m, 3H), 1.12 (s, 6H).

Example 148: methyl 1-((6-(4-isopropylcyclohexyloxy)naphthalen-2-yl)methyl)azetidine-3-carboxylate

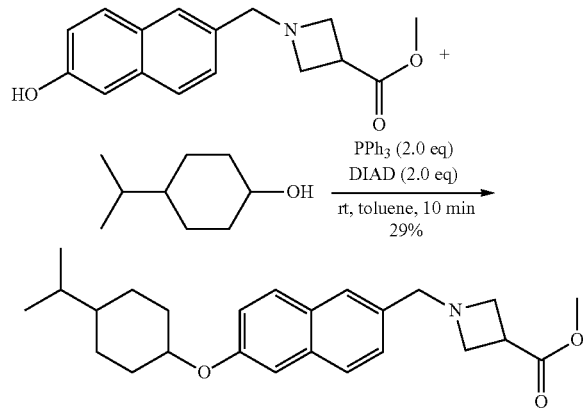

The preparation of the title compound was performed as described for methyl 1-((6-(4-(trifluoromethyl)cyclohexyloxy)naphthalen-2-yl)methyl)azetidine-3-carboxylate. ESI-MS (M+1)$^+$:396.3. $^1$H NMR (400 MHz, CD$_3$OD) δ: 7.73-7.64 (m, 3H), 7.38 (dd, 1H), 7.20-7.17 (m, 2H), 4.29-4.25 (m, 1H), 3.82 (s, 2H), 3.73-3.67 (m, 5H), 3.45-3.39 (m, 3H), 2.30-2.10 (m, 2H), 1.85-1.82 (m, 2H), 1.52-1.43 (m, 4H), 1.27-1.15 (m, 2H), 0.90 (d, 6H).

Example 149: 1-((6-(4-(trifluoromethyl)cyclohexyloxy)naphthalen-2-yl)methyl)azetidine-3-carboxylic acid

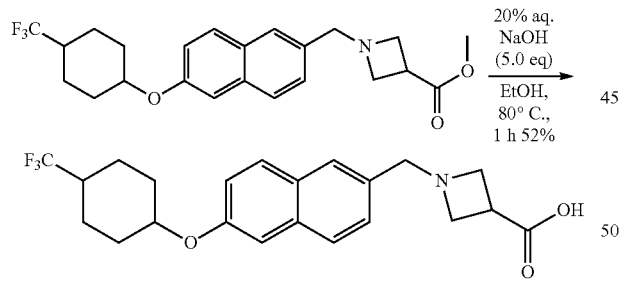

To a solution of methyl 1-((6-(4-(trifluoromethyl)cyclohexyloxy)naphthalen-2-yl)methyl)azetidine-3-carboxylate (100 mg, 0.26 mmol) in EtOH (15 mL) was added aqueous NaOH (3 mL, 20%, 5.0 eq.) and refluxed for 1 h. Then the reaction was cooled to 0° C., the pH of the solution was adjusted to 6 using 1M HCl, concentrated and the residue was dissolved in DCM, washed with water, dried and concentrated to give the title compound as a slight yellow solid (50 mg, yield: 52%). ESI-MS (M+1)$^+$: 408.2 HPLC: 94.97%. $^1$H NMR (400 MHz, CD$_3$OD) δ: 7.77 (d, 1H), 7.69 (d, 1H), 7.64 (s, 1H), 7.33 (d, 1H), 7.31 (s, 1H), 7.16 (dd, 1H), 4.80-4.71 (m, 1H), 3.57 (s, 2H), 3.25 (t, 2H), 3.09 (t, 2H), 2.79-2.73 (m, 1H), 2.41 (br, 1H), 2.07 (d, 2H), 1.80-1.60 (m, 6H).

Example 150: 1-((6-((trans)-4-(1,1-difluoroethyl)cyclohexyloxy)naphthalen-2-yl)methyl)azetidine-3-carboxylic acid

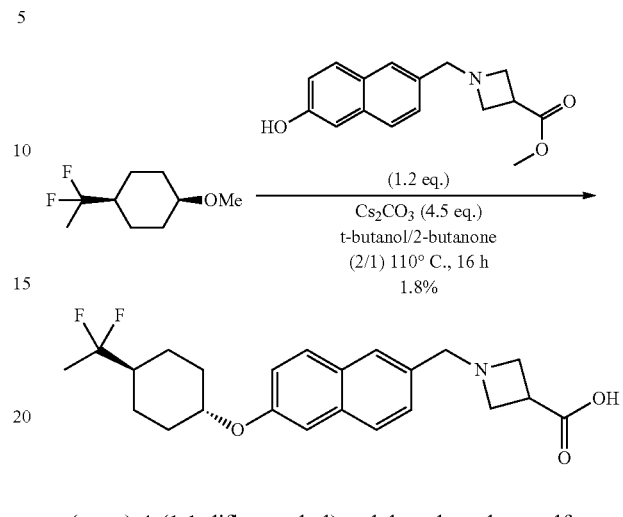

(trans)-4-(1,1-difluoroethyl)cyclohexyl methanesulfonate (WO 2010051030) (0.98 mmol, 236 mg, 1.0 eq.), methyl 1-((6-hydroxynaphthalen-2-yl)methyl)azetidine-3-carboxylate (1.17 mmol, 317 mg, 1.2 mmol) and Cs$_2$CO$_3$ (4.41 mmol, 1.4 g, 4.5 eq.) were dissolved in t-butanol (4 mL) and 2-butanone (2 mL). The mixture was stirred at 110° C. for 16 h. 1 M aq. HCl solution was added to the mixture to adjust pH=6. Then the mixture was extracted with EtOAc. The organic layer was purified by silica gel column chromatography using DCM/CH$_3$OH (10/1) as eluent to give product (7 mg, 1.8%) as a white solid. ESI-MS (M+1)$^+$: 404.1. HPLC: 89.46%. $^1$H NMR (400 MHz, CD$_3$OD) δ: 7.89 (s, 1H), 7.86-7.81 (m, 2H), 7.46 (dd, 1H), 7.31 (s, 1H), 7.19 (dd, 1H), 4.47 (s, 2H), 4.43-4.41 (m, 1H), 4.21 (d, 4H), 3.45~3.41 (m, 1H), 2.32-2.30 (m, 2H), 2.02-1.99 (m, 2H), 1.64-1.54 (m, 3H), 1.51-1.45 (m, 3H), 1.36-1.28 (m, 2H).

Example 151: 1-((6-((trans)-4-(1,1-difluoropropyl)cyclohexyloxy)naphthalen-2-yl)methyl)azetidine-3-carboxylic acid

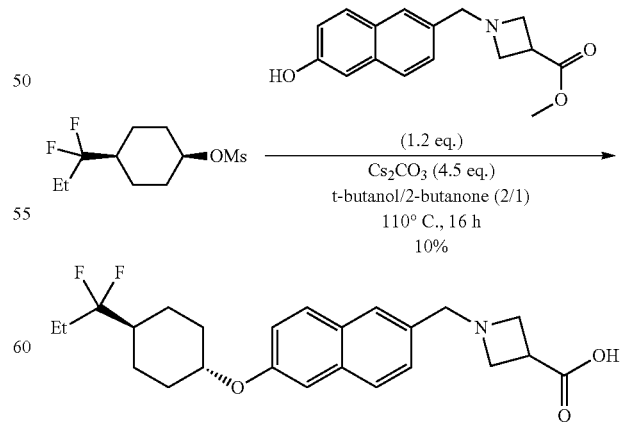

The preparation of the title compound was performed as described for 1-((6-((trans)-4-(1,1-difluoroethyl)cyclohexyloxy)naphthalen-2-yl)methyl)azetidine-3-carboxylic acid (Example 150). 22 mg, slight yellow solid, yield: 10%. ESI-MS (M+1)+: 418.1. HPLC: 93.94%. ¹H NMR (400 MHz, CD₃OD) δ: 7.91 (s, 1H), 7.87-7.82 (m, 2H), 7.46 (dd, 1H), 7.31 (s, 1H), 7.19 (dd, 1H), 4.53 (s, 2H), 4.44-4.40 (m, 1H), 4.34 (d, 4H), 3.74–3.69 (m, 1H), 2.32-2.30 (m, 2H), 1.98-1.85 (m, 5H), 1.51-1.46 (m, 4H), 1.02 (t, 3H).

Example 152: 1-((6-((1R,3s,5S)-bicyclo[3.1.0]hexan-3-yloxy)naphthalen-2-yl)methyl)azetidine-3-carboxylic acid

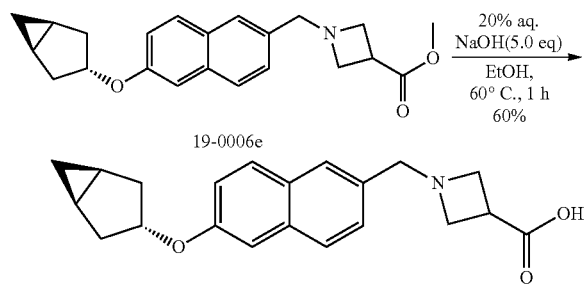

19-0006e

The preparation of the title compound was performed as described for methyl 1-((6-(4-(trifluoromethyl)cyclohexyloxy)naphthalen-2-yl)methyl)azetidine-3-carboxylic acid. 50 mg, slight yellow solid, yield: 60%. ESI-MS (M+1)+: 338.2. HPLC: 97.96%. ¹H NMR (400 MHz, CD₃OD) δ: 7.85 (s, 1H), 7.80-7.78 (m, 2H), 7.45 (d, 1H), 7.19 (dd, 1H), 7.14 (s, 1H), 4.65-4.58 (m, 1H), 4.41 (s, 2H), 4.21-4.15 (m, 4H), 3.39-3.37 (m, 1H), 2.48 (q, 2H), 2.04-1.98 (m, 2H), 1.46-1.42 (m, 2H), 0.56-0.53 (m, 1H), 0.17-0.15 (m, 1H).

Example 153: 1-((6-(bi(cyclohexan)-4-yloxy)naphthalen-2-yl)methyl)azetidine-3-carboxylic acid

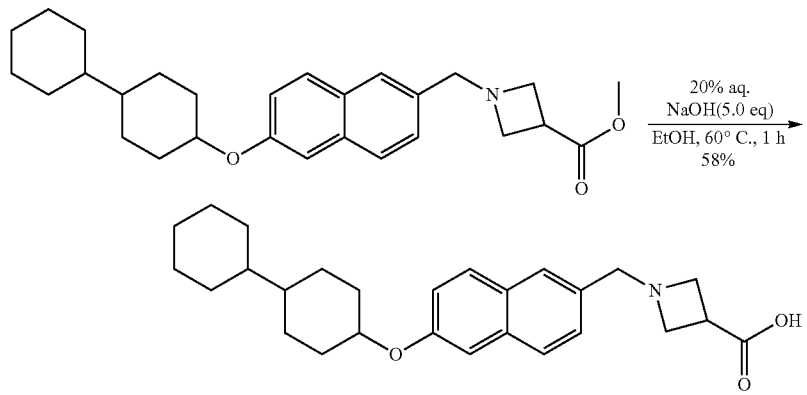

The preparation of the title compound was performed as described for methyl 1-((6-(4-(trifluoromethyl)cyclohexyloxy)naphthalen-2-yl)methyl)azetidine-3-carboxylic acid. 50 mg, slight yellow solid, yield: 58%. ESI-MS (M+1)+: 422.3 HPLC: 93.30%. ¹H NMR (400 MHz, CD₃OD) δ: 7.81-7.77 (m, 3H), 7.41 (d, 1H), 7.20 (s, 2H), 4.75-4.72 (m, 1H), 4.33 (s, 2H), 4.16-4.14 (m, 2H), 4.08-4.06 (m, 2H), 3.39-3.37 (m, 1H), 2.27 (d, 2H), 1.91-1.46 (m, 9H), 1.30-1.02 (m, 9H)

Example 154: 1-((6-(cyclohexyloxy)naphthalen-2-yl)methyl)azetidine-3-carboxylic acid

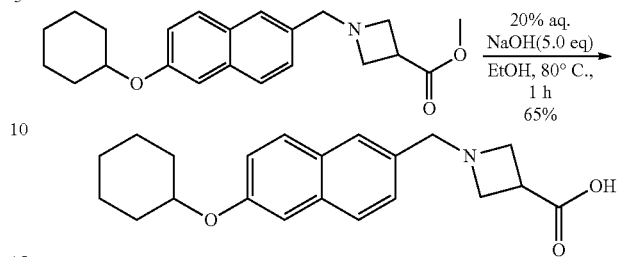

The preparation of the title compound was performed as described for methyl 1-((6-(4-(trifluoromethyl)cyclohexyloxy)naphthalen-2-yl)methyl)azetidine-3-carboxylic acid. 50 mg, slight yellow solid, yield: 65%. ESI-MS (M+1)+: 340.2 HPLC: 95.48%. ¹H NMR (400 MHz, CD₃OD) δ: 7.76-7.73 (m, 3H), 7.39 (d, 1H), 7.16 (dd, 2H), 4.45-4.40 (m, 1H), 4.21 (s, 2H), 3.97 (br, 4H), 3.37-3.32 (m, 1H), 2.04 (dd, 2H), 1.83 (dd, 2H), 1.63-1.48 (m, 3H), 1.46-1.33 (m, 3H)

Example 155: 1-((6-((trans)-4-cyclopentylcyclohexyloxy)naphthalen-2-yl)methyl)azetidine-3-carboxylic acid

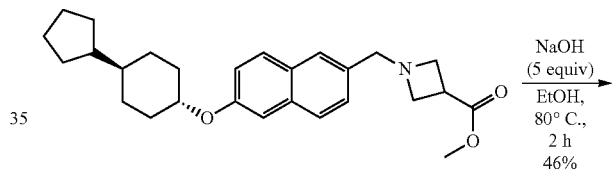

-continued

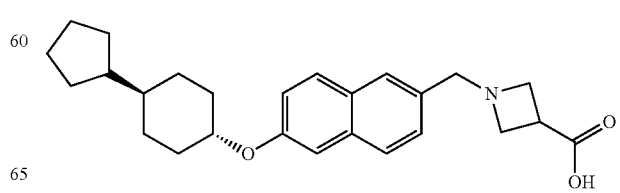

The preparation of the title compound was performed as described for methyl 1-((6-(4-(trifluoromethyl)cyclohexyloxy)naphthalen-2-yl)methyl)azetidine-3-carboxylic acid. 78 mg, slight yellow solid, yield: 46%. ESI-MS (M+1)⁺: 408.3 HPLC: 98.97%. ¹H NMR (400 MHz, CD₃OD) δ: 7.89 (s, 1H), 7.83 (dd, 2H), 7.44 (dd, 1H), 7.27 (d, 1H), 7.18 (dd, 1H), 4.51 (s, 2H), 4.42-4.37 (m, 1H), 4.33-4.31 (m, 4H), 3.72-3.64 (m, 1H), 2.21 (dd, 2H), 1.95 (dd, 2H) 1.83-1.78 (m, 2H), 1.65~1.42 (m, 7H), 1.22~1.14 (m, 5H)

Example 156: 1-((6-((trans)-4-tert-butylcyclohexyloxy)naphthalen-2-yl)methyl)azetidine-3-carboxylic acid

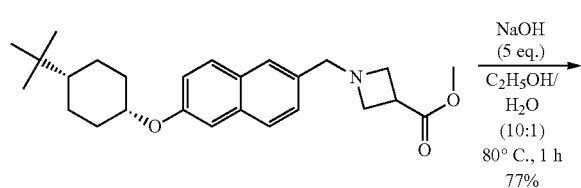

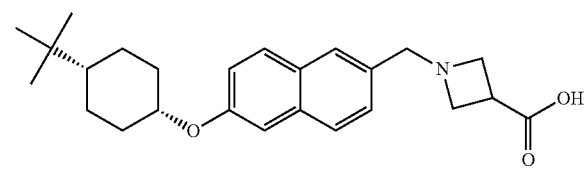

The preparation of the title compound was performed as described for methyl 1-((6-(4-(trifluoromethyl)cyclohexyloxy)naphthalen-2-yl)methyl)azetidine-3-carboxylic acid. 27 mg, slight yellow solid, yield: 77%. ESI-MS (M+1)⁺: 396.3 HPLC: 100%. ¹H NMR (400 MHz, CD₃OD) δ: 7.90 (s, 1H), 7.85 (dd, 2H), 7.45 (dd, 1H), 7.29 (d, 1H), 7.24 (dd, 1H), 4.77-4.75 (m, 1H), 4.47 (s, 2H), 4.22-4.20 (m, 4H), 3.45-3.40 (m, 1H), 2.20 (d, 2H), 1.65-1.49 (m, 6H), 1.20-1.14 (m, 1H), 0.93 (s, 9H)

Example 157: 1-((6-(4-methylcyclohexyloxy)naphthalen-2-yl)methyl)azetidine-3-carboxylic acid

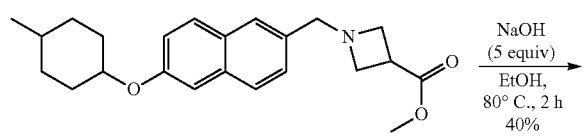

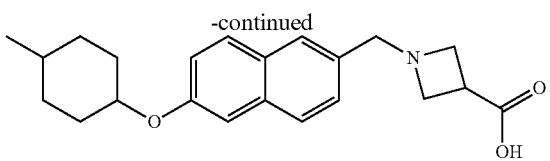

The preparation of the title compound was performed as described for methyl 1-((6-(4-(trifluoromethyl)cyclohexyloxy)naphthalen-2-yl)methyl)azetidine-3-carboxylic acid. 83 mg, slight yellow solid, yield: 40%. ESI-MS (M+1)⁺: 354.2 HPLC: 96.69%. ¹H NMR (400 MHz, CD₃OD) δ: 7.87 (s, 1H), 7.81 (dd, 2H), 7.43 (dd, 1H), 7.25 (d, 1H), 7.20 (dd, 1H), 4.73-4.69 (m, 1H), 4.50 (s, 2H), 4.35-4.30 (m, 4H), 3.71~3.64 (m, 1H), 2.02-1.98 (m, 2H), 1.83-1.38 (m, 7H), 0.94 (d, 3H).

Example 158: 1-((6-(4-propylcyclohexyloxy)naphthalen-2-yl)methyl)azetidine-3-carboxylic acid

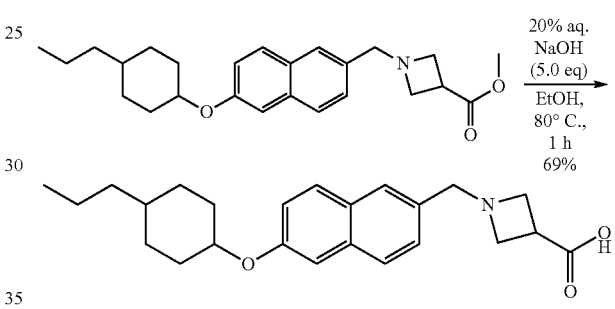

The preparation of the title compound was performed as described for methyl 1-((6-(4-(trifluoromethyl)cyclohexyloxy)naphthalen-2-yl)methyl)azetidine-3-carboxylic acid. 65 mg, yield: 69% ESI-MS (M+1)⁺: 382.2 HPLC: 96.32%. ¹H NMR (400 MHz, CD₃OD) δ: 7.85-7.78 (m, 3H), 7.43 (dd, 1H), 7.22-7.15 (m, 2H), 4.75-4.71 (m, 1H), 4.36 (s, 2H), 4.12-4.10 (m, 4H), 3.41-3.36 (m, 1H), 2.23-1.86 (m, 2H), 1.68-1.57 (m, 3H), 1.46-1.24 (m, 8H), 0.93 (t, 3H).

Example 159: 1-((6-(4-butylcyclohexyloxy)naphthalen-2-yl)methyl)azetidine-3-carboxylic acid

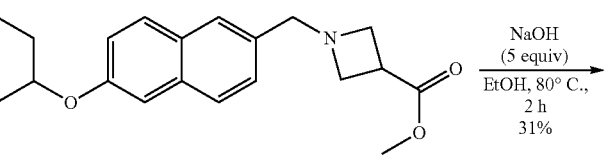

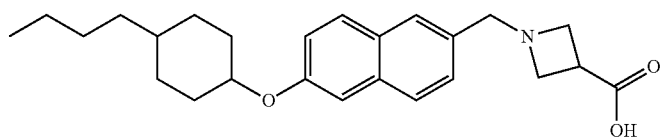

The preparation of the title compound was performed as described for methyl 1-((6-(4-(trifluoromethyl)cyclohexyloxy)naphthalen-2-yl)methyl)azetidine-3-carboxylic acid. 60 mg, slight yellow solid, yield: 31%. ESI-MS (M+1)⁺: 396.3 HPLC: 98.15%. ¹H NMR (400 MHz, DMSO-d₆) δ: 7.94 (s, 1H), 7.85 (dd, 2H), 7.53 (dd, 1H), 7.39 (dd, 1H), 7.20 (dd, 1H), 4.76-4.74 (m, 1H), 4.45 (s, 2H), 4.15-4.13 (m, 4H), 3.66-3.60 (m, 1H), 2.16 (d, 1H), 1.95 (d, 1H), 1.82 (d, 1H), 1.64-1.11 (m, 12H), 0.90 (t, 3H).

Example 160: 1-((6-((trans)-4-tert-pentylcyclohexyloxy)naphthalen-2-yl)methyl)azetidine-3-carboxylic acid The preparation of the title compound was performed as described for methyl 1-((6-(4-(trifluoromethyl)cyclohexyloxy)naphthalen-2-yl)methyl)azetidine-3-carboxylic acid. 60 mg, yield: 52% SI-MS (M+1)⁺: 412.2 PLC: 92.12%. ¹H NMR (400 MHz, CD₃OD) δ: 7.80-7.75 (m, 3H), 7.37 (d, 1H), 7.17-7.14 (m, 2H), 4.36-4.30 (m, 3H), 4.13-4.07 (m, 4H), 3.36-3.31 (m, 1H), 3.19 (s, 3H), 2.29-2.26 (m, 2H), 1.88-1.85 (m, 2H), 1.59-1.10 (m, 3H), 1.31-1.21 (m, 2H), 1.14 (s, 6H).

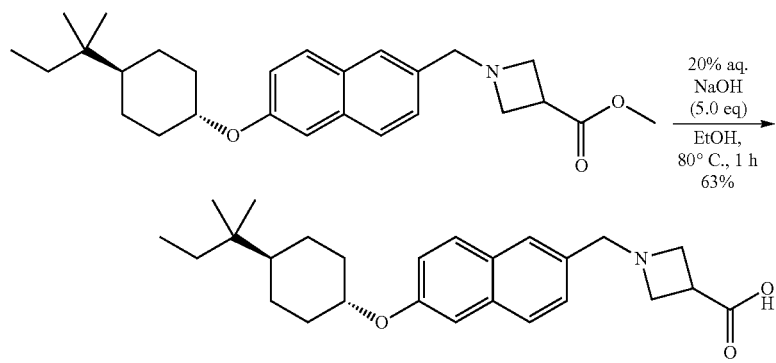

The preparation of the title compound was performed as described for methyl 1-((6-(4-(trifluoromethyl)cyclohexyloxy)naphthalen-2-yl)methyl)azetidine-3-carboxylic acid. 50 mg, yield: 63% ESI-MS (M+1)⁺: 410.3 HPLC: 93.22%. ¹H NMR (400 MHz, CD₃OD) δ: 7.91-7.82 (m, 3H), 7.46 (dd, 1H), 7.29 (d, 1H), 7.19 (dd, 1H), 4.53 (s, 2H), 4.39-4.34 (m, 5H), 3.74-3.70 (m, 1H), 2.30-2.27 (m, 2H), 1.89-1.86 (m, 2H), 1.45-1.26 (m, 7H), 0.85-0.88 (m, 9H).

Example 161: 1-((6-((trans)-4-(2-methoxypropan-2-yl)cyclohexyloxy)naphthalen-2-yl)methyl)azetidine-3-carboxylic acid Example 162: 1-((6-(4-isopropylcyclohexyloxy)naphthalen-2-yl)methyl)azetidine-3-carboxylic acid

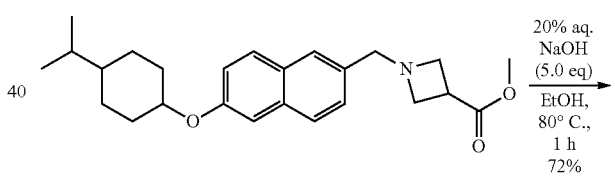

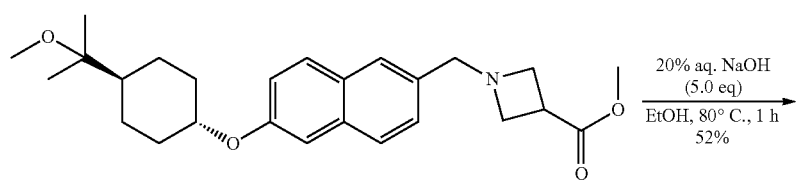

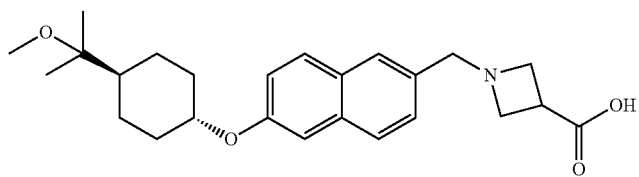

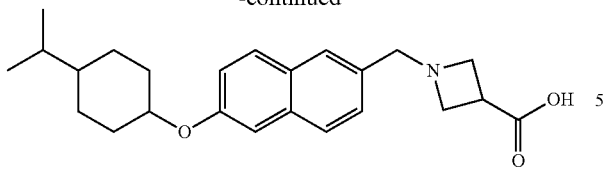

The preparation of the title compound was performed as described for methyl 1-((6-(4-(trifluoromethyl)cyclohexyloxy)naphthalen-2-yl)methyl)azetidine-3-carboxylic acid. 0 mg, yield: 72% SI-MS (M+1)+: 382.2 PLC: 92.20%. $^1$H NMR (400 MHz, CD$_3$OD) δ: 7.83-7.76 (m, 3H), 7.40 (dd, 1H), 7.23-7.15 (m, 2H), 4.39-4.34 (m, 3H), 4.16-4.11 (m, 4H), 4.38-4.34 (m, 1H), 2.26-2.10 (m, 2H), 1.87-1.84 (m, 1H), 1.61-1.43 (m, 5H), 1.22-1.16 (m, 2H), 0.94-0.90 (m, 6H).

Example 163:
6-Methoxy-2-methyl-4-trifluoromethyl-quinoline

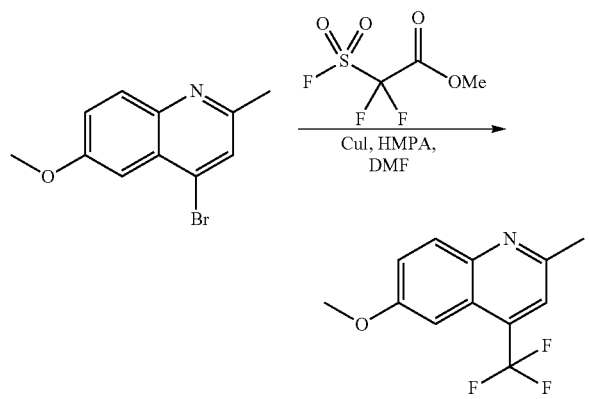

A solution of 4-Bromo-6-methoxy-2-methyl-quinoline (0.202 g, 0.801 mmol), Hexamethylphosphoramide (697 uL, 3.97 mmol) in N,N-Dimethylformamide (4.30 mL) was degassed by stirring under vacuum and replacing the vacuum with Argon (4 times). To this was added Copper(I) iodide (263 mg, 1.38 mmol) and Methyl fluorosulphonyldifluoroacetate (520 uL, 3.97 mmol) and the reaction was stirred under an atmosphere of Argon for 2 h @ 55° C., then at 80° C. for 16 hours. The reaction was evaporated, then diluted with methylene chloride. Silica gel was added and the solvent removed. The material was purified by silica gel chromatography using 0-50% ethyl acetate in hexanes as eluent (Rf=0.78 in 1:1 ethyl acetate/hexanes) to give the product in 40.5 mg yield (21%). ESI-MS(M+H+): 242.10.

Example 164:
2-Methyl-4-trifluoromethyl-quinolin-6-ol

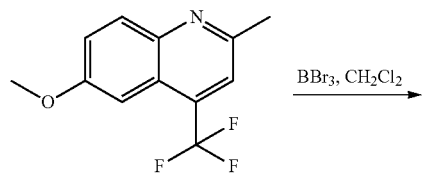

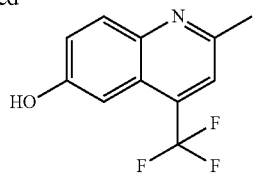

6-Methoxy-2-methyl-4-trifluoromethyl-quinoline (0.894 g, 3.71 mmol) was dissolved in Methylene chloride (60 mL), and cooled to −78° C. A solution of 1.0 M of Boron tribromide in Methylene chloride(11.0 mL, 11.0 mmol) was then added dropwise. The reaction mixture was then warmed up to 23° C. The reaction was allowed to stir 22 h at room temperature. After cooling in an ice bath, saturated sodium bicarbonate solution was added with stirring. The mixture was extracted with methylene chloride and ethyl acetate. The organics were dried over sodium sulfate, filtered and evaporated. The residue was purified by silica gel chromatography using 0-15% methanol in methylene chloride to give the product (Rf=0.49 in 10% methanol in methylene chloride) in 771 mg yield (92%). ESI-MS(M+H+): 228.10.

Example 165: 6-(trans-4-tert-Butyl-cyclohexyloxy)-2-methyl-4-trifluoromethyl-quinoline

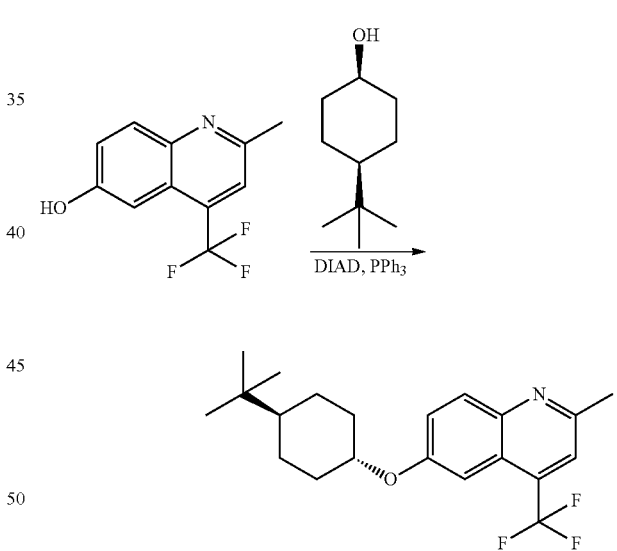

2-Methyl-4-trifluoromethyl-quinolin-6-ol (0.771 g, 0.00339 mol, cis-4-tert-Butyl-cyclohexanol (0.8570 g, 0.005484 mol) and Triphenylphosphine (1.423 g, 0.005425 mol) were placed in a flask, and dissolved in Toluene (25 mL). For the Mitsunobu reaction of certain analogs, THF was substituted for toluene as solvent. Diisopropyl azodicarboxylate (1.137 mL, 0.005430 mol) was then added dropwise. After 3 d stirring at RT, the reaction was evaporated to dryness. The residue was purified by silica gel chromatography using 0-30% ethyl acetate in hexanes as eluent (Rf=0.38 in 3:1 hexanes/ethyl acetate). Isolated was 0.739 g of product (60%). ESI-MS(M+H+): 366.20.

Example 166: 6-(trans-4-tert-Butyl-cyclohexyloxy)-4-trifluoromethyl-quinoline-2-carbaldehyde

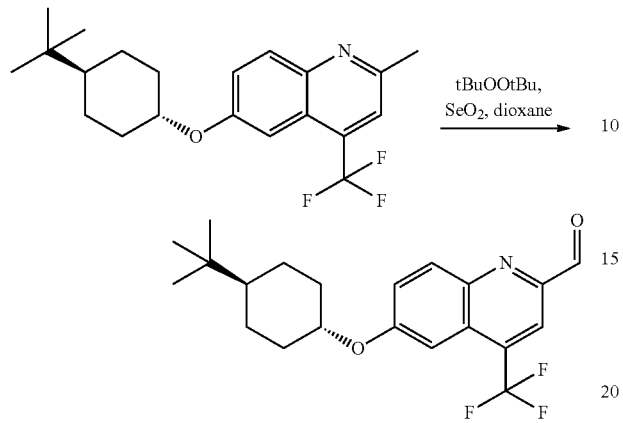

Di-tert-butyl peroxide (0.186 mL, 1.01 mmol) was added to a suspension of Selenium dioxide (0.252 g, 2.27 mmol) in 1,4-Dioxane (6.0 mL). The mixture was stirred for 30 minutes, then 6-(4-tert-Butyl-cyclohexyloxy)-2-methyl-4-trifluoromethyl-quinoline (0.366 g, 1.00 mmol) was added as a solution in 1,4-Dioxane (2.0 mL). The mixture was sealed and was heated at 50° C. for 20 h. The reaction was filtered through Celite and washed with dioxane. The solvent was evaporated and the residue was purified on silica gel column using 0-20% ethyl acetate in hexanes as eluent. Isolated was (Rf=0.70 in 3:1 hexanes/ethyl acetate) the product (212 mg, 56%). ESI-MS(M+H+): 380.20.

Example 167: 1-[6-(trans-4-tert-Butyl-cyclohexyloxy)-4-trifluoromethyl-quinolin-2-ylmethyl]-azetidine-3-carboxylic acid methyl ester

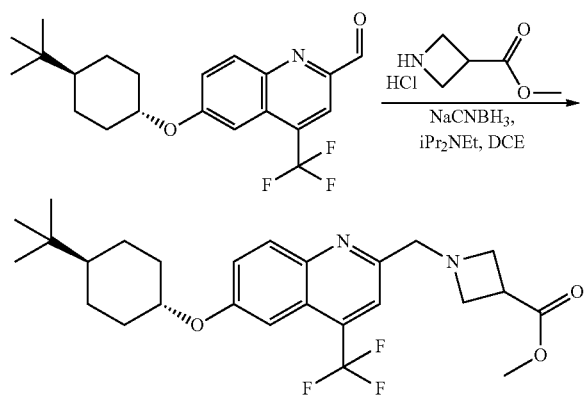

N,N-Diisopropylethylamine (39 uL, 0.22 mmol) was added to a solution of 6-(4-trans-tert-Butyl-cyclohexyloxy)-4-trifluoromethyl-quinoline-2-carbaldehyde (61 mg, 0.16 mmol) and Azetidine-3-carboxylic acid methyl ester hydrochloride salt (34 mg, 0.22 mmol) in 1,2-Dichloroethane (2.50 mL) and the mixture was stirred for 1 hour at room temperature. Sodium triacetoxyborohydride (54 mg, 0.25 mmol) was then added and stirring was continued. After 1.5 h, the reaction was diluted in methylene chloride and washed with saturated aq. sodium bicarbonate. The organic phase was dried over magnesium sulfate, filtered, evaporated and purified by flash chromatography (0-5% methanol in methylene chloride) to give the product (Rf=0.30 in 5% methanol/methylene chloride) in 65.8 mg yield (86%). ESI-MS (M+H+): 479.30.

Example 168: 1-[6-(trans-4-tert-Butyl-cyclohexyloxy)-4-trifluoromethyl-quinolin-2-ylmethyl]-azetidine-3-carboxylic acid

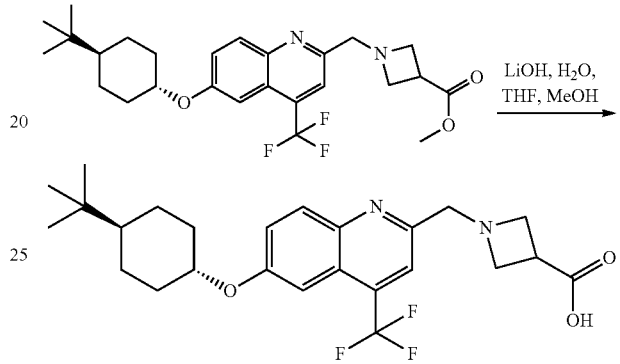

2 M of Lithium hydroxide, monohydrate in Water (0.500 mL, 1.00 mmol) was added to a solution of 1-[6-(4-trans-tert-Butyl-cyclohexyloxy)-4-trifluoromethyl-quinolin-2-ylmethyl]-azetidine-3-carboxylic acid methyl ester (0.0658 g, 0.137 mmol) in Tetrahydrofuran (0.500 mL) and Methanol (0.500 mL). The mixture was stirred at room temperature. After 1 hour, the solvent was concentrated under reduced pressure. The residue was dissolved in methylene chloride and treated with 1.00 M of Hydrogen chloride in water (1.00 mL). The organic phases were dried with magnesium sulfate, filtered and concentrated. Purification by preparative HPLC gave the product in 37.0 mg yield (39%) as bis-TFA salt. ESI-MS(M+H+): 465.3; 1H NMR (400 MHz, METHANOL-d4) Shift 8.16 (d, J=9.29 Hz, 1H), 7.83 (s, 1H), 7.58 (dd, J=2.51, 9.29 Hz, 1H), 7.39 (br. s., 1H), 4.90 (s, 2H), 4.35-4.44 (m, 1H), 3.83 (t, J=7.78 Hz, 1H), 2.29 (d, J=10.79 Hz, 2H), 1.89-2.00 (m, 2H), 1.42-1.56 (m, 2H), 1.08-1.34 (m, 3H), 0.94 (s, 9H). 1.6 TFA per molecule.

Example 169: 3-{[6-(trans-4-tert-Butyl-cyclohexyloxy)-4-trifluoromethyl-quinolin-2-ylmethyl]-amino}-propionic acid Synthesized as per 1-[6-(trans-4-tert-Butyl-cyclohexyloxy)-4-trifluoromethyl-quinolin-2-ylmethyl]-azetidine-3-carboxylic acid (Example 168) using the appropriate amine. ESI-MS(M+H+): 453.2; 1H NMR (400 MHz, METHANOL-d4) Shift 8.15 (d, J=9.29 Hz, 1H), 7.85 (s, 1H), 7.56 (dd, J=2.26, 9.29 Hz, 1H), 7.38 (br. s., 1H), 4.65 (s, 2H), 4.28-4.45 (m, 1H), 3.48 (t, J=6.65 Hz, 2H), 2.88 (t, J=6.78 Hz, 2H), 2.27 (d, J=10.79 Hz, 2H), 1.74-2.03 (m, 2H), 1.38-1.54 (m, 2H), 1.18-1.32 (m, 2H), 1.04-1.18 (m, 1H), 0.79-0.94 (m, 9H). 1.6 TFA per molecule.

Example 170: 1-[6-(trans-4-tert-Butyl-cyclohexyloxy)-4-trifluoromethyl-quinolin-2-ylmethyl]-pyrrolidine-3-carboxylic acid Synthesized as per 1-[6-(trans-4-tert-Butyl-cyclohexyloxy)-4-trifluoromethyl-quinolin-2-ylmethyl]-azetidine-3-carboxylic acid (Example 168) using the appropriate amine. ESI-MS(M+H+): 479.2; 1H NMR (400 MHz, METHANOL-d4) Shift 8.17 (d, J=9.29 Hz, 1H), 7.85 (s, 1H), 7.58 (dd, J=2.38, 9.41 Hz, 1H), 7.39 (br. s., 1H), 4.85 (br. s., 2H), 4.32-4.44 (m, 1H), 3.39-3.53 (m, 1H), 2.51 (br. s., 1H), 2.41 (br. s., 1H), 2.27 (d, J=10.79 Hz, 2H), 1.86-1.99 (m, 2H), 1.34-1.55 (m, 2H), 1.19-1.34 (m, 2H), 1.03-1.19 (m, 1H), 0.91 (s, 9H). 1.3 TFA per molecule.

Example 171: 4-Bromo-2-methyl-quinolin-6-ol

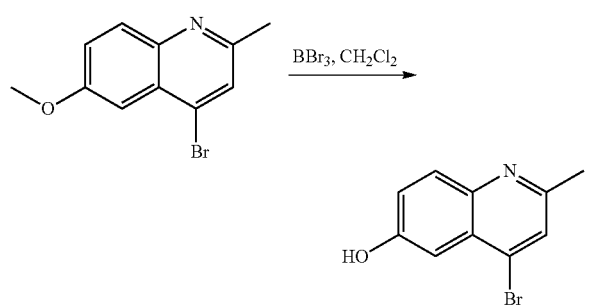

Synthesized as per 2-Methyl-4-trifluoromethyl-quinolin-6-ol using 4-Bromo-6-methoxy-2-methyl-quinoline as starting material. ESI-MS(M+H+): 238.00/240.00.

Example 172: 4-Bromo-6-(trans-4-tert-butyl-cyclohexyloxy)-2-methyl-quinoline

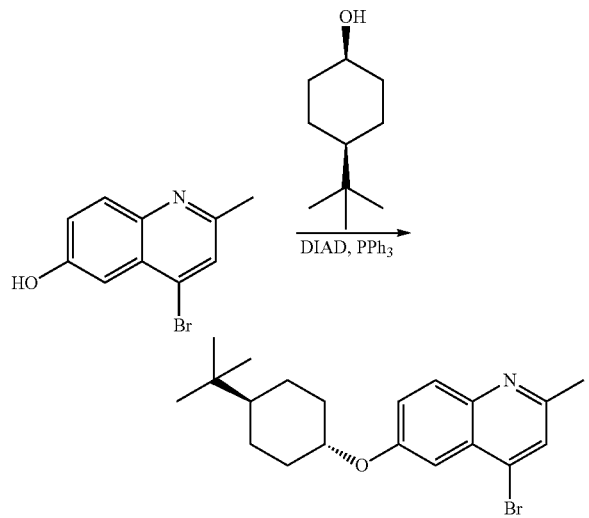

Synthesized as per 6-(trans-4-tert-Butyl-cyclohexyloxy)-2-methyl-4-trifluoromethyl-quinoline using 4-Bromo-2-methyl-quinolin-6-ol as starting material. ESI-MS(M+H+): 378.1.

Example 173: 4-Bromo-6-(trans-4-tert-butyl-cyclohexyloxy)-quinoline-2-carbaldehyde

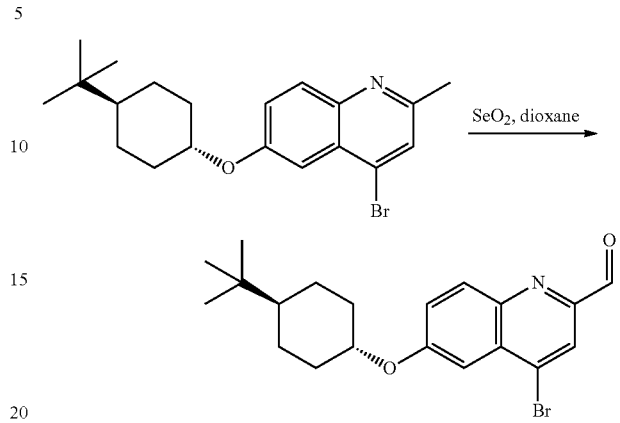

To a suspension of Selenium dioxide (0.333 g, 3.00 mmol) in 1,4-Dioxane (8.0 mL) was added a solution of 4-Bromo-6-(4-tert-butyl-cyclohexyloxy)-2-methyl-quinoline (0.469 g, 1.25 mmol) in 1,4-Dioxane (4.0 mL). The mixture was sealed and was heated at 50° C. in an oil bath. After 4 d, the reaction was filtered through Celite and washed with dioxane. The solvent was evaporated and the residue was purified on silica gel column using 0-25% ethyl acetate in hexanes as eluent. Isolated was the product (Rf=0.68 in 3:1 hexanes/ethyl acetate) in 362 mg yield, 74%. ESI(M+H+): 390.10/392.10.

Example 174: 1-[4-Bromo-6-(trans-4-tert-butyl-cyclohexyloxy)-quinolin-2-ylmethyl]-azetidine-3-carboxylic acid methyl ester

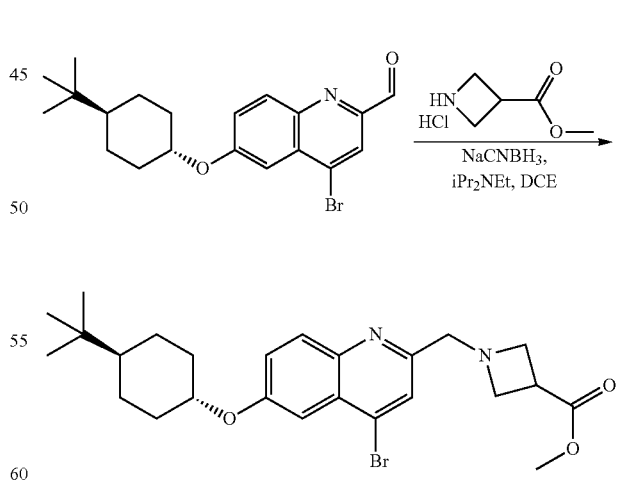

Synthesized as per 1-[6-(trans-4-tert-Butyl-cyclohexyloxy)-4-trifluoromethyl-quinolin-2-ylmethyl]-azetidine-3-carboxylic acid methyl ester using 4-Bromo-6-(trans-4-tert-butyl-cyclohexyloxy)-quinoline-2-carbaldehyde as starting material. ESI-MS(M+H+): 489.20/491.20.

Example 175: 1-[6-(trans-4-tert-Butyl-cyclohexyloxy)-4-methyl-quinolin-2-ylmethyl]-azetidine-3-carboxylic acid methyl ester

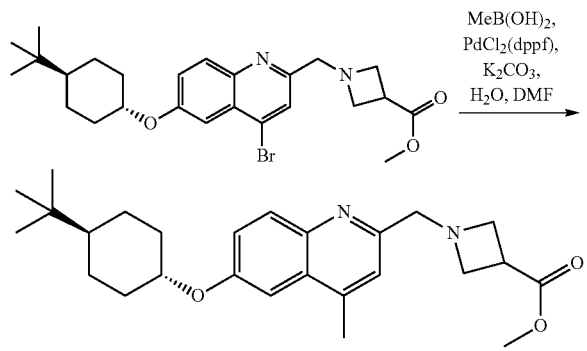

A mixture of 1-[4-Bromo-6-(trans-4-tert-butyl-cyclohexyloxy)-quinolin-2-ylmethyl]-azetidine-3-carboxylic acid methyl ester (0.100 g, 0.204 mmol), methylboronic acid (39 mg, 0.65 mmol), [1,1′-Bis(diphenylphosphino)ferrocene]dichloropalladium(II), complex with dichloromethane (1:1) (17 mg, 0.021 mmol), 2 M of Potassium carbonate in Water (0.306 mL, 0.613 mmol) and N,N-Dimethylformamide (2.5 mL) was added to a 40 mL vial equipped with a magnetic stir bar. The vial was degassed by stirring under a flow of Ar. The reaction mixture was stirred at 60° C. under Ar for 3 d. The reaction was cooled, diluted with water and extracted with ethyl acetate. The organics were washed with saturated sodium chloride, dried with sodium sulfate, filtered and evaporated. The residue was purified by silica gel chromatography using 0-10% methanol in methylene chloride as eluent (Rf=0.44 in 10% methanol/methylene chloride). Appropriate fractions were combined and evaporated. The product was further purified by preparative HPLC to give the product in 33 mg yield (25%) as bis-TFA salt. ESI-MS (M+H+): 425.30.

Example 176: 1-[6-(trans-4-tert-Butyl-cyclohexyloxy)-4-methyl-quinolin-2-ylmethyl]-azetidine-3-carboxylic acid

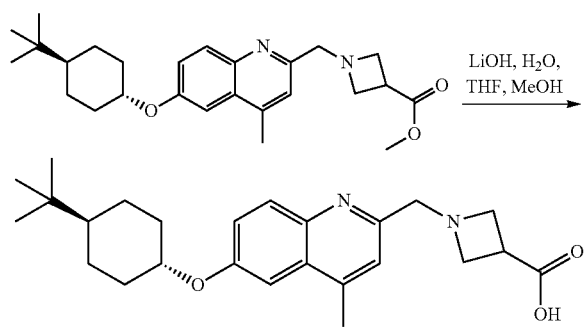

Synthesized as per 1-[6-(trans-4-tert-Butyl-cyclohexyloxy)-4-trifluoromethyl-quinolin-2-ylmethyl]-azetidine-3-carboxylic acid using 1-[6-(trans-4-tert-Butyl-cyclohexyloxy)-4-methyl-quinolin-2-ylmethyl]-azetidine-3-carboxylic acid methyl ester as starting material. ESI-MS (M+H+): 411.30; 1H NMR (400 MHz, METHANOL-d4) Shift 7.97 (d, J=9.29 Hz, 1H), 7.41 (dd, J=2.64, 9.16 Hz, 1H), 7.36 (d, J=2.51 Hz, 1H), 7.27 (s, 1H), 4.73 (s, 2H), 4.45-4.59 (m, 4H), 4.36-4.45 (m, 1H), 3.71-3.86 (m, 1H), 2.69 (s, 3H), 2.28 (d, J=11.29 Hz, 2H), 1.92 (d, J=10.79 Hz, 2H), 1.37-1.52 (m, 2H), 1.19-1.36 (m, 2H), 1.06-1.19 (m, 1H), 0.92 (s, 9H).

Example 177: 1-[6-(trans-4-tert-Butyl-cyclohexyloxy)-4-methyl-quinolin-2-ylmethyl]-pyrrolidine-3-carboxylic acid Synthesized as per 1-[6-(trans-4-tert-Butyl-cyclohexyloxy)-4-methyl-quinolin-2-ylmethyl]-azetidine-3-carboxylic acid using the appropriate amine. ESI-MS(M+H+): 425.3; 1H NMR (400 MHz, METHANOL-d4) Shift 8.00 (d, J=9.29 Hz, 1H), 7.43 (dd, J=2.51, 9.29 Hz, 1H), 7.38 (d, J=2.51 Hz, 1H), 7.32 (s, 1H), 4.63-4.76 (m, 2H), 4.36-4.49 (m, 1H), 3.68-3.90 (m, 2H), 3.54-3.68 (m, 2H), 3.37-3.51 (m, 1H), 2.71 (s, 3H), 2.45-2.57 (m, 1H), 2.34-2.45 (m, 1H), 2.29 (d, J=10.54 Hz, 2H), 1.87-1.98 (m, 2H), 1.37-1.53 (m, 2H), 1.20-1.37 (m, 2H), 1.07-1.20 (m, 1H), 0.92 (s, 9H).

Example 178: 3-{[6-(trans-4-tert-Butyl-cyclohexyloxy)-4-methyl-quinolin-2-ylmethyl]-amino}-propionic acid Synthesized as per 1-[6-(trans-4-tert-Butyl-cyclohexyloxy)-4-methyl-quinolin-2-ylmethyl]-azetidine-3-carboxylic acid using the appropriate amine. ESI-MS(M+H+): 399.3; 1H NMR (300 MHz, METHANOL-d4) Shift 7.88 (d, J=9.06 Hz, 1H), 7.26-7.35 (m, 2H), 7.21 (s, 1H), 4.40 (s, 2H), 4.27-4.38 (m, 1H), 3.31-3.38 (m, 2H), 2.77 (t, J=6.61 Hz, 2H), 2.61 (s, 3H), 2.19 (d, J=9.44 Hz, 2H), 1.77-1.89 (m, 2H), 1.28-1.43 (m, 2H), 1.10-1.26 (m, 2H), 0.97-1.10 (m, 1H), 0.83 (s, 9H).

Example 179: 1-[6-(trans-4-tert-Butyl-cyclohexyloxy)-4-cyclopropyl-quinolin-2-ylmethyl]-azetidine-3-carboxylic acid methyl ester

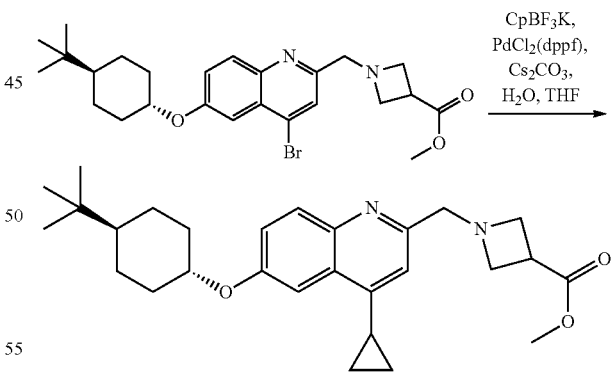

1-[4-Bromo-6-(trans-4-tert-butyl-cyclohexyloxy)-quinolin-2-ylmethyl]-azetidine-3-carboxylic acid methyl ester (0.100 g, 0.000204 mol), cyclopropyl trifluoroborate potassium salt (0.050 g, 0.00034 mol), [1,1′-Bis(diphenylphosphino)ferrocene]dichloropalladium(II), complex with dichloromethane (1:1) (0.019 g, 0.000023 mol), Cesium Carbonate (0.215 g, 0.000660 mol), Tetrahydrofuran (2.50 mL) and Water (0.25 mL) were added to a 40 mL vial equipped with a magnetic stir bar. The vial was degassed by stirring under a flow of Ar. The reaction was stirred under Ar for 3 d at 80° C. The reaction was cooled, diluted with water and extracted with ethyl acetate. The organics were washed with saturated sodium chloride, dried with sodium sulfate, filtered and evaporated. The residue was purified by silica gel chromatography using 0-10% methanol in DCM as eluent (Rf=0.44 in 10% methanol/DCM). The product was further purified by preparative HPLC. Appropriate fractions were combined to give the product in 76 mg yield (55%) as bis-TFA salt. ESI-MS(M+H+): 451.30.

Example 180: 1-[6-(trans-4-tert-Butyl-cyclohexyloxy)-4-cyclopropyl-quinolin-2-ylmethyl]-azetidine-3-carboxylic acid

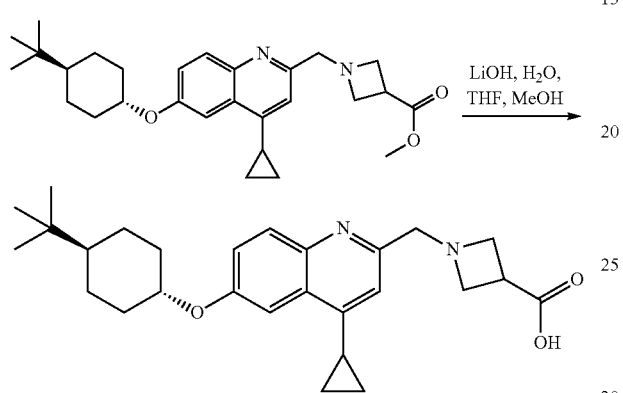

Synthesized as per 1-[6-(trans-4-tert-Butyl-cyclohexyloxy)-4-trifluoromethyl-quinolin-2-ylmethyl]-azetidine-3-carboxylic acid using 1-[6-(trans-4-tert-Butyl-cyclohexyloxy)-4-cyclopropyl-quinolin-2-ylmethyl]-azetidine-3-carboxylic acid methyl ester as starting material. ESI-MS (M+H+): 437.3; 1H NMR (400 MHz, METHANOL-d4) Shift 7.97 (d, J=9.04 Hz, 1H), 7.70 (d, J=2.76 Hz, 1H), 7.41 (dd, J=2.64, 9.16 Hz, 1H), 7.08 (s, 1H), 4.71 (s, 2H), 4.36-4.59 (m, 5H), 3.70-3.86 (m, 1H), 2.38-2.51 (m, 1H), 2.30 (d, J=10.54 Hz, 2H), 1.85-1.99 (m, 2H), 1.37-1.53 (m, 2H), 1.19-1.34 (m, 4H), 1.05-1.19 (m, 1H), 0.92 (s, 9H), 0.81-0.89 (m, 2H).

Example 181: 1-[6-(trans-4-tert-Butyl-cyclohexyloxy)-4-cyclopropyl-quinolin-2-ylmethyl]-pyrrolidine-3-carboxylic acid Synthesized as per 1-[6-(trans-4-tert-Butyl-cyclohexyloxy)-4-cyclopropyl-quinolin-2-ylmethyl]-azetidine-3-carboxylic acid using the appropriate intermediate available from the synthesis of 1-[6-(trans-4-tert-Butyl-cyclohehexyloxy)-4-methyl-quinolin-2-ylmethyl]-pyrrolidine-3-carboxylic acid). ESI-MS(M+H+): 451.3; 1H NMR (400 MHz, METHANOL-d4) Shift 7.99 (d, J=9.29 Hz, 1H), 7.70 (d, J=2.51 Hz, 1H), 7.42 (dd, J=2.64, 9.16 Hz, 1H), 7.13 (s, 1H), 4.60-4.72 (m, 2H), 4.35-4.49 (m, 1H), 3.81 (dd, J=6.53, 12.05 Hz, 1H), 3.72 (dd, J=8.66, 11.92 Hz, 1H), 3.50-3.66 (m, 2H), 3.37-3.49 (m, 1H), 2.42-2.55 (m, 2H), 2.38 (td, J=6.96, 13.68 Hz, 1H), 2.29 (d, J=10.29 Hz, 2H), 1.85-1.98 (m, 2H), 1.36-1.52 (m, 2H), 1.18-1.34 (m, 4H), 1.03-1.18 (m, 1H), 0.91 (s, 9H), 0.79-0.89 (m, 2H).

Example 182: 3-{[6-(trans-4-tert-Butyl-cyclohexyloxy)-4-cyclopropyl-quinolin-2-ylmethyl]-amino}-propionic acid Synthesized as per 1-[6-(trans-4-tert-Butyl-cyclohexyloxy)-4-cyclopropyl-quinolin-2-ylmethyl]-azetidine-3-carboxylic acid using the appropriate intermediate available from the synthesis of 3-{[6-(trans-4-tert-Butyl-cyclohexyloxy)-4-methyl-quinolin-2-ylmethyl]-amino}-propionic acid.) ESI-MS(M+H+): 425.3; 1H NMR (400 MHz, METHANOL-d4) Shift 8.00 (d, J=9.29 Hz, 1H), 7.72 (d, J=2.51 Hz, 1H), 7.43 (dd, J=2.64, 9.16 Hz, 1H), 7.14 (s, 1H), 4.50 (s, 2H), 4.40-4.49 (m, 1H), 3.44 (t, J=6.78 Hz, 2H), 2.87 (t, J=6.65 Hz, 2H), 2.44-2.54 (m, 1H), 2.32 (d, J=11.04 Hz, 2H), 1.91-1.99 (m, 2H), 1.42-1.54 (m, 2H), 1.21-1.36 (m, 4H), 1.07-1.21 (m, 1H), 0.94 (s, 9H), 0.84-0.92 (m, 2H).

Example 183: 6-Bromo-2-(4-tert-butyl-cyclohexyloxy)-quinoline

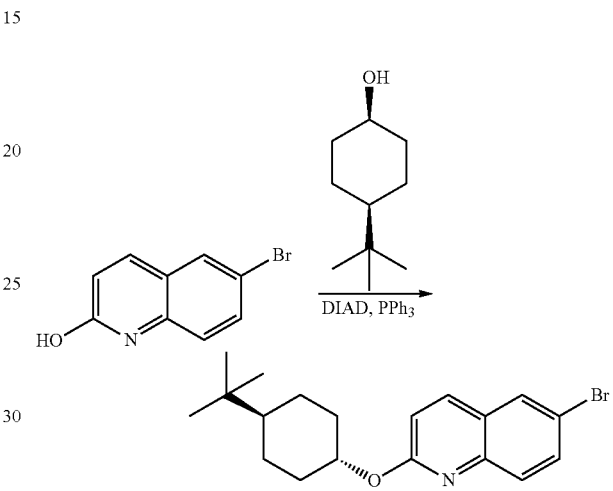

Synthesized as per 6-(trans-4-tert-Butyl-cyclohexyloxy)-2-methyl-4-trifluoromethyl-quinoline using 6-Bromo-quinolin-2-ol as starting material. Alkylation was confirmed to be on the oxygen by 2D NMR (HMQC) of the subsequent intermediate. ESI-MS(M+H+): 362.1/364.10).

Example 184: 2-(trans-4-tert-Butyl-cyclohexyloxy)-quinoline-6-carbaldehyde

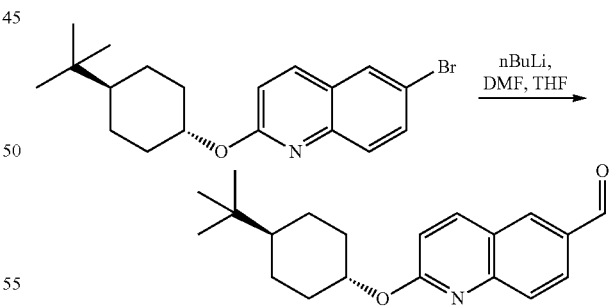

To 6-Bromo-2-(trans-4-tert-butyl-cyclohexyloxy)-quinoline (1.0933 g, 3.0176 mmol) in Tetrahydrofuran (24 mL) was added 1.6 M of n-Butyllithium in hexane (5.6 mL, 9.0 mmol) at −78° C. and the reaction was stirred for 15 min. N,N-Dimethylformamide (1.2 mL) was added and the reaction was stirred for 30 minutes. 1 M HCl was added and the reaction allowed to warm to RT. Saturated sodium bicarbonate solution was added and the mixture extracted with ethyl acetate. The organic layer was washed with saturated sodium chloride, dried with sodium sulfate, filtered and evaporated. The residue was purified by silica gel chromatography using hexanes/ethyl acetate (0-50%) as eluent to give product in 603 mg yield (64%). ESI-MS(M+H+): 312.20.

Example 185: 1-[2-(trans-4-tert-Butyl-cyclohexyloxy)-quinolin-6-ylmethyl]-azetidine-3-carboxylic acid methyl ester

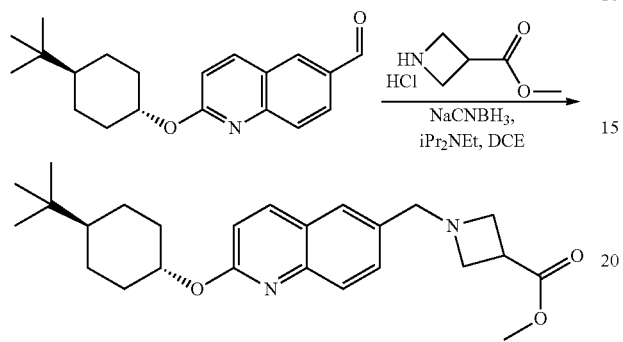

Synthesized as per 1-[6-(trans-4-tert-Butyl-cyclohexyloxy)-4-trifluoromethyl-quinolin-2-ylmethyl]-azetidine-3-carboxylic acid methyl ester using 2-(trans-4-tert-Butyl-cyclohexyloxy)-quinoline-6-carbaldehyde as starting material. ESI-MS(M+H+): 411.30.

Example 186: 1-[2-(trans-4-tert-Butyl-cyclohexyloxy)-quinolin-6-ylmethyl]-azetidine-3-carboxylic acid

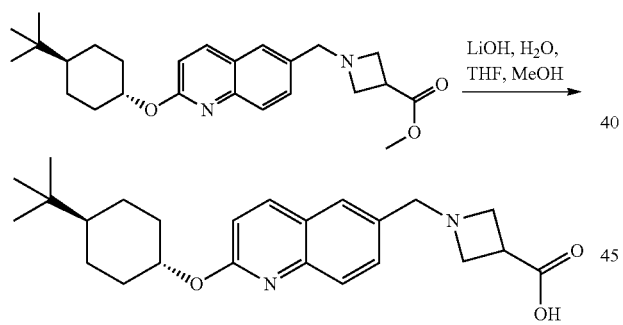

Synthesized as per 1-[6-(trans-4-tert-Butyl-cyclohexyloxy)-4-trifluoromethyl-quinolin-2-ylmethyl]-azetidine-3-carboxylic acid using 1-[2-(trans-4-tert-Butyl-cyclohexyloxy)-quinolin-6-ylmethyl]-azetidine-3-carboxylic acid methyl ester as starting material. ESI-MS(M+H+): 397.39; 1H NMR (400 MHz, METHANOL-d4) Shift 8.15 (d, J=8.78 Hz, 1H), 7.89-7.94 (m, 1H), 7.86 (d, J=8.78 Hz, 1H), 7.67 (dd, J=1.88, 8.66 Hz, 1H), 6.96 (d, J=8.78 Hz, 1H), 5.10-5.22 (m, 1H), 4.55 (s, 2H), 4.20-4.47 (m, 4H), 3.71 (quin, J=8.28 Hz, 1H), 2.28 (d, J=9.54 Hz, 2H), 1.92 (d, J=14.31 Hz, 2H), 1.36-1.52 (m, 2H), 1.19-1.36 (m, 2H), 1.06-1.19 (m, 1H), 0.92 (s, 9H).

Example 187: 1-[2-(trans-4-tert-Butyl-cyclohexyloxy)-quinolin-6-ylmethyl]-pyrrolidine-3-carboxylic acid Synthesized as per 1-[2-(trans-4-tert-Butyl-cyclohexyloxy)-quinolin-6-ylmethyl]-azetidine-3-carboxylic acid using the appropriate amine. ESI-MS(M+H+): 411.41; 1H NMR (400 MHz, METHANOL-d4) Shift 8.14 (d, J=8.78 Hz, 1H), 7.90-7.98 (m, 1H), 7.86 (d, J=8.53 Hz, 1H), 7.72 (dd, J=1.88, 8.66 Hz, 1H), 6.95 (d, J=8.78 Hz, 1H), 5.04-5.27 (m, 1H), 4.54 (br. s., 2H), 3.31-4.11 (m, 5H), 2.15-2.61 (m, 4H), 1.90 (d, J=13.05 Hz, 2H), 1.35-1.52 (m, 2H), 1.17-1.35 (m, 2H), 1.03-1.17 (m, 1H), 0.91 (s, 9H).

Example 188: 6-(trans-4-tert-butylcyclohexyloxy)-2-methylquinoline

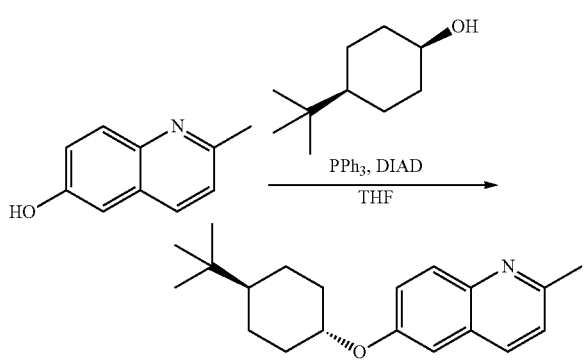

To a solution of 2-Methyl-quinolin-6-ol (4.13 g, 0.0259 mol), cis 4-tert-Butylcyclohexanol (4.86 g, 0.0311 mol) and triphenylphosphine (9.53 g, 0.0363 mol; Supplier=Aldrich) in tetrahydrofuran (100 mL, 1 mol; Supplier=Acros), cooled in an ice bath, was added diisopropyl azodicarboxylate (7.61 mL, 0.0363 mol; Supplier=Acros) in Tetrahydrofuran (10 mL, 0.1 mol; Supplier=Acros). The reaction mixture was stirred for 72 h allowing to reach room temperature. The solvent was removed under reduced pressure and the residue was taken up in methylene chloride, adsorbed onto silica gel and purified by flash chromatography (0-30% ethyl acetate in hexanes) to give the title compound in 56% yield. ESI-MS (M+H+): 298.3.

Example 189: 6-(trans-4-tert-butylcyclohexyloxy)quinoline-2-carbaldehyde

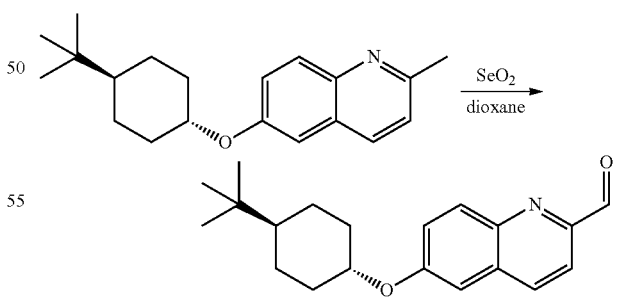

Di-tert-butyl peroxide (1.93 mL, 10.5 mmol) was added to a suspension of Selenium dioxide (2.68 g, 24.1 mmol) in 1,4-Dioxane (24.00 mL, 307.5 mmol). The mixture was stirred for 30 minutes, then 6-(trans-4-tert-Butyl-cyclohexyloxy)-2-methyl-quinoline (3.12 g, 10.5 mmol) was added as a solution in 1,4-Dioxane and the mixture was heated overnight at 50° C.

The reaction mixture was then cooled to room temperature, diluted in chloroform and filtered through a pad of celite. The filtrate was washed with water. The layers were separated and the combined organic phase was dried over MgSO$_4$, filtered, concentrated under reduced pressure, adsorbed onto silica gel and purified by flash chromatography (0-30% EtOAc in hexanes) to give the title compound as a pale yellow solid in 20% yield. ESI-MS (M+H+): 312.27.

Example 190: tert-butyl 3-((6-(trans-4-tert-butylcyclohexyloxy) quinolin-2yl) methylamino) propanoate

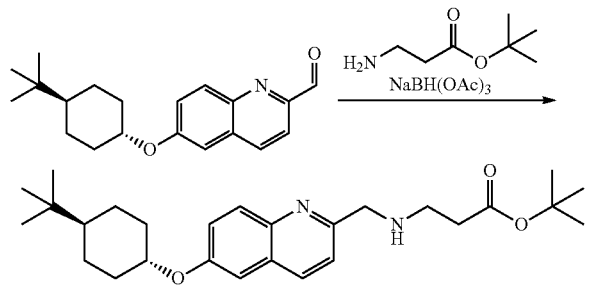

A solution of triethylamine (0.07356 mL, 0.5278 mmol), 6-(trans-4-tert-Butyl-cyclohexyloxy)-quinoline-2-carbaldehyde (0.1259 g, 0.4043 mmol) and β-alanine t-butyl ester HCl salt (0.08813 g, 0.4851 mmol) in 1,2-Dichloroethane (5.00 mL, 63.5 mmol) was stirred for 1 hour at room temperature. Sodium triacetoxyborohydride (0.1714 g, 0.8086 mmol) was then added and the mixture was stirred overnight. The reaction was diluted in methylene chloride and washed with saturated aq. sodium bicarbonate. The organic phase was dried over MgSO$_4$, filtered, adsorbed onto silica gel and purified by flash chromatography (0-5% MeOH in methylene chloride) to give the title compound in 66% yield. ESI-MS (M+H+): 441.50.

Example 191: 3-((6-((trans-4-tert-butylcyclohexyloxy) quinolin-2-yl) methylamino) propanoic acid

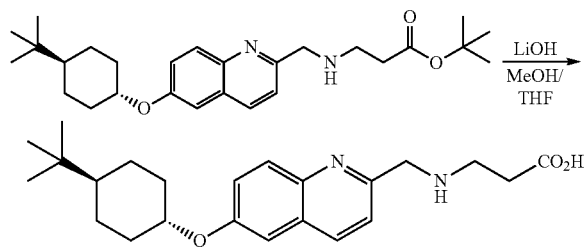

2 M of Lithium hydroxide, monohydrate in Water (1.00 mL, 2.00 mmol) was added to a solution of 3-{[6-(trans-4-tert-Butyl-cyclohexyloxy)-quinolin-2-ylmethyl]-amino}-propionic acid tert-butyl ester (0.2416 g, 0.5483 mmol) in Tetrahydrofuran (1.00 mL, 12.3 mmol) and Methanol (1.00 mL, 24.7 mmol). The mixture was stirred overnight at room temperature. The solvent was removed under reduced pressure and the residue was dissolved in methylene chloride and washed with water. The organic phase was concentrated under reduced pressure to give the title compound. ESI-MS (M+H+): 385.42. 1H NMR (400 MHz, MeOD) Shift 8.16 (d, J=8.53 Hz, 1H), 7.86 (d, J=9.04 Hz, 1H), 7.51 (d, J=8.53 Hz, 1H), 7.31 (dd, J=2.76, 9.04 Hz, 1H), 7.24 (d, J=2.51 Hz, 1H), 4.29-4.39 (m, 1H), 3.99 (s, 2H), 2.86 (t, J=6.90 Hz, 2H), 2.42 (t, J=6.90 Hz, 2H), 2.22-2.30 (m, 2H), 1.85-1.93 (m, 2H), 1.34-1.47 (m, 2H), 1.19-1.31 (m, 2H), 1.04-1.15 (m, 1H), 0.89 (s, 9H)

The following compounds were synthesized as 3-(6-(trans-4-tert-butylcyclohexyloxy)quinolin-2-yl) methylamino) propanoic acid using the appropriate cyclohexanols and aminoesters:

Example 192: 1-[6-(trans 4-tert-Butyl-cyclohexyloxy)-quinolin-2-ylmethyl]-pyrrolidine-3-carboxylic acid ESI-MS(M+H+): 411.64; 1H NMR (400 MHz, METHANOL-d4) Shift 8.56 (d, J=8.53 Hz, 1H), 8.11 (d, J=9.29 Hz, 1H), 7.75 (d, J=8.53 Hz, 1H), 7.55 (dd, J=2.76, 9.29 Hz, 1H), 7.48 (d, J=2.76 Hz, 1H), 4.90 (d, J=2.51 Hz, 2H), 4.40-4.51 (m, 1H), 3.78-3.93 (m, 2H), 3.60-3.74 (m, 2H), 3.45-3.55 (m, 1H), 2.54 (dt, J=6.96, 8.91 Hz, 1H), 2.37-2.47 (m, 1H), 2.29 (d, J=2.76 Hz, 2H), 1.89-1.98 (m, 2H), 1.41-1.53 (m, 2H), 1.24-1.37 (m, 2H), 1.11-1.20 (m, 1H), 0.92 (s, 9H)

Example 193: 1-[6-(trans 4-tert-Butyl-cyclohexyloxy)-quinolin-2-ylmethyl]-azetidine-3-carboxylic acid ESI-MS(M+H+): 397.44; 1H NMR (400 MHz, MeOD) Shift 8.26 (d, J=8.03 Hz, 1H), 7.97 (d, J=9.04 Hz, 1H), 7.37-7.42 (m, 2H), 7.30-7.34 (m, 1H), 4.79 (s, 2H), 4.48-4.59 (m, 4H), 4.34-4.44 (m, 1H), 2.66 (s, 1H), 2.25-2.33 (m, J=11.55 Hz, 2H), 1.89-1.97 (m, 2H), 1.38-1.51 (m, 2H), 1.22-1.35 (m, 2H), 1.07-1.19 (m, J=11.80 Hz, 1H), 0.93 (s, 9H)

Example 194: 1-[6-(trans 4-tert-Butyl-cyclohexyloxy)-quinolin-2-ylmethyl]-pyrrolidine-3-carboxylic acid Enantiomer 1, separated by chiral HPLC. ESI-MS(M+H+): 411.35; 1H NMR (400 MHz, DMSO-d6) Shift 8.16 (d, J=8.28 Hz, 1H), 7.83 (s, 1H), 7.50 (d, J=8.28 Hz, 1H), 7.38 (s, 1H), 7.31 (dd, J=2.76, 9.04 Hz, 1H), 4.31-4.42 (m, 1H), 3.77 (d, J=5.02 Hz, 2H), 2.80-2.90 (m, 1H), 2.69-2.77 (m, 1H), 2.52-2.67 (m, 4H), 2.15-2.24 (m, 2H), 1.88-2.00 (m, 2H), 1.76-1.85 (m, 2H), 1.28-1.40 (m, 2H), 1.14-1.27 (m, 2H), 0.87 (s, 9H)

Example 195: 1-[6-(trans 4-tert-Butyl-cyclohexyloxy)-quinolin-2-ylmethyl]-pyrrolidine-3-carboxylic acid Enantiomer 2, separated by chiral HPLC. ESI-MS(M+H+): 411.36; 1H NMR (400 MHz, DMSO-d6) Shift 8.16 (d, J=8.53 Hz, 1H), 7.82 (d, J=9.04 Hz, 1H), 7.50 (d, J=8.53 Hz, 1H), 7.38 (s, 1H), 7.28-7.34 (m, 1H), 4.32-4.42 (m, 1H), 3.78 (d, J=5.02 Hz, 2H), 2.83-2.92 (m, 1H), 2.71-2.77 (m, 1H), 2.51-2.68 (m, 4H), 2.17-2.24 (m, 2H), 1.89-2.00 (m, 2H), 1.77-1.85 (m, 2H), 1.29-1.41 (m, 2H), 1.14-1.27 (m, 2H), 0.87 (s, 9H)

Example 196: 1-[6-(trans 4-Cyclopentyl-cyclohexyloxy)-quinolin-2-ylmethyl]-pyrrolidine-3-carboxylic acid ESI-MS(M+H+): 423.33; 1H NMR (400 MHz, MeOD) Shift 8.29 (d, J=8.28 Hz, 1H), 8.01 (d, J=9.29 Hz, 1H), 7.40-7.48 (m, 2H), 7.34 (d, J=2.76 Hz, 1H), 4.77 (d, J=6.27 Hz, 2H), 4.38-4.49 (m, 1H), 3.79 (d, J=2.51 Hz, 2H), 3.65 (br. s., 2H), 3.43-3.52 (m, 1H), 2.52 (dq, J=7.02, 8.82 Hz, 1H), 2.43 (dt, J=6.87, 13.62 Hz, 1H), 2.20-2.29 (m, 2H), 1.93-2.02 (m, 2H), 1.78-1.89 (m, 2H), 1.41-1.71 (m, 7H), 1.11-1.30 (m, 5H)

Example 197: 1-[6-(trans 4-Cyclopentyl-cyclohexyloxy)-quinolin-2-ylmethyl]-azetidine-3-carboxylic acid ESI-MS(M+H+): 409.33; 1H NMR (400 MHz, MeOD) Shift 8.26 (d, J=8.53 Hz, 1H), 7.98 (d, J=9.29 Hz, 1H), 7.41-7.43 (m, 1H), 7.38-7.41 (m, 1H), 7.32 (d, J=2.51 Hz, 1H), 4.80 (s, 2H), 4.48-4.61 (m, 4H), 4.38-4.47 (m, 1H), 3.81 (quin, J=8.35 Hz, 1H), 2.20-2.28 (m, 2H), 1.93-2.01 (m, 2H), 1.79-1.88 (m, 2H), 1.40-1.71 (m, 7H), 1.12-1.29 (m, 5H)

Example 198: 3-{[6-(trans 4-Cyclopentyl-cyclohexyloxy)-quinolin-2-ylmethyl]-amino}-propionic acid ESI-MS(M+H+): 397.01; 1H NMR (400 MHz, MeOD) Shift 8.27 (d, J=8.28 Hz, 1H), 7.99 (d, J=9.29 Hz, 1H), 7.44 (d, J=8.53 Hz, 1H), 7.41 (dd, J=2.76, 9.29 Hz, 1H), 7.32 (d, J=2.76 Hz, 1H), 4.56 (s, 2H), 4.38-4.47 (m, 1H), 3.47 (t, J=6.65 Hz, 2H), 2.88 (t, J=6.78 Hz, 2H), 2.20-2.28 (m, 2H), 1.93-2.00 (m, 2H), 1.78-1.88 (m, 2H), 1.40-1.71 (m, 8H), 1.11-1.29 (m, 5H)

Example 199: 1-{6-[trans 4-(1,1-Dimethyl-propyl)-cyclohexyloxy]-quinolin-2-ylmethyl}-pyrrolidine-3-carboxylic acid ESI-MS(M+H+): 425.31; 1H NMR (400 MHz, MeOD) Shift 8.29 (d, J=8.28 Hz, 1H), 8.01 (d, J=9.29 Hz, 1H), 7.40-7.47 (m, 2H), 7.34 (d, J=2.76 Hz, 1H), 4.77 (d, J=6.02 Hz, 2H), 4.36-4.46 (m, 1H), 3.73-3.93 (m, 2H), 3.65 (br. s., 2H), 3.42-3.53 (m, 1H), 2.36-2.59 (m, 2H), 2.26-2.34 (m, 2H), 1.83-1.93 (m, 2H), 1.40-1.52 (m, 2H), 1.23-1.39 (m, 5H), 0.82-0.91 (m, 9H)

Example 200: 1-{6-[trans 4-(1,1-Dimethyl-propyl)-cyclohexyloxy]-quinolin-2-ylmethyl}-azetidine-3-carboxylic acid ESI-MS(M+H+): 411.32; 1H NMR (400 MHz, MeOD) Shift 8.26 (d, J=8.28 Hz, 1H), 7.97 (d, J=9.29 Hz, 1H), 7.41-7.43 (m, 1H), 7.37-7.40 (m, 1H), 7.32 (d, J=2.51 Hz, 1H), 4.80 (s, 2H), 4.48-4.60 (m, 4H), 4.35-4.44 (m, 1H), 3.81 (quin, J=8.35 Hz, 1H), 2.25-2.34 (m, 2H), 1.84-1.92 (m, 2H), 1.23-1.51 (m, 7H), 0.82-0.91 (m, 9H)

Example 201: 3-({6-[trans 4-(1,1-Dimethyl-propyl)-cyclohexyloxy]-quinolin-2-ylmethyl}-amino)-propionic acid ESI-MS(M+H+): 399.32; 1H NMR (400 MHz, MeOD) Shift 8.27 (d, J=8.28 Hz, 1H), 7.98 (d, J=9.29 Hz, 1H), 7.44 (d, J=8.53 Hz, 1H), 7.40 (dd, J=2.76, 9.29 Hz, 1H), 7.32 (d, J=2.76 Hz, 1H), 4.56 (s, 2H), 4.35-4.44 (m, 1H), 3.46 (t, J=6.78 Hz, 2H), 2.88 (t, J=6.78 Hz, 2H), 2.26-2.33 (m, 2H), 1.84-1.91 (m, 2H), 1.38-1.51 (m, 2H), 1.23-1.38 (m, 5H), 0.82-0.90 (m, 10H)

Example 202: (1S,2R)-2-{[6-(trans 4-tert-Butyl-cyclohexyloxy)-quinolin-2-ylmethyl]-amino}-cyclohexanecarboxylic acid ESI-MS(M+H+): 439.35; 1H NMR (400 MHz, MeOD) Shift 8.28 (d, J=8.28 Hz, 1H), 7.99 (d, J=9.04 Hz, 1H), 7.46 (d, J=8.28 Hz, 1H), 7.42 (dd, J=2.76, 9.29 Hz, 1H), 7.34 (d, J=2.76 Hz, 1H), 4.60 (s, 2H), 4.36-4.45 (m, 1H), 3.50 (dt, 1H), 2.04-2.35 (m, 2H), 1.89-1.99 (m, J=12.05 Hz, 3H), 1.59-1.69 (m, 2H), 1.40-1.53 (m, 3H), 1.14-1.36 (m, 3H), 0.93 (s, 9H)

Example 203: (1S,2S)-2-{[6-(trans-4-tert-Butyl-cyclohexyloxy)-quinolin-2-ylmethyl]-amino}-cyclohexanecarboxylic acid ESI-MS(M+H+): 439.36; 1H NMR (400 MHz, MeOD) Shift 8.29 (d, J=8.28 Hz, 1H), 7.98 (d, J=9.04 Hz, 1H), 7.47 (d, J=8.53 Hz, 1H), 7.41 (dd, J=2.76, 9.29 Hz, 1H), 7.34 (d, J=2.76 Hz, 1H), 4.69 (d, J=15.31 Hz, 1H), 4.56 (d, J=15.31 Hz, 1H), 4.36-4.46 (m, 1H), 3.48-3.60 (m, 1H), 2.65-2.75 (m, 1H), 2.26-2.39 (m, 4H), 1.90-1.99 (m, 3H), 1.86 (d, 1H), 1.36-1.60 (m, 5H), 1.24-1.36 (m, 2H), 1.17 (dt, 1H), 0.94 (s, 9H)

Example 204: (1S,2R)-2-{[6-(trans-4-tert-Butyl-cyclohexyloxy)-quinolin-2-ylmethyl]-amino}-cyclopentanecarboxylic acid ESI-MS(M+H+): 425.52; 1H NMR (400 MHz, MeOD) Shift 8.26-8.31 (m, 1H), 7.96-8.02 (m, 1H), 7.43-7.48 (m, 1H), 7.41 (dd, J=2.76, 9.29 Hz, 1H), 7.34 (d, J=2.76 Hz, 1H), 4.51-4.66 (m, 2H), 4.36-4.46 (m, 1H), 3.82-4.13 (m, 1H), 2.22-2.34 (m, 3H), 2.10-2.21 (m, 1H), 1.89-2.06 (m, 4H), 1.74-1.85 (m, 1H), 1.39-1.52 (m, 2H), 1.23-1.36 (m, 2H), 1.11-1.20 (m, 1H), 0.95 (s, 9H)

Example 205: 7-(trans 4-tert-butylcyclohexyloxy)-3-methylisoquinoline

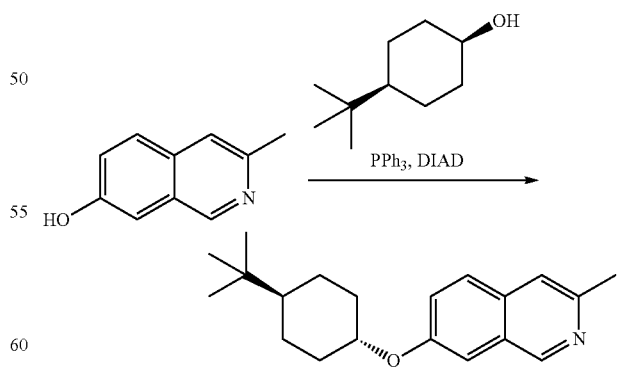

Triphenylphosphine (5.14 g, 19.6 mmol) was added to a solution of 3-Methyl-isoquinolin-7-ol (2.08 g, 13.1 mmol) and cis-4-tert-butylcyclohexanol (3.06 g, 19.6 mmol) in Toluene (60 mL, 600 mmol). The mixture was stirred for 15 minutes then Diisopropyl azodicarboxylate (3.86 mL, 19.6 mmol) was added. The mixture was then stirred at room temperature overnight. The solvent was removed under vacuum. The crude product was dissolved in methylene chloride, adsorbed onto silica gel and purified by flash chromatography (0-30% EtOAc in hexanes) to give the title compound in 52% yield. ESI-MS(M+H+): 298.46.

Example 206: 7-(trans-4-tert-butylcyclohexyloxy) isoquinoline-3-carbaldehyde

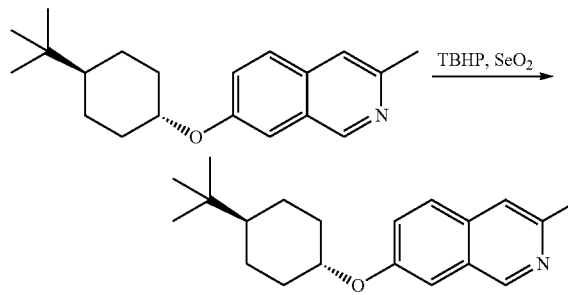

Selenium dioxide (2.25 g, 20.3 mmol) was added to a solution of 7-(trans-4-tert-Butyl-cyclohexyloxy)-3-methyl-isoquinoline (2.01 g, 6.76 mmol) in Diphenyl ether (50 mL, 300 mmol) and the mixture was heated at 200° C. in a sealed tube for 4 hours. The reaction was then cooled to room temperature. Silica gel was added and the flask was placed in a cold water bath to solidify the diphenylether solvent. This solid mixture containing the crude product was purified by flash chromatography (0-30% EtOAc in hexanes) to give the title compound in 50% yield. ESI-MS(M+H+): 312.27

Example 207: tert-butyl 3-((7-(trans-4-tert-butylcyclohexyloxy) isoquinolin-3-yl) methylamino) propanoate

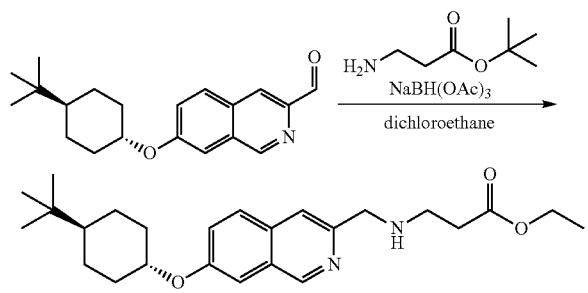

Triethylamine (0.07356 mL, 0.5278 mmol) was added to a solution of 7-(trans-4-tert-Butyl-cyclohexyloxy)-isoquinoline-3-carbaldehyde (0.1174 g, 0.3770 mmol) and 3-Amino-propionic acid ethyl ester HCl salt; (0.08107 g, 0.5278 mmol) in 1,2-Dichloroethane (5.00 mL, 63.5 mmol) and the mixture was stirred for 1 hour at room temperature. Sodium triacetoxyborohydride (0.1118 g, 0.5278 mmol) was then added and the mixture was stirred for 2 hours. The reaction was diluted in methylene chloride and washed with saturated aq. sodium bicarbonate. The organic phase was dried over MgSO4, filtered, adsorbed onto silica gel and purified by flash chromatography (0-5% MeOH in methylene chloride) to give the title compound in 97% yield. ESI-MS(M+H+): 413.35.

Example 208: 3-((7-(trans-4-tert-butylcyclohexyloxy) isoquinolin-3-yl) methylamino) propanoic acid

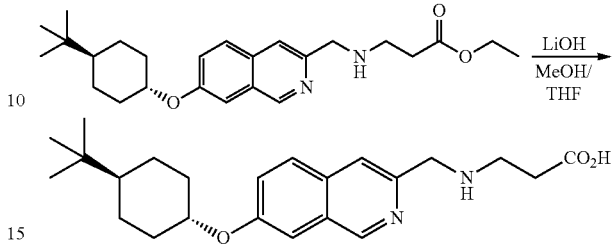

2 M of Lithium hydroxide, monohydrate in water (1.00 mL, 2.00 mmol) was added to a solution of 3-{[7-(trans-4-tert-butyl-cyclohexyloxy)-isoquinolin-3-ylmethyl]-amino}-propionic acid ethyl ester (0.1505 g, 0.3648 mmol) in Tetrahydrofuran (1.00 mL, 12.3 mmol) and Methanol (1.00 mL, 24.7 mmol). The mixture was stirred for 2 hours. The solvent was then evaporated under reduced pressure. The resulting residue was dissolved in methylene chloride and washed with a solution of 1 M of Hydrogen chloride in Water (1.999 mL, 1.999 mmol). The organic layer was then concentrated to dryness under reduced pressure. The crude product was dissolved in DMSO and purified by HPLC to give the title compound as a bis-TFA salt. ESI-MS(M+H+): 385.51 [M+1]. 1H NMR (400 MHz, MeOD) Shift 9.22 (s, 1H), 7.86 (d, J=9.04 Hz, 1H), 7.82 (s, 1H), 7.50 (d, J=2.51 Hz, 1H), 7.43 (dd, J=2.51, 9.04 Hz, 1H), 4.46 (s, 2H), 4.40-4.46 (m, 1H), 3.37 (t, J=6.65 Hz, 2H), 2.81 (t, J=6.78 Hz, 2H), 2.25-2.34 (m, 2H), 1.89-1.98 (m, 2H), 1.40-1.52 (m, 2H), 1.24-1.37 (m, 2H), 1.10-1.20 (m, 1H), 0.90-0.95 (m, 9H)

The following compounds were synthesized as 3-((7-(trans-4-tert-butylcyclohexyloxy) isoquinolin-3-yl) methylamino) propanoic acid using the appropriate cyclohexanols and aminoesters:

Example 209: 1-[7-(trans-4-tert-Butyl-cyclohexyloxy)-isoquinolin-3-ylmethyl]-pyrrolidine-3-carboxylic acid ESI-MS(M+H+): 411.33; 1H NMR (400 MHz, MeOD) Shift 9.23 (s, 1H), 7.87 (d, J=9.04 Hz, 1H), 7.83 (s, 1H), 7.51 (d, J=2.26 Hz, 1H), 7.44 (dd, J=2.51, 8.78 Hz, 1H), 4.56-4.68 (m, 2H), 4.39-4.49 (m, 1H), 3.61-3.78 (m, 2H), 3.52 (t, J=7.28 Hz, 2H), 3.37-3.47 (m, 1H), 2.33-2.52 (m, 2H), 2.25-2.33 (m, 2H), 1.88-1.97 (m, 2H), 1.39-1.51 (m, 2H), 1.23-1.35 (m, 2H), 1.09-1.18 (m, 1H), 0.91 (s, 9H)

Example 210: 1-[7-(trans-4-tert-Butyl-cyclohexyloxy)-isoquinolin-3-ylmethyl]-azetidine-3-carboxylic acid ESI-MS(M+H+): 397.32; 1H NMR (400 MHz, MeOD) Shift 9.20 (s, 1H), 7.87 (d, J=9.04 Hz, 1H), 7.80 (s, 1H), 7.50 (d, J=2.51 Hz, 1H), 7.44 (dd, J=2.51, 9.04 Hz, 1H), 4.65 (s, 2H), 4.39-4.50 (m, 5H), 3.70-3.81 (m, 1H), 2.26-2.35 (m, 2H), 1.90-1.99 (m, 2H), 1.41-1.53 (m, 2H), 1.30 (qd, 2H), 1.09-1.21 (m, J=2.54, 2.54, 11.48 Hz, 1H), 0.93 (s, 9H)

Example 211; 1-[7-(trans-4-Cyclopentyl-cyclohexyloxy)-isoquinolin-3-ylmethyl]-pyrrolidine-3-carboxylic acid ESI-MS(M+H+): 423.28; 1H NMR (400 MHz, MeOD) Shift 9.24 (s, 1H), 7.88 (d, J=9.04 Hz, 1H), 7.84 (s, 1H), 7.51

(d, J=2.26 Hz, 1H), 7.45 (dd, J=2.38, 8.91 Hz, 1H), 4.59-4.69 (m, 2H), 4.43-4.54 (m, 1H), 3.63-3.79 (m, 2H), 3.53 (t, J=7.28 Hz, 2H), 3.38-3.48 (m, 1H), 2.32-2.54 (m, 2H), 2.21-2.29 (m, 2H), 1.93-2.02 (m, 2H), 1.79-1.88 (m, 2H), 1.42-1.71 (m, 6H), 1.11-1.31 (m, 6H)

Example 212: 1-[7-(trans-4-Cyclopentyl-cyclohexyloxy)-isoquinolin-3-ylmethyl]-azetidine-3-carboxylic acid ESI-MS(M+H+): 409.29; 1H NMR (400 MHz, MeOD) Shift 9.20 (s, 1H), 7.87 (d, J=9.04 Hz, 1H), 7.80 (s, 1H), 7.49 (d, J=2.26 Hz, 1H), 7.44 (dd, J=2.38, 8.91 Hz, 1H), 4.65 (s, 2H), 4.39-4.52 (m, 5H), 3.70-3.81 (m, 1H), 2.25 (dd, J=3.64, 13.18 Hz, 2H), 1.93-2.01 (m, 2H), 1.78-1.88 (m, 2H), 1.41-1.71 (m, 7H), 1.11-1.31 (m, 5H)

Example 213: 3-{[7-(trans-4-Cyclopentyl-cyclohexyloxy)-isoquinolin-3-ylmethyl]-amino}-propionic acid ESI-MS(M+H+): 397.29; 1H NMR (400 MHz, MeOD) Shift 9.23 (s, 1H), 7.87 (d, J=8.78 Hz, 1H), 7.82 (s, 1H), 7.50 (d, J=2.26 Hz, 1H), 7.44 (dd, J=2.51, 9.04 Hz, 1H), 4.43-4.53 (m, 3H), 3.35-3.41 (m, 2H), 2.82 (t, J=6.65 Hz, 2H), 2.21-2.30 (m, 2H), 1.93-2.02 (m, 2H), 1.80-1.80 (m, OH), 1.79-1.88 (m, J=6.02 Hz, 2H), 1.41-1.71 (m, 7H), 1.12-1.30 (m, 5H)

Example 214: 1-(7-(trans-4-tert-pentylcyclohexyloxy) isoquinolin-3-yl) methyl) pyrrolidine-3-carboxylic acid ESI-MS(M+H+): 425.31; 1H NMR (400 MHz, MeOD) Shift 9.23 (s, 1H), 7.86 (d, J=9.04 Hz, 1H), 7.83 (s, 1H), 7.50 (d, J=2.26 Hz, 1H), 7.43 (dd, J=2.38, 8.91 Hz, 1H), 4.57-4.67 (m, 2H), 4.38-4.49 (m, 1H), 3.61-3.78 (m, 2H), 3.52 (t, J=7.28 Hz, 2H), 3.37-3.46 (m, 1H), 2.25-2.52 (m, 4H), 1.83-1.91 (m, 2H), 1.38-1.51 (m, 2H), 1.20-1.38 (m, 5H), 0.81-0.89 (m, 9H)

Example 215: 1-(7-(trans-4-tert-pentylcyclohexyloxy) isoquinolin-3-yl) methyl)-azetidine-3-carboxylic acid ESI-MS(M+H+): 411.31; 1H NMR (400 MHz, MeOD) Shift 9.20 (s, 1H), 7.86 (d, J=9.04 Hz, 1H), 7.80 (s, 1H), 7.49 (d, J=2.26 Hz, 1H), 7.43 (dd, J=2.51, 9.04 Hz, 1H), 4.65 (s, 2H), 4.39-4.49 (m, 5H), 3.70-3.80 (m, 1H), 2.26-2.34 (m, J=11.04 Hz, 2H), 1.84-1.92 (m, 2H), 1.39-1.51 (m, 2H), 1.21-1.39 (m, 5H), 0.83-0.90 (m, 9H)

Example 216: 3-((7-(trans-4-tert-pentylcyclohexyloxy)isoquinolin-3-yl) methylamino) propanoic acid ESI-MS(M+H+): 399.33; 1H NMR (400 MHz, MeOD) Shift 9.22 (s, 1H), 7.86 (d, J=8.78 Hz, 1H), 7.82 (s, 1H), 7.50 (d, J=2.51 Hz, 1H), 7.43 (dd, J=2.51, 9.04 Hz, 1H), 4.46 (s, 2H), 4.39-4.45 (m, 1H), 3.37 (t, J=6.65 Hz, 2H), 2.81 (t, J=6.65 Hz, 2H), 2.26-2.34 (m, J=2.76, 13.05 Hz, 2H), 1.83-1.91 (m, 2H), 1.39-1.51 (m, J=11.63, 11.63, 11.63 Hz, 2H), 1.20-1.38 (m, 5H), 0.82-0.90 (m, 9H).

Example 217: 6-bromo-2-(trans-4-tert-butylcyclohexyloxy)-1-(trifluoromethyl) naphthalene

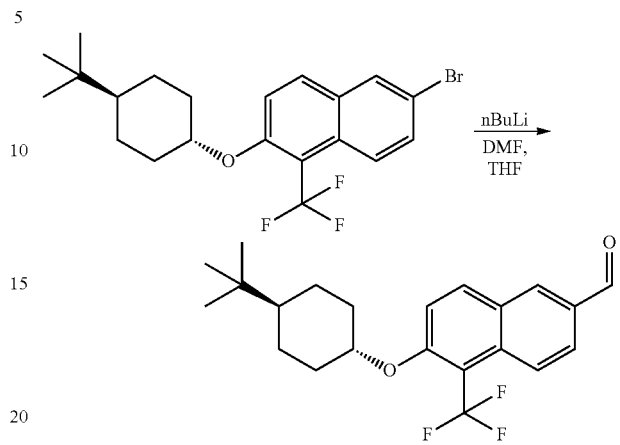

6-bromo-2-(trans-4-tert-butylcyclohexyloxy)-1-(trifluoromethyl)naphthalene (2.58 g, 6.01 mmol) was dissolved in Tetrahydrofuran (100 mL, 1000 mmol) and cooled to −78° C. in a dry ice/acetone bath. 1.6 M of n-Butyllithium in Hexane (7.512 mL, 12.02 mmol) was slowly added and the mixture was stirred for 30 minutes. N,N-Dimethylformamide (1.396 mL, 18.03 mmol) was then slowly added and the mixture was allowed to reach room temperature. The reaction mixture was poured into 1N HCl and extracted with ethyl acetate. The combined organic phase wash washed with sat. aq. sodium bicarbonate solution, brine, then dried over MgSO$_4$, filtered, concentrated and purified by flash chromatography (0-20% EtOAc in hexanes) to give the title compound in 80% yield. ESI-MS(M+H+): 379.41

Example 218: 2-{[6-(trans-4-tert-Butyl-cyclohexyloxy)-5-trifluoromethyl-naphthalen-2-ylmethyl]-amino}-ethanesulfonic acid

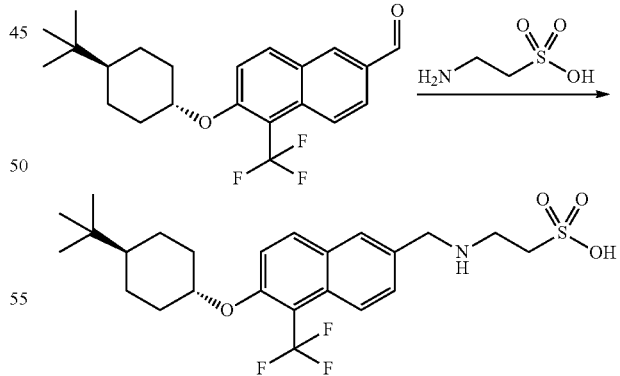

Taurine (0.03737 g, 0.2986 mmol) was added to a solution of 6-(trans-4-tert-butylcyclohexyloxy)-5-(trifluoromethyl)-2-naphthaldehyde (0.1130 g, 0.2986 mmol) in Ethanol (3.00 mL, 51.4 mmol) and the mixture was refluxed for 1 hour. The mixture was cooled to room temperature and Sodium cyanoborohydride (0.02252 g, 0.3583 mmol) was added. The mixture was then refluxed overnight. The reaction mixture was cooled to room temperature, washed with saturated aqueous citric acid solution (4 ml), then concentrated to dryness under reduced pressure. The resulting solid was washed with water and filtered. The residue was washed with water (10 mL), ether (10 mL) and hexane (10 mL) consecutively, then filtered. The residue was purified by prep HPLC to give the title compound. ESI-MS(M+H+): 488.3; 1H NMR (400 MHz, DMSO-d6) Shift 8.46-8.52 (m, 1H), 7.83-7.88 (m, 1H), 7.73-7.80 (m, 2H), 7.35-7.40 (m, 2H), 4.21-4.30 (m, 1H), 4.02 (br. s., 2H), 2.88 (t, J=6.78 Hz, 2H), 2.50 (d, J=13.80 Hz, 2H), 1.77-1.85 (m, 2H), 1.43-1.52 (m, 2H), 1.00-1.13 (m, 2H), 0.67-0.92 (m, 3H), 0.53 (s, 9H).

The following compound was synthesized as 2-{[6-(trans-4-tert-Butyl-cyclohexyloxy)-5-trifluoromethyl-naphthalen-2-ylmethyl]-amino}-ethanesulfonic acid using the appropriate aminosulfone:

Example 219: [6-(trans-4-tert-Butyl-cyclohexyloxy)-5-trifluoromethyl-naphthalen-2-ylmethyl]-(2-methanesulfonyl-ethyl)-amine ESI-MS(M+H+): 486.52; 1H NMR (400 MHz, MeOD) Shift 8.13 (dd, J=1.88, 8.91 Hz, 1H), 8.03 (d, J=9.29 Hz, 1H), 7.83 (d, J=1.51 Hz, 1H), 7.58 (dd, J=2.01, 9.04 Hz, 1H), 7.49 (d, J=9.04 Hz, 1H), 4.39-4.49 (m, 1H), 3.96 (s, 2H), 3.36 (d, J=7.78 Hz, 2H), 3.13 (t, J=6.27 Hz, 2H), 3.04 (s, 3H), 2.17-2.26 (m, 2H), 1.87-1.95 (m, 2H), 1.43-1.56 (m, 2H), 1.06-1.30 (m, 3H), 0.90 (s, 9H)

Example 220: 2-{[6-(trans-4-tert-Butyl-cyclohexyloxy)-naphthalen-2-ylmethyl]-amino}-ethanesulfonic acid A solution of 6-(trans-4-tert-Butyl-cyclohexyloxy)-naphthalene-2-carbaldehyde (0.1662 g, 0.5354 mmol) and Taurine (0.06700 g, 0.5354 mmol) in anhydrous Ethanol (4.00 mL, 68.5 mmol) was refluxed for 2 hours. The mixture was cooled to room temperature and Sodium cyanoborohydride (0.04037 g, 0.6425 mmol) was added. The mixture was then refluxed overnight. The reaction mixture was cooled to room temperature and washed with Sat. aqueous citric acid (4 mL). The mixture was then concentrated to dryness under reduced pressure. The resulting solid was suspended in water and filtered. The residue was washed with water, air-dried and purified by prep HPLC to give the title compound. ESI-MS(M+H+): 420.34; 1H NMR (400 MHz, DMSO-d6) Shift 8.68 (br. s., 1H), 7.84 (br. s., 1H), 7.73-7.81 (m, 2H), 7.45 (dd, J=1.76, 8.53 Hz, 1H), 7.32-7.35 (m, 1H), 7.12 (dd, J=2.51, 8.78 Hz, 1H), 4.29-4.38 (m, 1H), 4.24 (br. s., 2H), 3.13 (d, J=13.80 Hz, 2H), 2.76 (d, J=13.55 Hz, 2H), 2.10-2.18 (m, 2H), 1.72-1.80 (m, 2H), 1.23-1.36 (m, 2H), 1.09-1.22 (m, 2H), 0.96-1.06 (m, 1H), 0.81 (s, 9H)

The following compounds were synthesized as 2-{[6-(trans-4-tert-Butyl-cyclohexyloxy)-naphthalen-2-ylmethyl]-amino}-ethanesulfonic acid using the appropriate amines:

Example 221: 3-{[6-(trans-4-tert-Butyl-cyclohexyloxy)-naphthalen-2-ylmethyl]-amino}-propane-1-sulfonic acid ESI-MS(M+H+): 434.44; 1H NMR (400 MHz, MeOD) Shift 7.90 (br. s., 1H), 7.85 (d, J=8.53 Hz, 1H), 7.81 (d, J=9.04 Hz, 1H), 7.51 (dd, J=1.76, 8.53 Hz, 1H), 7.29 (d, J=2.26 Hz, 1H), 7.18 (dd, J=2.51, 9.04 Hz, 1H), 4.34-4.43 (m, 1H), 4.33 (s, 2H), 2.96 (t, J=6.65 Hz, 2H), 2.25-2.33 (m, 2H), 2.19 (quin, J=6.90 Hz, 2H), 1.89-1.97 (m, 2H), 1.38-1.50 (m, 2H), 1.23-1.35 (m, 2H), 1.08-1.19 (m, 1H), 0.92 (s, 9H)

Example 222: N-(2-{[6-(trans-4-tert-Butyl-cyclohexyloxy)-naphthalen-2-ylmethyl]-amino}-ethyl)-4-trifluoromethyl-benzenesulfonamide ESI-MS(M+H+): 563.50; 1H NMR (400 MHz, DMSO-d6) Shift 7.91-8.00 (m, 5H), 7.69-7.75 (m, 3H), 7.62-7.66 (m, 1H), 7.30-7.38 (m, 3H), 7.08-7.13 (m, 1H), 4.30-4.40 (m, 1H), 3.70-3.75 (m, 2H), 2.90 (t, J=6.53 Hz, 2H), 2.15-2.23 (m, 2H), 1.77-1.85 (m, 2H), 1.28-1.40 (m, 2H), 1.15-1.27 (m, 2H), 1.02-1.12 (m, 1H), 0.87 (s, 9H)

Example 223: 1-((6-(((trans)-4-tert-butylcyclohexyloxy)naphthalen-2-yl)methyl)-4-methylpyrrolidine-3-carboxylic acid

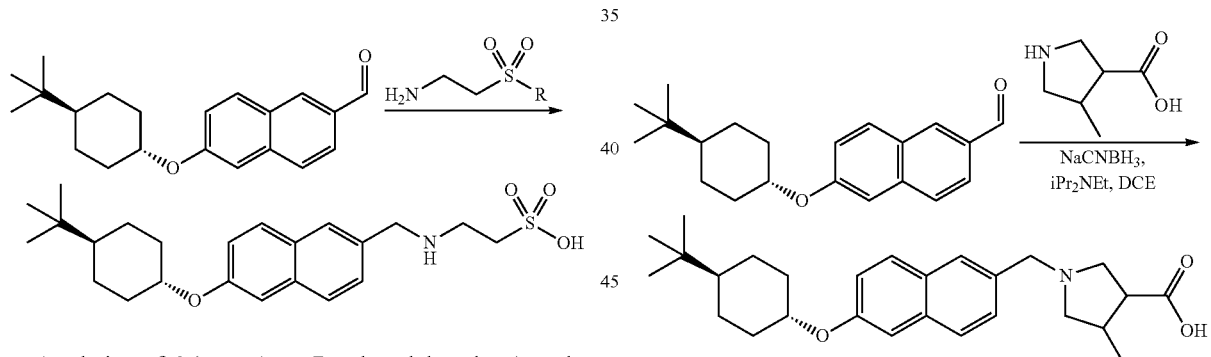

A solution of 6-(4-tert-Butyl-cyclohexyloxy)-naphthalene-2-carbaldehyde (140 mg, 0.46 mmol) and 4-methylpyrrolidine-3-carboxylic acid (60.1 mg, 0.465 mmol) in Ethanol (0.7 mL, 10 mmol) was heated to reflux for 2 h. The yellow solution was cooled to rt and Sodium cyanoborohydride (35.1 mg, 0.558 mmol) was added and was heated to reflux for 1 h. After cooled down to rt, DCM, water and citric acid were added along with some brine to clear up the layers. Concentration of the cloudy organic layer gave a precipitate that was dissolved in methanol and filtered before purification by preparative HPLC. $^1$H NMR (400 MHz, DMSO-d$_6$) δ 7.81-7.98 (m, 3H), 7.53 (d, J=7.28 Hz, 1H), 7.42 (d, J=2.26 Hz, 1H), 7.17-7.25 (m, J=2.38, 8.91 Hz, 1H), 4.34-4.55 (m, 3H), 3.61 (br. s., 2H), 3.05 (br. s., 1H), 2.94 (d, J=5.52 Hz, 1H), 2.63-2.80 (m, 1H), 2.21 (d, J=10.54 Hz, 2H), 1.83 (d, J=12.05 Hz, 2H), 1.29-1.43 (m, 2H), 1.19-1.28 (m, 2H), 1.02-1.18 (m, 5H), 0.88 (s, 9H) [M+1] 424.30.

The procedure used for 1-((6-(((1r,4r)-4-tert-butylcyclohexyloxy)naphthalen-2-yl)methyl)-4-methylpyrrolidine-3-carboxylic acid was used with the appropriate amine to make the following:

Example 224: N-(3-((6-((trans)-4-tert-butylcyclohexyloxy)naphthalen-2-yl)methylamino)propyl)methanesulfonamide $^1$H NMR (400 MHz, DMSO-$d_6$) δ 7.79-8.01 (m, 3H), 7.48-7.57 (m, 1H), 7.42 (d, J=2.01 Hz, 1H), 7.21 (dd, J=2.26, 9.04 Hz, 1H), 4.34-4.55 (m, 2H), 3.92-4.02 (m, 1H), 3.55-3.76 (m, 1H), 2.93-3.12 (m, 2H), 2.77-2.90 (m, 1H), 2.21 (d, J=10.54 Hz, 2H), 1.60-1.94 (m, 6H), 1.15-1.43 (m, 3H), 1.01-1.14 (m, 1H), 0.88 (s, 9H) [M+1] 447.30

Example 225: 2-((6-(((trans)-4-tert-butylcyclohexyloxy)naphthalen-2-yl)methyl)octahydrocyclopenta[c]pyrrole-3α-carboxylic acid $^1$H NMR (400 MHz, DMSO-$d_6$) δ 7.80-7.98 (m, 3H), 7.49-7.58 (m, 1H), 7.42 (d, J=2.01 Hz, 1H), 7.21 (dd, J=2.26, 9.04 Hz, 1H), 4.36-4.54 (m, 3H), 3.92-4.00 (m, 1H), 3.57-3.66 (m, 1H), 2.93-3.11 (m, 2H), 2.77-2.89 (m, 1H), 2.21 (d, J=10.54 Hz, 2H), 1.72-1.95 (m, 5H), 1.66 (br. s., 2H), 1.29-1.44 (m, 3H), 1.14-1.28 (m, 3H), 1.10 (d, J=11.55 Hz, 1H), 0.88 (s, 9H) [M+1] 450.30

Example 226: 1-((6-(((trans)-4-tert-butylcyclohexyloxy)naphthalen-2-yl)methyl)-4,4-dimethylpyrrolidine-3-carboxylic acid

[M+1] 438.30

Example 227: 1-((6-(((trans)-4-tert-butylcyclohexyloxy)naphthalen-2-yl)methyl)-3-methylpyrrolidine-3-carboxylic acid 1H NMR (400 MHz, DMSO-d6) Shift 7.93 (s, 1H), 7.85 (t, J=9.54 Hz, 2H), 7.54 (d, J=8.03 Hz, 1H), 7.41 (d, J=2.01 Hz, 1H), 7.20 (dd, J=2.38, 8.91 Hz, 1H), 4.34-4.50 (m, 2H), 2.21 (d, J=9.79 Hz, 2H), 1.82 (d, J=12.30 Hz, 2H), 1.29-1.43 (m, 6H), 1.14-1.28 (m, 2H), 1.10 (d, J=11.80 Hz, 1H), 0.88 (s, 9H) [M+1] 424.3

Example 228: 2-((6-(((trans)-4-tert-butylcyclohexyloxy)naphthalen-2-yl)methylamino)ethanesulfonamide $^1$H NMR (400 MHz, CHLOROFORM-d) δ 7.75-7.93 (m, 3H), 7.49 (d, J=8.03 Hz, 1H), 7.28 (br. s., 1H), 7.17 (d, J=8.78 Hz, 1H), 4.40 (br. s., 3H), 3.52 (d, J=4.02 Hz, 4H), 2.27 (d, J=10.79 Hz, 2H), 1.91 (d, J=11.55 Hz, 2H), 1.34-1.50 (m, 2H), 1.27 (d, J=12.55 Hz, 2H), 1.07-1.18 (m, 1H), 0.85-0.96 (m, 9H) [M+1] 441.3

Example 229: 3-(3-(6-(((trans)-4-tert-butylcyclohexyloxy)naphthalen-2-yl)oxetan-3-ylamino)propanoic acid

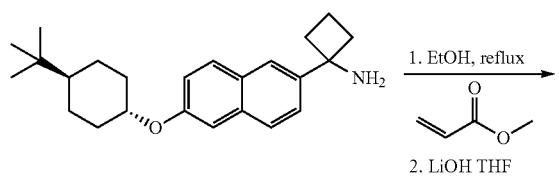

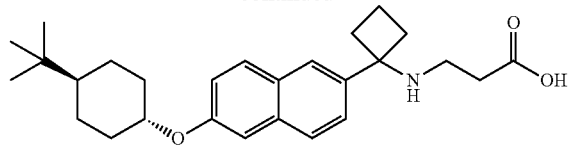

To a mixture of 3-[6-(4-tert-Butyl-cyclohexyloxy)-naphthalen-2-yl]-oxetan-3-ylamine (70 mg, 0.2 mmol) and Methyl acrylate (21 mg, 0.25 mmol) in Ethanol (1.0 mL, 17 mmol) was heated to reflux for 2 d. LCMS monitoring shows 1:1 starting material/product, new peak 1.63 min (m/z 440.30 [M+1], 20%). After concentration and HPLC gave product as a solid (18 mg, 20%). 1H NMR (400 MHz, MeOD) d=7.91 (d, J=8.7 Hz, 1H), 7.87 (s, 1H), 7.84 (d, J=9.0 Hz, 1H), 7.38 (dd, J=2.0, 8.6 Hz, 1H), 7.30 (d, J=2.3 Hz, 1H), 7.20 (dd, J=2.4, 9.0 Hz, 1H), 5.26 (d, J=8.4 Hz, 2H), 5.13 (d, J=8.5 Hz, 2H), 4.43-4.31 (m, 1H), 3.68 (s, 3H), 3.08 (t, J=6.3 Hz, 2H), 2.70 (t, J=6.3 Hz, 2H), 2.27 (d, J=10.4 Hz, 2H), 1.91 (d, J=13.0 Hz, 2H), 1.42 (q, J=12.9 Hz, 2H), 1.32-1.19 (m, 2H), 1.17-1.04 (m, 1H), 0.91 (s, 9H).

A solution of 3-{3-[6-(4-tert-Butyl-cyclohexyloxy)-naphthalen-2-yl]-oxetan-3-ylamino}-propionic acid methyl ester (18.0 mg, 0.0409 mmol) and Lithium hydroxide (6.41 mg, 0.268 mmol) in Tetrahydrofuran (0.6 mL, 8 mmol) and Water (0.2 mL, 9 mmol) was stirred at r.t. overnight. LCMS showed a single desired product peak M+Na at m/z 448.20, RT 1.56 min. The solvent was concentrated and neutralized with citric acid and concentrated and purified on HPLC to give product (5.8 mg, 33%). 1H NMR (400 MHz, MeOD) d=7.91 (d, J=8.4 Hz, 1H), 7.87 (s, 1H), 7.83 (d, J=8.9 Hz, 1H), 7.38 (d, J=8.2 Hz, 1H), 7.31 (s, 1H), 7.20 (d, J=6.8 Hz, 1H), 5.26 (d, J=7.9 Hz, 2H), 5.13 (d, J=7.7 Hz, 2H), 4.43-4.32 (m, 1H), 3.05 (t, J=5.1 Hz, 2H), 2.70-2.62 (m, 2H), 2.27 (d, J=11.2 Hz, 2H), 1.96-1.85 (m, 2H), 1.50-1.35 (m, 2H), 1.34-1.18 (m, 2H), 1.17-1.04 (m, 1H), 0.91 (s, 9H).

Example 230: 1-(6-(((trans)-4-tert-butylcyclohexyloxy)quinolin-2-yl)ethanone

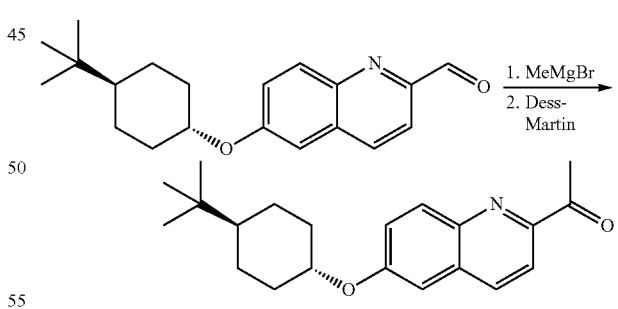

6-(trans-4-tert-butylcyclohexyloxy)quinoline-2-carbaldehyde (1.63 g, 5.23 mmol) was dissolved in Ether (17 mL, 160 mmol). At 0° C., 3.0 M of Methylmagnesium bromide in diethyl ether (2.62 mL, 7.85 mmol) was added. And after 2 h at r.t., Rochelle's salt was added. The reaction mixture was stirred and extracted with EtOAc. LCMS shows single peak. LCMS Rf=1.47 min, m/z 328.20 ([M+1], 100%). CC with MeOH/DCM gave product (1.73 g, 100%). 1H NMR (400 MHz CHLOROFORM-d) d=8.03 (d, J=8.5 Hz, 1H), 7.97 (d, J=9.1 Hz, 1H), 7.37 (dd, J=2.8, 9.2 Hz, 1H), 7.30 (d, J=8.5 Hz, 1H), 7.12 (d, J=2.7 Hz, 1H), 5.08-4.89 (m, 2H), 4.33-4.21 (m, 1H), 2.28 (d, J=14.5 Hz, 2H), 1.92 (d, J=11.1 Hz, 2H), 1.57 (d, J=6.4 Hz, 3H), 1.53-1.36 (m, 1H), 1.30-1.01 (m, 4H), 0.91 (s, 9H).

1-[6-(4-tert-Butyl-cyclohexyloxy)-quinolin-2-yl]-ethanol (1.40 g, 4.28 mmol) in Methylene chloride (24.5 mL, 382 mmol) was added Dess-Martin periodinane (3.2 g, 7.6 mmol) and was stirred at room temperature for 1 hour. After pass through si gel plug, the solvent was concentrated down to give product as an oil (1.29 g, 93%). LCMS 2.28 min at m/z 326.20 ([M+1], 100%).

Example 231: methyl 1-(1-(6-((trans)-4-tert-butyl-cyclohexyloxy)quinolin-2-yl)ethyl)azetidine-3-carboxylate

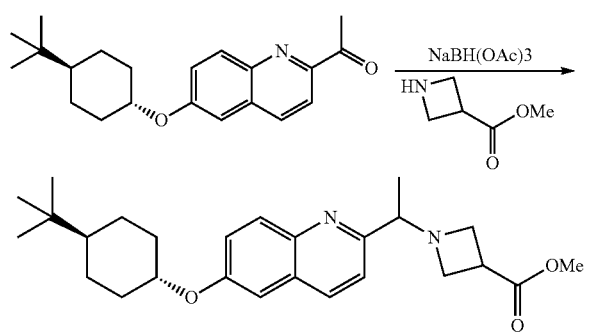

1-[6-(4-tert-Butyl-cyclohexyloxy)-quinolin-2-yl]-ethanone (68 mg, 0.00021 mol) and Azetidine-3-carboxylic acid methyl ester (23.9 mg, 0.000207 mol) was dissolved in Ethanol (0.50 mL, 0.0086 mol) and was heated to reflux for 2 hours. After cooling down to rt, Sodium cyanoborohydride (32.4 mg, 0.000516 mol) was added and was heated to reflux for 1 hour. After cooling down to rt and concentration, the mixture was dissolved into DCM and quenched with $NEt_3$ and concentrated. The residue was chromatographed with $MeOH/CH_2Cl_2$ to give product (57.2 mg, 65%). LCMS 1.66 min, at m/z 425.30 ([M+1], 100%).

Example 232: 1-(1-(6-((trans)-4-tert-butylcyclohexyloxy)quinolin-2-yl)ethyl)azetidine-3-carboxylic acid

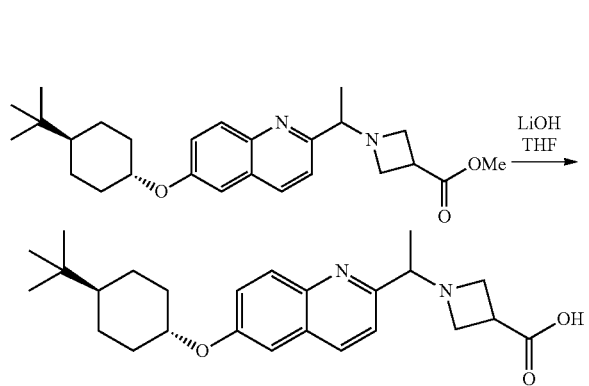

A solution of 1-{1-[6-(4-tert-Butyl-cyclohexyloxy)-quinolin-2-yl]-ethyl}-azetidine-3-carboxylic acid methyl ester (57.2 mg, 0.135 mmol) and Lithium hydroxide (20.9 mg, 0.874 mmol) in Tetrahydrofuran (2 mL, 20 mmol) and Water (0.5 mL, 30 mmol) was stirred at r.t. overnight. LCMS showed a single desired product peak RT 1.60 min M+1 at m/z 413.30, 100%. The solvent was concentrated and neutralized with citric acid and concentrated and Purified on HPLC to give product (26.2 mg, 37%). 1H NMR (300 MHz, MeOD) d=8.25 (d, J=8.3 Hz, 1H), 7.94 (d, J=9.4 Hz, 1H), 7.42 (d, J=8.3 Hz, 1H), 7.37 (dd, J=2.6, 9.1 Hz, 1H), 7.28 (d, J=3.0 Hz, 1H), 4.54-4.43 (m, 2H), 4.42-4.18 (m, 3H), 3.78-3.59 (m, 1H), 2.25 (d, J=10.2 Hz, 2H), 1.89 (d, J=11.3 Hz, 2H), 1.57 (d, J=6.8 Hz, 3H), 1.51-0.99 (m, 6H), 0.89 (s, 9H).

Example 233: (R,Z)—N-(1-(6-((trans)-4-tert-butyl-cyclohexyloxy)quinolin-2-yl)ethylidene)-2-methyl-propane-2-sulfinamide

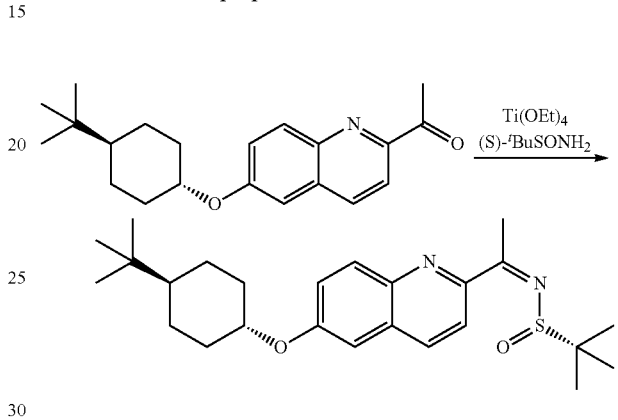

To the solution of 1-[6-(4-tert-Butyl-cyclohexyloxy)-quinolin-2-yl]-ethanone (0.2227 g, 0.0006843 mol) and (s)-(−)-2-Methyl-2-propanesulfinamide (0.0829 g, 0.000684 mol) in Methylene chloride (1.4 mL, 0.021 mol) was added Ti(OEt)4 (0.488 mL, 0.00171 mol). The reaction was stirred at room temperature for id. The mixture was then cooled to 0° C., added equal volume brine, filtrate through celite, and extracted with EtOAc. After died over $Na_2SO_4$, the residue was chromatographed 0-50% EA/HE gave product (132 mg, 45%). LCMS 2.39 min m/z 429.30 ([M+1], 100%).

Example 234: 2-(6-((trans)-4-tert-butylcyclohexyloxy)quinolin-2-yl)propan-2-amine

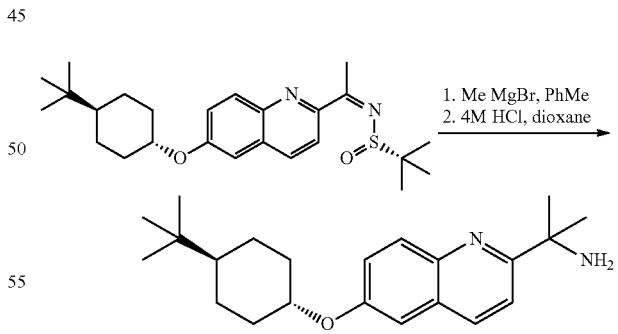

To a solution of (S)-2-Methyl-propane-2-sulfinic acid [1-[6-(4-tert-butyl-cyclohexyloxy)-quinolin-2-yl]-eth-(E)-ylidene]-amide (132.2 mg, 0.3084 mmol) in Toluene (1.0 mL, 9.4 mmol) at −25° C. under N2, MeMgBr (3M solution in ether, 0.41 mL/g 3, 4 equiv) was added dropwise. The reaction mixture was stirred at ~−20° C. for 15 minutes. TLC indicated a complete reaction. The reaction mixture was quenched by addition of saturated $NH_4Cl$ at 0° C. The quenched mixture was diluted with EtOAc. The aqueous layer was removed. The organic layer was washed with brine and dried over Na$_2$SO$_4$. The drying agent was removed and the dried solution was concentrated under vacuum to a residue, which was chromatographed to give product (76.3 mg, 56%). LCMS 1.82 min m/z 445.30 ([M+1], 100%).

2-Methyl-propane-2-sulfinic acid {1-[6-(4-tert-butyl-cyclohexyloxy)-quinolin-2-yl]-1-methyl-ethyl}-amide (76.3 mg, 0.172 mmol) in Methanol (1.9 mL, 48 mmol) was added 4.0 M of Hydrogen chloride in 1,4-Dioxane (0.97 mL, 3.9 mmol) and was stirred overnight. After removal of solvent, the residue was dissolved in DMSO, then HPLC give product as a gel (53 mg, 91%). LCMS Rf=1.58 min m/z 341.20 ([M+1], 100%). 1H NMR (400 MHz, CHLOROFORM-d) Shift=8.22 (d, J=8.4 Hz, 1H), 8.00 (d, J=9.2 Hz, 1H), 7.48 (d, J=8.3 Hz, 1H), 7.45 (dd, J=2.6, 9.2 Hz, 1H), 7.15 (s, 1H), 4.38-4.24 (m, 1H), 2.28 (d, J=10.4 Hz, 2H), 1.93 (d, J=12.9 Hz, 2H), 1.88 (s, 6H), 1.58-1.40 (m, 2H), 1.31-1.01 (m, 3H), 0.91 (s, 9H).

Example 235: 3-(2-(6-((trans)-4-tert-butylcyclohexyloxy)quinolin-2-yl)propan-2-ylamino)propanoic acid

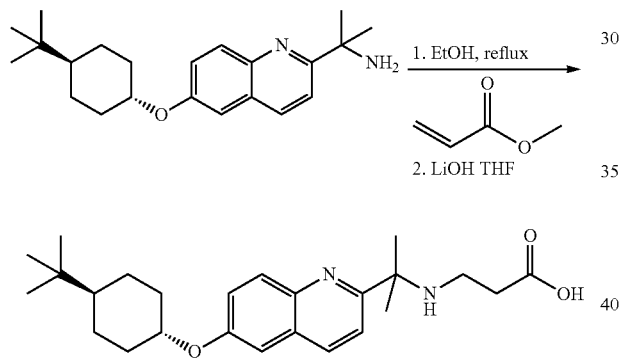

To a mixture of 1-[6-(4-tert-Butyl-cyclohexyloxy)-quinolin-2-yl]-1-methyl-ethylamine (53.0 mg, 0.156 mmol) and Methyl acrylate (0.014 mL, 0.16 mmol; Supplier=Aldrich) in Ethanol (0.32 mL, 5.5 mmol) was heated to reflux for overnight. LCMS monitoring shows new peak 1.60 min (m/z 427.30 [M+1], 20%). After concentration and cc with MeOH/DCM gave product as a oil (35 mg, 53%).

A solution of 3-{1-[6-(4-tert-Butyl-cyclohexyloxy)-quinolin-2-yl]-1-methyl-ethylamino}-propionic acid methyl ester (36.0 mg, 0.0844 mmol) and Lithium hydroxide (20.2 mg, 0.844 mmol) in Tetrahydrofuran (1 mL, 20 mmol) and Water (0.3 mL, 20 mmol) was stirred at r.t. overnight. LCMS showed a single desired product peak RT 1.57 min M+1 at m/z 413.30, 100%. The solvent was concentrated and neutralized with citric acid and concentrated and Purified on HPLC to give product (20 mg, 57%). 1H NMR (400 MHz, CHLOROFORM-d) d=8.30 (d, J=8.7 Hz, 1H), 7.97 (d, J=9.2 Hz, 1H), 7.59 (d, J=8.7 Hz, 1H), 7.39 (dd, J=2.7, 9.2 Hz, 1H), 7.30 (d, J=2.5 Hz, 1H), 4.43-4.28 (m, 1H), 3.23 (t, J=6.6 Hz, 2H), 2.84 (t, J=6.6 Hz, 2H), 2.26 (d, J=10.4 Hz, 2H), 1.90 (d, J=13.6 Hz, 2H), 1.79 (s, 6H), 1.49-1.32 (m, 2H), 1.32-1.17 (m, 2H), 1.17-1.00 (m, 1H), 0.90 (s, 9H).

Example 236: N-(2-Formyl-4-methoxyphenyl)acetamide

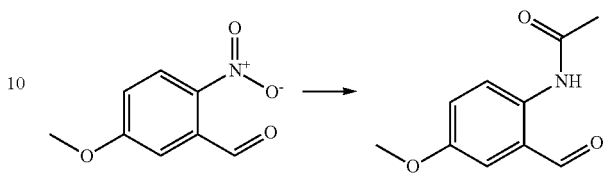

5-Methoxy-2-nitro-benzaldehyde (5.00 g, 0.0276 mol), Platinum dioxide (400 mg, 0.002 mol) and Sodium acetate trihydrate (300 mg, 0.002 mol) were placed in a pressure flask, followed by Ethyl acetate (200 mL, 2 mol). The reaction mixture was then purged under N$_2$ at least 3 times, and H$_2$ was introduced (purged 3 times) and maintained at 52 psi for 3 hours. The reaction mixture was then filtered, and cooled to at −20° C. N,N-Diisopropylethylamine (7.21 mL, 0.0414 mol) was added to the solution followed by Acetyl chloride (2.36 mL, 0.0331 mol). The reaction mixture was allowed to stir for 2 hours, and quenched with KHCO$_3$ (sat). Organic layer was separated, and washed with waster, brine and dried over Na$_2$SO$_4$. Removal of solvent gave a crude product, which was then purified via chromatography (SiO$_2$, 80 g, 0-100% ethyl acetate/hexanes; 4.28 g, 80%). $^1$H NMR (300 MHz, CHLOROFORM-d) δ ppm 2.25 (s, 3H) 3.88 (s, 3H) 7.10-7.26 (m, 2H) 8.69 (d, J=9.06 Hz, 1H) 9.90 (s, 1H) 10.75-11.04 (m, 1H). MS (ESI, M+1): 194.10.

Example 237: 6-Methoxy-2-methylquinazoline

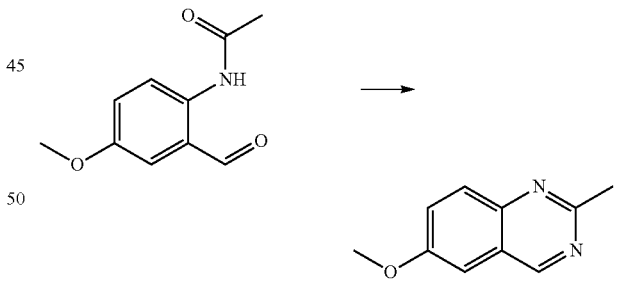

N-(2-Formyl-4-methoxyphenyl)acetamide (2, 2.50 g, 12.9 mmol) was dissolved in Ethanol (300 mL, 5000 mmol) and cooled to at −78° C. in a high pressure reactor. A solution of NH3 saturated in ethanol was added. The reaction mixture was then heated at 135° C. for 2 hours. Cooled to 23° C., and solvent was removed to give a crude product, which was then purified via chromatography (SiO$_2$, 120 g, 0-20% MeOH/DCM; 1.87 g, 83%). $^1$H NMR (400 MHz, CHLOROFORM-d) δ ppm 2.91 (s, 3H) 3.97 (s, 3H) 7.15 (d, J=2.51 Hz, 1H) 7.56 (dd, J=9.04, 2.51 Hz, 1H) 7.93 (d, J=9.04 Hz, 1H) 9.27 (s, 1H). MS (ESI, M+1): 175.10.

Example 238: 6-Methoxy-2-quinazolinylmethylaldehyde

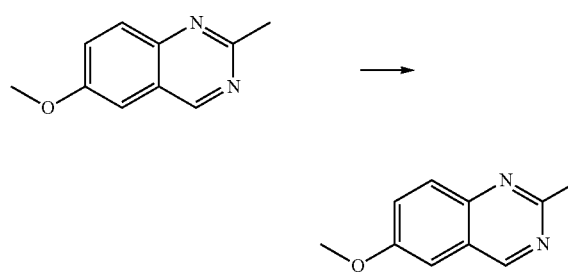

6-Methoxy-2-methyl-quinazoline (3, 2.50 g, 14.4 mmol) was dissolved in 1,4-Dioxane (200 mL, 3000 mmol), followed by Selenium dioxide (11.15 g, 100.4 mmol). The reaction mixture was then heated at 90° C. for 12 hours. The reaction mixture was filtered. Solvent was removed, and the crude mixture was purified via chromatography (SiO$_2$, 80 g, 0-100% ethyl acetate/hexanes; 1.85 g, 69%). $^1$H NMR (400 MHz, CHLOROFORM-d) Q ppm 4.02 (s, 3H) 7.23-7.31 (m, 1H) 7.69 (dd, J=9.29, 2.76 Hz, 1H) 8.16 (d, J=9.29 Hz, 1H) 9.49 (s, 1H) 10.23 (s, 1H). MS (ESI, M+1): 189.10.

Example 239: (R)-1-(6-Methoxyquinazolin-2-ylmethyl)pyrrolidine-3-carboxylic acid methyl ester

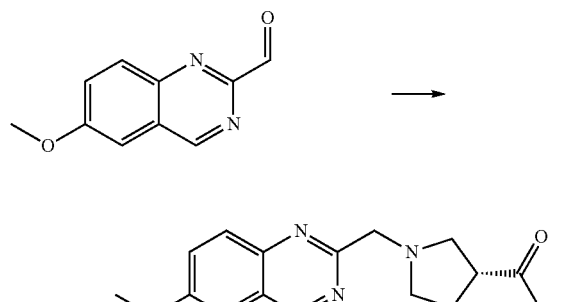

6-Methoxy-2-quinazolinylmethylaldehyde (4, 2.40 g, 12.7 mmol) was dissolved in Methanol (50 mL, 1000 mmol), followed by (R)-Pyrrolidine-3-carboxylic acid methyl ester (3.29 g, 25.5 mmol) at 23° C. The reaction mixture was stirred for 30 minutes, then Sodium cyanoborohydride (1.60 g, 25.5 mmol) was added at −30° C. The reaction mixture was gradually warmed up to 23° C., and stirred for 1 day. Solvent was removed, and the residue was treated with DCM/water. Organic layer was washed with washer (300×2 mL) and then brine and dried over Na$_2$SO$_4$. The product was purified via chromatography (SiO$_2$, 220 g, 0-10% MeOH/DCM) to give a pure product. 1H NMR (CHLOROFORM-d) δ ppm: 9.23 (s, 1H), 7.89 (d, J=9.3 Hz, 1H), 7.47 (d, J=9.3 Hz, 1H), 7.07 (br. s., 1H), 4.02 (d, J=3.3 Hz, 2H), 3.88 (s, 3H), 3.61 (s, 3H), 3.03-3.25 (m, 2H), 2.96 (d, J=4.5 Hz, 1H), 2.68 (t, J=8.2 Hz, 1H), 2.59 (q, J=8.0 Hz, 1H), 2.11 (d, 2H). MS (ESI, M+1): 302.10.

Example 240: (R)-1-(6-Hydroxy-quinazolin-2-ylmethyl)-pyrrolidine-3-carboxylic acid methyl ester

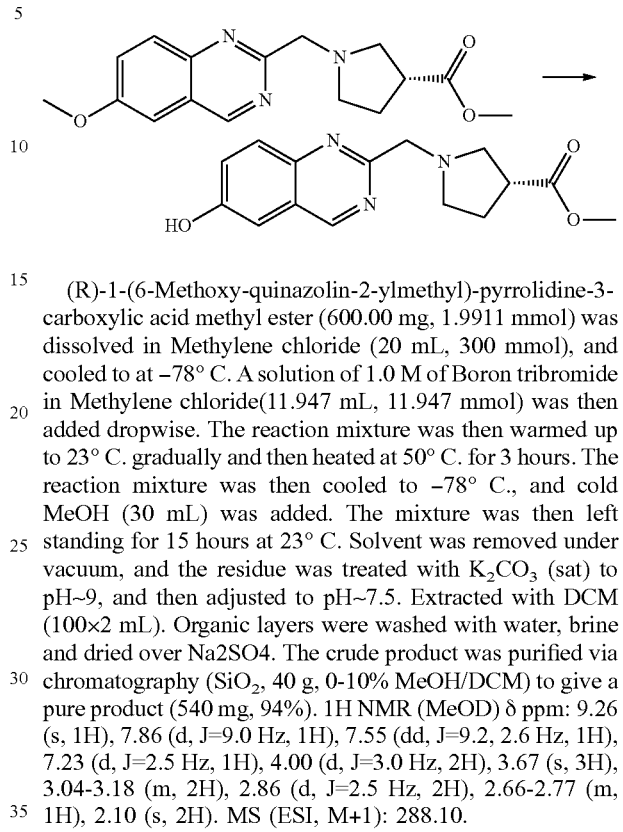

(R)-1-(6-Methoxy-quinazolin-2-ylmethyl)-pyrrolidine-3-carboxylic acid methyl ester (600.00 mg, 1.9911 mmol) was dissolved in Methylene chloride (20 mL, 300 mmol), and cooled to at −78° C. A solution of 1.0 M of Boron tribromide in Methylene chloride (11.947 mL, 11.947 mmol) was then added dropwise. The reaction mixture was then warmed up to 23° C. gradually and then heated at 50° C. for 3 hours. The reaction mixture was then cooled to −78° C., and cold MeOH (30 mL) was added. The mixture was then left standing for 15 hours at 23° C. Solvent was removed under vacuum, and the residue was treated with K$_2$CO$_3$ (sat) to pH~9, and then adjusted to pH~7.5. Extracted with DCM (100×2 mL). Organic layers were washed with water, brine and dried over Na2SO4. The crude product was purified via chromatography (SiO$_2$, 40 g, 0-10% MeOH/DCM) to give a pure product (540 mg, 94%). 1H NMR (MeOD) δ ppm: 9.26 (s, 1H), 7.86 (d, J=9.0 Hz, 1H), 7.55 (dd, J=9.2, 2.6 Hz, 1H), 7.23 (d, J=2.5 Hz, 1H), 4.00 (d, J=3.0 Hz, 2H), 3.67 (s, 3H), 3.04-3.18 (m, 2H), 2.86 (d, J=2.5 Hz, 2H), 2.66-2.77 (m, 1H), 2.10 (s, 2H). MS (ESI, M+1): 288.10.

Example 241: (R)-1-{6-[4-(1,1-Dimethylpropyl)cyclohexyloxy]quinazolin-2-ylmethyl}-pyrrolidine-3-carboxylic acid methyl ester

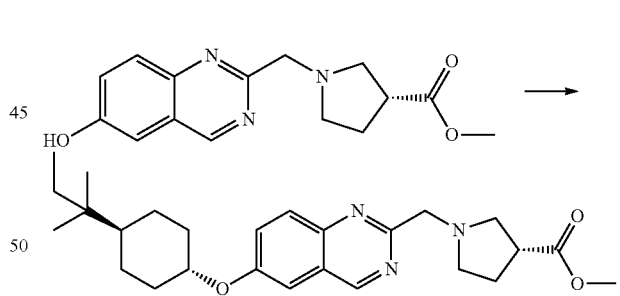

(R)-1-(6-Hydroxyquinazolin-2-ylmethyl)-pyrrolidine-3-carboxylic acid methyl ester (150.00 mg, 5.2208E-4 mol), cis-4-(1,1-dimethyl)propylcyclohexanol (133.36 mg, 7.8312E-4 mol) and Triphenylphosphine (273.87 mg, 0.0010442 mol) were placed in a 40 mL vial, followed by Toluene (5 mL, 0.04 mol). A solution of in THF (5 mL) was then added dropwise to the reaction mixture at 23° C. The reaction mixture was allowed to stir for 12 hours. The reaction mixture was then filtered through a celite pad, and concentrated. The crude mixture was purified via chromatography (SiO$_2$, 20 g, 0-35% ethyl acetate/hexanes) to give the desired product (388 mg, 80%). 1H NMR (CHLOROFORM-d) δ ppm: 9.25 (s, 1H), 7.93 (d, J=9.3 Hz, 1H), 7.50 (dd, J=9.3, 2.8 Hz, 1H), 7.13 (d, 1H), 4.28 (ddd, J=10.9, 6.6, 4.4 Hz, 1H), 3.99-4.16 (m, 2H), 3.67 (s, 3H), 3.22-3.34 (m, 1H), 3.16 (dd, J=8.9, 7.4 Hz, 1H), 2.98-3.10 (m, 1H), 2.76 (t, J=8.4 Hz, 1H), 2.66 (q, J=8.2 Hz, 1H), 2.26 (d, J=13.1 Hz, 2H), 2.06-2.21 (m, 2H), 1.76-1.92 (m, 2H), 1.36-1.55 (m, 2H), 1.29 (q, J=7.6 Hz, 2H), 1.09-1.24 (m, 3H), 0.72-0.90 (m, 9H). MS (ESI, M+1): 440.30.

Example 242: 1-{6-[4-(1,1-Dimethylpropyl)cyclohexyloxy]quinazolin-2-ylmethyl}pyrrolidine-3-carboxylic acid

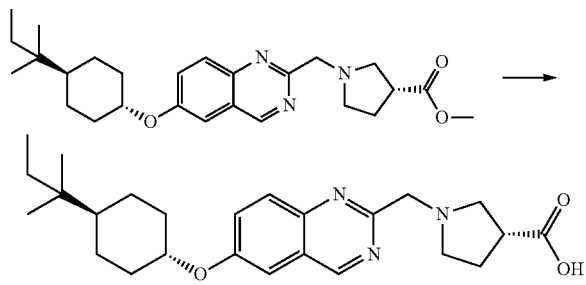

1-{6-[4-(1,1-Dimethyl-propyl)-cyclohexyloxy]-quinazolin-2-ylmethyl}-pyrrolidine-3-carboxylic acid methyl ester (229.50 mg, 5.2208E-4 mol) was dissolved in Methanol (5 mL, 0.1 mol) and Tetrahydrofuran (5 mL, 0.06 mol), followed by 2 M of Lithium hydroxide in Water (2 mL, 0.004 mol) at 23° C. for 10 minutes. Excess of solvents were removed under vacuum, and the solid residue was treated with HCl (2N, 3 mL), and extracted with DCM (20×3 mL). The organic layers were dried over Na$_2$SO$_4$. Removal of solvent gave a pure product (200 mg, 90%). 25 $^1$H NMR (400 MHz, CHLOROFORM-d) δ ppm 0.69-0.94 (m, 12H) 1.13-1.37 (m, 10H) 1.39-1.59 (m, 2H) 1.76-1.96 (m, 3H) 2.18-2.37 (m, 2H) 4.84 (br. s., 1H) 7.16-7.38 (m, 2H) 7.55-7.71 (m, 1H) 7.99 (br. s., 1H) MS (ESI, M+1): 426.30.

The two step procedure used to make 1-{6-[4-(1,1-Dimethylpropyl)cyclohexyloxy]quinazolin-2-ylmethyl}pyrrolidine-3-carboxylic acid was utilized with the appropriate alcohol to make the following:

Example 243: 1-[6-(4-tert-Butylcyclohexyloxy)quinazolin-2-ylmethyl]pyrrolidine-3-carboxylic acid (88% yield). $^1$H NMR (400 MHz, CHLOROFORM-d) δ ppm: 0.88-1.02 (m, 10H) 1.09-1.17 (m, 2H) 1.17-1.35 (m, 8H) 1.39-1.61 (m, 2H) 1.82-2.01 (m, 3H) 2.18-2.37 (m, 2H) 4.32 (br. s., 0H) 7.17-7.37 (m, 2H) 7.60 (br. s., 1H) 7.99 (br. s., 1H).

MS (ESI, M+1): 412.20.

Example 244: 1-[6-(4-Cyclopentylcyclohexyloxy)quinazolin-2-ylmethyl]pyrrolidine-3-carboxylic acid (95% yield). $^1$H NMR (400 MHz, CHLOROFORM-d) δ ppm: 1.00-1.19 (m, 10H) 1.37-1.57 (m, 8H) 1.57-1.70 (m, 2H) 1.70-1.87 (m, 2H) 1.87-2.02 (m, 3H) 2.21 (br. s., 2H) 4.34 (br. s., 1H) 7.10-7.34 (m, 1H) 7.55-7.68 (m, 1H) 7.85-8.07 (m, 2H) 9.24-9.44 (m, 1H). MS (ESI, M+1): 424.30.

Example 245: 1-[6-(4-tert-Butyl-cyclohexyloxy)-naphthalen-2-yl]-ethanone

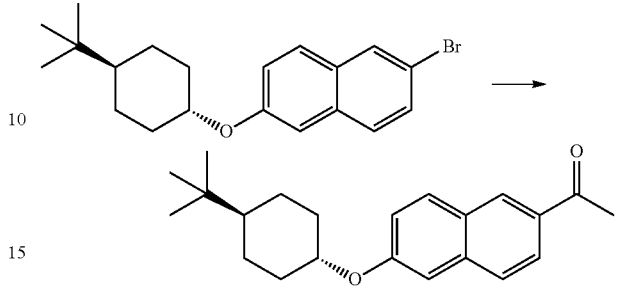

To a solution of 2-Bromo-6-(4-tert-butyl-cyclohexyloxy)-naphthalene (5 g, 0.01 mol) in 15 mL dry THF stirring at −78° C., was added 2.0 M of n-Butyllithium in hexane (8.3 mL, 0.017 mol) dropwise. The reaction was then stirred at −78° C. for 15 minutes, yellow color results. N-Methoxy-N-methyl-acetamide (1.6 mL, 0.015 mol) in 5 mL THF was then added dropwise while the reaction was stirred at −78° C. (rxn went colorless upon addition of B). Reaction was then quenched with water and extracted three times with ethyl ether. Organics were dried over MgSO$_4$, filtered, and concentrated to dryness under reduced pressure. Material was purified via column chromatography using a gradient of 0-10% EtOAC/Hexanes (ran neat hexanes for 5 min to elute desbromo SM) on 125 g of SiO$_2$ to give the title compound as a white solid.

Example 246: 1-N-Azetidine-3-ethoxycarbonyl-1-ethyl[6-(4-tert-Butyl-cyclohexyloxy)naphthalene

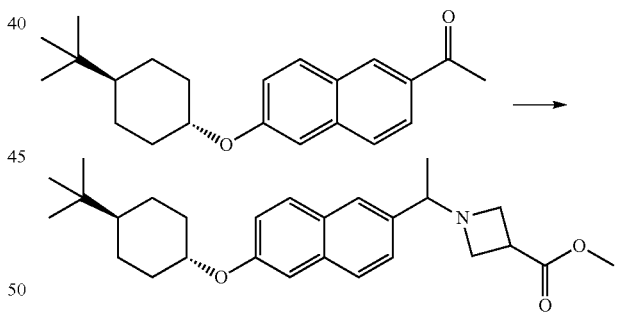

Azetidine-3-carboxylic acid ethyl ester (407.10 mg, 0.0031520 mol) (HCl salt) was combined with Potassium carbonate (653.01 mg, 0.0047249 mol) in Methanol (10 mL, 0.2 mol) and stirred for 15 minutes. The solids were removed via filtration. Acetic acid (8.9 uL, 0.00016 mol) was then added followed by 1-[6-(4-tert-Butyl-cyclohexyloxy)-naphthalen-2-yl]-ethanone (511.01 mg, 0.0015750 mol) and Sodium cyanoborohydride (245.55 mg, 0.0039074 mol) and the reaction was stirred overnight at RT. Solubility of SM was very poor. Added Methylene chloride (2.5 mL, 0.039 mol). Mixture became homogeneous after a few minutes. The reaction mixture was then heated to 50° C. for 5 hours. The reaction was then left stirring overnight at 50° C. The reaction was then quenched with water and extracted three times with ethyl ether. Organics were combined and dried over MgSO₄. Solids were removed via filtration and 5 g of SiO₂ was added. All solvent was then removed and the resulting silica was loaded onto a 24 g column and the reaction was purified using a gradient of 0-60% EtOAc/Hexanes and then dried on the highvac to give the title compound as a colorless oil. Material will be carried on without additional purification.

Example 247: 1-Ethyl[6-(4-tert-Butyl-cyclohexyloxy)naphthal-2-yl-N-azetidine-3-carboxylic acid

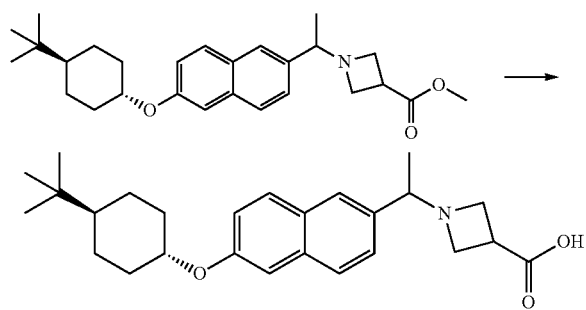

1-N-Azetidine-3-ethoxycarbonyl-1-ethyl[6-(4-tert-Butyl-cyclohexyloxy)naphthalene (140.1 mg, 0.3307 mmol) was dissolved in Ethanol (2 mL, 40 mmol) then treated with 1 M of Sodium hydroxide in Water (2 mL, 2 mmol). The mixture was stirred vigorously for 1 hour. LCMS shows about 10% conversion to new more polar spot RT=1.75 min M+1=410. Reaction left stirring overnight. LCMS indicates no SM remaining. pH was adjust to 3-4 with 3 N HCl and reaction was then extracted three times with EtOAc. Organics were combined then dried over MgSO₄, filtered and concentrated to dryness under reduced pressure. Ethyl ether was then added and a white ppt formed. The ppt. was removed via filtration to give a white solid that 99% pure by NMR and HPLC. ¹H NMR (400 MHz, CHLOROFORM-d) δ ppm 0.89 (s, 9H) 1.02-1.29 (m, 3H) 1.43 (q, J=11.38 Hz, 2H) 1.53-1.72 (m, 3H) 1.88 (d, J=11.55 Hz, 2H) 2.26 (d, J=10.54 Hz, 2H) 3.18-3.38 (m, 1H) 3.72-3.98 (m, 2H) 3.98-4.17 (m, 2H) 4.18-4.33 (m, 1H) 4.38 (br. s., 1H) 7.05-7.18 (m, 2H) 7.54 (d, J=8.28 Hz, 1H) 7.72 (t, J=8.28 Hz, 2H) 7.83 (br. s., 1H). MS (ESI, M+1): 410.30.

The same 2 step procedure utilized for 1-Ethyl[6-(4-tert-Butyl-cyclohexyloxy)naphthal-2-yl-N-azetidine-3-carboxylic acid was used to make the following compound with the appropriate amine.

Example 248: 3-{1-[6-(4-tert-Butyl-cyclohexyloxy)-naphthalen-2-yl]-ethylamino}-propionic acid ¹H NMR (400 MHz, DMSO-d₆) δ ppm 0.81 (br. s., 1H) 0.87 (s, 9H) 0.99-1.14 (m, 1H) 1.14-1.42 (m, 4H) 1.64 (d, J=6.78 Hz, 3H) 1.81 (d, J=12.05 Hz, 2H) 2.20 (d, J=10.29 Hz, 2H) 2.57-2.72 (m, 2H) 2.72-2.88 (m, 1H) 2.97 (br. s., 1H) 3.32 (br. s., 1H) 4.30-4.54 (m, 2H) 7.18 (dd, J=8.91, 2.13 Hz, 1H) 7.35-7.45 (m, 1H) 7.66 (d, J=7.78 Hz, 1H) 7.79 (d, J=8.78 Hz, 1H) 7.86 (d, J=8.53 Hz, 1H) 7.94 (s, 1H)

Example 249: (R)-1-[6-(4-tert-Butyl-cyclohexyloxy)-naphthalen-2-ylmethyl]-pyrrolidine-3-carboxylic acid

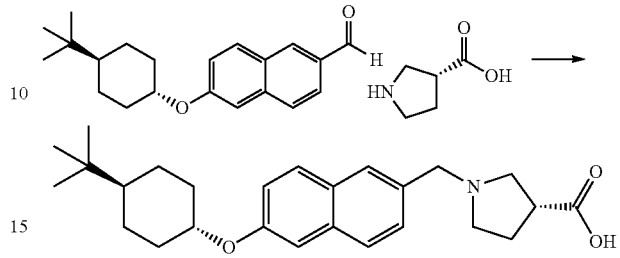

(R)-Pyrrolidine-3-carboxylic acid; compound with GENERIC INORGANIC NEUTRAL COMPONENT (98 mg, 0.65 mmol) was combined with Potassium carbonate (114.44 mg, 0.82203 mmol) in Methanol (5 mL, 100 mmol) and stirred for 15 min. The solids were then removed via filtration and 6-(4-tert-Butyl-cyclohexyloxy)-naphthalene-2-carbaldehyde (76.7 mg, 0.247 mmol) was added to the solution followed by Acetic acid (91 uL, 1.6 mmol). Solubility was poor so added Methylene chloride (0.6 mL, 10 mmol). Mixture was heated to 55° C. for 30 minutes and then cooled to RT. Sodium cyanoborohydride (0.077630 g, 1.2353 mmol) was then added in two small portions and the reaction was stirred at RT for 4 hours. Reaction was then treated with 2 additional eqs. of Sodium cyanoborohydride and heated to 55° C. overnight. Approximately 3 mL of MeOH was removed on the rotovap and the reaction mixture was treated with 2 mL DMSO to dissolve precipitated solids. The reaction was then purified directly via prep-HPLC on a 19×150 C18 column using a gradient of 10-100% CH₃CN/Water (0.1% TFA) to give the title compound. 1H NMR (400 MHz, MeOD) Shift=8.01-7.73 (m, 3H), 7.59-7.43 (m, 1H), 7.37-7.26 (m, 1H), 7.26-7.12 (m, 1H), 4.61-4.49 (m, 2H), 4.48-4.31 (m, 1H), 3.91-3.33 (m, 6H), 2.60-2.09 (m, 5H), 2.06-1.81 (m, 3H), 1.58-1.04 (m, 7H), 1.01-0.80 (m, 9H). MS (ESI, M+1): 410.30.

The procedure for (R)-1-[6-(4-tert-Butyl-cyclohexyloxy)-naphthalen-2-ylmethyl]-pyrrolidine-3-carboxylic acid was utilized to prepare the following compounds utilizing the appropriate amine.

Example 250: (R)-1-[6-(Bicyclohexyl-4-yloxy)-naphthalen-2-ylmethyl]-pyrrolidine-3-carboxylic acid 1H NMR (400 MHz, MeOD) Shift=7.98-7.71 (m, 3H), 7.59-7.45 (m, 1H), 7.39-7.09 (m, 2H), 4.69-4.48 (m, 1H), 4.48-4.32 (m, 1H), 2.51-2.08 (m, 4H), 1.83 (d, J=7.0 Hz, 7H), 1.71-1.38 (m, 7H), 1.12 (none, 6H). MS (ESI, M+1): 436.30.

Example 251: (R)-1-[6-(4-Cyclopentyl-cyclohexyloxy)-naphthalen-2-ylmethyl]-pyrrolidine-3-carboxylic acid ¹H NMR (400 MHz, METHANOL-d₄) δ ppm 1.05-1.34 (m, 7H) 1.40-1.70 (m, 8H) 1.72-1.88 (m, 2H) 1.89-2.07 (m, 2H) 2.23 (d, J=11.04 Hz, 2H) 3.41-3.53 (m, 2H) 3.53-3.68 (m, 2H) 4.35-4.48 (m, 1H) 4.53 (br. s., 2H) 7.20 (dd, J=8.91, 2.38 Hz, 1H) 7.25-7.34 (m, 1H) 7.52 (dd, J=8.53, 1.51 Hz, 1H) 7.87 (d, J=8.53 Hz, 1H) 7.82 (d, J=9.04 Hz, 1H) 7.93 (s, 1H). MS (ESI, M+1): 422.20.

Example 252: (S)-1-[6-(4-tert-Butyl-cyclohexyloxy)-naphthalen-2-ylmethyl]-pyrrolidine-3-carboxylic acid 1H NMR (400 MHz, MeOD) Shift=7.96-7.92 (m, 2H), 7.90-7.79 (m, 3H), 7.56-7.49 (m, 1H), 7.33-7.28 (m, 1H), 7.24-7.15 (m, 1H), 4.60-4.47 (m, 2H), 4.44-4.33 (m, 1H), 3.74-3.34 (m, 4H), 2.62-2.35 (m, 1H), 2.33-2.20 (m, 2H), 1.99-1.85 (m, 2H), 1.53-1.03 (m, 5H), 0.93 (s, 9H). MS (ESI, M+1): 410.30.

Example 252: (R)-1-[6-(trans-4-trifluoromethyl-cyclohexyloxy)-naphthalen-2-ylmethyl]-pyrrolidine-3-carboxylic acid $^1$H NMR (400 MHz, METHANOL-$d_4$) δ ppm 1.39-1.69 (m, 4H) 1.99-2.14 (m, 3H) 2.19-2.49 (m, 5H) 3.34-3.45 (m, 2H) 3.45-3.70 (m, 2H) 4.40-4.62 (m, 3H) 7.21 (dd, J=8.91, 2.38 Hz, 1H) 7.36 (d, J=2.01 Hz, 1H) 7.53 (dd, J=8.53, 1.51 Hz, 1H) 7.79-7.87 (m, 1H) 7.89 (d, J=8.28 Hz, 1H) 7.95 (s, 1H). MS (ESI, M+1): 422.20.

Example 253; (R)-1-[6-(cis-4-trifluoromethyl-cyclohexyloxy)-naphthalen-2-ylmethyl]-pyrrolidine-3-carboxylic acid $^1$H NMR (400 MHz, METHANOL-$d_4$) δ ppm 1.60-1.90 (m, 6H) 2.17-2.47 (m, 6H) 3.43-3.70 (m, 4H) 4.54 (br. s., 2H) 4.83 (br. s., 1H) 7.27 (dd, J=9.04, 2.26 Hz, 1H) 7.31-7.38 (m, 1H) 7.54 (dd, J=8.53, 1.51 Hz, 1H) 7.81-7.92 (m, 2H) 7.96 (s, 1H). MS (ESI, M+1): 422.20.

Example 254: 3-{[6-(4-Cyclopentylcyclohexyloxy)-naphthalen-2-ylmethyl]-amino}-propionic acid 1H NMR (400 MHz, DMSO-d6) Shift=7.87-7.61 (m, 3H), 7.56-7.39 (m, 1H), 7.32-7.20 (m, 1H), 7.15-6.96 (m, 1H), 4.39-4.25 (m, 1H), 4.20-4.04 (m, 2H), 3.20 (s, 2H), 3.09-2.83 (m, 3H), 2.71-2.49 (m, 3H), 2.14-1.90 (m, 3H), 1.88-1.55 (m, 6H), 1.16 (none, 10H).

Example 256: (R)-1-[6-(4-tert-Pentyl-cyclohexyloxy)-naphthalen-2-ylmethyl]-pyrrolidine-3-carboxylic acid 1H NMR (400 MHz, MeOD) Shift=7.91-7.66 (m, 2H), 7.43 (s, 1H), 7.20 (d, J=2.0 Hz, 1H), 4.43 (s, 1H), 4.35-4.21 (m, 1H), 3.72-3.25 (m, 4H), 2.18 (d, J=11.0 Hz, 3H), 1.75 (br. s., 1H), 1.38-1.06 (m, 5H), 0.88-0.62 (m, 6H). MS (ESI, M+1): 424.30.

Example 257: (R)-1-[6-(4-Ethyl-cyclohexyloxy)-naphthalen-2-ylmethyl]-pyrrolidine-3-carboxylic acid 1H NMR (400 MHz, MeOD) Shift=8.04-7.74 (m, 2H), 7.59-7.43 (m, 1H), 7.37-7.20 (m, 1H), 4.80-4.72 (m, 1H), 4.63-4.41 (m, 1H), 3.80-3.37 (m, 4H), 2.19-1.97 (m, 1H), 1.79-1.22 (m, 6H), 0.94 (s, 3H). MS (ESI, M+1): 382.20.

Example 258: (R)-1-[6-(4-Butyl-cyclohexyloxy)-naphthalen-2-ylmethyl]-pyrrolidine-3-carboxylic acid 1H NMR (400 MHz, MeOD) Shift=7.92-7.64 (m, 2H), 7.42 (d, J=7.5 Hz, 1H), 7.19 (d, J=1.8 Hz, 2H), 4.68-4.57 (m, 0H), 4.43 (s, 0H), 4.37-4.22 (m, 0H), 3.74-3.25 (m, 0H), 2.11 (br. s., 0H), 1.77 (br. s., 0H), 1.68-1.43 (m, 0H), 1.43-0.95 (m, 0H), 0.82 (t, J=6.3 Hz, 3H). MS (ESI, M+1): 410.30.

Example 259: (R)-1-[6-(4-Methoxymethyl-cyclohexyloxy)-naphthalen-2-ylmethyl]-pyrrolidine-3-carboxylic acid 1H NMR (400 MHz, MeOD) Shift=7.70-7.47 (m, 3H), 7.43-7.29 (m, 1H), 7.23-7.06 (m, 1H), 7.04-6.89 (m, 1H), 4.45-4.10 (m, 1H), 3.79-3.53 (m, 2H), 3.20-3.11 (m, 5H), 3.01-2.64 (m, 3H), 2.55-2.32 (m, 2H), 1.79 (s, 7H), 1.30 (none, 5H). MS (ESI, M+1): 398.10.

Example 260: {1-[6-(4-tert-Butyl-cyclohexyloxy)-naphthalen-2-ylmethyl]-pyrrolidin-3-yl}-acetic acid 1H NMR (400 MHz, MeOD) Shift=8.00-7.77 (m, 5H), 7.58-7.47 (m, 2H), 7.30 (d, J=1.5 Hz, 2H), 7.26-7.11 (m, 2H), 4.50 (s, 3H), 4.45-4.32 (m, 2H), 3.79-3.38 (m, 5H), 3.19-2.65 (m, 3H), 2.65-2.10 (m, 9H), 2.04-1.62 (m, 5H), 1.52-1.04 (m, 9H), 0.93 (s, 9H). MS (ESI, M+1): 424.30.

Example 261: 5-(4-tert-Butyl-cyclohexyloxy)-2-methyl-benzothiazole

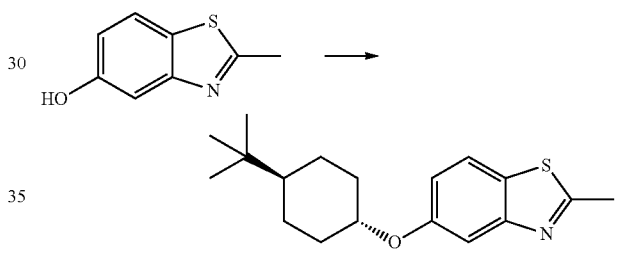

2-Methyl-benzothiazol-5-ol (2.5 g, 0.015 mol), cis-4-tert-butylcyclohexanol (2.84 g, 0.0182 mol), and Triphenylphosphine (4.76 g, 0.0182 mol) were combined in dry Toluene (100 mL, 1 mol) and stirred under nitrogen. Diisopropyl azodicarboxylate (3.6 mL, 0.018 mol) was added dropwise. The reaction was then stirred at RT overnight. Reaction was then concentrated to dryness and then residue was dissolved in DCM and 5 g of SiO$_2$ was added. Solvent was removed under reduced pressure and resulting powder was loaded onto a 40 g column and purified via column chromatography using a gradient of 0-60% EtOAC/Hexanes.

Example 262: 5-(4-tert-Butyl-cyclohexyloxy)-benzothiazole-2-aldehyde

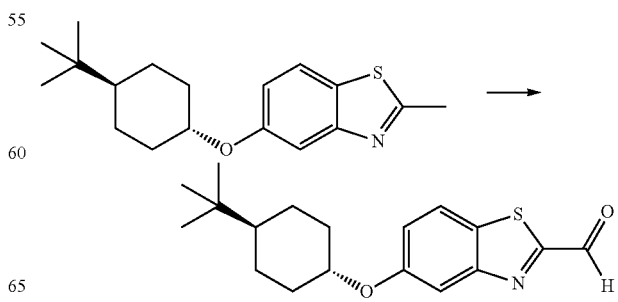

Selenium dioxide (180 mg, 1.6 mmol) was combined with 1,4-Dioxane (5 mL, 60 mmol) and Water (0.5 mL, 30 mmol) at room, temperature open to the atmosphere. The mixture was then treated with 5-(4-tert-Butyl-cyclohexyloxy)-2-methyl-benzothiazole (250 mg, 0.82 mmol) and resulting mixture was heated to 65° C. for 2 hours. The heat was increased to 90° C. and 4 additional eq. of $SeO_2$ were added. Reaction was stirred for additional 5 hours. LCMS shows nearly complete conversion. Reaction become dark and solids formed in reaction mixture. Reaction was cooled to RT and allowed to stand over night. Solids were removed via filtration. Concentrated to dryness then purified directly via column chromatography using a gradient of 0-40% Ethylacetate/hexane to give the title compound as a dark solid.

Example 263: (R)-1-[5-(4-tert-Butyl-cyclohexyloxy)-benzothiazol-2-ylmethyl]-pyrrolidine-3-carboxylic acid

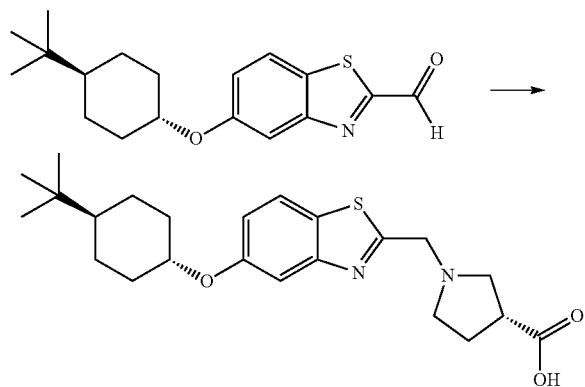

(R)-Pyrrolidine-3-carboxylic acid (100 mg, 0.9 mmol) (HCl salt) was combined with N,N-Diisopropylethylamine (300 uL, 2 mmol) in Methanol (4.0 mL, 98 mmol) and stirred for 15 min. 5-(4-tert-Butyl-cyclohexyloxy)-benzothiazole-2-carbaldehyde (1.0E2 mg, 0.33 mmol) was then added and the mixture was stirred at RT for 30 minutes. After 30 minutes the reaction was cooled to 0° C. and Sodium cyanoborohydride (100 mg, 2 mmol) was added in two portions. The reaction was then allowed to warm to RT while stirring overnight. The reaction was then purified directly on the Gilson (10-90% $CH_3CN/H_2O$ (0.1% TFA), 19×150 cm C18, RT=8.6 min) The product was then dried on the highvac to give the title compound as a white solid. 1H NMR (400 MHz, MeOD) Shift=8.00-7.78 (m, 1H), 7.69-7.51 (m, 1H), 7.27-7.05 (m, 1H), 5.09-4.93 (m, 3H), 4.39-4.21 (m, 1H), 4.01-3.39 (m, 4H), 2.65-2.18 (m, 3H), 2.01-1.80 (m, 2H), 1.53-1.04 (m, 6H), 0.92 (s, 9H). MS (ESI, M+1): 417.30.

Example 264: 1-[6-(4-tert-Butyl-cyclohexyloxy)-naphthalen-2-yl]-2,2,2-trifluoro-ethanone

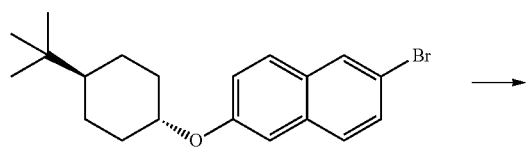

-continued

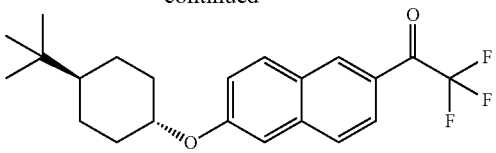

To a solution of 2-Bromo-6-(4-tert-butyl-cyclohexyloxy)-naphthalene (2 g, 0.006 mol) in 15 mL dry THF stirring at −78° C., was added dropwise. The reaction was then stirred at −78° C. for 15 minutes, yellow color results. 2,2,2-Trifluoro-N-methoxy-N-methyl-acetamide (1.0 mL, 0.0083 mol) in 10 mL THF was then added dropwise while the reaction was stirred at −78° C. Once all of the starting material was added reaction the reaction was allowed to warm to room temperature while stirring for 2 hours. The Reaction was then quenched with water and extracted three times with EtOAc. Organics were dried over $MgSO_4$, filtered, and concentrated to dryness under reduced pressure. Crude NMR shows about 80% purity (looks like desbromostarting material). Material was purified via column chromatography using a gradient of hexanes for one column volume followed by 0-10% EtOAC/Hexanes on 25 g of $SiO_2$ to give the title compound as a yellow solid. Material will be carried on without additional purification Example 265: 3-{1-[6-(4-tert-Butyl-cyclohexyloxy)-naphthalen-2-yl]-2,2,2-trifluoro-ethylamino}-propionic acid tert-butyl ester

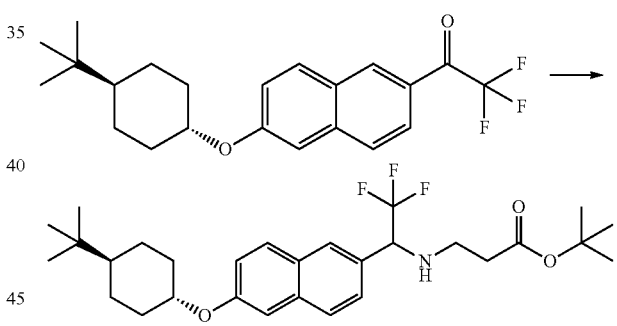

3-Amino-propionic acid tert-butyl ester (106 mg, 0.727 mmol) was combined with N,N-Diisopropylethylamine (575 uL, 3.30 mmol) and 1-[6-(4-tert-Butyl-cyclohexyloxy)-naphthalen-2-yl]-2,2,2-trifluoro-ethanone (250 mg, 0.66 mmol) in Methylene chloride (4 mL, 60 mmol). 1 M of Titanium(IV) chloride in Methylene chloride(727 uL, 0.727 mmol) was added and the mixture was stirred at RT for 5 hours. TLC (20% EtOAC/Hex) shows only traces of SM with new lower Rf spot. The reaction was cooled to 0° C. and Sodium cyanoborohydride (208 mg, 3.30 mmol) in methanol (5 mL) was added carefully in two portions (lots of bubbling so remove cap.) The reaction was then diluted with 10 mL DCM and the solids were removed via filtration. pH was adjust to 10 with 1 M NaOH and the reaction was extracted three times with methylene chloride. Organics were combined and dried over $MgSO_4$. Solids were removed via filtration and the crude reaction was absorbed onto silica (1 g) and purified via column chromatography on 12 g SiO2 using a gradient of 0-15% Ethylacetate/hexane to give material that was impure by NMR and LCMS (compound eluted around 1% EtOAc.) Material was repurified on 24 g ISCO gold column using a long gradient of 0-10% EtOAc/Hex over 30 minutes (desired compound was 2 nd major peak) to give the title compound as a colorless solid.

Example 266: 3-{1-[6-(4-tert-Butyl-cyclohexyloxy)-naphthalen-2-yl]-2,2,2-trifluoro-ethylamino}-propionic acid methyl ester

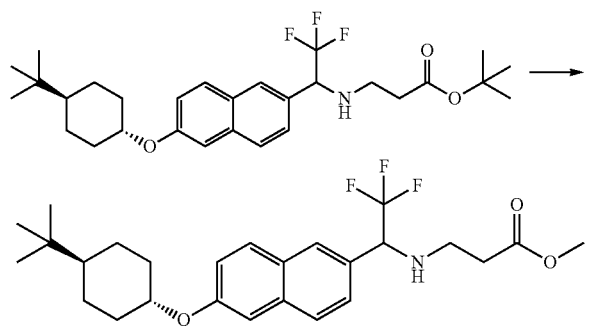

3-{1-[6-(4-tert-Butyl-cyclohexyloxy)-naphthalen-2-yl]-2,2,2-trifluoro-ethylamino}-propionic acid tert-butyl ester (0.174 g, 0.343 mmol) was dissolved in 4 M of Hydrogen chloride in 1,4-Dioxane (3 mL, 10 mmol) and stirred at RT for 2.5 hrs. ALL solvent is removed after purification of the previous step. Reaction was then concentrated to dryness under reduced pressure to give the title compound which was taken directly to the next step.

Example 267: 3-{1-[6-(4-tert-Butyl-cyclohexyloxy)-naphthalen-2-yl]-2,2,2-trifluoro-ethylamino}-propionic acid (BIO-021973)

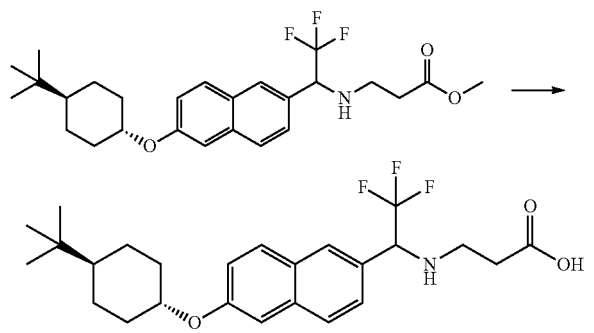

3-{1-[6-(4-tert-Butyl-cyclohexyloxy)-naphthalen-2-yl]-2,2,2-trifluoro-ethylamino}-propionic acid methyl ester (164 mg, 0.352 mmol) was dissolved in Ethanol (2 mL, 40 mmol) then treated with 1 M of Sodium hydroxide in Water (2 mL, 2 mmol). The mixture was stirred vigorously for 1 hour. pH was adjust to 3-4 with 6 N HCl and reaction was then extracted three times with EtOAc. Organics were combined then dried over MgSO₄, filtered and concentrated to dryness under reduced pressure. Ethyl ether was then added and a white ppt formed. The ppt. was removed via filtration to give a white solid that 99% pure by NMR and HPLC-traces of ethanol remain. $^1$H NMR (400 MHz, METHANOL-d$_4$) δ ppm 0.83 (s, 9H) 0.93-1.10 (m, 1H) 1.11-1.27 (m, 2H) 1.27-1.42 (m, 2H) 1.73-1.89 (m, 2H) 2.19 (d, J=10.29 Hz, 2H) 2.67 (t, J=6.53 Hz, 2H) 3.03-3.18 (m, 2H) 4.22-4.37 (m, 1H) 5.33-5.51 (m, 1H) 7.13 (dd, J=8.91, 2.38 Hz, 1H) 7.21-7.29 (m, 1H) 7.46 (d, J=8.78 Hz, 1H) 7.76 (d, J=9.04 Hz, 1H) 7.85 (d, J=8.78 Hz, 1H) 7.93 (s, 1H).

Example 268: 4-methoxypent-3-en-2-one

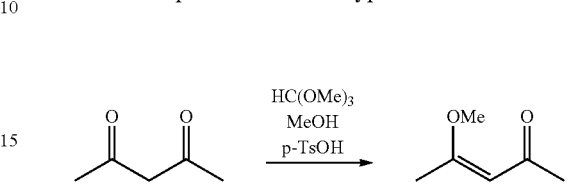

A solution of 2,4-pentanedione (100 g, 1 mol), trimethyl orthoformate (106 g, 1 mol), p-TsOH.H₂O (2.16 g, 11.4 mmol) in MeOH (248 mL) was heated at 55° C. for 5 hrs. The mixture was cooled to room temperature and concentrated. The residue was diluted with CCl₄ (100 mL) and the mixture was concentrated again to give the crude product as a dark-brown oil (~100 g). This residue was subjected to vacuum distillation to give colorless oil (58.0 g, yield: 50%). bp 32-33° C./3 torr).

Example 268: 3-methoxy-1-methylnaphthalene

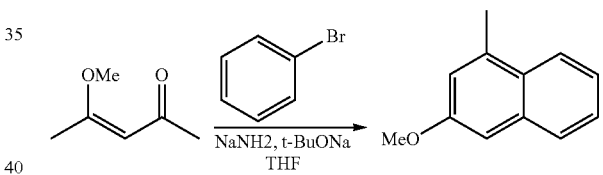

A solution of t-BuOH (44.5 g, 600 mmol) in dry THF (240 mL) was added dropwise to a suspension of NaNH₂ (84.4 g, 2.2 mmol) in dry THF (480 mL) under nitrogen. The resulting mixture was heated for 2 h at 40-45° C. After the mixture was cooled, a solution of 4-methoxypent-3-en-2-one (68.5 g, 600 mmol) in dry THF (480 mL) was added dropwise at 30-40° C. The resulting mixture was stirred at 45° C. for 2 h. A solution of bromobenzene (47.1 g, 300 mmol) in dry THF (240 mL) was added and the mixture was stirred at 55° C. for 6 h. The mixture was allowed to cool to room temperature overnight. The mixture was poured into ice, acidified with an aqueous 3 M HCl solution to pH 4-5 and extracted with EtOAc. The combined organic extracts were concentrated under reduced pressure, and the residue was diluted with acetone (480 mL) and stirred with conc. HCl solution (24 mL) for 10 min. The mixture was diluted with EtOAc (200 mL) and washed with saturated brine (200 mL). The aqueous layer was extracted with EtOAc, and the combined organic layers were dried over sodium sulfate, filtered, and concentrated. The residue was subjected to flash chromatography (700 g silica gel with dry-loading, eluting by 2% EtOAc in heptanes to give orange oil (19 g, yield: 37%).

Example 269: 4-Methylnaphthalen-2-ol

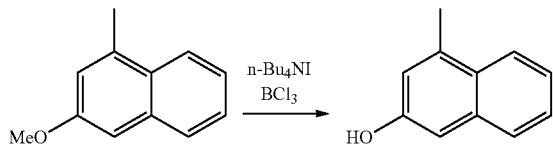

A solution of 4-methylnaphthalen-2-ol compound (22 g, 128 mmol) and n-Bu₄I (52 g, 141 mmol) in dry dichloromethane (650 mL) was added 1.0 M solution of BCl₃ in dichloromethane (192 mL, 192 mmol) at −78° C. under nitrogen. After 5 min, the solution was allowed to warm to 0° C. and stirred for 1 h. The reaction was quenched with cold water (200 mL) and extracted with dichloromethane. The combined extracts were washed with saturated brine, dried over sodium sulfate, filtered, and concentrated. The residue was subjected to flash chromatography, eluting with a gradient of 10% to 50% EtOAc in heptanes to give brown solid product (16 g, yield: 79%).

Example 270: 3-(4-tert-butyl-cyclohexyloxy)-1-methyl-naphthalene

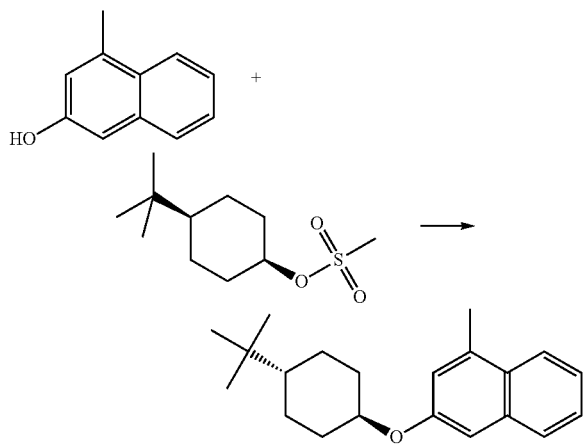

A mixture of 4-methyl-naphthalen-2-ol (0.60 g, 3.8 mmol), methanesulfonic acid 4-tert-butyl-cyclohexyl ester (1.9 g, 7.6 mmol) and cesium carbonate (3.7 g, 11 mmol) in t-BuOH (10 mL) and 2-butanone (7 mL) was heated at 80° C. overnight. After cooled to room temperature, the mixture was treated with water and ether. The organic phase was dried over MgSO₄, filtered and concentrated. The crude was treated with methanol to give solid product (0.55 g, yield: 48%). ESI-MS: 297.20 (M+H)⁺.

Example 271: 6-(4-tert-butyl-cyclohexyloxy)-8-methyl-naphthalene-2-carbaldehyde (13467-25)

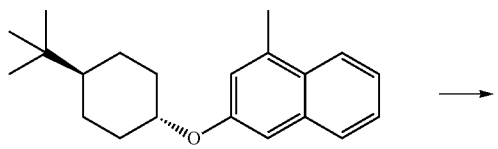

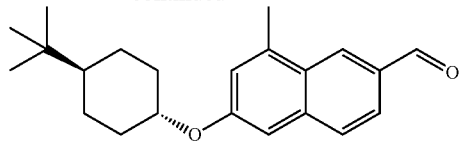

To a mixture of 3-(4-tert-butyl-cyclohexyloxy)-1-methyl-naphthalene (450 mg, 1.5 mmol) in 1,2-dichloroethane (9 mL) was added tin tetrachloride (236 uL, 2 mmol) at 0° C. After stirred at 0° C. for 1 hr, dichloromethyl methyl ether (183 uL, 2 mmol) was added. The solution was stirred at 0° C. for 1 hr and then warmed to room temperature. The mixture was added ice water and stirred for 1 hr, then the dark solution was diluted with dichloromethane and washed with water. The organic phase was washed with sodium bicarbonate aqueous, and dried over MgSO₄. The drying agent was filtered off and the solvent was concentrated to dryness to give dark solid product (0.48 g, yield: 97%). ESI-MS: 325.20 (M+H)⁺.

Example 272: {[6-(4-tert-butyl-cyclohexyloxy)-8-methyl-naphthalen-2-ylmethyl]-amino}-acetic acid methyl ester

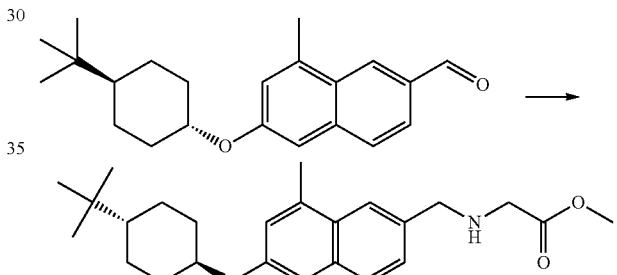

A solution of 6-(4-tert-butyl-cyclohexyloxy)-8-methyl-naphthalene-2-carbaldehyde (50 mg, 0.15 mmol), glycine methyl ester, hydrochloride (27 mg, 0.22 mmol) and N,N-diisopropylethylamine (DIEA) (34 uL) in 1,2-dichloroethane (2 mL) was stirred for 1 hour at room temperature. Then sodium triacetoxyborohydride (52 mg, 0.25 mmol) was added and stirred for 3 hrs. The reaction was diluted with methylene chloride and washed with saturated sodium bicarbonate aqueous, dried over MgSO₄, filtered, and concentrated. The crude was purified via silica gel column chromatography eluted 0-5% MeOH in methylene chloride to give the light brown solid (53 mg, yield: 86%). ESI-MS: 420.30 (M+23)⁺.

Example 273: {[6-(4-tert-butyl-cyclohexyloxy)-8-methyl-naphthalen-2-ylmethyl]-amino}-acetic acid

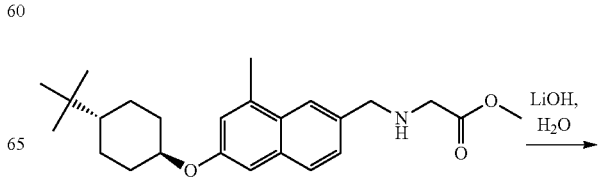

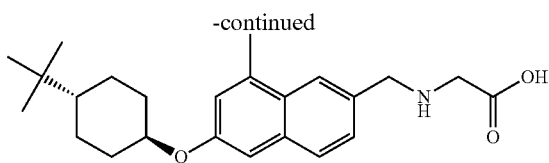

A solution of {[6-(4-tert-butyl-cyclohexyloxy)-8-methyl-naphthalen-2-ylmethyl]-amino}-acetic acid methyl ester (40 mg, 0.1 mmol) and lithium hydroxide (16 mg, 0.67 mmol) in THF (1.4 mL) and water (0.5) was stirred at 22° C. overnight. After the solvent was concentrated, the residue was treated with water. The resulting solid was filtered and washed with water and purified via HPLC to give white precipitate as TFA salt (24 mg, yield: 48%). ESI-MS: 406.30 (M+23)+; 1H NMR (400 MHz, MeOD) δ=8.075 (d, 1H), 8.065 (d, 1H), 7.62 (t, 1H), 7.48 (dd, 1H), 7.38 (s, 1H), 4.78 (s, 2H), 4.52 (m, 1H), 3.86 (s, 1H), 2.75 (s, 3H), 2.66 (s, 1H), 2.27 (d, 2H), 1.926 (d, 2H), 1.557 (m, 2H), 1.256 (m, 2H), 1.152 (m, 1H), 0.92 (s, 9H).

Example 274: 4-{[6-(4-tert-butyl-cyclohexyloxy)-8-methyl-naphthalen-2-ylmethyl]-amino}-butyric acid

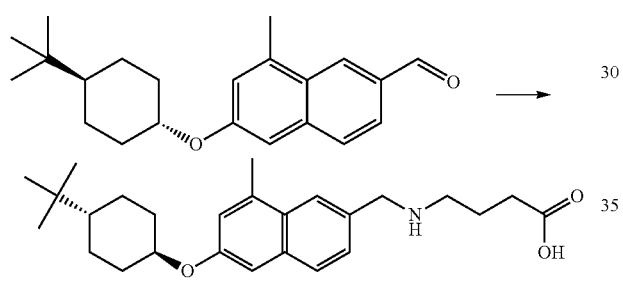

A solution of 6-(4-tert-butyl-cyclohexyloxy)-8-methyl-naphthalene-2-carbaldehyde (50 mg, 0.15 mmol) and 4-aminobutanoic acid (20 mg, 0.19 mmol) in ethanol (0.5 mL) was heated to reflux for 2 hrs. The yellow solution was cooled to room temperature and sodium cyanoborohydride (52 mg) was added. The mixture was heated at 50° C. overnight. The crude product was purified via HPLC to give white solid as TFA salt (9 mg, yield: 11%). ESI-MS: 412.30 (M+H)+; 1H NMR (400 MHz, MeOD) δ 8.06 (d, 1H), 8.03 (d, 1H), 7.58-7.65 (m, 1H), 7.48 (t, J=7.15 Hz, 1H), 7.38 (s, 1H), 4.68 (s, 2H), 4.53 (m, 1H), 3.20 (t, 2H), 2.75 (s, 3H), 2.48 (t, J=6.90 Hz, 2H), 2.29 (d, J=10.54 Hz, 2H), 2.04 (quin, J=7.34 Hz, 2H), 1.94 (d, 2H), 1.54 (m, 2H), 1.28 (m, 2H), 1.16 (m, 1H), 0.93 (s, 9H).

Example 275: 1-[6-(4-tert-butyl-cyclohexyloxy)-8-methyl-naphthalen-2-ylmethyl]-azetidine-3-carboxylic acid methyl ester

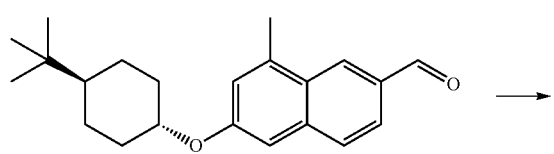

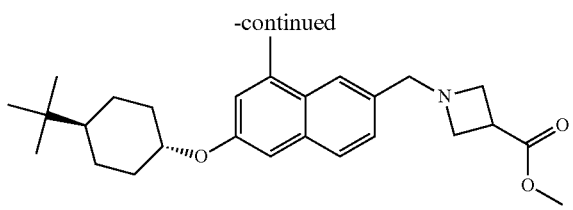

Synthesis was performed as described for {[6-(4-tert-butyl-cyclohexyloxy)-8-methyl-naphthalen-2-ylmethyl]-amino}-acetic acid methyl ester (40 mg, yield: 51%). ESI-MS: 424.30 (M+H)+.

Example 276: 1-[6-(4-tert-butyl-cyclohexyloxy)-8-methyl-naphthalen-2-ylmethyl]-azetidine-3-carboxylic acid

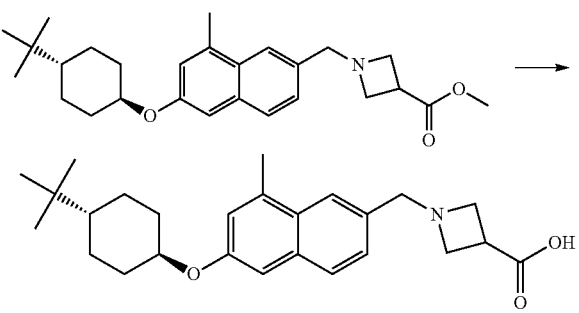

Synthesis was performed as described for {[6-(4-tert-butyl-cyclohexyloxy)-8-methyl-naphthalen-2-ylmethyl]-amino}-acetic acid. The product was treated with 1N HCl aqueous gave light yellow solid as HCl salt (30 mg, yield: 86%). ESI-MS: 410.30 (M+H)+. 1H NMR (400 MHz, DMSO) δ 8.10 (d, 1H), 7.97 (d, 1H), 7.55 (t, 1H), 7.47-7.41 (m, 2H), 4.60-4.45 (m, 2H), 3.97 (s, 3H), 3.50-3.33 (m, 2H), 2.68 (s, 3H), 2.16 (d, 2H), 1.81 (d, 2H), 1.47 (quin, 2H), 1.20 (quin, 2H), 1.09 (m, 2H), 0.88 (s, 9H).

Example 277: 3-{[6-(4-tert-butyl-cyclohexyloxy)-8-methyl-naphthalen-2-ylmethyl]-amino}-propionic acid ethyl ester

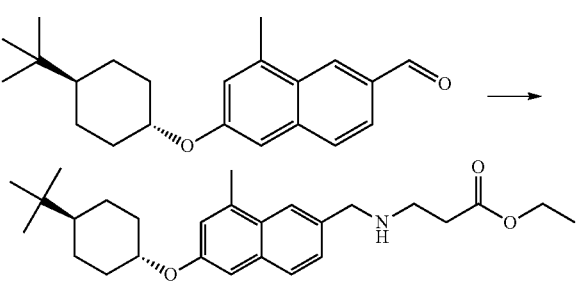

Synthesis was performed as described for {[6-(4-tert-butyl-cyclohexyloxy)-8-methyl-naphthalen-2-ylmethyl]-amino}-acetic acid methyl ester (38 mg, yield: 41%). ESI-MS: 426.30 (M+H)+.

Example 278: 3-{[6-(4-tert-butyl-cyclohexyloxy)-8-methyl-naphthalen-2-ylmethyl]-amino}-propionic acid

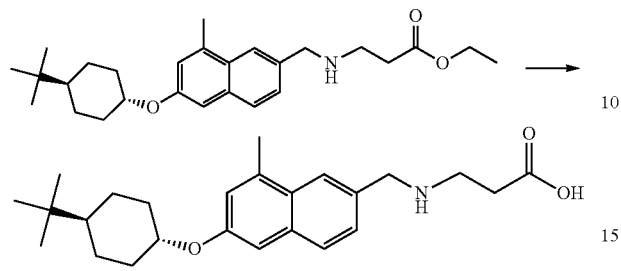

Synthesis was performed as described for {[6-(4-tert-butyl-cyclohexyloxy)-8-methyl-naphthalen-2-ylmethyl]-amino}-acetic acid. The crude was purified via HPLC to give white solid as TFA salt (22 mg, yield: 48%). ESI-MS: 398.20 (M+H)$^+$. $^1$H NMR (400 MHz, CDCl$_3$) δ 8.89 (s, 2H), 7.95 (d, 1H), 7.91 (d, 1H), 7.52 (m, 1H), 7.41 (t, 1H), 7.13 (s, 1H), 4.64 (s, 2H), 4.35 (m, 1H), 3.14 (s, 2H), 2.74-2.65 (m, 5H), 2.18 (d, 2H), 1.85 (d, 2H), 1.47 (m, 2H), 1.20-1.02 (m, 3H), 0.88 (s, 9H).

Example 279: 1-[6-(4-tert-butyl-cyclohexyloxy)-8-methyl-naphthalen-2-ylmethyl]-pyrrolidine-3-carboxylic acid methyl ester

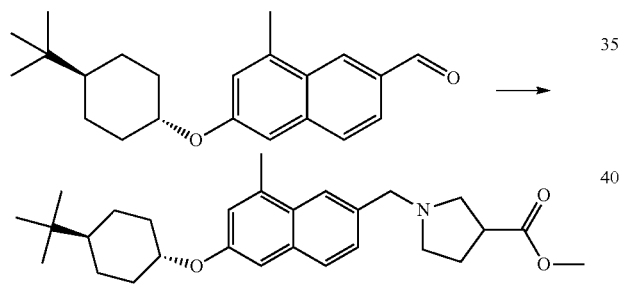

Synthesis was performed as described for {[6-(4-tert-butyl-cyclohexyloxy)-8-methyl-naphthalen-2-ylmethyl]-amino}-acetic acid methyl ester as sticky oil (57 mg, yield: 70%). ESI-MS: 438.30 (M+H)$^+$.

Example 280: 1-[6-(4-tert-butyl-cyclohexyloxy)-8-methyl-naphthalen-2-ylmethyl]-pyrrolidine-3-carboxylate

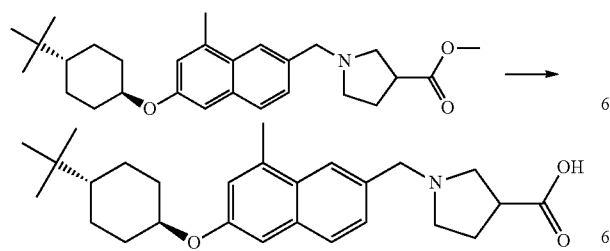

Synthesis was performed as described for {[6-(4-tert-butyl-cyclohexyloxy)-8-methyl-naphthalen-2-ylmethyl]-amino}-acetic acid. (36 mg, yield: 69%). ESI-MS: 424.30 (M+H)$^+$. $^1$H NMR (400 MHz, DMSO) δ 8.14 (d, 1H), 7.88 (d, 1H), 7.44 (t, 1H), 7.35 (m, 1H), 7.27 (s, 1H), 4.31 (m, 1H), 3.89 (s, 2H), 2.73 (t, 1H), 2.62 (s, 3H), 2.53 (m, 3H), 2.36 (m, 1H), 2.12 (d, 2H), 1.90 (m, 1H), 1.78 (d, 2H), 1.64 (m, 1H), 1.36 (m, 2H), 1.20-1.00 (m, 3H), 0.85 (s, 9H).

Example 281: 3-(4-tert-butyl-cyclohexyloxy)-1-iodo-naphthalene

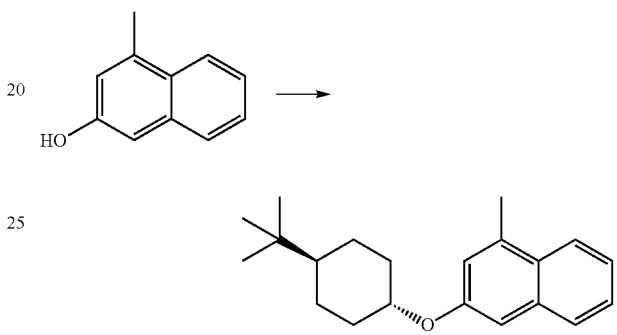

A mixture of 4-iodo-naphthalen-2-ol (1.0 g, 3.7 mmol) (See, for example, Australian Journal of Chemistry (1963), 16 401-10. b. Journal of the Chemical Society (1943), 468-9, which is incorporated by reference in its entirety), methanesulfonic acid 4-tert-butyl-cyclohexyl ester (1.8 g, 7.4 mmol) and cesium carbonate (3.6 g, 11 mmol) in tert-butyl alcohol (10 mL) and 2-butanone (7 mL) was heated in a sealed vial at 100° C. for 4 hrs. The mixture was partitioned between water and dichloromethane. The organic phase was washed with brine, dried over MgSO$_4$, filtered and concentrated. The residue was purified via a silica gel column eluted with EtOAc in hexanes from 0 to 30% to give light yellow precipitate (1.10 g, yield: 73%). ESI-MS: 409.10 (M+H)$^+$.

Example 282: 6-(4-tert-butyl-cyclohexyloxy)-8-iodo-naphthalene-2-carbaldehyde

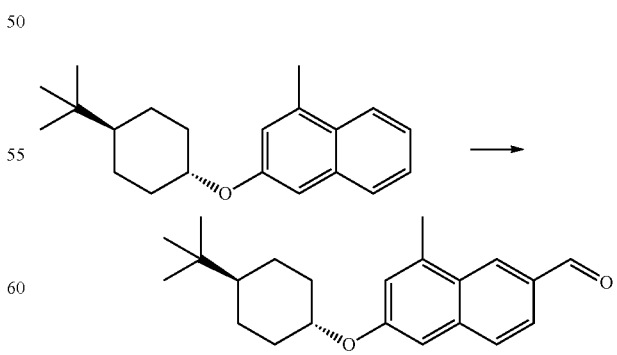

Synthesis was performed as described for 6-(4-tert-butyl-cyclohexyloxy)-8-methyl-naphthalene-2-carbaldehyde (sticky oil, 700 mg, yield: 98%). ESI-MS: 437.10 (M+H)$^+$.

Example 283: 3-{[6-(4-tert-butyl-cyclohexyloxy)-8-iodo-naphthalen-2-ylmethyl]-amino}-propionic acid ethyl ester

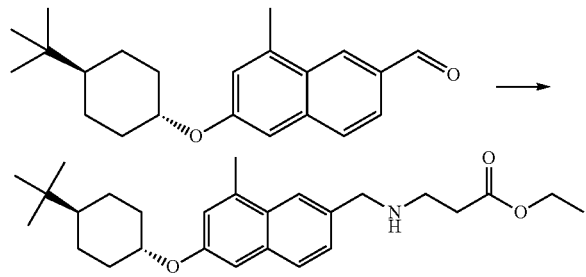

Synthesis was performed as described for {[6-(4-tert-butyl-cyclohexyloxy)-8-methyl-naphthalen-2-ylmethyl]-amino}-acetic acid methyl ester (light brown solid, 110 mg, yield: 40%). ESI-MS: 538.20 (M+H)$^+$.

Example 284; 3-{[6-(4-tert-Butyl-cyclohexyloxy)-8-iodo-naphthalen-2-ylmethyl]-amino}-propionic acid; compound with trifluoro-acetic acid

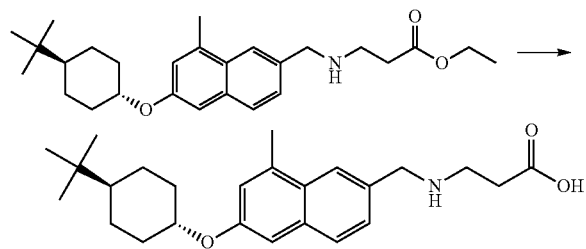

Synthesis was performed as described for {[6-(4-tert-butyl-cyclohexyloxy)-8-methyl-naphthalen-2-ylmethyl]-amino}-acetic acid. The crude was purified via HPLC to give white solid as TFA salt (7 mg, yield: 30%). ESI-MS: 510.20 (M+H)$^+$. $^1$H NMR (400 MHz, MeOD) δ 8.13 (d, 1H), 8.12 (s, 1H), 8.05 (d, 1H), 7.66 (m, 1H), 7.54 (m, 1H), 4.72 (s, 2H), 4.54 (m, 1H), 3.14 (t, 2H), 2.81 (t, 1H), 2.66 (s, 1H), 2.28 (d, 2H), 1.94 (d, 2H), 1.60 (m, 2H), 1.30 (m, 2H), 1.16 (m, 1H), 0.93 (s, 9H).

Example 285: [6-(4-tert-Butyl-cyclohexyloxy)-naphthalen-2-yl]-acetic acid ethyl ester

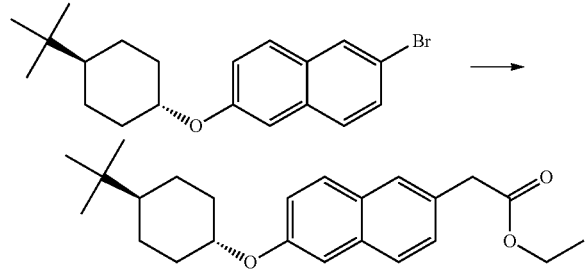

A solution of 2-bromo-6-(4-tert-butyl-cyclohexyloxy)-naphthalene (2 g, 5.5 mmol) in ether (10 mL) under nitrogen was added 1.6 M n-butyllithium in hexane (4 mL, 6.4 mmol) at 0° C. The solution was stirred for 30 min at 0° C., then treated with copper(I) bromide-dimethyl sulfide complex (0.8 g, 3.9 mmol). After 2 hrs stirring, a solution of ethyl bromoacetate (0.7 mL, 6 mmol) in ether (4 mL) was added. The solution was stirred at 0° C. for 2 hrs, then warmed to room temperature for 3 hrs. The reaction was quenched with 10% HCl aqueous then the insoluble was filtered off. The organic layer was washed with water, sodium bicarbonate aqueous, dried over MgSO$_4$, filtered and concentrated. The crude was purified via silica gel column eluted with EtOAc in hexanes from 0 to 10% to give light yellow solid (0.45 g, yield: 22% yield). ESI-MS: 369.20 (M+H)$^+$.

Example 286: 2-[6-(4-tert-Butyl-cyclohexyloxy)-naphthalen-2-yl]-ethanol

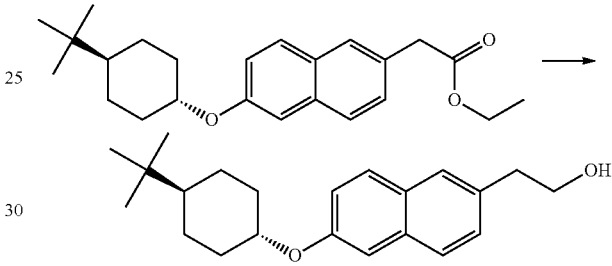

To a solution of [6-(4-tert-butyl-cyclohexyloxy)-naphthalen-2-yl]-acetic acid ethyl ester (250 mg, 0.68 mmol) in THF (10 mL) was added 1.0 M of lithium tetrahydroaluminate in THF (2 mL, 2 mmol) at 0° C. After stirred at room temperature for 2 hrs, the solution was quenched with ethyl acetate (1 mL), then added Rochelle's salt aqueous (1.5 mL). The solution was stirred for 1 hr, then extracted with ethyl acetate. The organic phase was dried over MgSO$_4$, filtered and concentrated. The resulting crude was purified via a silica gel column eluted with EtOAc in hexanes from 0 to 60% to give white precipitate (0.17 g, yield: 77%). ESI-MS: 327.20 (M+H)$^+$.

Example 287: [6-(4-tert-Butyl-cyclohexyloxy)-naphthalen-2-yl]-acetaldehyde

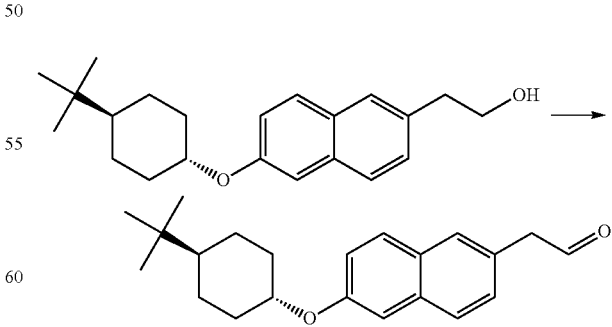

A solution of 2-[6-(4-tert-butyl-cyclohexyloxy)-naphthalen-2-yl]-ethanol (170 mg, 0.52 mmol) in methylene chloride (5 mL) was added Dess-Martin periodinane (0.31 g, 0.73 mmol).

After stirred at room temperature for 1 hour, the solution was diluted with methylene chloride, washed with sodium thiosulfate aqueous, dried over Na₂SO₄, and concentrated. The crude was purified via silica gel column to afford white solid (120 mg, yield: 70%). ESI-MS: 325.20 (M+H)⁺.

Example 288: 3-{2-[6-(4-tert-butyl-cyclohexyloxy)-naphthalen-2-yl]-ethylamino}-propionic acid tert-butyl ester

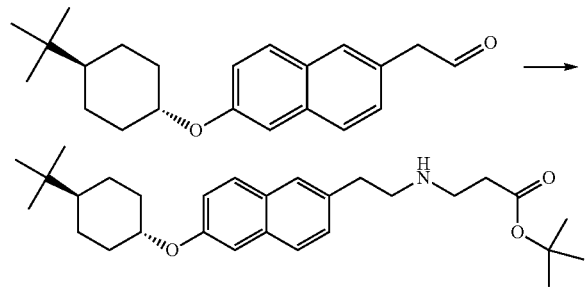

Synthesis was performed as described for {[6-(4-tert-butyl-cyclohexyloxy)-8-methyl-naphthalen-2-ylmethyl]-amino}-acetic acid methyl ester as white solid (13 mg, yield: 30%). ESI-MS: 454.40 (M+H)⁺.

Example 289: 3-{2-[6-(4-tert-Butyl-cyclohexyloxy)-naphthalen-2-yl]-ethylamino}-propionic acid

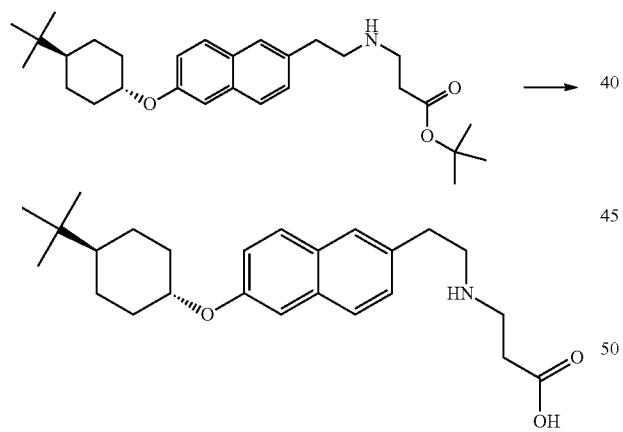

A solution of 3-{2-[6-(4-tert-butyl-cyclohexyloxy)-naphthalen-2-yl]-ethylamino}-propionic acid tert-butyl ester (13 mg, 0.028 mmol) in 4 M of HCl in 1,4-dioxane (0.50 mL) was stirred at room temperature overnight. After the solvent was concentrated, the crude was purified via HPLC to give white solid (7 mg, yield: 49%). ESI-MS: 398.30 (M+H)⁺. ¹H NMR (400 MHz, MeOD) δ 7.73 (d, 1H), 7.70 (d, 1H), 7.65 (s, 1H), 7.33 (dd, 1H), 7.21 (d, 1H), 7.09 (dd, 1H), 4.31 (m, 1H), 3.41-3.31 (m, 4H), 3.14 (t, 2H), 2.74 (t, 2H), 2.25 (d, 2H), 1.89 (d, 2H), 1.40 (m, 2H), 1.24 (m, 2H), 1.10 (m, 1H), 0.90 (s, 9H).

Example 290: (R)-1-{2-[6-(4-tert-Butyl-cyclohexyloxy)-naphthalen-2-yl]-ethyl}-pyrrolidine-3-carboxylic acid

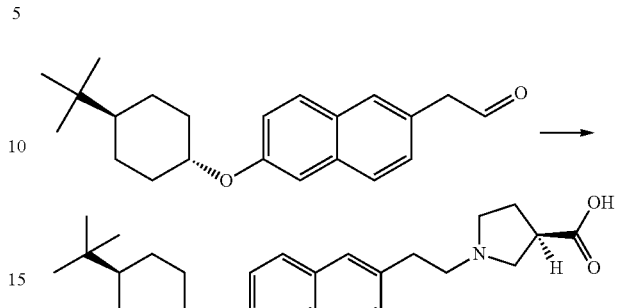

A mixture of (R)-pyrrolidine-3-carboxylic acid, HCl salt (54 mg, 0.35 mmol) and potassium carbonate (0.11 g, 0.79 mmol) in methanol (1.4 mL) was stirred for 15 min. The solids were then removed via filtration, and the filtrate was concentrated. The residue was added [6-(4-tert-butyl-cyclohexyloxy)-naphthalen-2-yl]-acetaldehyde (57 mg, 0.18 mmol) and sodium triacetoxyborohydride (200 mg, 1 mmol) in 1,2-dichloroethane (2 mL) and acetic acid (0.14 mL, 2.4 mmol). After heating at 80° C. for 2 hrs, the reaction was diluted with dichloromethane and washed with 5% of citric acid aqueous. The organic phase was concentrated and residue was purified via HPLC to give solid as TFA salt (42 mg, yield: 44%). ESI-MS: 424.30 (M+H)⁺;

Example 291: 6-hydroxy-3,4-dihydro-1H-isoquinoline-2-carboxylic acid tert-butyl ester

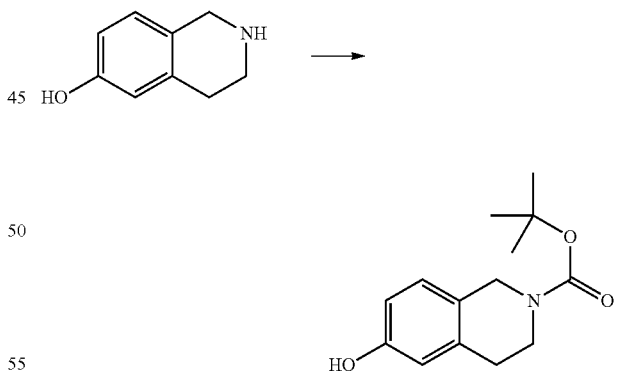

A solution of 1,2,3,4-tetrahydro-isoquinolin-6-ol, HCl salt (2 g, 10 mmol) and di-tert-butyldicarbonate (4 g, 18 mmol) in saturated aqueous sodium bicarbonate solution (20 mL) and chloroform (20 mL) was stirred at room temperature overnight. The organic phase was washed with water, dried over MgSO₄, filtered and concentrated. The crude was purified via a silica gel column eluted with EtOAc in hexanes from 0 to 100% to give desired product (1.7 g, yield: 65%).

Example 292: 6-(4-tert-Butyl-cyclohexyloxy)-3,4-dihydro-1H-isoquinoline-2-carboxylic acid tert-butyl ester

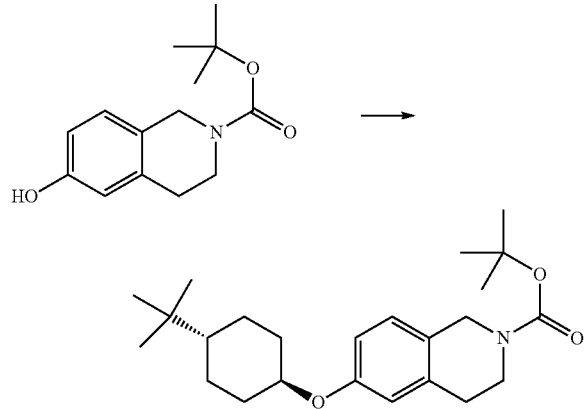

A mixture of 6-hydroxy-3,4-dihydro-1H-isoquinoline-2-carboxylic acid tert-butyl ester (1.1 g, 4.4 mmol), cesium carbonate (4.3 g, 13 mmol), and methanesulfonic acid 4-tert-butyl-cyclohexyl ester (2.2 g, 8.8 mmol). in t-BuOH (12 mL) and 2-butanone (6.0 mL) was heated in a sealed vial at 100° C. overnight. The mixture was partitioned between water and ether. The organic phase was washed with water, dried over MgSO$_4$, filtered and concentrated. The residue was purified via a silica gel column eluted with EtOAc in hexanes from 0 to 30% to give white precipitate (1.0 g, yield: 58%). $^1$H NMR (400 MHz, CDCl$_3$) δ 6.99 (d, 1H), 6.74 (dd, 1H), 6.67 (d, 1H), 4.49 (s, 2H), 4.07 (m, 1H), 3.61 (s, 2H), 2.78 (m, 2H), 2.18 (d, 2H), 1.85 (d, 2H), 1.48 (s, 9H), 1.37 (m, 2H), 1.18-1.00 (m, 3H), 0.87 (s, 9H).

Example 293: 6-(4-tert-Butyl-cyclohexyloxy)-1,2,3,4-tetrahydro-isoquinoline

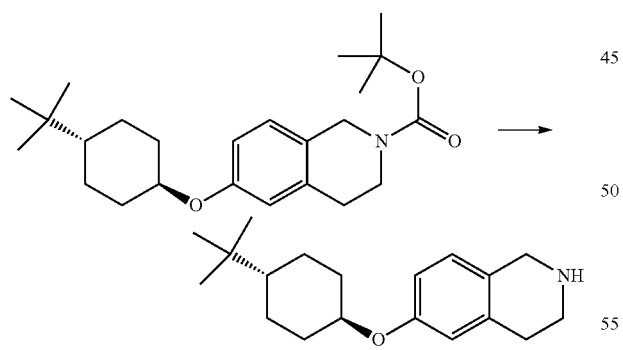

A solution of 6-(4-tert-butyl-cyclohexyloxy)-3,4-dihydro-1H-isoquinoline-2-carboxylic acid tert-butyl ester (0.89 g, 2.3 mmol) in 4 M of HCl in 1,4-dioxane (10 mL, 40 mmol) and ether (40 mL) was stirred at room temperature for 3 hrs to form white precipitate. The solid was collected by filtration to give desired product as HCl salt (0.73 g, yield: 98%). (400 MHz, DMSO) δ 7.09 (d, 1H), 6.81 (d, 1H), 6.80 (s, 1H), 4.20 (m, 1H), 4.14 (m, 2H), 3.31 (m, 2H), 2.95 (t, 2H), 2.09 (d, 2H), 1.77 (d, 2H), 1.27 (m, 2H), 1.20-0.98 (m, 3H), 0.85 (s, 9H).

Example 294: 3-tert-butoxycarbonylamino-4-[6-(4-tert-butyl-cyclohexyloxy)-3,4-dihydro-1H-isoquinolin-2-yl]-4-oxo-butyric acid tert-butyl ester

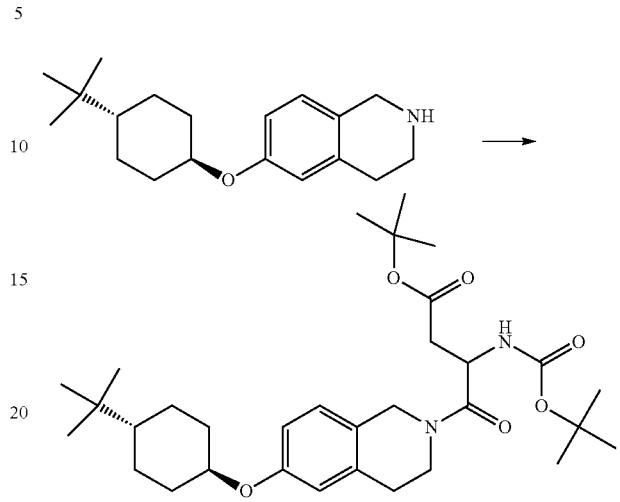

A mixture of 6-(4-tert-butyl-cyclohexyloxy)-1,2,3,4-tetrahydro-isoquinoline HCl salt, (80 mg, 0.25 mmol), 2-tert-butoxycarbonylamino-succinic acid 4-tert-butyl ester (143 mg, 0.49 mmol), triethylamine (41 uL), N-(3-dimethylaminopropyl)-N'-ethylcarbodiimide hydrochloride (57 mg, 0.30 mmol) and HOBT monohydrate (10 mg, 0.06 mmol) in DMF (2.0 mL) was heated at 50° C. for 4 hrs. The solution was diluted with ether and washed with water. The organic phase was dried over MgSO$_4$, filtered and concentrated. The residue was purified via a silica gel column eluted with EtOAc in hexanes from 0 to 20% to give desired product (90 mg, yield: 65%).

Example 295: 3-amino-4-[6-(4-tert-butyl-cyclohexyloxy)-3,4-dihydro-1H-isoquinolin-2-yl]-4-oxo-butyric acid

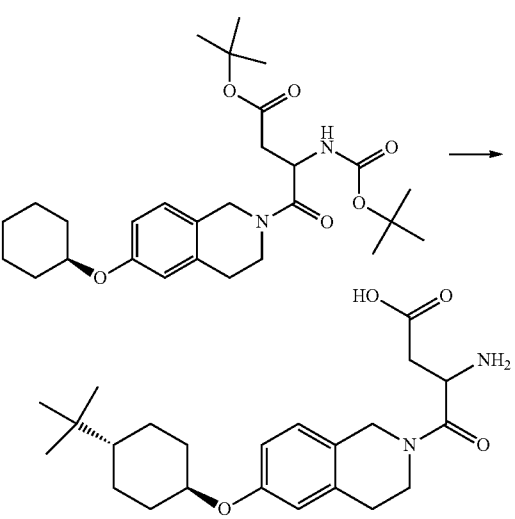

A solution of 3-tert-butoxycarbonylamino-4-[6-(4-tert-butyl-cyclohexyloxy)-3,4-dihydro-1H-isoquinolin-2-yl]-4-oxo-butyric acid tert-butyl ester (90 mg, 0.16 mmol) in methylene chloride (1.0 mL) and trifluoroacetic acid (0.3 mL) was stirred at room temperature overnight. After the solvent was concentrated, the residue was purified via HPLC to give white solid as TFA salt (48 mg, yield: 58%). ESI-MS: 403.80 (M+H)$^+$; 1H NMR (400 MHz, CDCl$_3$) δ 6.95 (dd, 1H), 6.70 (d, 1H), 6.62 (d, 1H), 4.86 (m, 1H), 4.61-4.41 (m, 2H), 4.04 (m, 1H), 3.73-3.51 (m, 2H), 2.95-2.75 (m, 3H), 2.70 (m, 1H), 2.14 (d, 2H), 1.83 (d, 2H), 1.34 (q, 2H), 1.17-0.99 (m, 3H), 0.86 (s, 9H).

Example 296:
5-hydroxy-2,3-dihydro-indole-1-carboxylic acid tert-butyl ester

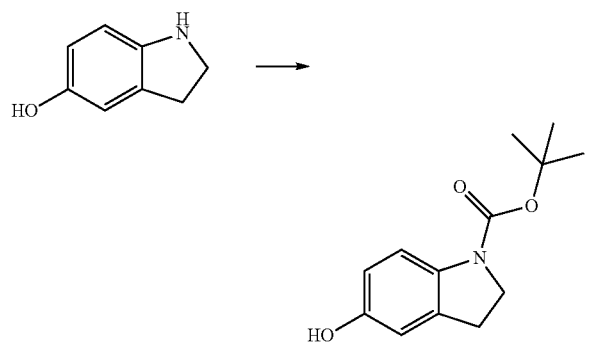

Synthesis was performed as described for 6-hydroxy-3,4-dihydro-1H-isoquinoline-2-carboxylic acid tert-butyl ester (1.1 g, yield: 60%). ESI-MS: 258.10 (M+23)$^+$.

Example 297: 5-(4-Trifluoromethyl-cyclohexyloxy)-2,3-dihydro-indole-1-carboxylic acid tert-butyl ester

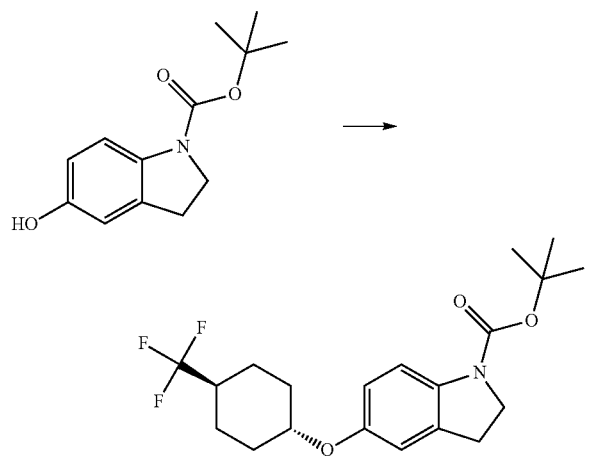

A mixture of 5-hydroxy-2,3-dihydro-indole-1-carboxylic acid tert-butyl ester (0.33 g, 1.4 mmol), cesium carbonate (0.93 g, 2.8 mmol), and methanesulfonic acid 4-trifluoromethyl-cyclohexyl ester (0.70 g, 2.8 mmol) in t-BuOH (5 mL) and 2-butanone (2.5 mL) was heated in a sealed vial at 100° C. overnight. The mixture was treated with dichloromethane to form precipitate. The solid was filtered off and the filtrate was concentrated. The residue was treated with minimum of amount dichloromethane to form solid during 2 days. The solid was filtered and washed with ether to give desired product (200 mg, yield: 40%). ESI-MS: 408.20 (M+23)$^+$.

Example 298: 5-(4-Trifluoromethyl-cyclohexyloxy)-2,3-dihydro-1H-indole

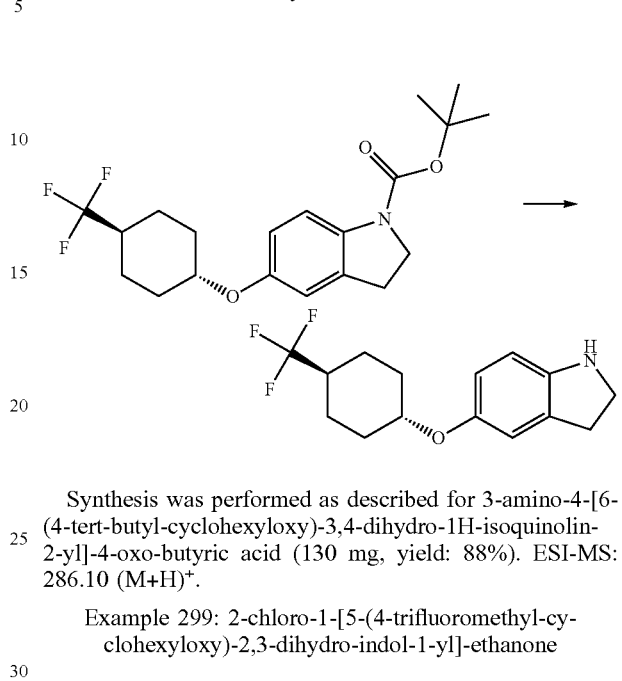

Synthesis was performed as described for 3-amino-4-[6-(4-tert-butyl-cyclohexyloxy)-3,4-dihydro-1H-isoquinolin-2-yl]-4-oxo-butyric acid (130 mg, yield: 88%). ESI-MS: 286.10 (M+H)$^+$.

Example 299: 2-chloro-1-[5-(4-trifluoromethyl-cyclohexyloxy)-2,3-dihydro-indol-1-yl]-ethanone

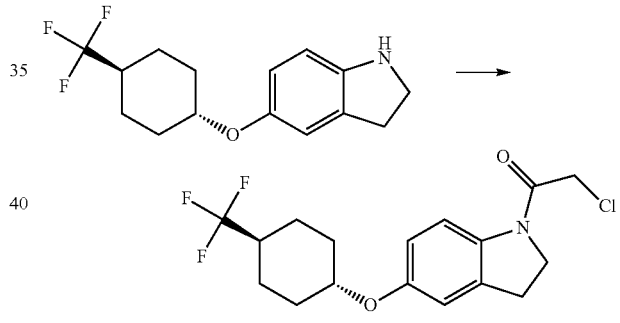

A mixture of 5-(4-trifluoromethyl-cyclohexyloxy)-2,3-dihydro-1H-indole (130 mg, 0.46 mmol) and DIEA (103 uL) in methylene chloride (2 mL) was added chloroacetyl chloride (47 uL, 0.59 mmol) at room temperature. The black solution was stirred for 30 min. The solvent was concentrated to give crude product. The crude was used directly for next step without further purification (80 mg, yield: 77%). ESI-MS: 362.10 (M+H)$^+$.

Example 300: 3-{2-oxo-2-[5-(4-trifluoromethyl-cyclohexyloxy)-2,3-dihydro-indol-1-yl]-ethyl-amino}-propionic acid ethyl ester

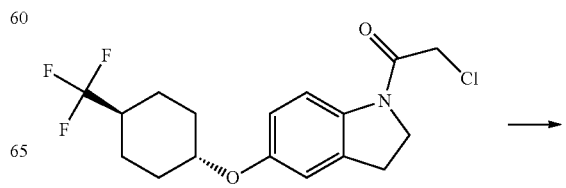

-continued

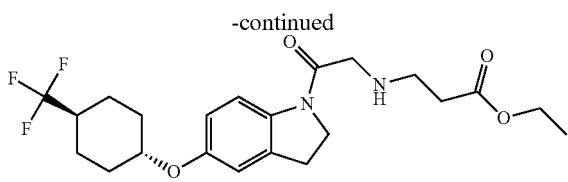

A mixture of crude 2-chloro-1-[5-(4-trifluoromethyl-cyclohexyloxy)-2,3-dihydro-indol-1-yl]-ethanone (80 mg, 0.22 mmol), 3-amino-propionic acid ethyl ester as HCl salt (68 mg, 0.44 mmol) and potassium carbonate (98 mg, 0.71 mmol) in acetonitrile (2 mL) was heated to reflux for 4 hrs. The mixture was treated with water and extracted with ether. The organic phase was dried over MgSO$_4$, concentrated, and purified via a silica gel column to give desired product (11 mg, yield 10%). ESI-MS: 443.20 (M+H)$^+$.

Example 301: 3-{2-oxo-2-[5-(4-trifluoromethyl-cyclohexyloxy)-2,3-dihydro-indol-1-yl]-ethyl-amino}-propionic acid

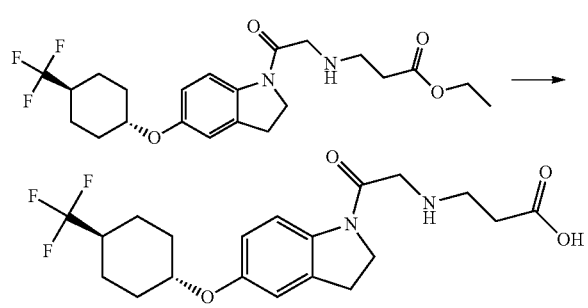

Synthesis was performed as described for {[6-(4-tert-butyl-cyclohexyloxy)-8-methyl-naphthalen-2-ylmethyl]-amino}-acetic acid (3.8 mg, yield: 35%). ESI-MS: 415.20 (M+H)$^+$. $^1$H NMR (400 MHz, MeOD) δ 8.03 (d, 1H), 6.89 (s, 1H), 6.78 (dd, 1H), 4.58 (m, 1H), 4.15-4.03 (m, 4H), 3.22 (t, 2H), 2.79 (q, 1H), 2.64 (t, 2H), 2.22 (m, 1H), 2.11 (d, 2H), 1.78-1.69 (m, 5H), 1.67-1.56 (m, 2H).

Example 302: 2-((trans)-4-tert-butylcyclohexyloxy)quinoline-6-carbaldehyde

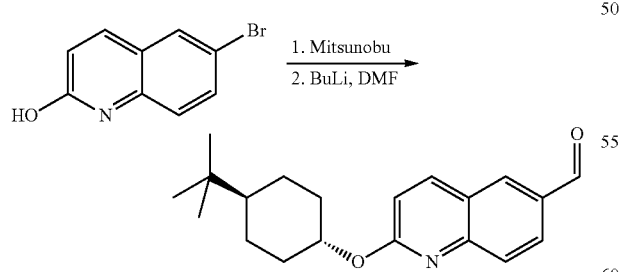

The mixture of 6-bromo-quinolin-2-ol (500 mg, 0.002 mol), cis-tert-butylcyclohexanol (418.5 mg, 0.002678 mol), and triphenylphosphine (702.4 mg, 0.002678 mol) in toluene (4.754 mL, 0.04463 mol) was heated to reflux, and diisopropyl azodicarboxylate (0.5273 mL, 0.002678 mol) was added dropwise and was stirred and refluxed for 6 hours. The mixture was taken up into DCM and subjected to chromatography purification with EtOAc/hexane (0:100 to 40:60) to give product as a white solid (253 mg, 30%). LCMS Rt=2.82 min (m/z=364.45, M+2, 100%).

6-Bromo-2-(4-tert-butyl-cyclohexyloxy)-quinoline (115 mg, 0.317 mmol) in tetrahydrofuran (2.6 mL, 32 mmol) was added 2.0 M of n-butyllithium in cyclohexane (0.48 mL, 0.95 mmol) at −78° C. and was stirred for 15 min. N,N-dimethylformamide (0.12 mL, 1.6 mmol) was added and was stirred for 30 minutes. When the reaction completed, 1 M HCl was added and after 5 min at −78° C., sat. NaHCO$_3$ was added and extracted with EtOAc. The organic layer was concentrated and purified by silica gel chromatography using PE/EA (0-50%) as eluent to give product as a gel (30.6 mg, 31%). LCMS Rt=2.49 min m/z=312.51 ([M+1], 100%).

Example 303: 3-((2-((trans)-4-tert-butylcyclohexyloxy)quinolin-6-yl)methylamino)propanoic acid

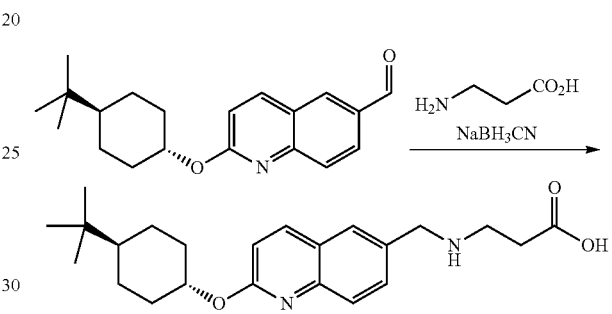

A solution of 2-(4-tert-butyl-cyclohexyloxy)-quinoline-6-carbaldehyde (30.6 mg, 0.0983 mmol) and Beta-alanine (8.75 mg, 0.0983 mmol) in ethanol (0.7 mL, 10 mmol) was heated to reflux for 2 h. The yellow solution was cooled to rt and sodium cyanoborohydride (7.41 mg, 0.118 mmol) was added and was heated to reflux for 1 h. After cooled down to rt, citric acid was added and concentrated down. The solid was suspended in water and filtrate, and the collected solid was washed thoroughly with water. HPLC purification of the solid give the product (7.5 mg, 15%). LCMS Rt=1.60 min m/z=385.49 [M+1]. 1H NMR (400 MHz, MeOD) δ=8.14 (d, J=8.8 Hz, 1H), 7.92 (s, 1H), 7.88 (d, J=8.7 Hz, 1H), 7.72 (d, J=10.7 Hz, 1H), 6.96 (d, J=8.8 Hz, 1H), 5.29-5.09 (m, 1H), 4.40 (s, 2H), 3.36 (t, J=5.8 Hz, 2H), 2.79 (t, J=6.7 Hz, 2H), 2.30 (d, J=10.9 Hz, 2H), 1.94 (d, J=12.9 Hz, 2H), 1.55-1.06 (m, 5H), 0.94 (s, 9H).

Example 304: methyl 6-(spiro[4.5]decan-8-yloxy)-2-naphthoate

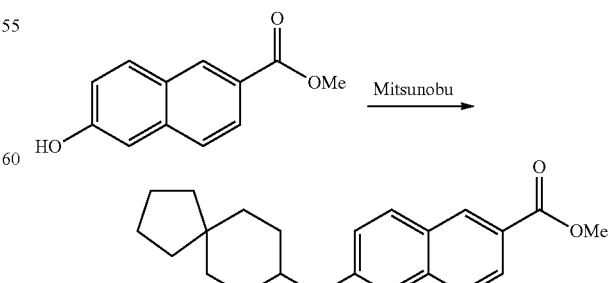

The mixture of spiro[4.5]decan-8-ol (0.915 g, 0.00593 mol), 6-hydroxy-naphthalene-2-carboxylic acid methyl ester (1.00 g, 0.00494 mol) and triphenylphosphine (1.56 g, 0.00593 mol) in toluene (10 mL, 0.1 mol) was heated to reflux, and diisopropyl azodicarboxylate (1.17 mL, 0.00593 mol) was added dropwise and was stirred and refluxed for 6 hours. The mixture was taken up into DCM and subjected to chromatography purification with EtOAc/hexane (0:100 to 40:60) to give product as a white solid (1.02 g, 61%). LCMS Rt=2.58 min, m/z=339.34, (M+1, 100%).

Example 305: (6-(spiro[4.5]decan-8-yloxy)naphthalen-2-yl)methanol

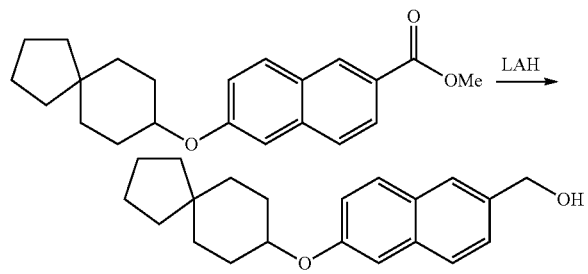

6-(Spiro[4.5]dec-8-yloxy)-naphthalene-2-carboxylic acid methyl ester (0.312 g, 0.000922 mol) in tetrahydrofuran (9 mL, 0.1 mol) and 1.0 M of lithium tetrahydroaluminate in tetrahydrofuran (2.76 mL, 0.00276 mol) was added at 0° C. After stirring at rt for 2 h, quench with EtOAc, then Rochele's salt was added and stirred at rt for 1 h. Extraction with EtOAc, c/c give the product as a white solid (257.2 mg, 90%). LCMS Rt=2.21 min m/z=293.30 ([M-17], 100%).

Example 306: 6-(spiro[4.5]decan-8-yloxy)-2-naphthaldehyde

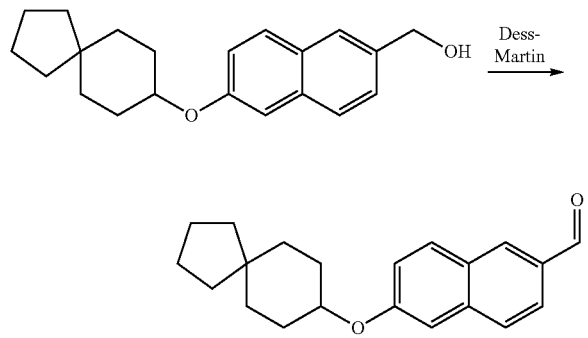

[6-(Spiro[4.5]dec-8-yloxy)-naphthalen-2-yl]-methanol (257.2 mg, 0.8285 mmol) in methylene chloride (9 mL, 100 mmol) was added Dess-Martin periodinane (0.492 g, 1.16 mmol) and was stirred at room temperature for 1 hour. After pass through si gel plug, the solvent was concentrated down to give product as a solid (256 mg, 100%). LCMS Rt=2.44 min m/z=309.56 ([M+1], 100%).

Example 307: 3-((6-(spiro[4.5]decan-8-yloxy)naphthalen-2-yl)methylamino)propanoic acid

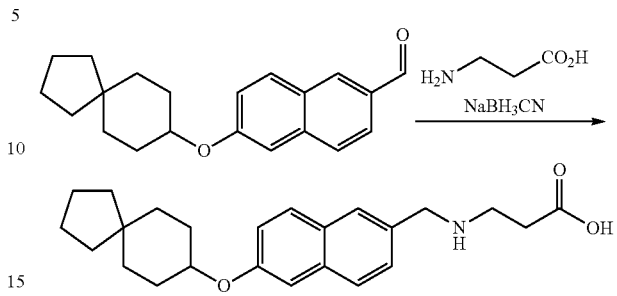

A solution of 6-(Spiro[4.5]dec-8-yloxy)-naphthalene-2-carbaldehyde (229.5 mg, 0.7441 mmol) and Beta-alanine (66.3 mg, 0.744 mmol) in ethanol (1 mL, 20 mmol) was heated to reflux for 2 h. The yellow solution was cooled to rt and sodium cyanoborohydride (56.1 mg, 0.893 mmol) was added and was heated to reflux for 1 h. After cooled down to rt, citric acid was added and concentrated down. Extraction with DCM and prep HPLC gave product as a white solid (88 mg, 31%). LCMS Rt=1.52 min m/z=382.30 [M+1]. $^1$H NMR (400 MHz, MeOD) δ=7.89 (s, 1H), 7.83 (d, J=8.5 Hz, 1H), 7.80 (d, J=9.0 Hz, 1H), 7.48 (dd, J=1.7, 8.5 Hz, 1H), 7.27 (s, 1H), 7.19 (dd, J=2.3, 8.9 Hz, 1H), 4.55-4.44 (m, 1H), 4.35 (s, 2H), 3.36-3.32 (m, 2H), 2.76 (t, J=6.8 Hz, 2H), 2.09-1.33 (m, 16H).

The sequence used to make 3-((6-(spiro[4.5]decan-8-yloxy)naphthalen-2-yl)methylamino)propanoic acid was utilized to synthesize the compound below using the appropriate alcohol as starting material.

Example 308: 3-((6-(spiro[5.5]undecan-3-yloxy)naphthalen-2-yl)methylamino)propanoic acid

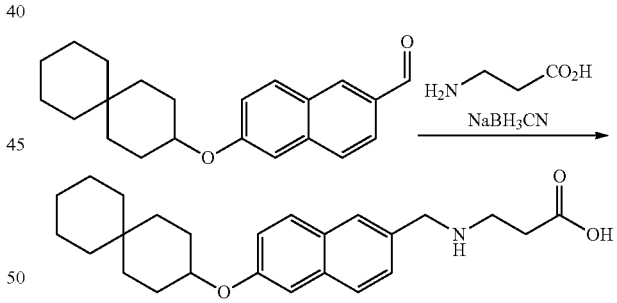

A solution of 6-(spiro[5.5]undec-3-yloxy)-naphthalene-2-carbaldehyde (150 mg, 0.46 mmol) and Beta-alanine (41.4 mg, 0.465 mmol) in ethanol (0.7 mL, 10 mmol) was heated to reflux for 2 h. The yellow solution was cooled to rt and sodium cyanoborohydride (35.1 mg, 0.558 mmol) was added and was heated to reflux for 1 h. After cooled down to rt, citric acid was added and concentrated down. LCMS shows 1.59 min 396.30 [M+1]. The solid was suspended in water and extracted with DCM. CC with prep HPLC gave product (42 mg, 23%). LCMS Rt =1.59 min m/z=396.30 [M+1]. 1H NMR (400 MHz, MeOD) D=7.89 (br. s., 1H), 7.86-7.74 (m, 2H), 7.48 (d, J=8.3 Hz, 1H), 7.26 (br. s., 1H), 7.19 (br. s., 1H), 4.48 (br. s., 1H), 4.35 (br. s., 2H), 3.34 (s, 2H), 2.76 (s, 2H), 1.91 (br. s., 2H), 1.68 (br. s., 4H), 1.55-1.21 (m, 10H).

Example 309: Further Compounds of Formula (I)

Each of the following additional compounds of formula (I) were prepared analogously to those described above:
4-(((2-(trans-4-tert-butylcyclohexyloxy)naphthalen-6-yl)methyl)amino)butyric acid;
(R)-1-((2-(trans-4-tert-butylcyclohexyloxy)naphthalen-6-yl)methyl)piperidine-3-carboxylic acid;
(S)-1-((2-(trans-4-tert-butylcyclohexyloxy)naphthalen-6-yl)methyl)piperidine-3-carboxylic acid;
4-((2-(trans-4-tert-butylcyclohexyloxy)naphthalen-6-yl)methyl)butyric acid;
5-((2-(trans-4-tert-butylcyclohexyloxy)naphthalen-6-yl)methyl)pentanoic acid;
6-((2-(trans-4-tert-butylcyclohexyloxy)naphthalen-6-yl)methyl)hexanoic acid;
4-(6-(trans-4-tert-butylcyclohexyloxy)-3,4-dihydroisoquinolin-2(1H)-yl)butanoic acid;
4-(6-(cis-4-tert-butylcyclohexyloxy)-3,4-dihydroisoquinolin-2(1H)-yl)butanoic acid;
2-(2-(5-(trans-4-tert-butylcyclohexyloxy)indolin-1-yl)-2-oxoethylamino)ethylphosphonic acid; and
3-amino-4-(5-(trans-4-tert-butylcyclohexyloxy)indolin-1-yl)-4-oxo-butanoic acid.

Example 310: Further Compounds of Formula (I)

Each of the following additional compounds of formula (I) are prepared analogously to those described above:
1-((6-(spiro[5.5]undecan-3-yloxy)naphthalen-2-yl)methyl)azetidine-3-carboxylic acid;
1-((6-(trans-4-tert-butylcyclohexyloxy)naphthalen-2-yl)sulfonyl)azetidine-3-carboxylic acid;
3-(((6-(trans-4-tert-butylcyclohexyloxy)naphthalen-2-yl)methyl)amino)-N-(methylsulfonyl)propionamide;
5-(2-(((6-(trans-4-tert-butylcyclohexyloxy)naphthalen-2-yl)methyl)amino)ethyl)tetrazole;
1-hydroxy-2-(((6-(trans-4-tert-butylcyclohexyloxy)naphthalen-2-yl)methyl)amino)ethylphosphonic acid;
3-(((6-(trans-4-tert-butylcyclohexyloxy)naphthalen-2-yl)methyl)amino)propylphosphonic acid;
3-(((6-(trans-4-tert-butylcyclohexyloxy)quinoxalin-2-yl)methyl)amino)propionic acid;
3-(((7-(trans-4-tert-butylcyclohexyloxy)quinolin-3-yl)methyl)amino)propionic acid;
3-(((7-(trans-4-tert-butylcyclohexyloxy)cinnolin-3-yl)methyl)amino)propionic acid;
3-(((5-(trans-4-tert-butylcyclohexyloxy)-1-methylindol-2-yl)methyl)amino)propionic acid;
3-(((6-(trans-4-tert-butylcyclohexyloxy)-1-methylindol-2-yl)methyl)amino)propionic acid;
3-(((2-(trans-4-tert-butylcyclohexyloxy)quinazolin-6-yl)methyl)amino)propionic acid;
3-(((2-(trans-4-tert-butylcyclohexyloxy)-1-methylindol-6-yl)methyl)amino)propionic acid;
3-(((2-(trans-4-tert-butylcyclohexyloxy)-1-methylindol-5-yl)methyl)amino)propionic acid; and
3-(((3-(trans-4-tert-butylcyclohexyloxy)-1-methylindol-6-yl)methyl)amino)propionic acid.

Example 310: Calcium Mobilization

Compounds that are not specific for the $S1P_1$ receptor, e.g., have $S1P_3$ activity, can cause undesirable side effects. Accordingly, compounds are tested to identify those that are specific for $S1P_1$ activity and have little or no activity, or are antagonists of, $S1P_3$ activity. Accordingly, the test compounds are tested in a calcium mobilization assay to determine agonist activity at either the human $S1P_1$ or human $S1P_3$ receptor, and antagonist activity only at the human $S1P_3$ receptor. The procedure is essentially as described in Davis et al. (2005) *Journal of Biological Chemistry*, vol. 280, pp. 9833-9841, which is incorporated by reference in its entirety with the following modifications. Calcium mobilization assays were performed in recombinant CHEM cells expressing human $S1P_1$, $S1P_2$, $S1P_3$, $S1P_4$, or $S1P_5$ purchased from Millipore (Billerica, Mass.). To detect free intracellular calcium, $S1P_1$, $S1P_2$, $S1P_3$, $S1P_4$, or $S1P_5$ cells were loaded with FLIPR Calcium 4 dye from Molecular Devices (Sunnyvale, Calif.). Cells were imaged for calcium mobilization using a FLIPR$^{TETRA}$ equipped with a 96-well dispense head.

Example 311: In Vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVET™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of formula (I) can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

Example 312: Assessment of Heart Effect

One reported undesirable effect of an S1P agonist can be, e.g., bradycardia. Assays are conducted to determine the effect of test compounds on heart function. The effects of compounds on cardiac function are monitored using the ECG genie recording system. ECGs are recorded in conscious mice (C57bl/6 male, 6-10 week-old) before and after compound administration. Compounds were administered by oral gavage. Three mice are used to assess heart rate effect of each compound. Compounds are found to have little or no effect on heart rate at therapeutic levels.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

The invention claimed is:

1. A method for treatment of multiple sclerosis in a mammal comprising administering to said mammal an effective amount of a compound of formula (IIa):

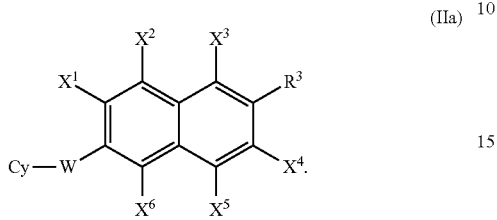

or a pharmaceutically acceptable salt thereof, wherein:
each of $X^1$, $X^2$, $X^3$, $X^4$, $X^5$, and $X^6$, independently, is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —N($R^f R^g$), —N($R^f$)$SO_2R^g$, —$SO_2R^f$, —S(O)$_2$N($R^f R^g$), —$CO_2R^f$, trialkylamino, aryl, or heteroaryl;
W is —O—;
Cy has the formula:

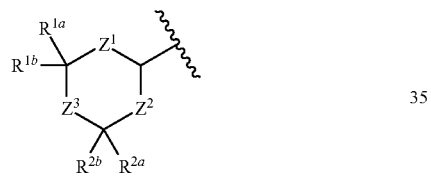

wherein:
$Z^1$ is —CH$_2$CH$_2$—;
$Z^2$ is —CH$_2$—;
$Z^3$ is a bond;
$R^{1a}$ and $R^{1b}$, independently, are hydrogen, halo, hydroxy, nitro, cyano, —N$R^f R^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;
or $R^{1a}$ and $R^{1b}$, when taken together, are $C_2$-$C_5$ alkylene or $C_2$-$C_5$ alkenylene;
$R^{2a}$ and $R^{2b}$, independently, are hydrogen, halo, hydroxy, nitro, cyano, —N$R^f R^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;
or $R^{1a}$ and $R^{2a}$, when taken together, are $C_1$-$C_5$ alkylene or $C_2$-$C_5$ alkenylene;

wherein $R^{1a}$, $R^{1b}$, $R^{2a}$, and $R^{2b}$ are each, independently, substituted with 0-5 substituents selected from halo, hydroxy, nitro, cyano, —N$R^f R^g$, or —$CO_2R^f$;
$R^3$ is -$L^1$-J-$L^2$-$T^1$;
$L^1$ is —C($R^f R^g$)—;
J is —N($R^f$)—; or J is

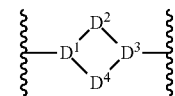

wherein
each of $D^1$ and $D^3$, independently, is

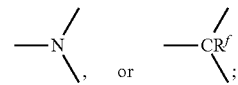

$D^2$ is —[C($R^f R^g$)]$_k$—, —[C($R^f R^g$)]$_k$—N($R^f$)—, —[C($R^f R^g$)]$_k$—O—, —N($R^f$)—, or —N($R^f$)—[(C$R^f R^g$)]$_k$—; and
$D^4$ is —[C($R^f R^g$)]$_m$—;
wherein k is 1 or 2; and m is 0, 1, 2, or 3;
provided that no more than 2 ring atoms of $D^1$-$D^4$ are N or O;
$L^2$ is —C($R^f R^g$)—, —C($R^f$G)-, —C(G)$_2$-, —C($R^f R^g$)—C($R^f R^g$)—, —C($R^f R^g$)—C($R^f$G)-, —C($R^f R^g$)—C(G)$_2$-, or a bond;
$T^1$ is —C(O)(O$R^f$), —C(O)N($R^f$)S(O)$_2R^f$, tetrazolyl, —S(O)$_2$O$R^f$, —C(O)NHC(O)—$R^f$, —Si(O)OH, —B(OH)$_2$, —N($R^f$)S(O)$_2R^f$, —S(O)$_2$N$R^f$, —O—P(O)(O$R^f$)O$R^f$, or —P(O)$_2$(O$R^f$);
each G, independently, is hydrogen, hydroxy, a halogen, or trifluoromethyl;
each $R^f$, independently, is hydrogen, hydroxy, halo, alkyl, haloalkyl, alkenyl, alkynyl, cycloalkyl, cycloalkenyl, aryl, heteroaryl, heterocyclyl or NH$_2$;
wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CG$_3$, —OH, —NO$_2$, alkyl, —OCG$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and
each $R^g$, independently, is hydrogen, hydroxy, halo, alkyl, haloalkyl, alkenyl, alkynyl, cycloalkyl, cycloalkenyl, aryl, heteroaryl, or heterocyclyl;
wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CG$_3$, —OH, —NO$_2$, alkyl, —OCG$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

2. The method of claim 1, wherein $T^1$ is —C(O)(O$R^f$), —C(O)N($R^f$)S(O$_2R^f$), —O—P(O)(O$R^f$)O$R^f$, —P(O)$_2$(O$R^f$), tetrazolyl or —S(O)$_2$O$R^f$.

3. The method of claim 1, wherein $R^{1a}$ and $R^{2a}$ are both hydrogen, and $R^{1b}$ is fluoro, chloro, bromo, iodo, methyl, triflurormethyl, ethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

4. The method of claim 1, or a pharmaceutically acceptable salt thereof, wherein:

J is

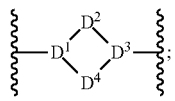

and $T^1$ is —C(O)(OR$^f$), —C(O)N(R)S(O$_2$R), —O—P(O)(OR$^f$)OR$^f$, —P(O$_2$)(OR$^f$), tetrazolyl, or —S(O)$_2$OR$^f$.

5. A method for treatment of multiple sclerosis in a mammal comprising administering to said mammal an effective amount of a compound of formula (IIa), (IIIa) or (IIIb):

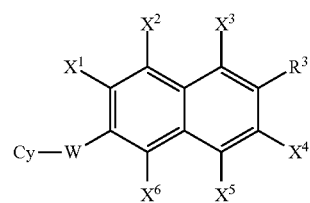
(IIa)

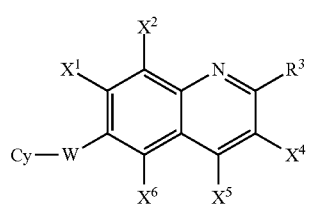
(IIIa)

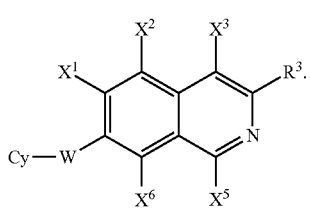
(IIIb)

or a pharmaceutically acceptable salt thereof, wherein:
each of $X^1$, $X^2$, $X^3$, $X^4$, $X^5$, and $X^6$, independently, is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —N(R$^f$R$^g$), —N(R$^f$)SO$_2$R$^g$, —SO$_2$R$^f$, —S(O)$_2$N(R$^f$R$^g$), —CO$_2$R$^f$, trialkylamino, aryl, or heteroaryl;
W is —O—;

Cy has the formula:

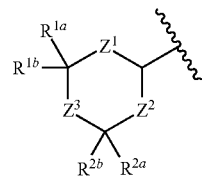

wherein:
$Z^1$ is —CH$_2$CH$_2$—;
$Z^2$ is —CH$_2$—;
$Z^3$ is a bond;
$R^{1a}$ and $R^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;
or $R^{1a}$ and $R^{1b}$, when taken together, are C$_2$-C$_5$ alkylene or C$_2$-C$_5$ alkenylene;
$R^{2a}$ and $R^{2b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;
or $R^{1a}$ and $R^{2a}$, when taken together, are C$_1$-C$_5$ alkylene or C$_2$-C$_5$ alkenylene;
wherein $R^{1a}$, $R^{1b}$, $R^{2a}$, and $R^{2b}$ are each, independently, substituted with 0-5 substituents selected from halo, hydroxy, nitro, cyano, —NR$^f$R$^g$, or —CO$_2$R$^f$;
$R^3$ is -L$^1$-J-L$^2$-T$^1$;
$L^1$ is —C(R$^f$R$^g$)—;
J is —N(R$^f$)—; or J is

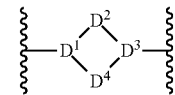

wherein
each of $D^1$ and $D^3$, independently, is

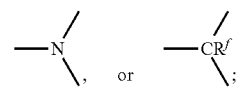

$D^2$ is —[C(R$^f$R$^g$)]$_k$—, —[C(R$^f$R$^g$)]$_k$—N(R$^f$)—, —[C(R$^f$R$^g$)]$_k$—O—, —N(R$^f$)—, or —N(R$^f$)—[(CR$^f$R$^g$)]$_k$—; and
$D^4$ is —[C(R$^f$R$^g$)]$_m$—;
wherein k is 1 or 2; and m is 0, 1, 2, or 3;
provided that no more than 2 ring atoms of $D^1$-$D^4$ are N or O;

L² is —C(RᶠRᵍ)—, —C(RᶠG)-, —C(G)₂-, —C(RᶠRᵍ)—C(RᶠRᵍ)—, —C(RᶠRᵍ)—C(RᶠG)-, —C(RᶠRᵍ)—C(G)₂-, or a bond;

T¹ is —C(O)(ORᶠ), —C(O)N(Rᶠ)S(O)₂Rᶠ, tetrazolyl, —S(O)₂ORᶠ, —C(O)NHC(O)—Rᶠ, —Si(O)OH, —B(OH)₂, —N(Rᶠ)S(O)₂Rᶠ, —S(O)₂NRᶠ, —O—P(O)(ORᶠ)ORᶠ, or —P(O)₂(ORᶠ);

each G, independently, is hydrogen, hydroxy, a halogen, or trifluoromethyl;

each Rᶠ, independently, is hydrogen, hydroxy, halo, alkyl, haloalkyl, alkenyl, alkynyl, cycloalkyl, cycloalkenyl, aryl, heteroaryl, heterocyclyl or NH₂; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CG₃, —OH, —NO₂, alkyl, —OCG₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl; and each Rᵍ, independently, is hydrogen, hydroxy, halo, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CG₃, —OH, —NO₂, alkyl, —OCG₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

6. The method of claim 5, wherein T¹ is —C(O)(ORᶠ), —C(O)N(Rᶠ)S(O₂Rᶠ), —O—P(O)(ORᶠ)ORᶠ, —P(O₂)(ORᶠ), tetrazolyl or —S(O)₂ORᶠ.

7. The method of claim 5, wherein R¹ᵃ and R²ᵃ are both hydrogen, and R¹ᵇ is fluoro, chloro, bromo, iodo, methyl, triflurormethyl, ethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

8. The method of claim 5, or a pharmaceutically acceptable salt thereof, wherein:
J is

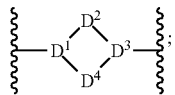

and
T¹ is —C(O)(ORᶠ), —C(O)N(Rᶠ)S(O₂Rᶠ), —O—P(O)(ORᶠ)ORᶠ, —P(O₂)(ORᶠ), tetrazolyl, or —S(O)₂ORᶠ.

9. The method of claim 1, wherein the compound is selected from the group consisting of:
3-((6-(trans-4-tert-butylcyclohexyloxy)naphthalen-2-yl)methylamino)-N-(phenylsulfonyl)propanamide;
3-((6-(trans-4-tert-butylcyclohexyloxy)-5-(trifluoromethyl)naphthalen-2-yl)methylamino)-N-(phenylsulfonyl)propanamide;
2-((6-(trans-4-tert-butylcyclohexyloxy)naphthalen-2-yl)methylamino)propanoic acid;
3-((6-(trans-4-tert-butylcyclohexyloxy)naphthalen-2-yl)methylamino)butanoic acid;
2-(((6-(trans-4-tert-butylcyclohexyloxy)naphthalen-2-yl)methyl)(methyl)amino) acetic acid;
3-((6-(trans-4-tert-butylcyclohexyloxy)naphthalen-2-yl)methylamino)propanoic acid;
3-(((6-(trans-4-tert-butylcyclohexyloxy)naphthalen-2-yl)methyl)(methyl)amino) propanoic acid;
1-((6-(trans-4-tert-butylcyclohexyloxy)naphthalen-2-yl)methyl)azetidine-3-carboxylic acid;
1-((6-(trans-4-tert-butylcyclohexyloxy)naphthalen-2-yl)methyl)pyrrolidine-3-carboxylic acid;
1-((6-(trans-4-tert-butylcyclohexyloxy)naphthalen-2-yl)methyl)piperidine-4-carboxylic acid;
1-((6-(trans-4-tert-butylcyclohexyloxy)-5-(trifluoromethyl)naphthalen-2-yl)methyl)azetidine-3-carboxylic acid;
3-((6-(trans-4-tert-butylcyclohexyloxy)-5-(trifluoromethyl)naphthalen-2-yl)methylamino)propanoic acid;
3-((6-(trans-4-tert-butylcyclohexyloxy)naphthalen-2-yl)methylamino)-2,2-difluoropropanoic acid;
2,2-difluoro-3-((6-(spiro[5.5]undecan-3-yloxy)naphthalen-2-yl)methylamino)propanoic acid;
2-(((2-(trans-4-tert-butylcyclohexyloxy)naphthalen-6-yl)methyl)amino)acetic acid;
4-(((2-(trans-4-tert-butylcyclohexyloxy)naphthalen-6-yl)methyl)amino)butyric acid;
4-(((2-(trans-4-tert-butylcyclohexyloxy)naphthalen-6-yl)methyl)amino)butyric acid;
(R)-1-((2-(trans-4-tert-butylcyclohexyloxy)naphthalen-6-yl)methyl)piperidine-3-carboxylic acid;
(S)-1-((2-(trans-4-tert-butylcyclohexyloxy)naphthalen-6-yl)methyl)piperidine-3-carboxylic acid;
4-((2-(trans-4-tert-butylcyclohexyloxy)naphthalen-6-yl)methyl)butyric acid;
5-((2-(trans-4-tert-butylcyclohexyloxy)naphthalen-6-yl)methyl)pentanoic acid;
6-((2-(trans-4-tert-butylcyclohexyloxy)naphthalen-6-yl)methyl)hexanoic acid;
4-(6-(trans-4-tert-butylcyclohexyloxy)-3,4-dihydroisoquinolin-2(1H)-yl)butanoic acid;
4-(6-(cis-4-tert-butylcyclohexyloxy)-3,4-dihydroisoquinolin-2(1H)-yl)butanoic acid;
2-(((2-(trans-4-tert-butylcyclohexyloxy)naphthalen-6-yl)methyl)amino)ethylphosphonic acid;
2-(2-(5-(trans-4-tert-butylcyclohexyloxy)indolin-1-yl)-2-oxoethylamino)ethylphosphonic acid;
3-amino-4-(5-(trans-4-tert-butylcyclohexyloxy)indolin-1-yl)-4-oxo-butanoic acid;
3-{[6-(4-tert-butyl-cyclohexyloxy)-8-methyl-naphthalen-2-ylmethyl]-amino}-propionic acid;
{[6-(4-tert-butyl-cyclohexyloxy)-8-methyl-naphthalen-2-ylmethyl]-amino}-acetic acid;
4-{[6-(4-tert-butyl-cyclohexyloxy)-8-methyl-naphthalen-2-ylmethyl]-amino}-butyric acid;
1-[6-(4-tert-butyl-cyclohexyloxy)-8-methyl-naphthalen-2-ylmethyl]-azetidine-3-carboxylic acid; and
1-[6-(4-tert-butyl-cyclohexyloxy)-8-methyl-naphthalen-2-ylmethyl]-pyrrolidine-3-carboxylate;
or a pharmaceutically acceptable salt thereof.

10. The method of claim 1, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulator, an antipsoriatic, and an antidiabetic.

* * * * *